(12) United States Patent
Johnson et al.

(10) Patent No.: US 10,716,858 B2
(45) Date of Patent: Jul. 21, 2020

(54) BRANCHED MULTI-FUNCTIONAL MACROMONOMERS AND USES THEREOF

(71) Applicant: Massachusetts Institute of Technology, Cambridge, MA (US)

(72) Inventors: Jeremiah A. Johnson, Boston, MA (US); Nolan Gallagher, Cambridge, MA (US); Farrukh Vohidov, Arlington, MA (US); Yivan Jiang, Stow, MA (US); Hung Vanthanh Nguyen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/024,662

(22) Filed: Jun. 29, 2018

(65) Prior Publication Data
US 2019/0038751 A1    Feb. 7, 2019

Related U.S. Application Data

(60) Provisional application No. 62/528,010, filed on Jun. 30, 2017.

(51) Int. Cl.
| | | |
|---|---|---|
| A61K 47/18 | (2017.01) | |
| C08G 61/08 | (2006.01) | |
| A61K 47/59 | (2017.01) | |
| A61P 35/00 | (2006.01) | |
| C07D 403/14 | (2006.01) | |
| C07D 405/14 | (2006.01) | |
| C08G 83/00 | (2006.01) | |
| C08L 71/02 | (2006.01) | |
| A61K 47/34 | (2017.01) | |
| B01J 31/22 | (2006.01) | |
| C08G 69/48 | (2006.01) | |
| G01N 33/574 | (2006.01) | |

(52) U.S. Cl.
CPC ............ *A61K 47/18* (2013.01); *A61K 47/34* (2013.01); *A61K 47/595* (2017.08); *A61P 35/00* (2018.01); *B01J 31/2278* (2013.01); *C07D 403/14* (2013.01); *C07D 405/14* (2013.01); *C08G 61/08* (2013.01); *C08G 69/48* (2013.01); *C08G 83/00* (2013.01); *C08L 71/02* (2013.01); *G01N 33/574* (2013.01); *B01J 2523/821* (2013.01); *C08G 2261/135* (2013.01); *C08G 2261/136* (2013.01); *C08G 2261/1414* (2013.01); *C08G 2261/1424* (2013.01); *C08G 2261/1426* (2013.01); *C08G 2261/1432* (2013.01); *C08G 2261/418* (2013.01); *C08G 2261/76* (2013.01)

(58) Field of Classification Search
None
See application file for complete search history.

(56) References Cited

U.S. PATENT DOCUMENTS

| | | | |
|---|---|---|---|
| 4,359,425 | A | 11/1982 | Totani et al. |
| 5,811,515 | A | 9/1998 | Grubbs et al. |
| 8,067,505 | B2 | 11/2011 | Harris et al. |
| 9,381,253 | B2 | 7/2016 | Johnson et al. |
| 9,447,129 | B2 | 9/2016 | Johnson et al. |
| 9,822,216 | B2 | 11/2017 | Mahanthappa et al. |
| 10,023,536 | B2 | 7/2018 | Johnson et al. |
| 10,105,449 | B2 | 10/2018 | Johnson et al. |
| 10,153,513 | B2 | 12/2018 | Grubbs et al. |
| 10,159,749 | B2 | 12/2018 | Johnson et al. |
| 2002/0183473 | A1 | 12/2002 | Matyjaszewski et al. |
| 2002/0198328 | A1 | 12/2002 | L'Alloret |
| 2003/0065023 | A1 | 4/2003 | Swindell et al. |
| 2005/0109976 | A1 | 5/2005 | Fuchs et al. |
| 2011/0243848 | A1 | 10/2011 | Appel et al. |
| 2011/0300219 | A1 | 12/2011 | Lippard et al. |
| 2013/0296491 | A1 | 11/2013 | Xia |
| 2013/0324666 | A1 | 12/2013 | Yan et al. |
| 2014/0142249 | A1 | 5/2014 | Cho et al. |
| 2014/0308234 | A1 | 10/2014 | Johnson et al. |
| 2015/0225438 | A1 | 8/2015 | Johnson |
| 2016/0024246 | A1 | 1/2016 | Mahanthappa et al. |
| 2016/0289392 | A1 | 10/2016 | Grubbs et al. |
| 2016/0296631 | A1 | 10/2016 | Johnson |
| 2016/0361702 | A1 | 12/2016 | Cohen et al. |
| 2017/0000909 | A1 | 1/2017 | Gianneschi et al. |
| 2017/0073311 | A1 | 3/2017 | Johnson et al. |
| 2017/0348431 | A1 | 12/2017 | Johnson et al. |
| 2018/0030213 | A1 | 2/2018 | Johnson et al. |
| 2018/0036415 | A9 | 2/2018 | Johnson et al. |

(Continued)

FOREIGN PATENT DOCUMENTS

| CN | 101412792 A | 4/2009 |
|---|---|---|
| KR | 20120113694 A | 10/2012 |

(Continued)

OTHER PUBLICATIONS

International Search Report and Written Opinion dated Aug. 29, 2014 for Application No. PCT/US2014/33554.

(Continued)

*Primary Examiner* — Brian J Davis
(74) *Attorney, Agent, or Firm* — Wolf, Greenfield & Sacks, P.C.

(57) ABSTRACT

Disclosed are methods, compositions, reagents, systems, and kits to prepare and utilize branched multi-functional macromonomers, which contain a ring-opening metathesis polymerizable norbornene group, one or more reactive sites capable of undergoing click chemistry, and a terminal acyl group capable of undergoing a coupling reaction; branched multi-cargo macromonomers; and the corresponding polymers are disclosed herein. Various embodiments show that the macromonomers and polymers disclosed herein display unprecedented control of cargo loading of agents. These materials have the potential to be utilized for the treatment of diseases and conditions such as cancer and hypertension.

31 Claims, 87 Drawing Sheets

(56) References Cited

U.S. PATENT DOCUMENTS

| | | |
|---|---|---|
| 2019/0030067 A1 | 1/2019 | Johnson et al. |
| 2019/0038751 A1 | 2/2019 | Johnson et al. |
| 2019/0038782 A1 | 2/2019 | Johnson et al. |
| 2019/0054187 A1 | 2/2019 | Johnson et al. |
| 2019/0192672 A1 | 6/2019 | Johnson et al. |

FOREIGN PATENT DOCUMENTS

| | | |
|---|---|---|
| WO | WO 2010/047765 A2 | 4/2010 |
| WO | WO 2013/169739 A1 | 11/2013 |
| WO | WO 2014/169073 A1 | 10/2014 |
| WO | WO 2016/023036 A1 | 2/2016 |

OTHER PUBLICATIONS

Anderson, Late Transition Metal Complexes of Pentafluorophenylphosphino-Pincer Ligands. Doctoral Thesis. Victoria University of Wellington. 2012:ii, iii, 32.

Huynh, Novel Polymeric Micelles via RAFT Polymerization for Platinum Drug Delivery. Doctoral Thesis. The University of New South Wales. 2012:i, 57-58.

Johnson et al., Core-clickable PEG-branch-azide bivalent-bottlebrush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Li et al., Surface Properties of Bottlebrush Polymer Thin Films. Macromolecules. 2012;45(17):7118-7127.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

U.S. Appl. No. 14/249,254, filed Apr. 9, 2014, Johnson et al.
U.S. Appl. No. 15/190,018, filed Jun. 22, 2016, Johnson et al.
U.S. Appl. No. 15/616,498, filed Jun. 7, 2017, Johnson et al.
U.S. Appl. No. 16/167,412, filed Oct. 22, 2018, Johnson et al.
U.S. Appl. No. 16/024,665, filed Jun. 29, 2018, Johnson et al.
U.S. Appl. No. 16/024,643, filed Jun. 29, 2018, Johnson et al.
PCT/US2014/033554, Oct. 22, 2015, International Preliminary Report on Patentability.
EP 14782253.0, Nov. 11, 2016, Extended European Search Report.
PCT/US2017/036447, Sep. 7, 2017, International Search Report and Written Opinion.
PCT/US2017/036447, Dec. 20, 2018, International Preliminary Report on Patentability.
PCT/US2017/064784, Mar. 1, 2018, International Search Report and Written Opinion.
PCT/US2018/040488, Oct. 15, 2018, International Search Report and Written Opinion.
PCT/US2018/040494, Oct. 10, 2018, International Search Report and Written Opinion.
PCT/US2018/040496, Nov. 21, 2018, Invitation to Pay Additional Fees.
International Preliminary Report on Patentability for PCT/US2014/033554, dated Oct. 22, 2015.
Extended European Search Report for EP 14782253.0, dated Nov. 11, 2016.
International Search Report and Written Opinion for PCT/US2017/036447, dated Sep. 7, 2017.
International Preliminary Report on Patentability for PCT/US2017/036447, dated Dec. 20, 2018.
International Search Report and Written Opinion for PCT/US2017/064784, dated Mar. 1, 2018.
International Search Report and Written Opinion for PCT/US2018/040488, dated Oct. 15, 2018.
International Search Report and Written Opinion for PCT/US2018/040494, dated Oct. 10, 2018.
Invitation to Pay Additional Fees for PCT/US2018/040496, dated Nov. 21, 2018.

Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.

Aime et al., Lanthanide(III) chelates for NMR biomedical applications. Chem. Soc. Rev., 1998;27:19-29.

Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.

Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.

Altintas et al., Constructing star polymersvia modular ligation strategies. Polym. Chem., 2012;3:34-45. DOI: 10.1039/C1PY00249J.

Amouri et al., Host-guest interactions: design strategy and structure of an unusual cobalt cage that encapsulates a tetrafluoroborate anion. Angew Chem Int Ed Engl. Jul. 18, 2005;44(29):4543-6.

Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.

Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.

Anraku et al., Size-controlled long-circulating PICsome as a ruler to measure critical cut-off disposition size into normal and tumor tissues. Chem Commun (Camb). Jun. 7, 2011;47(21):60546. doi: 10.1039/c1cc11465d. Epub Apr. 26, 2011.

Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.

Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.

Bapat et al., Dynamic-covalent nanostructures prepared by Diels—Alder reactions of styrene-maleic anhydride-derived copolymers obtained by one-step cascade block copolymerization. Polym. Chem., 2012;3:3112-3120. DOI: 10.1039/C2PY20351K.

Bapat et al., Redox-Responsive Dynamic-Covalent Assemblies: Stars and Miktoarm Stars. Macromolecules, 2013;46(6):2188-2198. DOI: 10.1021/ma400169m.

Barbour et al., an intermolecular (H2O)10 cluster in a solid-state supramolecular complex. Nature. 1998;393(6686): 671-673.

Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. EpubSep. 14, 2016.

Barrett et al., pH-Based Regulation of Hydrogel Mechanical Properties Through Mussel-Inspired Chemistry and Processing. Advanced Functional Materials. Mar. 6, 2013;23(9):1111-1119.

Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.

Beck et al., Multistimuli, multiresponsive metallo-supramolecular polymers. J Am Chem Soc. Nov. 19, 2003;125(46):13922-3.

Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.

Blencowe et al., Core cross-linked star polymers via controlled radical polymerisation. Polymer Jan. 2009;50(1):5-32.

(56) References Cited

OTHER PUBLICATIONS

Bunco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983;147(3):781-8.
Brummelhuis et al., Stimuli-responsive star polymers through thiol-yne core functionalization/crosslinking of block copolymer micelles. Polym. Chem., 2011;2:1180-1184. DOI: 10.1039/C1PY00002K.
Budil et al., Nonlinear-Least -Squares Analysis of Slow-Motion EPR Spectra in One and Two Levenberg-Marquardt Algorithm. Elsevier. Journal of Magnetic.Dimensions Using a Modified Resonance, Series A. Jun. 1996;120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Burts et al., Using EPR to Compare PEG-branch-nitroxide "Bivalent-Brush Polymers" and Traditional PEG Bottle—Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caiolfa et al., Polymer-bound camptothecin: initial biodistribution and antitumour activity studies. J Control Release. Mar. 1, 2000;65(1-2):105-19.
Campos-Fernandez et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.
Campos-Fernandez et al., Fine-tuning the ring-size of metallacyclophanes: a rational approach to molecular pentagons. J Am Chem Soc. Jan. 31, 2001;123(4):773-4.
Caravan et al., Gadolinium(III) Chelates as MRI Contrast Agents: Structure, Dynamics, and Applications. Chem Rev. Sep. 8, 1999;99(9):2293-352.
Castilla et al., Stereochemistry in subcomponent self-assembly. Acc Chem Res. Jul. 15, 2014;47(7):2063-73. doi: 10.1021/ar5000924. Epub May 2, 2014.
Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metal-locage encapsulating a nitrate ion. Chem Commun (Camb). Sep. 7, 2001;(17):1652-3.
Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.
Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.
Chen et al., Synthesis of superporous hydrogels: hydrogels with fast swelling and superabsorbent properties. J Biomed Mater Res. Jan. 1999;44(1):53-62.
Cheon et al., Synergistically integrated nanoparticles as multimodal probes for nanobiotechnology.Acc Chem Res. Dec. 2008;41(12):1630-40. doi: 10.1021/ar800045c.
Chifotides et al., Anion-.pi. interactions in supramolecular architectures. Acc Chem Res. Apr. 16, 2013;46(4):894-906. doi: 10.1021/ar300251k. Epub Mar. 11, 2013.
Choi et al., Self-confirming "AND" logic nanoparticles for fault-free MRI. J Am Chem Soc. Aug. 18, 2010;132(32):11015-7. doi: 10.1021/ja104503g.
Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.
Clever et al., Inclusion of anionic guests inside a molecular cage with palladium(II) centers as electrostatic anchors. Angew Chem Int Ed Engl. 2009;48(38):7010-2. doi: 10.1002/anie.200902717.
Cok et al., Synthesis of Model Network Hydrogels via Tetrazine-Olefin Inverse Electron Demand Diels-Alder Cycloaddition. Macromolecular Symposia. Jul. 2013;329(1):108-112.
Conrad et al., Tunable, temperature-responsive polynorbornenes with side chains based on an elastin peptide sequence. Angew Chem Int Ed Engl. 2009;48(44):8328-30. doi: 10.1002/anie.200903888.
Cordier et al., Self-healing and thermoreversible rubber from supramolecular assembly. Nature. Feb. 21, 2008;451(7181):977-80. doi: 10.1038/nature06669.
Davies et al., Environmentally responsive MRI contrast agents. Chem Commun (Camb). Oct. 28, 2013;49(84):9704-21. doi: 10.1039/c3cc44268c.
Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.
Davis et al., Nanoparticle therapeutics: an emerging treatment modality for cancer. Nat Rev Drug Discov. Sep. 2008;7(9):771-82. doi: 10.1038/nrd2614.
Desmarets et al., Design, Self-Assembly, and Molecular Structures of 3D Copper(II) Capsules Templated by BF4—Guest Anions. European Journal of Inorganic Chemistry. Oct. 2009;(2930):4396-4400. doi: 10.1002/ejic.200900606.
Detape et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.
Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.
Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.
Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.
Doane et al., the unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.
Duncan et al., The dawning era of polymer therapeutics. Nat Rev Drug Discov. May 2003;2(5):347-60.
Duncan, The dawning era of polymer therapeutics. Nat Rev Drug Discov. May 2003;2(5):347-60.

(56) References Cited

OTHER PUBLICATIONS

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.

Eryazici et al., Two Large-Pore Metal-Organic Frameworks Derived from a Single Polytopic Strut. Crystal Growth & Design. Mar. 7, 2012;12(3):1075-1080.

Feng et al., A metabonomic analysis of organ specific response to USPIO administration. Biomaterials. Sep. 2011;32(27):6558-69. doi: 10.1016/j.biomaterials.2011.05.035.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Forgan et al., Chemical topology: complex molecular Rev. Sep. 14, 2014;111(9):5434-64. doi: 10.1021/cr200034u. knots, links, and entanglements. Chem 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Fullenkamp et al., Mussel-Inspired Histidine-Based Transient Network Metal Coordination Hydrogels. Macromolecules. Jan. 18, 2013;46(3):1167-1174.

Gao et al., Development of star polymers as unimolecular containers for nanomaterials. Macromol Rapid Commun. May 14, 2012;33(9):722-34. doi: 10.1002/marc.201200005. Epub Mar. 14, 2012.

Gao et al., Modular Approaches to Star and Miktoarm Star Polymers by ATRP of Cross-Linkers. Macromol. Symp., 291-292: 12-16. doi:10.1002/masy.201050502.

Gao et al., Synthesis of Acid-Labile PEG and PEG-Doxorubicin-Conjugate Nanoparticles via Brush-First ROMP. ACS Macro Lett., 2014;3(9):854-857. DOI: 10.1021/mz5004097.

Gao et al., Synthesis of functional polymers with controlled architecture by CRP of monomers in the presence of cross-linkers: From stars to gels. Progress in Polymer Science Apr. 2009;34(4):317-350.

Gao et al., Synthesis of Star Polymers by a New "Core-First" Method: Sequential Polymerization of Cross-Linker and Monomer. Macromolecules, 2008;41(4):1118-1125. DOI: 10.1021/ma702560f.

Ge et al., A Pyrene-functionalized Polynorbornene for Ratiometric Fluorescence Sensing of Pyrophosphate. Chem. Asian J. 2016;11:687.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Glunde et al., Magnetic resonance spectroscopy in metabolic and molecular imaging and diagnosis of cancer. Chem Rev. May 12, 2010;110(5):3043-59. doi: 10.1021/cr9004007.

Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.

Greenwald et al., Effective drug delivery by PEGylated drug conjugates. Adv Drug Deliv Rev. Feb. 10, 2003;55(2):217-50.

Grumbley et al., Photoresponsive Polymers Containing Nitrobenzyl Esters via Ring-Opening Metathesis Polymerization. Macromolecules. 2011;44(20):7956-61.

Hackelbusch et al., Chain Dynamics in Supramolecular Polymer Networks. Macromolecules. 2013;46(15):6273-6286.

Hackelbusch et al., Multiresponsive Polymer Hydrogels by Orthogonal Supramolecular Chain Cross-Linking. Macromolecules. 2014;47(12):4028-4036.

Haddleton et al., Well-defined oligosaccharide-terminated polymers from living radical polymerization. Biomacromolecules. 2000 Summer;1(2):152-6.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Han et al., Recent Development of Peptide Coupling Reagents in Organic Synthesis. Tetrahedron, 2004;60:2447-2467.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Hao et al., Dendrimers as scaffolds for multifunctional reversible addition—fragmentation chain transfer agents: Syntheses and polymerization. J. Polym. Sci. A Polym. Chem., 2004;42:5877-5890. doi:10.1002/pola.20434.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Harrison et al., A multimeric MR-optical contrast agent for multimodal imaging. Chem Commun (Camb). Oct. 9, 2014;50(78):11469-71. doi: 10.1039/c4cc05651e.

Harrison et al., Multimeric Near IR-MR Contrast Agent for Multimodal in Vivo Imaging. J Am Chem Soc. Jul. 22, 2015;137(28):9108-16. doi: 10.1021/jacs.5b04509. Epub Jul. 14, 2015.

Harvey et al., Lanthanide Complexes as Paramagnetic Probes for 19F Magnetic Resonance. Eur. J. Inorg. Chem., 2012: 2015-2022. doi:10.1002/ejic.201100894.

Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.

Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.

Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.

Helms et al., One-Pot Reaction Cascades Using Star Polymers with Core-Confined Catalysts. Angewandte Chemie, 2005;44:6384-6387. doi:10.1002/ange.200502095.

Hirakawa et al., Removal of Perchlorate Anion from an Aqueous Solution by Encapsulation in an Anion-templated Self-assembled Molecular Capsule. Chemistry Letters. 2009;38(3):290-291.

Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

(56) References Cited

OTHER PUBLICATIONS

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Huinink et al., Topotecan versus paclitaxel for the treatment of recurrent epithelial ovarian cancer. J Clin Oncol. Jun. 1997;15(6):2183-93.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jamieson et al., Structure, Recognition, and Processing of Cisplatin-DNA Adducts. Chem Rev. Sep. 8, 1999;99(9):2467-98.

Jesberger et al., Hyperbranched polymers as scaffolds for multi-functional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi200-40219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20,2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Mussel-Inspired Adhesives and Coatings. Annu Rev Mater Res. Aug. 1, 2011;41:99-132.

Lee et al., Single-molecule mechanics of mussel adhesion. Proc Natl Acad Sci U S A. Aug. 29, 2006;103(35):12999-3003. Epub Aug. 18, 2006.

Lee et al., Stimuli-responsive molecular brushes. Progress in Polymer Science (Oxford), 35(1-2), 24-44. DOI: 10.1016/j.progpolymsci.2009.11.002.

Leininger et al., Self-assembly of discrete cyclic nanostructures mediated by transition metals. Chem Rev. Mar. 8, 2000;100(3):853-908.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Polycatechol Nanoparticle MRI Contrast Agents. Small, 2016;12(5):668-677. https://doi.org/10.1002/smll.201502754.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Liang et al., The copper(I)-catalyzed alkyne-azide cycloaddition (CuAAC) "click" reaction and its applications. An overview. Coordination Chemistry Reviews Dec. 2011;255(23-24):2933-2945.

(56) References Cited

OTHER PUBLICATIONS

Liao et al., A Convergent Synthetic Platform for Single-Nanoparticle Combination Cancer Therapy: Ratiometric Loading and Controlled Release of Cisplatin, Doxorubicin, and Camptothecin. J. Am. Chem. Soc., 2014;136(16):5896-5899. DOI: 10.1021/ja502011g.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 4, 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457460.

Liu et al., Nuts and bolts of chemical exchange saturation transfer MRI. NMR Biomed. Jul. 2013;26(7):810-28. doi: 10.1002/nbm.2899. Epub Jan. 10, 2013.

Liu et al., Particles without a Box: Brush-first Synthesis of Photodegradable PEG Star Polymers under Ambient Conditions. J Vis Exp. 2013;80:e50874, doi:10.3791/50874.

Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805. doi: 10.1021/acsnano.6b07196.

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Ma et al., Nanoparticles for combination drug therapy. ACS Nano. Nov. 26, 2013;7(11):951825. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., Oximes as reversible links in polymer chemistry: dynamic macromolecular stars. Polym. Chem., 2014;5:6923-6931. DOI: 10.1039/C4PY01282H.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Nair et al., Modulating mechanical properties of self-assembled polymer networks by mult-ifunctional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

(56) References Cited

OTHER PUBLICATIONS

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer as the Supporting Ligand for Ruthenium-Catalyzed Chemoselective Hydrogen Transfer Reduction of Ketones. Organometallics, 2012;31(14):5074-5080. DOI: 10.1021/om300417v.

Paletta et al., Synthesis and Reduction Kinetics of Sterically Shielded Pyrrolidine Nitroxides. Org. Lett., 2012;14(20):5322-5325. DOI: 10.1021/ol302506f.

Park et al.,Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Qiu et al., Efficient and versatile synthesis of star polymers in water and their use as emulsifiers. Chem. Commun., 2011;47:12685-12687. DOI: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Rizzo et al., in vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

Rzayev et al., Molecular Bottlebrushes: New Opportunities in Nanomaterials Fabrication. ACS Macro Lett., 2012;1(9):1146-1149. DOI: 10.1021/m7300402x.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host—guest self-assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shellock et al., Safety of magnetic resonance imaging contrast agents. J Magn Reson Imaging. Sep. 1999;10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Skomski et al., Redox-active on-surface assembly of metal-organic chains with single-site Pt(II). *J Am Chem Soc. Jul. 16, 2014;136(28):9862-5. doi: 10.1021/ja504850f. Epub Jul. 1, 2014.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications2014;5:Article No. 5460.

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

(56) References Cited

OTHER PUBLICATIONS

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sulistio et al., Star polymers composed entirely of amino acid building blocks: a route towards stereospecific, biodegradable and hierarchically functionalized stars. Chem. Commun., 2011;47:1151-1153. DOI: 10.1039/COCC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Thompson et al., Labelling polymers and micellar nanoparticles via initiation, propagation and termination with ROMP. Polym. Chem., 2014;5:1954-1964.

Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.

Tolmasoff et al., Superoxide dismutase: correlation with life-span and specific metabolic rate in primate species. Proc Natl Acad Sci U S A. May 1980;77(5):2777-81.

Tominaga et al., Finite, spherical coordination networks that self-organize from 36 small components. Angew Chem Int Ed Engl. Oct. 25, 2004;43(42):5621-5.

Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.

Tsuji et al., Facile Palladium catalyzed decarboxylative allylation of active methylene compounds under neutral conditions using allylic carbonates. Tetrahedron Letters. 1982;23(46):4809-12.

Tu et al., Multimodal magnetic-resonance/optical-imaging contrast agent sensitive to NADH. Angew Chem Int Ed Engl. 2009;48(35):6547-51. doi: 10.1002/anie.200900984.

Valeur et al., Amide bond formation: beyond the myth of coupling reagents. Chem. Soc. Rev., 2009;38:606-631. DOI: 10.1039/B701677H.

Verduzco et al., Correction: Structure, function, self-assembly, and applications of bottlebrush copolymers. Chem Soc Rev. Nov. 7, 2015;44(21):7916. doi: 10.1039/c5cs90099a.

Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.

Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.

Wang et al., Advances of cancer therapy by nanotechnology. Cancer Res Treat. Mar. 2009;41(1):1-11. doi: 10.4143/crt.2009.41.1.1. Epub Mar. 31, 2009.

Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol5024491].

Wei et al., Exceedingly small iron oxide nanoparticles as positive MRI contrast agents. Proc. Natl. Acad. Sci. USA 2017;114(9):2325-2330.

Weng et al., Control of Gel Morphology and Properties of a Class of Metallo-Supramolecular Polyers by Good/Poor Solvent Environments. Macromolecules. 2009;42(1):236-246.

Weng et al., Effect of monomer structure on the gelation of a class of metallo-supramolecular polymers. Soft Matter. 2009;5(23):4647-4657.

Weng et al., Structural origin of the thixotropic behavior of a class of metallosupramolecular gels. Tetrahedron. Jul. 30, 2007;63(31):7419-7431.

Weng et al., Understanding the mechanism of gelation and stimuli-responsive nature of a class of metallo-supramolecular gels. J Am Chem Soc. Sep. 6, 2006;128(35):11663-72.

Westhaus et al., Triggered release of calcium from lipid vesicles: a bioinspired strategy for rapid gelation of polysaccharide and protein hydrogels. Biomaterials. Mar. 2001;22(5):453-62.

Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.

Wong et al., Quantitative formation of core cross-linked star polymers via a one-pot two-step single electron transfer-living radical polymerization. Polym. Chem., 2013;4:4562-4565. DOI: 10.1039/C3PY00726J.

Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.

Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.

Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.

Xia et al., EPR study of spin labeled brush polymers in organic solvents. J Am Chem Soc. Dec. 14, 2011;133(49):19953-9. doi: 10.1021/ja2085349. Epub Nov. 21, 2011.

Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Epub Aug. 28, 2012.

Xing et al., A stable metal coordination polymer gel based on a calix[4]arene and its 'uptake' of non-ionic organic molecules from the aqueous phase. Chem Commun (Camb). Feb. 21, 2002;(4):362-3.

Xing et al., Design of coordination polymer as stable catalytic systems. Chemistry. Nov. 4, 2002;8(21):5028-32.

Xing et al., Spontaneous Enrichment of Organic Molecules from Aqueous and Gas Phases into a Stable Metallogel. Langmuir. 2002;18:9654-9658.

Xu et al., Mechanism of Shear Thickening in Reversibly Cross-linked Supramolecular Polymer Networks. Macromolecules. Apr. 13, 2010;43(7):3556-3565.

Xu et al., Scaling Laws in Supramolecular Polymer Networks. Macromolecules. 2011;44(13):5465-5472.

Xu et al., Strain Hardening and Strain Softening of Reversibly Cross-linked Supramoleecular Polymer Networks. Macromolecules. Sep. 27, 2011;44(18):7478-7488.

Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.

(56) References Cited

OTHER PUBLICATIONS

Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.
Yang et al., Luminescent chemodosimeters for bioimaging. Chem Rev. Jan. 9, 2013;113(1):192270. doi: 10.1021/cr2004103. Epub Jun. 18, 2012.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.
Yount et al., Small-molecule dynamics and mechanisms polymer underlying the macroscopic mechanical properties of coordinatively cross-linked networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.
Zhang et al., Active cross-linkers that lead to active gels. Angew Chem Int Ed Engl. Oct. 25, 2013;52(44):11494-8. doi: 10.1002/anie.201304437. Epub Sep. 12, 2013.
Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.
Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.
Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.
Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.
Zhang et al., Redox-Responsive, Core Cross-Linked Polyester Micelles. ACS Macro Lett., 2013;2(1):40-44. DOI: 10.1021/mz300522n.
Zhao et al., Rheological Behavoir of Shear-Responsive Metallo-Supramolecular Gels. Macromolecules. 2004;37(10):3529-3531.
Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.
Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.
Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.
Zhou et al., Counting primary loops in polymer gels. Proc Natl Acad Sci U S A. Nov. 20, 2012;109(47):19119-24. doi: 10.1073/pnas.1213169109. Epub Nov. 6, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
PCT/US2014/33554, Aug. 29, 2014, International Search Report and Written Opinion.
U.S. Appl. No. 16/231,166, filed Dec. 21, 2018, Johnson et al.
U.S. Appl. No. 15/725,036, filed Oct. 4, 2017, Johnson et al.
U.S. Appl. No. 16/080,503, filed Aug. 28, 2018, Johnson et al.
PCT/US2017/048641, Nov. 9, 2017, International Search Report and Written Opinion.
PCT/US2017/048641, Mar. 7, 2019, International Preliminary Report on Patentability.
PCT/US2018/040496, Jan. 14, 2019, International Search Report and Written Opinion.
International Search Report and Written Opinion for PCT/US2017/055145, dated Jan. 23, 2018.
International Preliminary Report on Patentability for PCT/US2017/055145, dated Apr. 18, 2019.
International Preliminary Report on Patentability for PCT/US2017/064784, dated Jun. 20, 2019.
International Search Report for PCT/US2017/48641, dated Nov. 9, 2017.
International Preliminary Report on Patentability for Application No. PCT/US2017/48641 dated Mar. 7, 2019.
International Search Report and Written Opinion for Application No. PCT/US2018/040496 dated Jan. 14, 2019.
Bates et al., Polarity-switching top coats enable orientation of sub-10-nm block copolymer domains. Science. Nov. 9, 2012;338(6108):775-9. doi: 10.1126/science.1226046.
Bohbot-Raviv et al., Discovering new ordered phases of block copolymers. Phys Rev Lett. Oct. 16, 2000;85(16):3428.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Burts et al., Using EPR to Compare PEG-branch-nitroxide "Bivalent-Brush Polymers" and Traditional PEG Bottle-Brush Polymers: Branching Makes a Difference. Macromolecules, Oct. 2012;45(20):8310-8318.
Cheng et al., Well-defined diblock macromonomer with a norbornene group at block junction: anionic living linking synthesis and ring-opening metathesis polymerization. Macromol. Mar. 4, 2010;43(7):3153-5.
Dalsin et al., Bottlebrush block polymers: Quantitative theory and experiments. ACS Nano. Nov. 6, 2015;9(12):12233-45.
Davis et al., Atom transfer radical polymerization of tert-butyl acrylate and preparation of block copolymers. Macromol. May 30, 2000;33(11):4039-47.
Frechet. Functional polymers and dendrimers: reactivity, molecular architecture, and interfacial energy. Science. Mar. 25, 1994;263(5154):1710-5.
Gestwicki et al., Influencing receptor-ligand binding mechanisms with multivalent ligand architecture. J Am Chem Soc. Dec. 18, 2002;124(50):14922-33.
Godugu et al., Abstract 2139: Effect of telmisartan on triple negative breast cancer (TNBC) and lung cancer tumor progression and intratumoral distribution of nanoparticles. Cancer Res. 2013;73(8). 4 pages.
Grahovac et al., Abstract B41: The angiotensin receptor blocker telmisartan inhibits the growth of pancreatic ductal adenocarcinoma and improves survival. Cancer Res. 2016;76(24). 4 pages.

(56) References Cited

OTHER PUBLICATIONS

Grason et al., Geometric theory of diblock copolymer phases. Phys Rev Lett. Jul. 31, 2003;91(5):058304. 4 pages.

Gu et al., PolyMOF Nanoparticles: Dual Roles of a Multivalent polyMOF Ligand in Size Control and Surface Functionalization. Angewandte Chemie Int. Ed. 2019;58:2-8. Epub Sep. 10, 2019.

Hawker et al., Preparation of polymers with controlled molecular architecture. A new convergent approach to dendritic macromolecules. J Am Chem Soc. Oct. 1990;112(21):7638-47.

Heroguez et al., Novel Styrene-Butadiene Copolymers by Ring-Opening Metathesis Polymerization. Macromol. Oct. 3, 2000;33(20):7241-8.

Hoogenboom et al., 1-Lactide Polymerization Utilizing a Hydroxy-Functionalized 3,6-Bis(2-pyridyl)pyridazine as Supramolecular (Co)initiator: Construction of Polymeric [2×2] Grids. Macromolecules, 2003;36(13):4743-9. DOI: 10.1021/ma034119e.

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.

Jakubowski et al., Activators regenerated by electron transfer for atom transfer radical polymerization of styrene. Macromol. Jan. 10, 2006;39(1):39-45.

Jeong et al., Highly tunable self-assembled nanostructures from a poly (2-vinylpyridine-b-dimethylsiloxane) block copolymer. Nano Lett. Sep. 27, 2011;11(10):4095-101.

Jiang et al., Morphology and Phase Diagram of Comb Block Copolymer A m+1 (BC) m. J Phys Chem B. May 7, 2009;113(21):7462-7.

Jung et al., Orientation-controlled self-assembled nanolithography using a polystyrene-polydimethylsiloxane block copolymer. Nano Lett. Jul. 11, 2007;7(7):2046-50.

Kale et al., Supramolecular assemblies of amphiphilic homopolymers. Langmuir. May 19, 2009;25(17):9660-70.

Kawamoto et al., Loops versus branch functionality in model click hydrogels. Macromol. Dec. 1, 2015;48(24):8980-8.

Lee et al., Novel phase morphologies in a microphase-separated dendritic polymer melt. Macromol. Jan. 12, 2009;42(3):849-59.

Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.

Li et al., Dynamic cylindrical assembly of triblock copolymers by a hierarchical process of covalent and supramolecular interactions. J Am Chem Soc. Jan. 4, 2011;133(5):1228-31.

Li et al., Efficient synthesis of narrowly dispersed amphiphilic double-brush copolymers through the polymerization reaction of macromonomer micelle emulsifiers at the oil-water interface. Polym Chem. 2016;7(27):4476-85.

Li et al., Facile syntheses of cylindrical molecular brushes by a sequential RAFT and ROMP "grafting-through" methodology. J Polym Sci A Polym Chem. Oct. 15, 2009;47(20):5557-5563.

Li et al., Synthesis of Hetero-Grafted Amphiphilic Diblock Molecular Brushes and Their Self-Assembly in Aqueous Medium. Macromolecules. 2010;43(3):1182-1184.

Li et al., Well-defined amphiphilic double-brush copolymers and their performance as emulsion surfactants. Macromol. May 18, 2012;45(11):4623-9.

Luo et al., Toroidal structures from brush amphiphiles. Chem Commun. 2014;50(5):536-8.

Rangadurai et al., Temporal and triggered evolution of host-guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Runge et al., "Synthesis and Self-Assembly of Bottlebrush Block Copolymers" PMSEPreprints, 2005, 92, 5-6.

Rzayev Synthesis of polystyrene-polylactide bottlebrush block copolymers and their melt self-assembly into large domain nanostructures. Macromol. Feb. 20, 2009;42(6):2135-41.

Sides et al., Parallel algorithm for numerical self-consistent field theory simulations of block copolymer structure. Polymer. Sep. 1, 2003;44(19):5859-66.

Sinturel et al., High χ-low N block polymers: how far can we go?. ACS Macro Lett. Sep. 2, 2015;4:1044-50.

Sowers et al., Redox-responsive branched-bottlebrush polymers for in vivo MRI and fluorescence imaging. Nat Commun. Nov. 18, 2014;5:5460.

Theodorakis et al., Interplay between chain collapse and microphase separation in bottle-brush polymers with two types of side chains. Macromol. May 4, 2010;43(11):5137-48.

Verduzco et al., Structure, function, self-assembly, and applications of bottlebrush copolymers. Chem. Soc. Rev., 2015;44:2405-20.

Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.

Yuan et al., One-pot syntheses of amphiphilic centipede-like brush copolymers via combination of ring-opening polymerization and "click" chemistry. Macromol. Jan. 27, 2010;43(4):1739-46.

Zhao et al., Polystyrene-Polylactide Bottlebrush Block Copolymer at the Air/Water Interface. Macromol. Sep. 28, 2009;42(22):9027-33.

Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.

Zheng et al., Morphology of ABC triblock copolymers. Macromol. Oct. 1995;28(21):7215-23.

Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

International Preliminary Report on Patentability for PCT/US2018/040488, dated Jan. 9, 2020.

International Preliminary Report on Patentability for PCT/US2018/040494, dated Jan. 9, 2020.

International Preliminary Report on Patentability for PCT/US2018/040496, dated Jan. 9, 2020.

Fenlon et al., The Thread & Cut Method: Syntheses of Molecular Knot Precursors. Eur J Org Chem. Jun. 2008;2008(18):3065-3068.

BRANCHED MULTI-FUNCTIONAL MACROMONOMERS AND USES THEREOF

RELATED APPLICATIONS

This application claims priority under 35 U.S.C. § 119(e) to U.S. Provisional Application, U.S. Ser. No. 62/528,010, filed Jun. 30, 2017, which is incorporated herein by reference.

BACKGROUND OF THE INVENTION

Bottlebrush polymers have found widespread applications in fields ranging from drug delivery and molecular imaging to novel materials and stimuli responsive networks.[1-3] Graft-through ring-opening metathesis polymerization (ROMP) offers distinct advantages over other bottlebrush synthesis methods.[4,5] The fast-initiating Grubb's $3^{rd}$ generation catalyst (G3-Cat) has been shown to sustain propagation of polymer chain reactions with exceptionally high tolerance towards a wide range of sterically-hindered multivalent macromonomers (MMs), reaching high degrees of polymerization and low dispersity values, even at low millimolar concentrations.[6,7] Furthermore, using G3-Cat, it is possible to control composition, morphology, and size of final macromolecules, allowing the preparation of remarkable polymeric architectures, such as bottlebrush polymers and star polymers.[7-11] Due to the high packing density of their side-chains, the backbones of bottlebrush polymers are very rigid and adopt extended morphologies with minimal side-chain entanglement.[6] Recently, self-assembly behaviors of bottlebrush block copolymers (BBCPs) have become an active area of research, as these macromolecules readily undergo phase separation and can be used to design materials with novel mechanical properties in bulk.[6,12]

Polymeric star nanoarchitectures, on the other hand, offer several different valuable features, such as tunable nanoscale sizes and shapes that mimic globular biomacromolecules, allowing for extended blood circulation and efficient biodistribution and/or tumor accumulation.[13-15] These properties make star polymers particularly well-suited for biological applications.[16]

The development of bottlebrush and star polymeric structures (e.g., brush-arm star polymers (BASPs)) is a growing field of research because these polymeric structures have broad applications. Previous work has reported preparation of multi-component MMs that can be used in graft-through ROMP; these MMs contain side-chains with a multitude of functions and properties, which can either be on different MMs, or branching off the same MM.[9,11,12,14,16,17] In particular, the branched platform consists of a ROMP-compatible norbornene group on a molecule that also contains two orthogonally functionalizable sites: an alkyne, for which copper (I)-catalyzed alkyne-azide cycloaddition (CuAAC) can be applied,[18-20] and a carboxylic acid group, compatible with carbodiimide coupling chemistry,[21-25] both of which are efficient, and known modes of conjugations. The side-chains can be functionalized with two dissimilar polymers that self-assemble into various morphologies or a polymer chain containing an agent (e.g., a therapeutic agent (e.g., drug), a diagnostic agent (e.g., imaging agent), a prophylactic agent, or a biological ligand); resulting polymers are reported to demonstrate interesting characteristics across multiple applications, including self-assembly, drug delivery, and molecular imaging.[8,9,11,26-28]

SUMMARY OF THE INVENTION

Adapting new classes of polymers and/or small molecules as side-chains of graft-through bottlebrushes facilitates the discovery of new polymeric macromolecules. However, further elaboration in various applications and optimization studies requires large amounts of core monomers, especially for material development requiring large quantities of polymers for investigation of their properties in bulk. Typical macromonomers are commercially available or accessible via short and simple synthetic protocols, but complex macromonomers, such as those containing multifunctional platforms or one or more agents requires more effort to develop synthetic protocols that are efficient, simple, and scalable, especially from an industrial point of view.

While the previously reported system, hereby referred to as Generation 1 macromonomer, or G1-M (such as the macromonomer shown in FIG. 1A), had several interesting properties as mentioned above,[29] there are issues regarding the synthetic protocol for making G1-M: a linear preparation route, non-trivial reaction conditions and purifications, as well as the inability to be efficiently scaled up (FIG. 1A). Consequently, these synthetic limitations will likely hinder further research and limit widespread use of these types of macromonomers, and consequently, the polymers and materials that can be produced from these macromonomers.

Described herein are methods for the synthesis of novel macromonomers, which retain the advantageous core properties and functions of G1-M, and the corresponding polymers. Given the synthetic challenges of G1-M, the branched norbornene monomer preparation route was re-examined in an attempt to increase its ease of access both in academic and industrial settings. Utilizing simple and scalable chemistry, Generation 2 branched macromonomer (G2-M such as G2-Nb-yne-OtBu) was synthesized on hundred-gram scale via a convergent route with double the net yield (87% from 43%, FIGS. 1A and 1B) as well as minimal purification efforts compared to the previous design; the original system's three core functions were also retained: the ring-opening metathesis polymerizable norbornene group, along with two orthogonal functional groups: a click-chemistry handle and a terminal acyl group capable of undergoing a coupling reaction. In certain embodiments, the click-chemistry handle is an alkyne group for CuAAC chemistry, and the terminal acyl group is a carboxylic acid group for carbodiimide coupling.[29] Furthermore, it is demonstrated that these $2^{nd}$ Generation MMs undergo efficient ROMP and yield well-controlled star polymeric nanoparticles (NP) as well as BBCPs. In certain, embodiments, the BBCPs exhibit ordered self-assembly.

In addition, the simple and scalable synthetic route developed for G2-M allows for the efficient synthesis of derivatives of G2-M via carbodiimide coupling of the carboxylic acid group of G2-M with one or more compounds containing an alkyne group (FIG. 1B). This synthetic protocol allows for the generation of macromonomers with multiple sites capable of undergoing click chemistry (FIG. 35). Therefore, macromonomers with multiple agents per macromonomer can be synthesized and further reacted to provide polymers with higher cargo loading of agents than previous polymers synthesized from macromonomers only capable of single cargo loading of agents (i.e., G1-M).

Furthermore, a related strategy for increasing the number of agents per macromonomer is disclosed pertaining to the development of azides of Formula (III), designed to contain multiple agents, capable of undergoing CuAAC coupling with alkyne groups of G1-M, G2-M, and related derivatives disclosed herein (FIGS. 46, 50, and 51). Consequently, these azides allow for the synthesis of macromonomers and polymers with controllable cargo loading of agents to produce more effective therapeutic, diagnostic, and prophylactic materials.

Methods, compositions, systems, and kits that allow for the preparation and utilization of branched multi-functional macromonomers, which contain one or more reactive sites capable of undergoing click chemistry (e.g., CuAAC coupling), branched multi-cargo macromonomers, and the corresponding polymers are disclosed herein. Specifically, the macromonomers and polymers disclosed herein can be synthesized more efficiently and/or contain a higher cargo loading of agents than previously reported macromonomers (i.e., G1-M) and the corresponding polymers.

In one aspect, the macromonomers of the disclosure G2-M macromonomers are of the Formula (I):

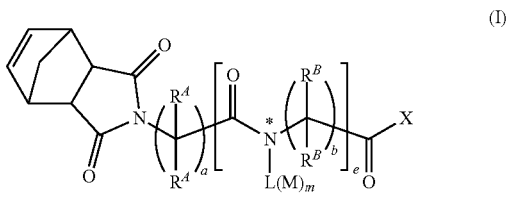

or a salt thereof, wherein:

each instance of $R^A$ is independently hydrogen, halogen, or substituted or unsubstituted, $C_{1-6}$ alkyl;

a is an integer from 1 to 20, inclusive;

each instance of M is independently hydrogen or an agent;

each instance of m is independently an integer from 1 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

provided that when each instance of M is hydrogen, at least one instance of -L(M)$_m$- comprises a click-chemistry handle;

each instance of $R^B$ is independently hydrogen, halogen, or substituted or unsubstituted $C_{1-6}$ alkyl;

each instance of b is independently an integer from 1 to 20, inclusive;

e is an integer from 1 to 10, inclusive; and

X is $OR^C$ or $N(R^D)_2$, wherein $R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, two $R^D$ are taken together to form a substituted or unsubstituted heterocyclyl or substituted or unsubstituted heteroaryl moiety, or a nitrogen protecting group.

In another aspect, the macromonomers of the disclosure are of the Formula (II):

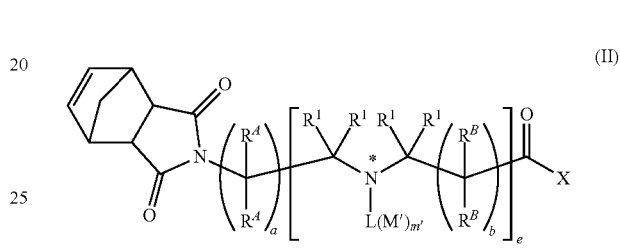

or a salt thereof, wherein:

each instance of $R^A$ is independently hydrogen, halogen, or substituted or unsubstituted $C_{1-6}$ alkyl;

a is an integer from 1 to 20, inclusive;

each instance of M' is independently an agent;

each instance of m' is independently an integer from 2 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein: optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive;

X is $OR^C$ or $N(R^D)_2$, wherein: $R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}^-$ heteroalkenyl, substituted or unsubstituted, $C_{2-1000}$ heteroalkynyl, two $R^D$ are taken together to form a substituted or unsubstituted heterocyclyl or substituted or unsubstituted heteroaryl moiety, or a nitrogen protecting group; and each instance of $R^1$ is independently hydrogen, halogen, substituted or unsubstituted, $C_{1-6}$ alkyl, or two $R^1$ bonded to the same carbon are taken together to form an oxo group.

In yet another aspect, the compounds of the disclosure are of Formula (III):

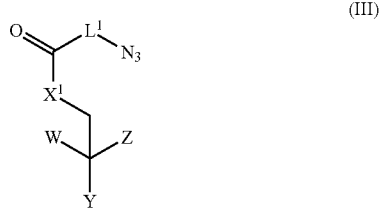

(III)

or a salt thereof, wherein:

each instance of $L^1$ is independently substituted or unsubstituted, $C_{1-20}$ alkylene, or substituted or unsubstituted, $C_{2-20}$ heteroalkylene;

$X^1$ is O or $NR^I$, wherein $R^I$ is independently hydrogen, substituted or unsubstituted, $C_{1-10}$ alkyl, substituted or unsubstituted, $C_{2-10}$ alkenyl, substituted or unsubstituted, $C_{1-10}$ heteroalkyl, substituted or unsubstituted, $C_{2-10}$ heteroalkenyl, or a nitrogen protecting group;

W, Y, and Z are each independently hydrogen, substituted or unsubstituted, $C_{1-100}$ alkylene, substituted or unsubstituted, $C_{2-100}$ heteroalkylene, or a group of Formula (i), provided that at least one instance of W, Y, or Z is a group of Formula (i), wherein Formula (i) is:

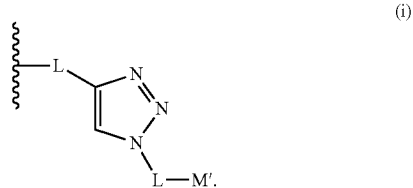

(i)

In other embodiments, the present disclosure provides methods of preparing macromonomers describe herein. In certain embodiments, methods are provided to prepare macromonomers, or a salt thereof, by utilizing a carbodiimide coupling. In certain embodiments, the coupling reaction is a carbodiimide coupling reaction. In certain embodiments, methods are provided to prepare macromonomers, or a salt thereof, by utilizing a click coupling. In certain embodiments, the click coupling is a copper(I)-catalyzed azide-alkyne cycloaddition (CuAAC). In certain embodiments, the macromonomers contain one or more M moieties, which can be hydrogen or an agent. In certain embodiments, the macromonomers contain one or more M' moieties, which can be an agent. In certain embodiments, the agent is a pharmaceutical agent. In certain embodiments, the pharmaceutical agent is a therapeutical agent, a diagnostic agent, or a prophylactic agent.

In other embodiments, the present disclosure provides polymers and methods for preparing polymers describe herein. In certain embodiments, polymers are disclosed which are prepared by polymerizing a macromonomer, or a salt thereof, as described herein in the presence of a metathesis catalyst. In certain embodiments, methods are provided to prepare polymers by polymerizing a macromonomer, or a salt thereof, as described herein in the presence of a metathesis catalyst. In certain embodiments, the polymers are prepared by polymerizing more than one type of macromonomer, wherein at least one instance of M or M' of one macromonomer is different from at least one instance of M or M' of another macromonomer. In certain embodiments, the metathesis catalyst is a transition metal catalyst or Grubbs catalyst.

In some embodiments, the present disclosure provides pharmaceutical compositions comprising a polymer described herein and optionally a pharmaceutically acceptable excipient.

In further embodiments, the present disclosure provides kits comprising a macromonomer or a polymer or a pharmaceutical composition described herein; and instructions for using the macromonomer, polymer, or pharmaceutical composition.

The present disclosure also provides methods of use for polymers and pharmaceutical compositions described herein. In certain embodiments, methods of delivering a therapeutic agent, a diagnostic agent, or a prophylactic agent to a subject comprising administering to the subject a polymer or a pharmaceutical composition described herein are provided. In certain embodiments, methods of delivering a therapeutic agent, a diagnostic agent, or a prophylactic agent to a cell comprising contacting the cell with a polymer or a pharmaceutical composition described herein are provided. In some embodiments, methods of treating, preventing, or diagnosing a disease in a subject comprising administering to or implanting in the subject a therapeutically effective amount, prophylactically effective amount, or diagnostically effective amount, respectively, of a polymer or a pharmaceutical composition described herein; wherein at least one instance of M or M' is a therapeutic agent, prophylactic agent, or diagnostic agent.

The details of certain embodiments of the invention are set forth in the Detailed Description of Certain Embodiments, as described below. Other features, objects, and advantages of the invention will be apparent from the Definitions, Figures, Examples, and Claims.

BRIEF DESCRIPTION OF THE DRAWINGS

(FIG. 1A) Synthesis of previously reported G1-M. *Macromolecules*, 2010, 43, 10326. (FIG. 1B) Synthesis of G2-M. (FIG. 1C) Synthesis summary of G1-M and G2-M.

(FIG. 4A) Schematic of the BF-ROMP process for the generation of BASP NPs. (FIG. 4B) Gel permeation chromatography (GPC) traces of reaction mixture of G2-MMs in comparison with their G1-MMs counterparts. * denotes residual unconverted brushes, and ** denotes residual MMs. (FIG. 4C) Transmission electron microscopy (TEM) images of G2-based BASP NPs in comparison with their G1-based BASP NPs counterparts.

(FIG. 5B) GPC traces of reaction mixtures of BMM. (FIG. 5C) Small-angle X-ray scattering (SAXS) profile of BBCP prepared from BMM.

(FIG. 37A) Full MALDI spectrum for Nb-yneIII-MM. (FIG. 37B) Close-up MALDI spectrum for Nb-yneIII-MM.

(FIG. 81A) Computational analysis of EPR spectra of G2-chex-MM. (FIG. 81B) Computational analysis of EPR spectra of G2-chex$_2$-MM. (FIG. 81C) Computational analysis of EPR spectra of G2-chex$_3$-MM. (FIG. 81D) Relevant data acquired from simulations for G2-chex-MM, G2-chex$_2$-MM, and G2-chex$_3$-MM.

(FIG. 85A) Synthesis of BMM for BBCP formation via graft-through ROMP. (FIG. 85B) Schematic of the synthesis and self-assemble of BBCP. (FIG. 85C) GPC traces of reaction mixture of BMM. (FIG. 85D) SAXS profile of BBCP prepared from BMM.

(FIG. 87A) Synthesis of MMM. (FIG. 87B) Graft-through ROMP schematics of MMM.

(FIG. 88A) Characterization of G2-Nb-TEG$_n$-PEG. (FIG. 88B) GPC of G2-Nb-TEG$_n$-PEG at DP=40. (FIG. 88C) GPC of G2-Nb-TEG$_3$-PEG at varying DPs. MM-to-BP conversions were determined to be >90% for all cases.

(FIG. 89A) Chemical structure of G2-Nb-chex$_n$-PEG. G2-chex-MM: $C_{175}H_{330}N_8O_{74}$: calcd m/z=3728.48; Found: 3729.711 [M+H]$^+$. G2-chex$_2$-MM: $C_{199}H_{366}N_{14}O_{77}$: calcd m/z=4191.78; Found: 4190.456 [M+Li]$^+$. G2-chex$_3$-MM: $C_{223}H_{404}N_{20}O_{80}$: calcd m/z=4643.06; Found: 4643.578 [M+H]$^+$. (FIG. 89B) Normalized EPR of G2-Nb-chex$_n$-PEG. G2-chex-MM, G2-chex$_2$-MM, and G2-chex$_3$-MM. (FIG. 89C) MALDI characterization of G2-Nb-chex$_n$-PEG. G2-chex-MM, G2-chex$_2$-MM, and G2-chex$_3$-MM. (FIG. 89D) GPC of G2-Nb-chex$_n$-PEG at DP=40. (FIG. 89E) GPC of G2-Nb-chex$_3$-PEG at varying DPs.

DEFINITIONS

Figure 1A:
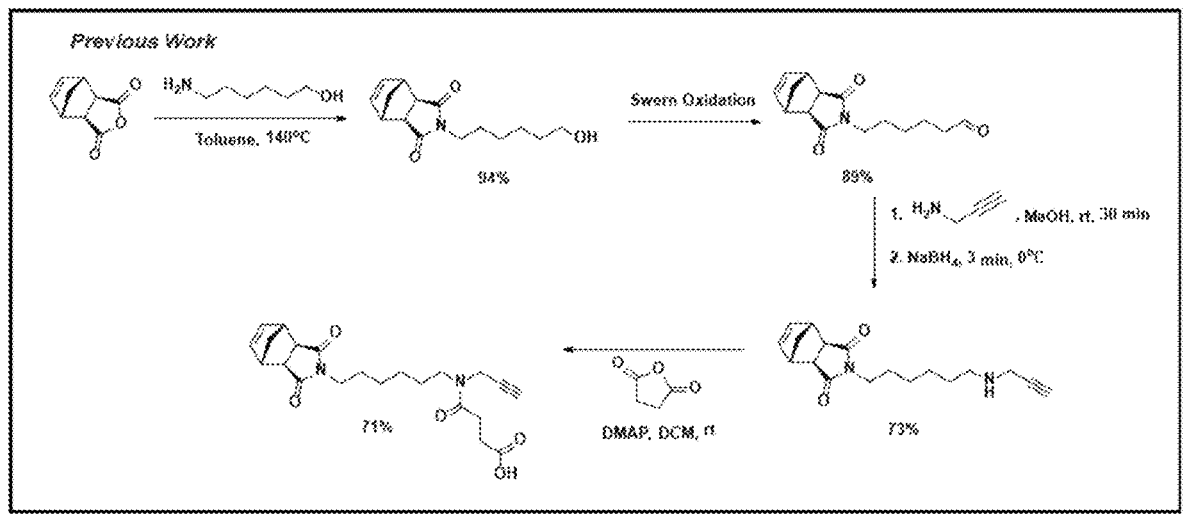
FIGS. 1A to 1C show a summary of current and past work in the development of the synthetic protocols for G1-M and G2-M.

For convenience, certain terms employed herein, in the specification, examples and appended claims are collected herein.

Unless otherwise required by context, singular terms shall include pluralities, and plural terms shall include the singular.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry,* Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations,* VCH Publishers, Inc., New York, 1989; and Carruthers, Some Modern Methods of Organic Synthesis, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$O_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-$C_{500}$ alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C=C double bond for which the stereochemistry is not specified (e.g., —CH=CHCH$_3$,

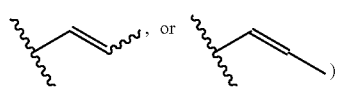

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and for more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and for more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("hetero$C_1$-$C_{1000}$ alkenyl"), 1 to 900 carbon atoms and 1 or more heteroatoms within the parent chain ("hetero$C_1$-$C_{900}$ alkenyl"), 1 to 800 carbon atoms and 1 or more heteroatoms within the parent chain ("hetero$C_1$-$C_{800}$ alkenyl"), 1 to 700 carbon atoms and 1 or more heteroatoms within the parent chain ("hetero$C_1$-$C_{700}$ alkenyl"), 1 to 600 carbon atoms and 1 or more heteroatoms within the parent chain ("hetero$C_1$-$C_{600}$ alkenyl"), 1 to 500 carbon atoms and 1 or more heteroatoms within the parent chain ("hetero$C_1$-$C_{500}$ alkenyl"), 1 to 400 carbon atoms and for more heteroatoms within the parent chain ("hetero$C_1$-$C_{400}$ alkenyl"), 1 to 300 carbon atoms and 1 or more heteroatoms within the parent chain ("hetero$C_1$-$C_{300}$ alkenyl"), 1 to 200 carbon atoms and 1 or more heteroatoms within the parent chain ("hetero$C_1$-$C_{200}$ alkenyl"), or 1 to 100 carbon atoms and 1 or more heteroatoms within the parent chain ("hetero$C_1$-$C_{100}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("hetero$C_1$-$C_{1000}$ alkynyl"), 1 to 900 carbon atoms and 1 or more heteroatoms within the parent chain ("hetero$C_1$-$C_{900}$ alkynyl"), 1 to 800 carbon atoms and 1 or more heteroatoms within the parent chain ("hetero$C_1$-$C_{800}$ alkynyl"), 1 to 700 carbon atoms and 1 or more heteroatoms within the parent chain ("hetero$C_1$-$C_{700}$ alkynyl), 1 to 600 carbon atoms and 1 or more heteroatoms within the parent chain ("hetero$C_1$-$C_{600}$ alkynyl"), 1 to 500 carbon atoms and 1 or more heteroatoms within the parent chain ("hetero$C_1$-$C_{500}$ alkynyl"), 1 to 400 carbon atoms and for more heteroatoms within the parent chain ("hetero$C_1$-$C_{400}$ alkynyl"), 1 to 300 carbon atoms and 1 or more heteroatoms within the parent chain ("hetero$C_1$-$C_{300}$ alkynyl"), 1 to 200 carbon atoms and 1 or more heteroatoms within the parent chain ("hetero$C_1$-$C_{200}$ alkynyl"), or 1 to 100 carbon atoms and 1 or more heteroatoms within the parent chain ("hetero$C_1$-$C_{100}$ alkynyl"). In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 r electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6,10, or 14 r electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 R$^{dd}$ groups;

each instance of e is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —C, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, the carbon atom substituents are independently halogen, substituted or unsubstituted $C_{1-6}$ alkyl, —$OR^{aa}$, —$SR^{aa}$, —N($R^{bb}$)$_2$, —CN, —SCN, —NO$_2$, —C(=O)$R^{aa}$, —CO$_2$$R^{aa}$, —C(=O)N($R^{bb}$)$_2$, —OC(=O)$R^{aa}$, —OCO$_2$$R^{aa}$, —OC(=O)N($R^{bb}$)$_2$, —$NR^{bb}$C(=O)$R^{aa}$, —$NR^{bb}$CO$_2$$R^{aa}$, or —$NR^{bb}$C(=O)N($R^{bb}$)$_2$. In certain embodiments, the carbon atom substituents are independently halogen, substituted or unsubstituted $C_{1-6}$ alkyl, —$OR^{aa}$, —$SR^{aa}$, —N($R^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=$NR^{bb}$)$R^{aa}$, —C(=$NR^{cc}$)$OR^{aa}$, —C(=$NR^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=$NR^{cc}$)$R^{aa}$, —C(=$NR^{cc}$)$OR^{aa}$, —C(=$NR^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$, are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4- pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$,
wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4$^1$,4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —$NH_2$.

As used herein, the term "polyethylene glycol" or "PEG" refers to an ethylene glycol polymer that contains about 20 to about 2,000,000 linked monomers, typically about 50-1,000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG3350, PEG4000, PEG4600, PEG5000, PEG6000, PEG8000, PEG11000, PEG12000, PEG2000000, and any mixtures thereof.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4{}^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —$OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

"Click chemistry" refers to a chemical approach to conjugation introduced by Sharpless in 2001 and describes chemistry tailored to generate substances quickly and reliably by joining units together. See, e.g., Kolb, Finn and Sharpless *Angewandte Chemie International Edition* 2001 40, 2004-2021; *Evans, Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition reactions); and Diels-Alder reactions (e.g., tetrazine [4+2] cycloaddition). Examples of click chemistry reactions and click-chemistry handles can be found in, e.g., Kolb, H. C.; Finn, M. G. and Sharpless, K. B. *Angew. Chem. Int. Ed.* 2001, 40, 2004-2021. Kolb, H. C. and Sharless, K. B. *Drug Disc. Today,* 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057; Manetsch, R. et al., *J. Am. Chem. Soc.* 2004, 126, 12809-12818; Mocharla, V. P. et al. *Angew. Chem., Int. Ed.* 2005, 44, 116-120.

Any methods known in the art of bioconjugation can be used (e.g., click chemistry reactions). For example, the nanoparticle may comprise a click chemistry handle on its outer shell, which can react with a click chemistry handle on a targeting agent, thereby covalently linking the nanoparticle with the targeting agent. In certain embodiments, the one or more nanoparticles are conjugated to the targeting agent via click chemistry, and therefore the linker comprises a moiety derived from a click chemistry reaction (e.g., triazole, diazole, diazine, sulfide bond, maleimide ring, succinimide ring, ester, amide).

The term "average molecular weight" may encompass the number average molecular weight ($M_n$), weight average molecular weight ($M_w$), higher average molecular weight ($M_z$ or $M_z+1$), GPC/SEC (gel permeation chromatography/size-exclusion chromatography)-determined average molecular weight ($M_p$), and viscosity average molecular weight ($M_v$).

The term "average hydrodynamic diameter" ($D_H$) as used herein refers to the average size of a conjugate or particle. The average hydrodynamic diameter may or may not encompass the solvation layers of conjugate or particle, and may be determined through a number of methods including dynamic light scattering, electron microscopy (e.g., scanning electron microscopy, transmission electron microscopy), atomic force microscopy, and X-ray diffraction. The hydrodynamic diameter measured by dynamic light scattering (DLS) is defined as "the size of a hypothetical hard sphere that diffuses in the same fashion as that of the particle being measured". In practice though, particles or macromolecules in solution are non-spherical, dynamic (tumbling), and solvated. Because of this, the diameter calculated from the diffusional properties of the particle will be indicative of the apparent size of the dynamic hydrated/solvated particle. Hence the terminology, Hydrodynamic diameter. The hydrodynamic diameter, or Stokes diameter, therefore is that of a sphere that has the same translational diffusion coefficient as the particle being measured, assuming a hydration layer surrounding the particle or molecule. The measured data in a dynamic light scattering (DLS) experiment is the correlation curve which should be a smooth, single exponential decay function for a mono-size particle dispersion (Chu, B., *Annual Review of Physical Chemistry,* 1970, 21, 145-174). Embodied within the correlation curve is all of the information regarding the diffusion of particles within the sample being measured. By fitting the correlation curve to an exponential function, the diffusion coefficient (D) can be calculated (D is proportional to the lifetime of the exponential decay). With the diffusion coefficient (D) now known, the hydrodynamic diameter can be calculated by using a variation of the Stokes-Einstein equation. For a polydisperse sample this curve is a sum of exponential decays.

The term "average polydispersity" (PDI) as used herein refers to a measure of the distribution of molecular size in a mixture, e.g., as determined by a chromatographic method, such as gel permeation chromatography or size exclusion chromatography, or through dynamic light scattering. Polydispersity (PDI) is a measure of the distribution of molecular mass in a given polymer. Polydispersity is calculated by: PDI=$M_w/M_n$ (Stepto, R. F. T., et al., *Pure Appl. Chem.,* 2009, 81, 351-353). $M_n$ is more sensitive to molecules of low molecular mass, while $M_w$ is more sensitive to molecules of high molecular mass. The dispersity indicates the distribution of individual molecular masses in a bath of polymers. D has a value equal to or greater than 1.

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the macromonomers, conjugates, or particles disclosed herein comprise an agent(s), e.g., a first therapeutic agent (e.g., at least one (including, e.g., at least two, at least three). In some embodiments, the BASP-compositions (e.g., macromonomers, conjugates, or particles) can further comprise a second therapeutic agent, a targeting moiety, a diagnostic moiety, e.g., as described herein. The agent(s) can be coupled to the conjugate or particle. In other embodiments, the agent(s) can be associated with a conjugate or particle. In some embodiments, a first agent can be coupled to the conjugate or particle, and a second agent, targeting moiety, and/or diagnostic moiety can be non-covalently associated with the conjugate or particle. Any of the agents disclosed herein can be used in the macromonomers, conjugates, particles and other compositions and methods disclosed herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent, e.g., a therapeutic agent, can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs.

In some embodiments, the agent, e.g., a therapeutic agent, a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents, e.g., a therapeutic agents, in the BASP-compositions include, but are not limited to, those found in *Harrison's Principles of Internal Medicine*, 13th Edition, Eds. T. R. Harrison et al. McGraw-Hill N.Y., NY; *Physicians' Desk Reference*, 50th Edition, 1997, Oradell N.J., Medical Economics Co.; *Pharmacological Basis of Therapeutics*, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, exemplary therapeutic agents in the BASP-compositions include, but are not limited to, one or more of the agents listed in Paragraph [0148] of U.S. Pat. No. 9,381,253, incorporated by reference herein.

In other embodiments, exemplary therapeutic agents in the BASP-compositions include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenviroment modulators disclosed, e.g., in Paragraphs 113-121, of WO 2013/169739, incorporated herein by reference. In some embodiments, the BASP-composition comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics, and immunotherapies) in a tumor or tumor vasculature, in the subject.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The term "crosslinker" refers to a compound that allows for two or more molecules or polymers to be joined by covalent bonds. In certain embodiments, the crosslinker results in a covalent attachment between two polymers.

The term "ring-opening metathesis polymerization (ROMP)" refers to a type of olefin metathesis chain-growth polymerization that is driven by the relief of ring strain in cyclic olefins (e.g. norbornene or cyclopentene). The catalysts used in the ROMP reaction include $RuCl_3$/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium (II), dichloro[1,3-Bis(2-methylphenyl)-2-imidazolidinylidene](benzylidene)(tricyclohexylphosphine) ruthenium (II), dichloro[1,3-bis(2,4,6-trimethylphenyl)-2-imidazolidinylidene][3-(2-pyridinyl)propylidene]ruthenium (II), dichloro(3-methyl-2-butenylidene)bis(tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium (II) (Grubbs II), and dichloro[1,3-bis(2,4,6-trimethylphenyl)-2-imidazolidinylidene] (benzylidene)bis(3-bromopyridine)ruthenium(II) (Grubbs III).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "ratiometric" refers to the situation where $C_1^i$ is substantially equal to $C_0^i$, wherein $C_0^i$ refers to the ratio of the amount of a first agent before the first agent is delivered to a subject, tissue, or cell, to the total amount of two or more agents (including the first agent) before the two or more agents are delivered to the subject, tissue, or cell; and $C_1^i$ refers to the ratio of the amount of the first agent that is delivered to the subject, tissue, or cell, to the total amount of the two or more agents (including the first agent) that are delivered to the subject, tissue, or cell. In certain embodiments, the delivery of each one of the two or more agents is ratiometric.

The term "orthogonal" refers to the situation where a first agent and a second agent, each of which is included in a BASP described herein, is independently released from the BASP. In certain embodiments, under condition A, the first agent, but not the second agent, is released from the BASP. For example, an orthogonal release or orthogonal delivery of the first and second agents includes: under condition A, the first agent, but not the second agent, is released from the BASP; under condition B, the second agent, but not the first agent, is released from the BASP. The release or delivery of the first and second agents is not orthogonal when, for example, under condition C, both the first and second agents are released from the BASP.

The term "self-assembly" refers to a process in which a disordered system of pre-existing components forms an organized structure or pattern as a consequence of specific, local interactions among the components themselves, without external direction. When the constitutive components are molecules, the process is termed molecular self-assembly. Self-assembly can be classified as either static or dynamic. In static self-assembly, the ordered state forms as a system approaches equilibrium, reducing its free energy. However, in dynamic self-assembly, patterns of pre-existing components organized by specific local interactions are not commonly described as "self-assembled" by scientists in the associated disciplines. These structures are better described as "self-organized", although these terms are often used interchangeably.

The disclosure is not intended to be limited in any manner by the above exemplary listing of substituents. Additional terms may be defined in other sections of this disclosure.

DETAILED DESCRIPTION OF CERTAIN EMBODIMENTS

Before the disclosed systems, compositions, methods, reagents, and kits are described in more detail, it should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

The present disclosure provides macromonomers, compounds, polymers, compositions, systems, reagents, kits, and methods focused on the syntheses or uses of star polymers. In certain embodiments, the star polymers are brush-arm star polymers (BASPs). In certain embodiments, the BASPs contain one more agents. In certain embodiments, the BASPs containing one more agents are used to treat, prevent, and/or diagnose a diseade or condition in a subject.

Macromonomers and Compounds

The present disclosure describes macromonomers of Formula (I) and Formula (II), and compounds of Formula (III) as described herein.

In certain embodiments, the macromonomer is a macromonomer of Formula (I):

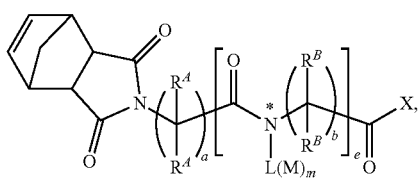

(I)

or a salt thereof, wherein:
each instance of $R^A$ is independently hydrogen, halogen, or substituted or unsubstituted, $C_{1-6}$ alkyl;
a is an integer from 1 to 20, inclusive;
each instance of M is independently hydrogen or an agent;
each instance of m is independently an integer from 1 to 10, inclusive;
each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:
optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
provided that when each instance of M is hydrogen, at least one instance of -L(M)$_m$ comprises a click-chemistry handle;
each instance of $R^B$ is independently hydrogen, halogen, or substituted or unsubstituted, $C_{1-6}$ alkyl;
each instance of b is independently an integer from 1 to 20, inclusive;
e is an integer from 1 to 10, inclusive;
X is OR$^C$ or N(R$^D$)$_2$, wherein:
R$^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and
each instance of R$^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, two R$^D$ are taken together to form a substituted or unsubstituted heterocyclyl or substituted or unsubstituted heteroaryl moiety, or a nitrogen protecting group.

In certain embodiments, the macromonomer is a macromonomer of Formula (II):

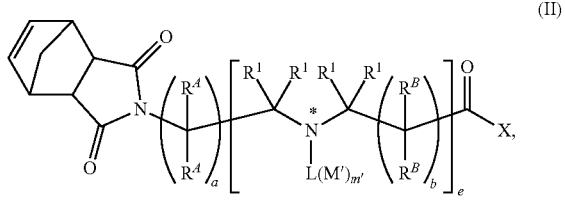

(II)

or a salt thereof, wherein:
each instance of $R^A$ is independently hydrogen, halogen, or substituted or unsubstituted, $C_{1-6}$ alkyl;
a is an integer from 1 to 20, inclusive;
each instance of M' is independently an agent;

each instance of m' is independently an integer from 2 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive;

X is $OR^C$ or $N(R^D)_2$, wherein:

$R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group;

each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, two $R^D$ are taken together to form a substituted or unsubstituted heterocyclyl or substituted or unsubstituted heteroaryl moiety, or a nitrogen protecting group; and each instance of $R^1$ is independently hydrogen, halogen, substituted or unsubstituted, $C_{1-6}$ alkyl, or two $R^1$ bonded to the same carbon are taken together to form an oxo group.

In certain embodiments, the compound is a compound of Formula (III):

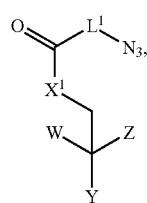

or a salt thereof, wherein:

each instance of $L^1$ is independently substituted or unsubstituted, $C_{1-20}$ alkylene, or substituted or unsubstituted, $C_{2-20}$ heteroalkylene;

$X^1$ is O or $NR^I$, wherein:

$R^I$ is independently hydrogen, substituted or unsubstituted, $C_{1-10}$ alkyl, substituted or unsubstituted, $C_{2-10}$ alkenyl, substituted or unsubstituted, $C_{1-10}$ heteroalkyl, substituted or unsubstituted, $C_{2-10}$ heteroalkenyl, or a nitrogen protecting group;

W, Y, and Z are each independently hydrogen, substituted or unsubstituted, $C_{1-100}$ alkylene, substituted or unsubstituted, $C_{2-100}$ heteroalkylene, or a group of Formula (i), provided that at least one instance of W, Y, or Z is a group of Formula (i), wherein Formula (i) is:

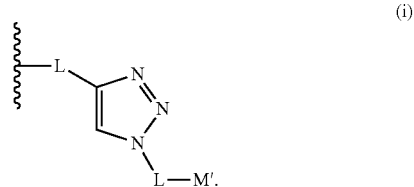

In certain embodiments, each instance of $R^A$ is hydrogen. In certain embodiments, at least one instance of $R^A$ is hydrogen. In certain embodiments, each instance of $R^A$ is halogen. In certain embodiments, at least one instance of $R^A$ is halogen. In certain embodiments, each instance of $R^A$ is unsubstituted $C_{1-6}$ alkyl. In certain embodiments, at least one instance of $R^A$ is unsubstituted $C_{1-6}$ alkyl. In certain embodiments, each instance of $R^A$ is substituted $C_{1-6}$ alkyl. In certain embodiments, at least one instance of $R^A$ is substituted $C_{1-6}$ alkyl.

In certain embodiments, each instance of $R^B$ is hydrogen. In certain embodiments, at least one instance of $R^B$ is hydrogen. In certain embodiments, each instance of $R^B$ is halogen. In certain embodiments, at least one instance of $R^B$ is halogen. In certain embodiments, each instance of $R^B$ is unsubstituted $C_{1-6}$ alkyl. In certain embodiments, at least one instance of $R^B$ is unsubstituted $C_{1-6}$ alkyl. In certain embodiments, each instance of $R^B$ is substituted $C_{1-6}$ alkyl. In certain embodiments, at least one instance of $R^B$ is substituted $C_{1-6}$ alkyl.

In certain embodiments, each instance of $R^1$ is hydrogen. In certain embodiments, at least one instance of $R^1$ is hydrogen. In certain embodiments, each instance of $R^1$ is halogen. In certain embodiments, at least one instance of $R^1$ is halogen. In certain embodiments, each instance of $R^1$ is unsubstituted $C_{1-6}$ alkyl. In certain embodiments, at least one instance of $R^1$ is unsubstituted $C_{1-6}$ alkyl. In certain embodiments, each instance of $R^1$ is substituted $C_{1-6}$ alkyl. In certain embodiments, at least one instance of $R^1$ is substituted $C_{1-6}$ alkyl. In certain embodiments, the macromonomer is a macromonomer of formula:

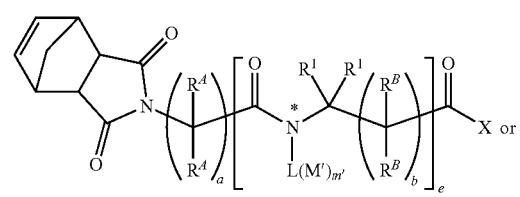

-continued

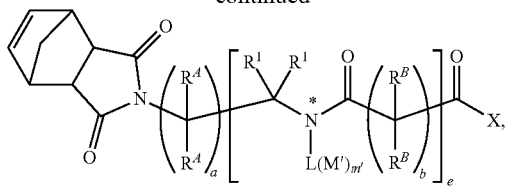

wherein two R¹ bonded to the same carbon have been taken together to form an oxo group. In certain embodiments, the macromonomer is a macromonomer of formula

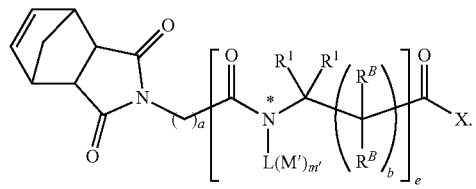

In certain embodiments, the macromonomer is a macromonomer of formula

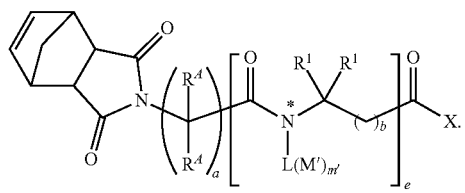

In certain embodiments, the macromonomer is a macromonomer of formula

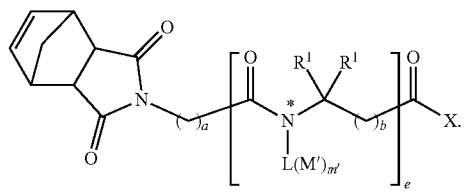

In certain embodiments, the macromonomer is a macromonomer of formula

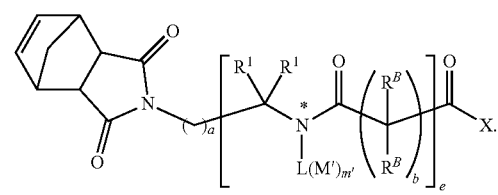

In certain embodiments, the macromonomer is a macromonomer of formula

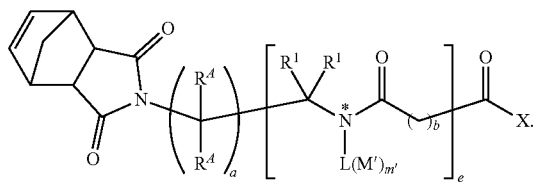

In certain embodiments, the macromonomer is a macromonomer of formula

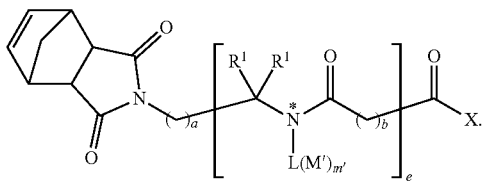

In certain embodiments, a is selected from the group of integers consisting of 1, 2, 3, 4, 5, 6, 7, 8, 9, 10, 11, 12, 13, 14, 15, 16, 17, 18, 19, and 20.

In certain embodiments, M is a hydrogen or an agent. In certain embodiments, at least one instance of M is a hydrogen. In certain embodiments, each instance of M is a hydrogen. In certain embodiments, M or M' is an agent. An agent can be a molecule, group of molecules, complex or substance administered to an organism for diagnostic, therapeutic, preventative medical, or veterinary purposes. In certain embodiments, the agent is a pharmaceutical agent. In certain embodiments the pharmaceutical agent is a therapeutic agent, a diagnostic agent, or a prophylactic agent. In certain embodiments, the therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF), and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the anti-cancer agent is paclitaxel.

In certain embodiments, the agent is an anti-hypertension agent. Exemplary anti-hypertension agents include, but are not limited to, amiloride, amlodipine, atenolol, azilsartan, benazepril, bendroflumethiazide, betaxolol, bisoprolol, bucindolol, bumetanide, candesartan, captopril, carteolol, carvedilol, chlorothiazide, chlorthalidone, cilnidipine, clevidipine, diltiazem, doxazosin, enalapril, epitizide, eplerenone, eprosartan, ethacrynic acid, felodipine, Fimasartan, fosinopril, furosemide, hydrochlorothiazide, indapamide, indoramin, irbesartan, isradipine, labetalol, lercanidipine, levamlodipine, lisinopril, losartan, methyclothiazide, metolazone, metoprolol, moexipril, nadolol, nebivolol, nicardipine, nifedipine, nimodipine, nisoldipine, nitrendipine, olmesartan, oxprenolol, penbutolol, perindopril, pindolol, phenoxybenzamine, phentolamine, polythiazide, prazosin, propranolol, quinapril, ramipril, spironolactone, telmisartan, terazosin, timolol, tolazoline, torsemide, trandolapril, triamterene, valsartan, and verapamil. In certain embodiments, the anti-hypertension agent is telmisartan.

Exemplary diagnostic agents include, but are not limited to, fluorescent molecules; gases; metals; imaging agents, such as commercially available imaging agents used in positron emissions tomography (PET), computer assisted tomography (CAT), single photon emission computerized tomography, x-ray, fluoroscopy, and magnetic resonance imaging (MRI); and contrast agents, such as magnetic-resonance signal enhancing agents, X-ray attentuatung agents, ultrasound scattering agent, and ultrasound frequency shifting agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, the diagnostic agent is a metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, the diagnostic agent is an organic compound. In certain embodiments, the diagnostic agent is metal-free. In certain embodiments, the diagnostic agent is a metal-free organic compound.

In certain embodiments, the imaging agent is a magnetic resonance imaging (MRI) agent. In certain embodiments, the MRI agent is gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}Cu$ diacetyl-bis($N^4$-methylthiosemicarbazone) ($^{64}Cu$-ASTM), $^{18}F$-fluorodeoxyglucose (FDG), $^{18}F$-fluoride, 3'-deoxy-3'-[$^{18}F$]fluorothymidine (FLT), $^{18}F$-fluoromisonidazole (FMISO), gallium, technetium-99m, and thallium.

In certain embodiments, the imaging agent is radiographic imaging agent. In certain embodiments, the radiographic imaging agent is selected from the group consisting of barium, gastrografin, and iodine contrast agent.

In certain embodiments, the imaging agent is a radical-containing compound. In certain embodiments, the imaging agent is a nitroxide radical-containing compound. In certain embodiments, the imaging agent or diagnostic agent is of the formula:

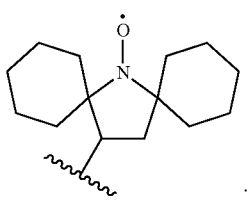

In certain embodiments, the imaging agent or diagnostic agent is an organic compound. In certain embodiments, the imaging agent is a salt of an organic compound. In certain embodiments, the imaging agent or diagnostic agent is of the formula:

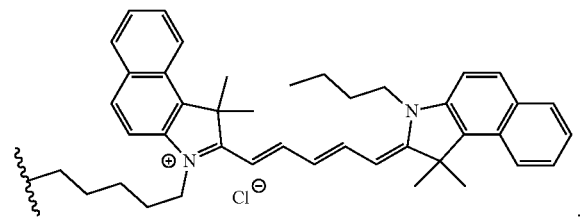 [SMILES: *CCCCC[N+]1=C(/C=C/C=C/C=C2\N(CCCC)c3ccc4ccccc4c3C2(C)C)C(C)(C)c2c1ccc1ccccc21 ; [Cl-] ; "."]

In certain embodiments, the diagnostic agent may comprise a fluorescent molecule, a metal chelate, a contrast agent, a radionuclide, or a positron emission tomography (PET) imaging agent, an infrared imaging agent, a near-IR imaging agent, a computer assisted tomography (CAT) imaging agent, a photon emission computerized tomography imaging agent, an X-ray imaging agent, or a magnetic resonance imaging (MRI) agent.

In some embodiments, the diagnostic agent is a fluorescent molecule. In some embodiments, the fluorescent molecule comprises an acridine dye, a cyanine dye, a rhodamine dye, a BODIPY dye, a fluorescein dye, a dansyl dye, an Alexa dye, an atto dye, a quantum dot, or a fluorescent protein. In some embodiments, the fluorescent molecule is a cyanine dye (e.g., Cy3, Cy 3.5, Cy5, Cy5.5, Cy7, or Cy7.5).

In some embodiments, the diagnostic agent is an MRI agent (e.g., a contrast agent). Examples of suitable materials for use as MRI agents (e.g., contrast agents) include gadolinium chelates, as well as iron, magnesium, manganese, copper, and chromium.

In some embodiments, the diagnostic agent is a CAT imaging agent or an X-ray imaging agent. Examples of materials useful for CAT and X-ray imaging include iodine-based materials.

In some embodiments, the diagnostic agent is a PET imaging agent. Examples of suitable PET imaging agents include compounds and compositions comprising the positron emitting radioisotopoes $^{18}F$, $^{15}O$, $^{13}N$, $^{11}C$, $^{82}Rb$, $^{64}Cu$, and $^{68}Ga$, e.g., fludeoxyglucose ($^{18}F$-FDG), $^{68}Ga$-DOTA-psuedopeptides (e.g., $^{68}Ga$-DOTA-TOC), $^{11}C$-metomidate, $^{11}C$-acetate, $^{11}C$-methionine, $^{11}C$-choline, $^{18}F$-fluciclovine, $^{18}F$-fluorocholine, $^{18}F$-fluorodeoxysorbitol, $^{18}F$-3'-fluoro-3'-deoxythymidine, $^{11}C$-raclopride, and $^{18}F$-desmethoxyfallypride.

In some embodiments, the diagnostic agent is a near-IR imaging agent. Examples of near-IR imaging agents include Pz 247, DyLight 750, DyLight 800, cyanine dyes (e.g., Cy5, Cy5.5, Cy7), AlexaFluor 680, AlexaFluor 750, IRDye 680, IRDye 800CW, and Kodak X-SIGHT dyes.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present disclosure include, but are not limited to, $^{123}I$, $^{125}I$, $^{130}I$, $^{131}I$, $^{133}I$, $^{135}I$, $^{47}Sc$, $^{72}As$, $^{72}Sc$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99m}Tc$, $^{14}C$, $^{13}N$, $^{15}O$, $^{32}P$, $^{33}P$, or $^{18}F$.

Prophylactic agents that can be included in the conjugates of the disclosure include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

In certain embodiments, m is selected from the group of integers consisting of 1, 2, 3, 4, 5, 6, 7, 8, 9, and 10. In certain embodiments, m' is selected from the group of integers consisting of 2, 3, 4, 5, 6, 7, 8, 9, and 10. In certain embodiments, m or m' is independently 2, 3, 4, or 5.

In certain embodiments, b is selected from the group of integers consisting of 1, 2, 3, 4, 5, 6, 7, 8, 9, 10, 11, 12, 13, 14, 15, 16, 17, 18, 19, and 20. In certain embodiments, each instance of b is 2.

In certain embodiments, e is selected from the group of integers consisting of 1, 2, 3, 4, 5, 6, 7, 8, 9, and 10. In certain embodiments, e is 1.

In certain embodiments, X is $OR^C$ or $N(R^D)_2$, wherein $R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group.

In certain embodiments, $R^C$ is hydrogen, substituted or unsubstituted, $C_{1-6}$ alkyl, an oxygen protecting group, or a leaving group; and at least one instance of $R^D$ is hydrogen, substituted or unsubstituted, $C_{1-6}$ alkyl, or a nitrogen protecting group. In certain embodiments, X is —$OR^C$, wherein $R^C$ is an oxygen protecting group or a leaving group. In certain embodiments, X is —OH. In certain embodiments, $R^C$ or at least one instance of $R^D$ is substituted or unsubstituted, $C_{50-1000}$ heteroalkyl. In certain embodiments, $R^C$ or at least one instance of $R^D$ is

wherein: n is an integer from 1 to 300, inclusive; and $R^F$ is hydrogen, substituted or unsubstituted, $C_{1-6}$ alkyl, or an oxygen protecting group. In certain embodiments, wherein $R^C$ or at least one instance of $R^D$ is

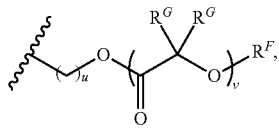

wherein: u is 1, 2, 3, 4, 5, or 6; each instance of $R^G$ is independently hydrogen, halogen, or substituted or unsubstituted, $C_{1-6}$ alkyl; v is an integer from 1 to 300, inclusive; and $R^F$ is hydrogen, substituted or unsubstituted, $C_{1-6}$ alkyl, or an oxygen protecting group.

In certain embodiments, $X^1$ is O or $NR^I$. In certain embodiments, $X^1$ is O. In certain embodiments, $X^1$ is $NR^I$, wherein: $R^I$ is independently hydrogen, substituted or unsubstituted, $C_{1-10}$ alkyl, substituted or unsubstituted, $C_{2-10}$ alkenyl, substituted or unsubstituted, $C_{1-10}$ heteroalkyl, substituted or unsubstituted, $C_{2-10}$ heteroalkenyl, or a nitrogen protecting group.

In certain embodiments, L is substituted or unsubstituted, $C_{2-200}$ alkynylene. In certain embodiments, L is substituted or unsubstituted, $C_{2-200}$ heteroalkynylene. In certain embodiments, L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with substituted or unsubstituted heteroarylene. In certain embodiments, L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with

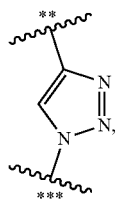 [SMILES: *c1cn(*)nn1]

wherein the nitrogen atom labeled with "*" (for compounds of Formula (I) and Formula (II)) is closer to the attachment point labeled with "" than the attachment point labeled with "*". In certain embodiments, L is substituted or unsubstituted, $C_{2-200}$ heteroalkylene, wherein one carbon or one heteroatom, of the substituted or unsubstituted, $C_{2-200}$ heteroalkylene, is replaced with

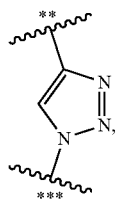 [SMILES: *c1cn(*)nn1]

wherein the nitrogen atom labeled with "*" (for compounds of Formula (I) and Formula (II)) is closer to the attachment point labeled with "" than the attachment point labeled with "*". In certain embodiments, at least one instance of L comprises

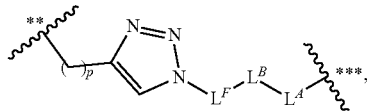

wherein: each instance of p is independently an integer from 1 to 10, inclusive; each instance of $L^F$ is independently substituted or unsubstituted, $C_{2-180}$ heteroalkylene; each instance of $-L^B-L^A-$ is independently $-C(=O)O-$, $-OC(=O)-$, $-C(=O)NR^E-$, or $-NR^E C(=O)-$, wherein each instance of $R^E$ is independently hydrogen, substituted or unsubstituted, $C_{1-6}$ alkyl, or a nitrogen protecting group; and the nitrogen atom labeled with "*" (for compounds of Formula (I) and Formula (II)) is closer to the attachment point labeled with "" than the attachment point labeled with "*". In certain embodiments, L is

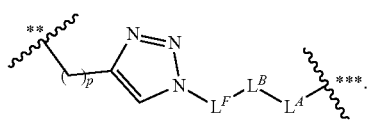

In certain embodiments, L comprises

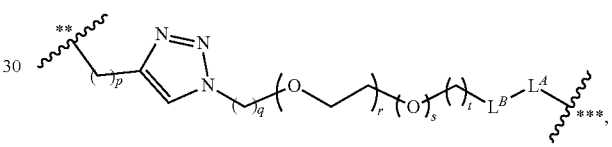

wherein: each instance of p is independently an integer from 1 to 10, inclusive; each instance of q is independently an integer from 1 to 10, inclusive;

each instance of r is independently an integer from 0 to 10, inclusive; each instance of s is independently 0 or 1; each instance of t is independently an integer from 0 to 10, inclusive; each instance of $-L^B-L^A-$ is independently $-C(=O)O-$, $-OC(=O)-$, $-C(=O)NR^E-$, or $-NR^E C(=O)-$, wherein each instance of $R^E$ is independently hydrogen, substituted or unsubstituted, $C_{1-6}$ alkyl, or a nitrogen protecting group; and the nitrogen atom labeled with "*" (for compounds of Formula (I) and Formula (II)) is closer to the attachment point labeled with "" than the attachment point labeled with "*". In certain embodiments, L is

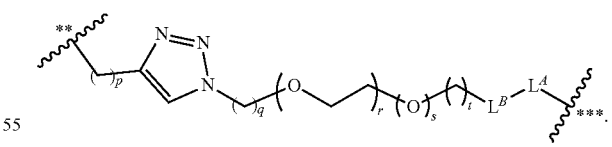

In certain embodiments, L comprises

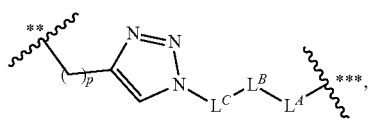

wherein: each instance of p is independently an integer from 1 to 10, inclusive; each instance of $L^C$ is independently substituted or unsubstituted, $C_{1-180}$ alkylene; each instance of -L$^B$-L$^A$- is independently —C(═O)O—, —OC(═O)—, —C(═O)NR$^E$—, or —NR$^E$C(═O)—, wherein each instance of R$^E$ is independently hydrogen, substituted or unsubstituted, C$_{1-6}$ alkyl, or a nitrogen protecting group; and the nitrogen atom labeled with "*" (for compounds of Formula (I) and Formula (II)) is closer to the attachment point labeled with "" than the attachment point labeled with "*". In certain embodiments, L is

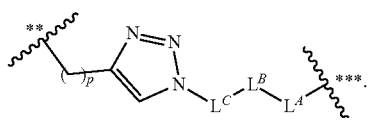

Figure 89:
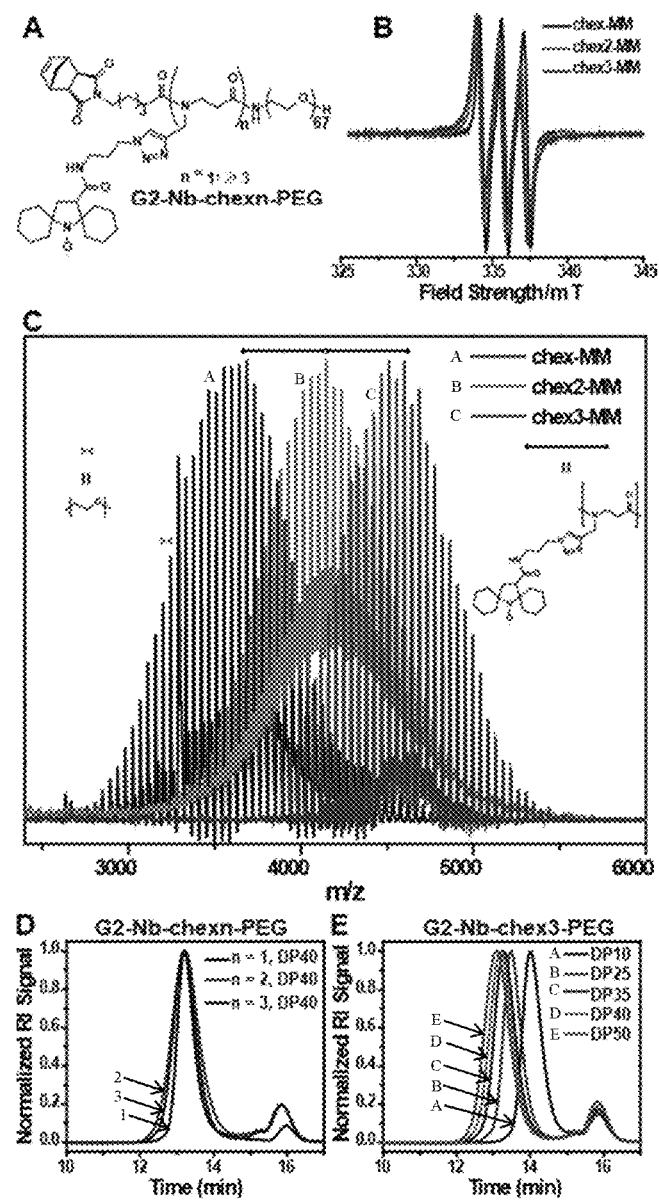
FIGS. 89A to 89E show.

In certain embodiments, L$^C$ is independently C$_{1-180}$ alkylene substituted with one or more instances of: substituted or unsubstituted phenyl and/or substituted or unsubstituted, C$_{1-6}$ alkyl. In certain embodiments, L is exemplified in compounds and macromonomers illustrated throughout FIGS. 1 to 89.

In certain embodiments, at least two instances of L are different from each other. In certain embodiments, all instances of L are different from each other. In certain embodiments, all instances of L are the same.

In certain embodiments, L$^1$ is substituted or unsubstituted, C$_{1-20}$ alkylene. In certain embodiments, L$^1$ is substituted or unsubstituted, C$_{2-20}$ heteroalkylene.

In certain embodiments, at least one instance of L or L$^1$ comprises a polymer chain. In some embodiments, at least one instance of the polymer chain is a polyethylene glycol (PEG), a polyethylene oxide (PEO), a polypropylene glycol (PPG), a polyglycerol (PG), a poloxamine (PDX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester. In some embodiments, at least one instance of the polymer chain is polyethylene glycol (PEG). In some embodiments, the PEG has a molecular weight of between about 100 and about 6000 g/mol (e.g., PEG 100, PEG200, PEG400, PEG600, PEG800, PEG1000, PEG1500, PEG2000, PEG3000, PEG4000, or PEG6000). In some embodiments, the PEG is PEG100. In some embodiments, the PEG is PEG200. In some embodiments, the PEG is PEG400. In some embodiments, the PEG is PEG600. In some embodiments, the PEG is PEG800. In some embodiments, the PEG is PEG1000. In some embodiments, the PEG is PEG2000. In some embodiments, the PEG is PEG3000. In some embodiments, the PEG is PEG4000. In some embodiments, the PEG is PEG6000.

In certain embodiments, the polymer chain is in the form of a conjugate, BASP, or particle (e.g., nanoparticle or microparticle). The agent is covalently bound to the polymer chain, through a cleavable linker (which can also be referred to herein as a "sensitive linker"). In certain embodiments, at least one instance (e.g., each instance) of L comprises a cleavable linker. In certain embodiments, at least one instance (e.g., each instance) of L is a cleavable linker. A cleavable linker is "cleaved" or "degraded" when one or more bonds of the cleavable linker are broken, e.g., resulting in release of an agent, e.g., from the conjugate or particle. Linker cleavage or agent release need not be 100%, e.g., a cleavage or release of at least 10%, 20%, 30%, 40%, 50%, 60%, 70%, 80%, 90%, 95%, or higher, e.g., over a period of seconds, minutes, hours (e.g., 6 hours, 12 hours, or 24 hours), days (e.g., 2 days or 7 days), weeks, or months is encompassed by this term.

In some embodiments, the cleavable linker is cleavable by or is sensitive to an enzyme (e.g., an esterase or a protease), pH (e.g., acidic pH, basic pH), light (e.g., ultraviolet light), a nucleophile, reduction, or oxidation. In some embodiments, the cleavable linker is cleavable by or is sensitive to an enzyme (e.g., an esterase or a protease) or pH (e.g., acidic pH, basic pH). In some embodiments, the cleavable linker is not cleavable by light (e.g., ultraviolet light).

In some embodiments, the cleavable linker comprises an ester, an acetal, a ketal, a phosphoramidite, a hydrazone, an imine, an oxime, a disulfide, or a silyl moiety, a combination of acetal or ketal with ester group, an oligo-acetal or oligo-ketal group, a combination of the oligo-ketal and silyl ether group, or a combination of the oligo-ketal and vinyl ether group. In some embodiments, the cleavable linker comprises an ester. In some embodiments, the cleavable linker comprises an acetal. In some embodiments, the cleavable linker comprises a phosphoramidite. In some embodiments, the cleavable linker comprises a hydrazine. In some embodiments, the cleavable linker comprises an imine. In some embodiments, the cleavable linker comprises an oxime. In some embodiments, the cleavable linker comprises a silyl moiety. In some embodiments, the cleavable linker comprises a disulfide.

In other embodiments, the cleavable linker is chosen from a combination of acetal or ketal with cis-aconityl, hydrazine, oxime, imidazole, or trityl groups. Any of the aforesaid groups or combination of groups can modified to enhance the pH sensitivity of the cleavable linker, e.g., as described herein.

In some embodiments, the cleavable linker is an amide, urea, carbamate, carbonate, or disulfide.

In some embodiments, the cleavable linker comprises: —OC(O)—, —C(O)O—,

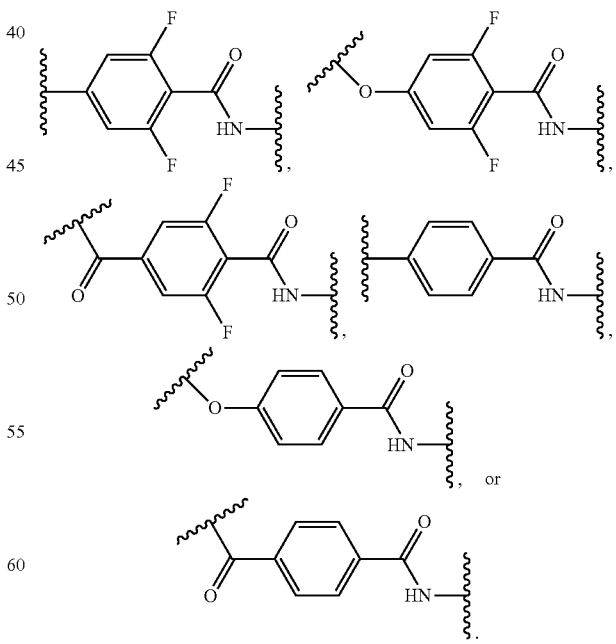

The cleavable linker may include an atom or a part of a moiety that is derived in part from the agent (e.g., a therapeutic agent).

In some embodiments, the cleavable linker is cleaved or degraded, e.g., preferentially cleaved or degraded, upon exposure to a first set of conditions relative to a second set of conditions. For example, the cleavable linker can be "preferentially cleaved" or "preferentially degraded" in a first set of conditions relative to a second set of conditions if at least 10%, 20%, 30%, 40%, 50%, 60%, 70%, 80%, 90%, 95%, or more of a bond or bonds of the cleavable linker are broken, or the agent is released, in the first set of conditions relative to the second set of conditions.

In some embodiments, the cleavable linker is degraded or hydrolyzed at physiological conditions. In some embodiments, the linker is pH sensitive or cleaved at a certain pH. In some embodiments, the linker is degraded or hydrolyzed through the action of an enzyme (e.g., a protease or esterase). For example, in some embodiments, the cleavable linker is preferentially cleaved in a tissue microenvironment, e.g., a tumor microenvironment, which is referred to herein as a "tissue microenvironment cleavable linker." In embodiments, the tissue (e.g., tumor) microenvironment cleavable linker is preferentially cleaved or degraded upon exposure to a first desired tissue or tumor microenvironment relative to a second tissue or non-tumor tissue. A tissue (e.g., tumor) microenvironment cleavable linker can be preferentially cleaved if at least 10%, 20%, 30%, 40%, 50%, 60%, 70%, 80%, 90%, 95% or more of a bond or bonds of the linker are broken, or the agent is released, in a desired tissue or tumor microenvironment relative to another tissue or non-tumor tissue. In one embodiments, the tissue (e.g., tumor) microenvironment cleavable linker is preferentially cleaved or degraded if one or more of the bonds of the linker are broken, or the agent is released, at least 2, 5, 10, 20, 30, 40, 50, 60, 70, 80, or 100 times faster upon exposure to a first desired tissue or tumor microenvironment relative to a second tissue or non-tumor tissue. The tissue (e.g., tumor) microenvironment can have a particular set of conditions, e.g., pH, enzymes, that cause the cleavage or degradation of the linker.

In some embodiments, the cleavable linker is a peptide. In some embodiments, the linker is a peptide, and the peptide sequence is comprised of naturally occurring amino acids. In some embodiments, the linker is a peptide, and the peptide sequence comprises at least one synthetically derived amino acids, e.g., at least 2, at least 3, at least 4, at least 5, at least 8, at least 10, at least 15, at least 20, or more synthetically derived amino acids (unnatural amino acid). In some embodiments, the peptide has a linear structure. In some embodiments, the peptide has a branched structure. In some embodiments, the peptide has a branced structure with, e.g., at least 2, at least 3, at least 4, at least 5, at least 6, at least 7, or at least 8 branching points. In some embodiments, the peptide has a cyclic structure.

In some embodiments, the cleavable linker is a peptide, and the peptide sequence comprises at least 2 amino acid residues. In some embodiments, the peptide sequence comprises at least 3, at least 4, at least 5, at least 6, at least 7, at least 8, at least 9, or at least 10 amino acid residues. In some embodiments, the peptide sequence is from about 1 to about 10 amino acid residues. In some embodiments, the peptide sequence is from about 1 to about 15, about 20, about 25, about 30, about 40, about 50, about 60, about 70, about 80, about 90, or about 100 amino acid residues. In some embodiments, the peptide sequence is from about 10 to about 100 amino acid residues. In some embodiments, the peptide sequence is from about 25 to about 100 amino acid residues. In some embodiments, the peptide sequence is from about 50 to about 100 amino acid residues.

In some embodiments, the cleavable linker comprises a substrate peptide that is cleaved, e.g., activated, by a matrix metalloprotease (MMP) selected from a sequence disclosed in U.S. Patent Application No. 2015/0087810 with a publication date of Mar. 26, 2015. In some embodiments, the substrate peptide comprises a protease substrate comprising an amino acid sequence selected from the group consisting of SEQ ID NOs: 353-363, 372-375, 376-378, 395-401, 411-419, 426-433, 437-449, 454-456, 459-469, 475-482, 487-495, 318-323, 325-327, 330-335, 341-347, 14-33, and 159, e.g., as described in U.S. Patent Application No. 2015/0087810. In some embodiments, the linker comprises a substrate peptide derived from a sequence disclosed in U.S. Pat. No. 8,541,203, e.g., a substrate peptide chosen from an enzyme selected from the group consisting of MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the linker comprises a sequence disclosed in U.S. Pat. No. 8,513,390. In some embodiments, the linker comprises a sequence disclosed in International Patent Publication No. WO2003/079972. In some embodiments, the linker comprises a sequence disclosed in U.S. Pat. No. 7,495,099. In some embodiments, the linker comprises a sequence disclosed in U.S. Pat. No. 8,580,244. In some embodiments, the linker comprises a sequence disclosed in one of the following articles: van Kempen, et al. *Eur Cancer* (2006) 42:728-734; Desnoyers, L. R. et al. *Sci Transl Med* (2013) 5:207ra144; Rice, J. J. et al. *Protein Sci* (2006) 15:825-836; Boulware, K. T. and Daugherty, P. S. *Proc Natl Acad Sci USA* (2006) 103:7583-7588; Deperthes, D. *Biol Chem* (2002) 383:1107-1112; Harris, J. L. *Proc Natl Acad Sci USA* (2000) 97:7754-7759; Salmaso S. and Caliceti, P. *J Drug Deliv* (2013) 2013:1-19; and Eckhard, U et al. *Matrix Biol* (2015) doi: 10.1016/j.matbio.2015.09.003 (epub ahead of print). The contents of any of the publications referenced herein are hereby expressly incorporated by reference.

In some embodiments, the cleavable linker comprises a substrate peptide that is cleaved, e.g., activated, by a protease, e.g., a protease present in a tumor or fibrotic microenvironment (e.g, a matrix metalloprotease (MMP), e.g., as described by Desnoyers, L. R. et al. *Sci Transl Med* (2013) 5:207ra144; Eckhard, U et al *Matrix Biol* (2015) doi: 10.1016/j.matbio.2015.09.003 (epub ahead of print); and van Kempen, et al. *Eur Cancer* (2006) 42:728-734. In one embodiments, the linker includes the amino acid sequence of a substrate for uPA, e.g., comprises the amino acid sequence LSGRSDNH (SEQ ID NO:1), e.g., as described in U.S. Pat. No. 8,513,390. In some embodiments, the linker sequence further includes a Gly-Ser- containing peptide linker, at either end, or both ends to the substrate peptide. Additional exemplary proteases that may be upregulated in a tumor microenvironment include, but are not limited to, urokinase-type plasminogen activator (uPA), which is upregulated in human carcinomas (S. Ulisse, et al. *Curr. Cancer Drug Targets* 9, 32-71 (2009)), membrane-type serine protease 1 (MT-SP1/matriptase) (K. Uhland Cell. Mol. *Life Sci.* 63, 2968-2978 (2006); A. M. LeBeau, et al. *Proc. Natl. Acad. Sci. U.S.A.* 110, 93-98 (2013)), and legumain, a lysosomal protease found to be released and active in the acidic extracellular tumor microenvironment (C. Liu, et al. *Cancer Res.* 63, 2957-2964 (2003)). In some embodiments, the protease is produced by an inflammatory cell, e.g., a tumor infiltrating leukocyte (e.g., a leukocyte-derived MMP), e.g., as described by van Kempen, et al. *Eur Cancer* (2006) 42:728-734. In other embodiments, the MMP is chosen from MMP1, MMP2, MMP3, MMP1, MMP8, MMP9, MMP12, MMP13 or MMP14, e.g., as described by Eckhard, U et al. supra.

In some embodiments, the substrate peptide is derived from a CLiPS library (as described in, e.g., K. T. Boulware, P. S. Daugherty, *Proc. Natl. Acad. Sci. U.S.A.* 103, 7583-7588 (2006)). In other embodiments, the substrate peptide specificity is evaluated using combinatorial fluorogenic substrate libraries, e.g., as described by Harris, J. L. *Proc Natl Acad Sci USA* (2000) 97:7754-7759. In other embodiments, the substrate peptide is derived from a phage display library (e.g., it is a phase display substrate), e.g., as described by Deperthes, D. *Biol Chem* (2002) 383:1107-1112. For example, a phage display substrate is exposed to a plurality of proteases; peptides released through specific cleavage can be amplified in an expression system. In other embodiments, the substrate peptide is derived from a bacterial display library, e.g., as described by Rice, J. J. et al. *Protein Sci* (2006) 15:825-836.

In one embodiments, the tissue (e.g., tumor) microenvironment cleavable linker is cleavable by an enzyme. In some embodiments, the enzyme comprises an esterase or a protease. Exemplary proteases include MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, or TACE.

In other embodiments, the tissue microenvironment cleavable linker is cleavable at a particular pH. In some embodiments, the tissue microenvironment cleavable linker is cleavable at a pH between about 5.0 and about 7.4, between 5.0 and 7.0, between 5.0 and 6.5, between 5.0 and 5.5, or between 5.9 and 6.2. In one embodiment, the tissue microenvironment cleavable linker is cleavable at a pH between about 6.0 and about 7.0, between about 6.2 and about 6.9, between about 6.5 and about 6.8, or between about 6.5 and about 6.7. In one embodiment, the tissue microenvironment cleavable linker is cleavable at a pH between about 5.5 and about 6.5, e.g., between 5.9 and 6.2. In one embodiment, the tissue microenvironment cleavable linker is cleavable at a hypoxic pH, e.g., a pH about 6.7 to 6.9, e.g., compared to a physiological pH of about 7.4.

In some embodiments, the tissue microenvironment cleavable linker is cleavable is cleaved at a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the tissue microenvironment cleavable linker is preferentially cleaved or degraded upon exposure to a first pH relative to a second pH. In one embodiment, the tissue microenvironment cleavable linker is cleaved or degraded at least 2, 5, 10, 20, 30, 40, 50, 60, 70, 80, or 100 times faster upon exposure to a first pH relative to a second pH. In other embodiments, the tissue microenvironment cleavable linker shows a greater release or degradation rate at a first acidic pH (e.g., pH=6.7) relative to a second more basic pH (e.g., pH=7.4). In one embodiment, ratio of release or degradation rate of the tissue microenvironment cleavable linker at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the tissue microenvironment cleavable linker at pH=6.7 relative to pH=7.4 is greater than 2.

In one embodiment, the tissue microenvironment cleavable linker shows increased pH-sensitivity in a hypoxic microenvironment, e.g., in a tumor, or fibrotic tissue.

In some embodiments, the tissue microenvironment cleavable linker exhibits an increased release rate or increased release yield of the agent at a desired site (e.g., a tumor), e.g., relative to the release rate or release yield at another site. In one embodiment, the tissue microenvironment cleavable linker comprises an electron withdrawing group (e.g., an electron withdrawing group that enhances the cleavage rate or yield.

In certain embodiments, at least one instance of -L(M)$_m$ comprises 1, 2, 3, 4, or 5 click-chemistry handles. In certain embodiments, each instance of -L(M)$_m$ comprises independently a click-chemistry handle. In certain embodiments, at least one instance of the click-chemistry handle comprises an alkenylene group or alkynylene group. In certain embodiments, at least one instance of the click-chemistry handle comprises an internal alkenylene group or alkynylene group. In certain embodiments, at least one instance of the click-chemistry handle comprises an terminal alkenylene group or alkynylene group. In certain embodiments, at least one instance of the click-chemistry handle is —CCH, substituted or unsubstituted cyclooctynyl optionally fused independently with one or more instances of substituted or unsubstituted phenyl, substituted or unsubstituted cyclopropenyl, substituted or unsubstituted cyclobutenyl, substituted or unsubstituted trans-cyclooctenyl optionally fused independently with one or more instances of substituted or unsubstituted phenyl, or substituted or unsubstituted

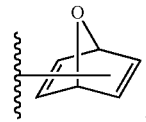

In certain embodiments, each instance of the click-chemistry handle is —CCH. In certain embodiments, at least one instance of -L(M)$_m$ is —(CH$_2$)$_p$—CCH, wherein each instance of p is independently an integer from 1 to 10, inclusive. In certain embodiments, at least one instance of -L(M)- comprises 2, 3, 4, or 5 instances of —(CH$_2$)$_p$—CCH, wherein each instance of p is independently an integer from 1 to 10, inclusive. Each instance of p is independently an integer selected from the group consisting of 1, 2, 3, 4, 5, 6, 7, 8, 9, and 10.

In certain embodiments, at least one instance of -L(M)$_m$ comprises:

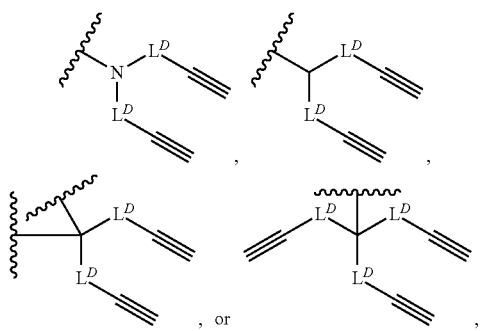

, or wherein each instance of $L^D$ is independently substituted or unsubstituted, $C_{1-10}$ alkylene, or substituted or unsubstituted, $C_{2-10}$ heteroalkylene. In certain embodiments, at least one instance of $-L(M)_m$ comprises:

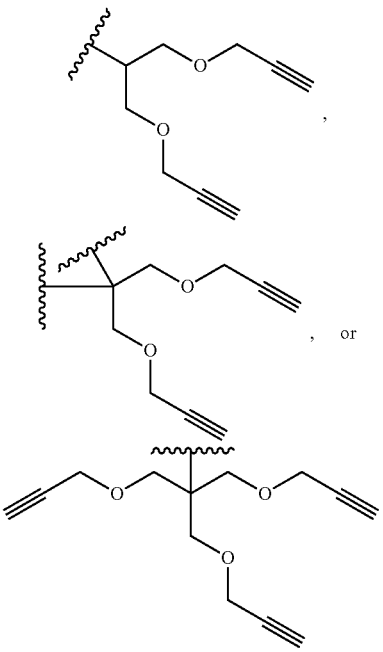

In certain embodiments, at least one instance of $-L(M)_m$ comprises:

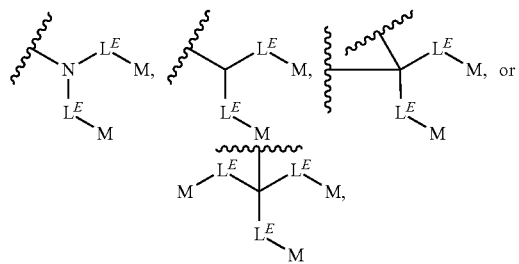

wherein each instance of $L^E$ is independently substituted or unsubstituted, $C_{1-50}$ alkylene, substituted or unsubstituted, $C_{2-50}$ alkenylene, substituted or unsubstituted, $C_{2-50}$ alkynylene, substituted or unsubstituted, $C_{2-50}$ heteroalkylene, substituted or unsubstituted, $C_{2-50}$ heteroalkenylene, or substituted or unsubstituted, $C_{2-50}$ heteroalkynylene, wherein: optionally one or more carbons of each instance of the substituted or unsubstituted, $C_{1-50}$ alkylene, substituted or unsubstituted, $C_{2-50}$ alkenylene, substituted or unsubstituted, $C_{2-50}$ alkynylene, substituted or unsubstituted, $C_{2-50}$ heteroalkylene, substituted or unsubstituted, $C_{2-50}$ heteroalkenylene, and substituted or unsubstituted, $C_{2-50}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms of each instance of the substituted or unsubstituted, $C_{2-50}$ heteroalkylene, substituted or unsubstituted, $C_{2-50}$ heteroalkenylene, and substituted or unsubstituted, $C_{2-50}$ heteroalkynylene are independently replaced with substituted or unsubstituted carbocyclylene, substituted or unsubstituted heterocyclylene, substituted or unsubstituted arylene, or substituted or unsubstituted heteroarylene.

Exemplary macromonomers may be described by a number of properties, including molecular weight (kDa) and hydrodynamic diameter (nm). In some embodiments, the molecular weight of the macromonomer is between about 1 kDa and about 10 kDa, e.g., between about 2 kDa and about 8 kDa or about 3 kDa and about 6 kDa, e.g., as detected by mass spectrometry. In some embodiments, the molecular weight of the macromonomer is between about 3 kDa and about 6 kDa. In some embodiments, the molecular weight of the macromonomer is about 2 kDa, about 3 kDa, about 4 kDa, about 5 kDa, or about 6 kDa. In some embodiments, the hydrodynamic diameter of the macromonomer is between about 0.5 nm and about 3 nm, e.g., about 1 nm and about 2 nm, e.g., as detected by dynamic light scattering.

Polymers

The present disclosure describes polymers (e.g., conjugates, particles, brush-arm star polymers (BASPs)) and materials produced from polymerizing macromonomers of Formula (I) and Formula (II), and compounds of Formula (III).

In certain embodiments, the terms "polymer", "conjugate", and "particle" are used interchangeably. Exemplary conjugates or particles may be described by a number of properties, including, $M_n$=average molecular weight (kDa), $D_H$=average hydrodynamic diameter (nm), and PDI=polydispersity.

In certain embodiments, the $M_n$ is determined with gel permeation chromatography, viscometry via the (Mark-Houwink equation), colligative methods (such as vapor pressure osmometry), end-group determination, or proton NMR. In certain embodiments, the $M_w$ is determined with static light scattering, small angle neutron scattering, X-ray scattering, and sedimentation velocity. In some embodiments, the average molecular weight of the conjugate is between about 10 kDa and about 100 kDa, e.g., between about 15 kDa and about 85 kDa, about 20 kDa and about 60 kDa, or about 30 kDa and about 50 kDa, e.g., as determined by gel permeation chromatography. In one embodiment, the average molecular weight of the conjugate is between about 20 kDa and about 60 kDa. In one embodiment, the average molecular weight of the conjugate is between about 30 kDa and about 50 kDa.

In some embodiments, the average molecular weight of the conjugate is less than about 100 kDa (e.g., less than about 95 kDa, about 90 kDa, about 85 kDa, about 80 kDa, about 75 kDa, about 70 kDa, about 65 kDa, about 60 kDa, about 55 kDa, or about 50 kDa), e.g., as determined by gel permeation chromatography. In some embodiments, the average molecular weight of the conjugate is less than about 75 kDa (e.g., less than about 70 kDa, about 65 kDa, about 60 kDa, about 55 kDa, or about 50 kDa).

In some embodiments, the average molecular weight of the particle is between about 100 kDa and about 1,000 kDa, e.g., between about 200 kDa and about 700 kDa or about 300 kDa and about 500 kDa, e.g., as determined by gel permeation chromatography. In one embodiment, the average molecular weight of the particle is between about 2000 kDa and about 70 kDa. In one embodiment, the average molecular weight of the particle is between about 300 kDa and about 500 kDa.

In some embodiments, the average molecular weight of the particle is less than about 1,000 kDa (e.g., less than about 950 kDa, about 900 kDa, about 850 kDa, about 800 kDa, about 750 kDa, about 700 kDa, about 650 kDa, about 600 kDa, about 550 kDa, or about 500 kDa), e.g., as determined by gel permeation chromatography. In some embodiments, the average molecular weight of the particle is less than about 750 kDa (e.g., less than about 700 kDa, about 650 kDa, about 600 kDa, about 550 kDa, or about 500 kDa). In some embodiments, the average molecular weight of the particle is less than about 500 kDa (e.g., less than about 450 kDa, about 400 kDa, about 350 kDa, or 300 kDa).

In some embodiments, the average hydrodynamic diameter of the conjugate is less than 50 nm (e.g., less than about 45 nm, about 40 nm, about 35 nm, about 25 nm, about 20 nm, about 15 nm, about 10 nm, about 7.5 nm, or less), e.g., as determined by dynamic light scattering. In some embodiments, the average hydrodynamic diameter of the conjugate is between about 1 nm and about 20 nm (e.g., between about 2.5 nm and about 17.5 nm, or about 5 nm and about 15 nm). In some embodiments, the average hydrodynamic diameter of the conjugate is between about 5 nm and about 15 nm.

In some embodiments, the average hydrodynamic diameter of the particle is less than 100 nm (e.g., less than about 90 nm, about 80 nm, about 75 nm, about 70 nm, about 65 nm, about 60 nm, about 55 nm, about 50 nm, about 45 nm, about 40 nm, about 35 nm, about 25 nm, or less), e.g., as determined by dynamic light scattering. In some embodiments, the average hydrodynamic diameter of the particle is between about 5 nm and about 100 nm (e.g., between about 7.5 nm and about 75 nm, about 10 nm and about 50 nm, about 12.5 nm and about 40 nm, or about 15 nm and about 30 nm). In some embodiments, the average hydrodynamic diameter of the particle is between about 10 nm and about 50 nm. In some embodiments, the average hydrodynamic diameter of the particle is between about 15 nm and about 30 nm.

In some embodiments, the average polydispersity of the conjugate or particle is less than about 0.5 (e.g., less than about 0.4, about 0.35, about 0.3, about 0.25, about 0.2, about 0.15, or less). In some embodiments, the average polydispersity of the conjugate or particle is less than about 0.3. In some embodiments, the average polydispersity of the conjugate or particle is less than about 0.2. In some embodiments, the conjugate or particle is monodisperse. In some embodiments, the conjugate or particle is about 50% monodisperse (e.g., about 55%, about 60%, about 65%, about 70%, about 75%, about 80%, about 85%, about 90%, about 95%, about 99%, or about 99.9% monodisperse).

In some embodiments, the conjugate or particle is substantially soluble in water (e.g., hydrophilic). In some embodiments, the conjugate or particle is substantially insoluble in water (e.g., hydrophobic). In some embodiments, the conjugate or particle is substantially insoluble in water and greater than about 10,000 parts water are required to dissolve 1 part polymer. In one embodiment, the conjugate or particle is amphiphilic. In one embodiment, the conjugate or particle comprises a segment that is hydrophobic and a segment that is hydrophilic.

In some cases, the polymers (i.e., BASPs) are in the form of particles (e.g., nanoparticles, i.e., the particle have a characteristic dimension of less than about 1 micrometer). In certain embodiments, the characteristic dimension of a particle is the diameter of a perfect sphere having the same volume as the particle. In certain embodiments, the BASP particle has a characteristic dimension of less than about 300 nm. In certain embodiments, the BASP particle has a characteristic dimension of less than about 200 nm. In certain embodiments, the BASP particle has a characteristic dimension of less than about 150 nm. In certain embodiments, the BASP particle has a characteristic dimension of less than about 100 nm. In certain embodiments, the BASP particle has a characteristic dimension of less than about 50 nm. In certain embodiments, the BASP particle has a characteristic dimension of less than about 30 nm. In certain embodiments, the BASP particle has a characteristic dimension of less than about 20 nm. In certain embodiments, the BASP particle has a characteristic dimension of less than about 10 nm. In certain embodiments, the BASP particle has a characteristic dimension between 6 and 250 nm, inclusive. In certain embodiments, the BASP particle has a characteristic dimension between 8 and 200 nm, inclusive. In certain embodiments, the BASP particle has a characteristic dimension between 12 and 200 nm, inclusive. In certain embodiments, the BASP particle has a characteristic dimension between 50 and 200 nm, inclusive.

The BASPs described herein may be able to deliver multiple agents ratiometrically and/or orthogonally. Different chemical and/or physical conditions may be employed to individually release the multiple agents upon delivery. The convergent synthesis of BASPs allow the attachment of different agents to the BASPs through different linkers (e.g., linkers cleavable by reduction, hydrolysis (such as esters), oxidation, and UV irradiation (such as the moiety

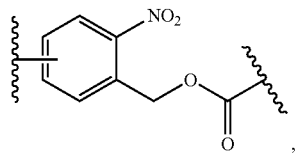

wherein the moiety may be further substituted)). The hydrolyzation, oxidation, UV irradiation, and reduction may be performed in any order and at the same time or different times.

In certain embodiments, the BASP is a polymer comprising at least 100 repeating units selected from Formula (Ia), Formula (IIa), and Formula (Za):

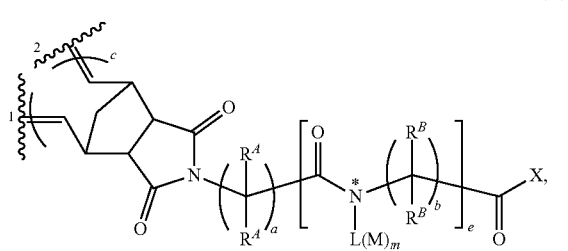

Formula (Ia)

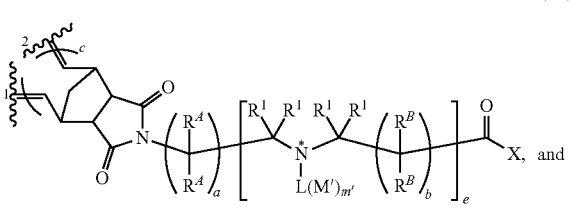

Formula (IIa)

55

-continued

Formula (Za)

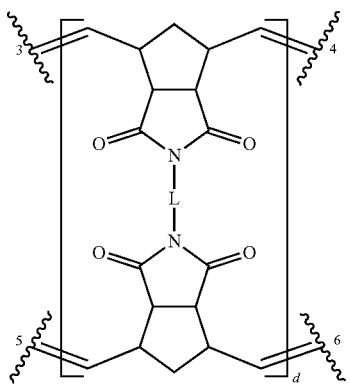

or a salt thereof, wherein:

each of "1", "2", "3", "4", "5", and "6" is independently a terminal group selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio; or represents a bond to a structure of Formula (Ia), Formula (IIa), or Formula (Za). In certain embodiments, the polymer comprises repeating units selected from Formula (Ia) and Formula (Za). In certain embodiments, the polymer comprises repeating units selected from Formula (IIa) and Formula (Za). In certain embodiments, the polymer comprises repeating units selected from Formula (Ia), Formula (IIa) and Formula (Za).

Methods of Preparation of Macromonomers and Polymers

The present disclosure describes methods of preparing macromonomers of Formula (I) and Formula (II) as well as methods for producing polymers described herein.

In certain embodiments, a method of preparing a macromonomer is described, which comprises coupling a compound of Formula (D): or (D)

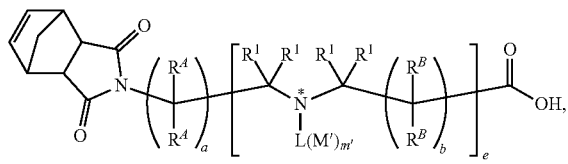

a salt thereof, with a compound of the formula: HOR$^C$ or HN(R$^D$)$_2$, or a salt thereof. In certain embodiments, a method of preparing a macromonomer is described, which comprises coupling a compound of Formula (E):

(E)

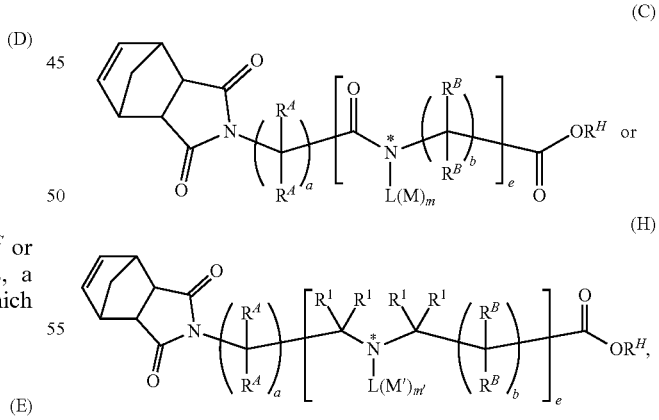

or a salt thereof, with a compound of the formula: HOR$^C$ or HN(R$^D$)$_2$, or a salt thereof. In certain embodiments, a

56 method of preparing a macromonomer is described, which comprises coupling a compound of the formula:

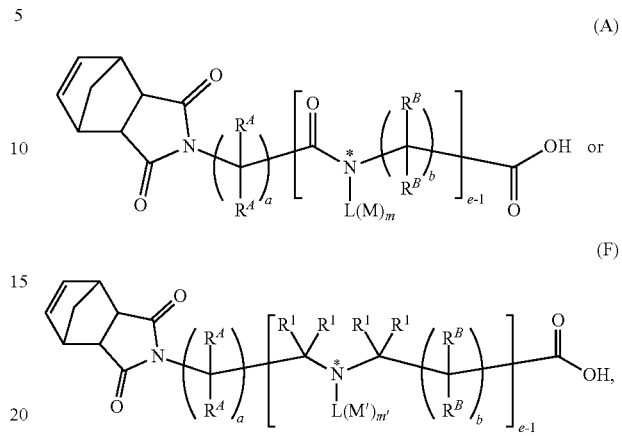

or a salt thereof, with a compound of the formula:

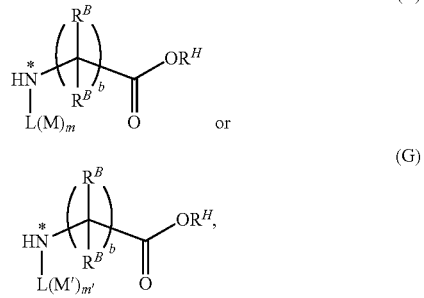

or a salt thereof, to provide a compound of the formula:

(C)

(H)

or a salt thereof, wherein R$^H$ is an oxygen protecting group; and further comprising deprotecting the compound of Formula (C) or Formula (H), or a salt thereof, to provide the compound of Formula (D) or Formula (E), or a salt thereof.

In certain embodiments, a method of preparing a macromonomer is described, which comprises coupling a macromonomer of the formula:

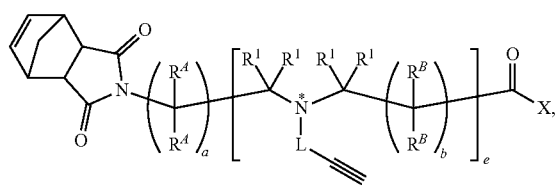

or salt thereof, with a compound of Formula (III) to provide a macromonomer of Formula (II).

In certain embodiments, a reagent for coupling a carboxylic acid with an alcohol or amine is N-(3-dimethylaminopropyl)-N'-ethylcarbodiimide (EDC), dicyclohexylcarbodiimide (DCC), 1-ethyl-3-(3-dimethylaminopropyl) carbodiimide hydrochloride (WSC/HCl), diphenylphosphorylazide (DPPA), carbonyldiimidazole (CDI), diethylcyanophosphonate (DEPC), benzotriazole-1-yloxy-trispyrrolidinophosphonium (DIPCI), benzotriazole-1-yloxy-trispyrrolidinophosphonium hexafluorophosphate (PyB OP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), or 3,4-dihydro-3-hydrodi-4-oxa-1,2,3-benzotriazine (Dhbt), or a salt thereof; or a combination (e.g., a combination of two) thereof. In certain embodiments, the reagent for coupling a carboxylic acid with an alcohol or amine is DCC. In certain embodiments, the reagent for coupling a carboxylic acid with an alcohol or amine is EDC, or a salt thereof.

The reagent for coupling a carboxylic acid with an alcohol or amine is used in an amount of about 1 to 20 equivalents of the compound of Formula (D) or Formula (E). In certain embodiments, the reagent for coupling a carboxylic acid with an alcohol or amine is used in an amount of about 1 to 10 equivalents. In certain embodiments, the activator is used in an amount of about 1 to 5 equivalents.

Any suitable solvent for coupling reactions can be used to perform coupling reactions described herein. Examples of useful solvents in the coupling reaction are DMSO, DMF, and methylene chloride. Additional exemplary solvents include acetonitrile, chloroform, tetrahydrofuran, and acetone.

The coupling reaction can be conducted at 0 to 50° C. In certain embodiments, the coupling reaction is conducted at room temperature for about 10 minutes to about 30 hours. In certain embodiments, the coupling reaction is conducted for about 15 minutes to about 24 hours.

In certain embodiments, the preparation of compounds of Formula (III) comprises a conjugation reaction. For instance, EDC-NHS chemistry (1-ethyl-3-(3-dimethylaminopropyl) carbodiimide hydrochloride and N-hydroxysuccinimide), or a reaction involving a maleimide or a carboxylic acid, which can be conjugated to one end of a thiol, an amine, or a similarly functionalized polyether. The conjugation can be performed in an organic solvent, such as, but not limited to, methylene chloride, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting the agent that includes a hydroxyl, thiol, or amino group with a polymer comprising a carboxylic acid functional group. Such a reaction may occur as a single-step reaction, i.e., the conjugation is performed with or without using intermediates such as N-hydroxysuccinimide or a maleimide. The conjugation reaction between the amine-containing, thiol-containing, or hydroxyl-containing moiety and the carboxylic acid-terminated polymer may be achieved in one embodiment, by adding the amine-containing, thiol-containing, or hydroxyl-containing moiety, solubilized in an organic solvent such as, but not limited to, dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously in some cases. Unconjugated macromonomers may be washed away after such reactions, and the polymer may be precipitated in solvents such as, for instance, ethyl ether, hexane, methanol, or ethanol.

In certain embodiments, the methods for preparing the polymers (i.e., BASPs) described herein may involve a metathesis reaction. In certain embodiments, the metathesis reaction is a ring-opening metathesis polymerization (ROMP) (Liu et al. *J. Am. Chem. Soc.* 2012, 134, 16337; Liu, J.; Gao, A. X.; Johnson, J. A. *J Vis Exp* 2013, e50874). In certain embodiments, the polymers described herein are prepared by polymerization of one or more macromonomers of Formula (I) and/or Formula (II) in the presence of a metathesis catalyst. In certain embodiments, the polymers described herein are prepared by polymerization of one or more macromonomers of Formula (I) and/or Formula (II) in the presence of a metathesis catalyst followed by in situ crosslinking with bis-norbornene crosslinkers. The preparation methods described herein are versatile and have little limitations, e.g., in terms of the different agents that can be built into the BASPs. In certain embodiments, an agent that can be built into the BASPs includes functional groups that are compatible with ROMP.

In certain embodiments, the metathesis catalyst (e.g., ROMP catalyst) is a tungsten (W), molybdenum (Mo), or ruthenium (Ru) catalyst. In certain embodiments, the ROMP catalyst is a ruthenuim catalyst. ROMP catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the ROMP catalyst is a Grubbs catalyst. In certain embodiments, the Grubbs catalyst is selected from the group consisting of:

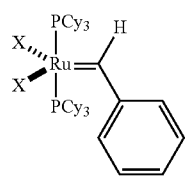

X = Cl; Br; I
Cy = cyclohexyl

Benzylidenebis-(tricyclohexylphosphine)-dichlororuthenium (X=Cl); Benzylidenebis-(tricyclohexylphosphine)-dibromoruthenium (X=Br); Benzylidenebis-(tricyclohexylphosphine)-diiodoruthenium (X=I);

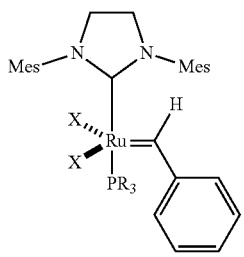

X = Cl; Br; I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl); 1,3-(Bis(mesityl)-2-imidazolidinylidene)dibromo-(phenylmethylene) (tricyclohexyl-phosphine)ruthenium (X=Br; R=cyclohexyl); 1,3-(Bis(mesityl)-2-imidazolidinylidene)diiodo-(phenylmethylene) (tricyclohexyl-phosphine)ruthenium (X=I; R=cyclohexyl); 1,3-(Bis(mesityl)-2-imidazolidinylidene)dichloro-(phenylmethylene) (triphenylphosphine)ruthenium (X=Cl; R=phenyl); 1,3-(Bis(mesityl)-2-imidazolidinylidene)dichloro-(phenylmethylene) (tribenzylphosphine)ruthenium (X=Cl; R=benzyl);

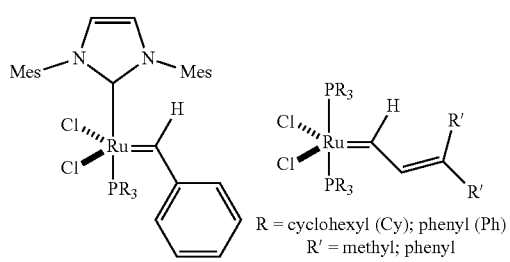

R = cyclohexyl (Cy); phenyl (Ph)
R' = methyl; phenyl

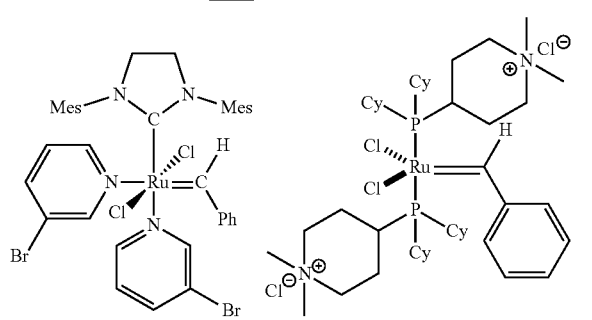

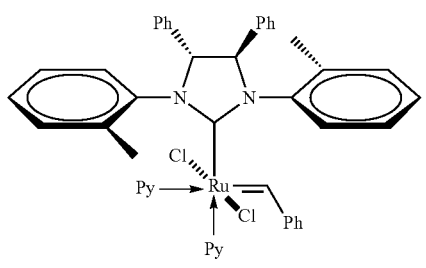

Py = pyridine
Ph = phenyl

In certain embodiments, the ROMP catalyst is a Grubbs-Hoveyda catalyst. In certain embodiments, the Grubbs-Hoveyda catalyst is selected from the group consisting of:

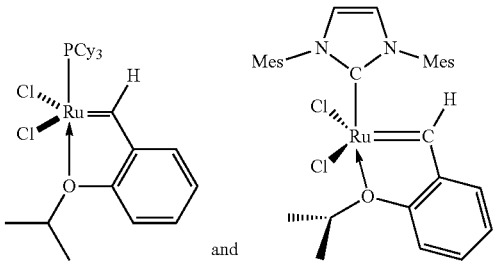

and

In certain embodiments, the ROMP catalyst is selected from the group consisting of:

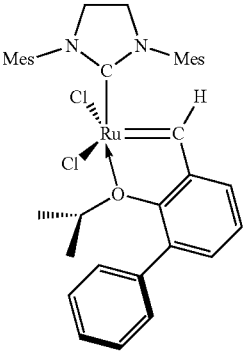

Blechart Catalyst;

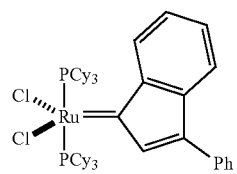

Neolyst™ M1; and

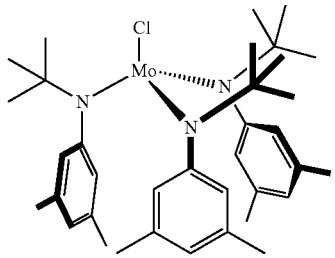

Furstner Catalyst.

In certain embodiments, the ROMP catalyst is of the formula:

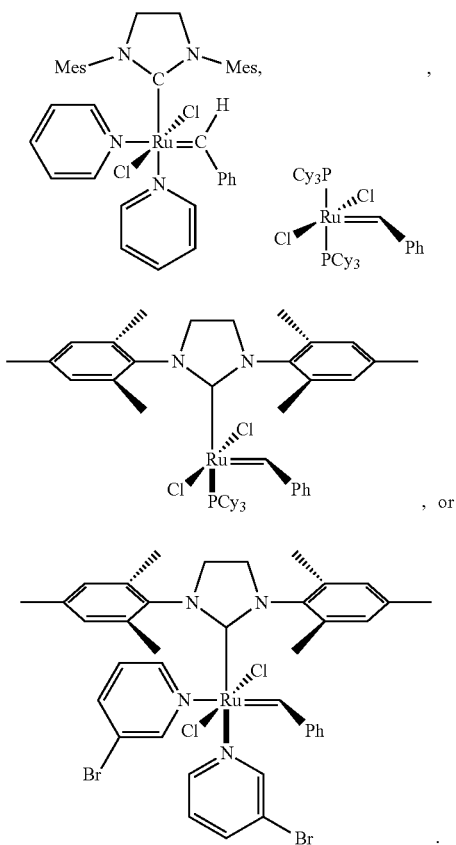

, or

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

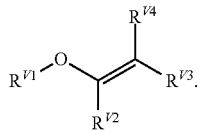

Each of $R^{V1}$, $R^{V2}$, $R^{V3}$, and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$, and $R^{V4}$ is conjugated with a diagnostic agent as defined above. In certain embodiments, the ROMP is quenched by ethyl vinyl ether. Excess ethyl vinyl ether can be removed from the BASPs by vacuum.

Compositions and Kits

The present disclosure provides compositions (e.g., pharmaceutical compositions) comprising a polymer of described herein, and optionally an excipient (e.g., pharmaceutically acceptable excipient). In certain embodiments, the composition is a pharmaceutical composition. In certain embodiments, the excipient is a pharmaceutically acceptable excipient.

In certain embodiments, the pharmaceutical compositions are useful for delivering an agent (e.g., to a subject or cell). In certain embodiments, the pharmaceutical compositions are useful for treating a disease in a subject in need thereof. In certain embodiments, the pharmaceutical compositions are useful for preventing a disease in a subject. In certain embodiments, the pharmaceutical compositions are useful for diagnosing a disease in a subject.

In certain embodiments, the polymer described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., proliferative disease, hematological disease, neurological disease, painful condition, psychiatric disorder, or metabolic disorder) in a subject in need thereof. In certain embodiments, the effective amount is an amount effective for inhibiting the activity (e.g., aberrant activity, such as increased activity) of a protein kinase in a subject or cell.

In certain embodiments, the cell is in vitro. In certain embodiments, the cell is in vivo.

Pharmaceutical compositions described herein can be prepared by any method known in the art of pharmacology. In general, such preparatory methods include bringing the polymer described herein (which may includes a therapeutic agent (the "active ingredient")) into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients, such as cocoa butter and suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a polymer described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Polymers provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The polymers and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the polymer or pharmaceutical composition described herein is suitable for topical administration to the eye of a subject.

The exact amount of a polymer required to achieve an effective amount will vary from subject to subject, depending, for example, on species, age, and general condition of a subject, severity of the side effects or disorder, identity of the particular polymer, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a polymer described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer described herein. In certain embodiments, a dose described herein includes independently between 1 mg and 3 mg, inclusive, of a polymer described herein. In certain embodiments, a dose described herein includes independently between 3 mg and 10 mg, inclusive, of a polymer described herein. In certain embodiments, a dose described herein includes independently between 10 mg and 30 mg, inclusive, of a polymer described herein. In certain embodiments, a dose described herein includes independently between 30 mg and 100 mg, inclusive, of a polymer described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A polymer or composition, as described herein, can be administered in combination with one or more additional pharmaceutical agents (e.g., therapeutically and/or prophylactically active agents). The polymers or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a polymer described herein and an additional pharmaceutical agent shows a synergistic effect that is absent in a pharmaceutical composition including one of the polymer and the additional pharmaceutical agent, but not both.

The polymer or composition can be administered concurrently with, prior to, or subsequent to one or more additional pharmaceutical agents, which are different from the polymer or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the polymer described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the polymers described herein or pharmaceutical compositions can be administered in combination with an anti-cancer therapy including surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or polymer described herein and instructions for use. The kits may further comprise a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or polymer described herein. In some embodiments, the pharmaceutical composition or polymer described herein provided in the first container and the second container are combined to form one unit dosage form.

In some embodiments, the percentage of the conjugates or particles that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the conjugates that comprise an agent is less than about 50%, e.g., less than about 40%, less than about 35%, less than about 30%, less than about 25%, less than about 20%, less than about 15%, or less than about 10%. In some embodiments, the percentage of the conjugates (e.g., in a particle) that comprise an agent is between about 5% and about 50%, about 5% and about 40%, about 5% and about 30%, about 5% and about 25%, or about 5% and about 20%. In some embodiments, the percentage of the conjugates (e.g., in a particle) that comprise an agent is between about 5% and 90%. In some embodiments, the percentage of the conjugates (e.g., in a particle) that comprise an agent is between about 5% and about 75%. In the some embodiments, the the conjugates (e.g., in a particle) that comprise an agent is between about 5% and about 50%. In the some embodiments, the percentage of the conjugates (e.g., in a particle) that comprise an agent is between about 10% and about 25%.

In some embodiments, the total amount of the agent present in the conjugate or particle is greater than about 5% (e.g., about 6%, about 7%, about 8%, about 9%, about 10%, about 12%, about 15%, about 20%, about 25%, about 30%, or more) of the total size or weight of the conjugate or particle. In some embodiments, the total amount of the agent present in the conjugate or particle is greater than about 10% (e.g., about 12%, about 15%, about 20%, about 25%, about 30%, or more) of the total size or weight of the conjugate or particle.

Without being bound by theory, the conjugates or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a polymer, conjugate or particle described herein).

Without being bound by theory, due to the localized delivery of the BASP compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent. In one embodiment, the agent are incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). In some embodiments, since the particle described herein releases the agent at a target site based on pH microenvironment, other non-target sites (e.g., blood vessels) with different pH would be less likely to be exposed to the agent.

In another aspect, provided are kits including a first container comprising a polymer or pharmaceutical composition described herein. In certain embodiments, the kits are useful for delivering an agent (e.g., to a subject or cell). In certain embodiments, the kits are useful for treating a disease (e.g., proliferative disease, hematological disease, neurological disease, painful condition, psychiatric disorder, or metabolic disorder) in a subject in need thereof. In certain embodiments, the kits are useful for preventing a disease (e.g., proliferative disease, hematological disease, neurological disease, painful condition, psychiatric disorder, or metabolic disorder) in a subject in need thereof. In certain embodiments, the kits are useful for reducing the risk of developing a disease (e.g., proliferative disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein kinase in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for delivering an agent. In certain embodiments, the kits and instructions provide for treating a disease (e.g., proliferative disease, hematological disease, neurological disease, painful condition, psychiatric disorder, or metabolic disorder) in a subject in need thereof. In certain embodiments, the kits and instructions provide for preventing a disease (e.g., proliferative disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

Methods of Treatment and Uses

The present disclosure also provides methods of using the polymers described herein, or a pharmaceutical composition thereof, for delivering an agent. The present disclosure also provides methods of using the polymers described herein, or a pharmaceutical composition thereof, for the treatment, prevention, or diagnosis of a disease or condition.

In certain embodiments, the methods described herein include administering to a subject with an effective amount of the polymers described herein, or a pharmaceutical composition thereof. In certain embodiments, the methods described herein include implanting to a subject with an effective amount of the polymers described herein, or a pharmaceutical composition thereof. In certain embodiments, the methods described herein comprise treating a disease or condition in a subject in need thereof by administering to or implanting in the subject a therapeutically effective amount of: a polymer described herein; or a pharmaceutical composition thereof; wherein at least one instance of M or M' is a therapeutic agent. In certain embodiments, the methods described herein comprise preventing a disease or condition in a subject in need thereof by administering to or implanting in the subject a prophylactically effective amount of: a polymer described herein; or a pharmaceutical composition thereof; wherein at least one instance of M or M' is a prophylactic agent. In certain embodiments, the methods described herein comprise diagnosing a disease or condition in a subject in need thereof by administering to or implanting in the subject a diagnostically effective amount of: a polymer described herein; or a pharmaceutical composition thereof; wherein at least one instance of M or M' is a diagnostic agent.

In certain embodiments, the disease or condition is a proliferative disease, hematological disease, neurological disease, painful condition, psychiatric disorder, metabolic disorder, or a long-term medical condition. In certain embodiments, the disease is cancer (e.g. lung cancer, large bowel cancer, pancreas cancer, biliary tract cancer, or endometrial cancer), benign neoplasm, angiogenesis, inflammatory disease, autoinflammatory disease, or autoimmune disease. In certain embodiments, the long-term medical condition is hypertension.

In some embodiments, the polymers described herein, or a pharmaceutical composition thereof are useful in treating a cancer. In some embodiments, the polymers described herein, or a pharmaceutical composition thereof, are useful to delay the onset of, slow the progression of, or ameliorate the symptoms of cancer. In some embodiments, the polymers described herein, or a pharmaceutical composition thereof, are administered in combination with other compounds, drugs, or therapeutics to treat cancer.

In some embodiments, the polymers described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma, heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the polymers described herein, or a pharmaceutical composition thereof, are useful in treating lung cancer, head-and-neck cancer, esophagus cancer, stomach cancer, breast cancer, pancreas cancer, liver cancer, kidney cancer, prostate caner, glioblastomas, metastatic melanomas, peritoneal or pleural mesotheliomas.

In some embodiments, the proliferative disease is a benign neoplasm. All types of benign neoplasms disclosed herein or known in the art are contemplated as being within the scope of the disclosure. In some embodiments, the proliferative disease is associated with angiogenesis. All types of angiogenesis disclosed herein or known in the art are contemplated as being within the scope of the disclosure. In certain embodiments, the proliferative disease is an inflammatory disease. All types of inflammatory diseases disclosed herein or known in the art are contemplated as being within the scope of the disclosure. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the disclosure. In some embodiments, the proliferative disease is an autoimmune disease. All types of autoimmune diseases disclosed herein or known in the art are contemplated as being within the scope of the disclosure.

In some embodiments, the polymers herein, or a pharmaceutical composition thereof contain at least one instance of M or M' useful in treating cancer. In certain embodiments, M or M' is a therapeutic agent. In certain embodiments, the therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g., mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (RESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In some embodiments, the polymers described herein, or a pharmaceutical composition thereof contain at least one instance of M or M' useful in treating hypertension. In certain embodiments, M or M' is a therapeutic agent. In certain embodiments, the therapeutic agent is an anti-hypertension agent. Exemplary anti-hypertension agents include, but are not limited to, amiloride, amlodipine, atenolol, azilsartan, benazepril, bendroflumethiazide, betaxolol, bisoprolol, bucindolol, bumetanide, candesartan, captopril, carteolol, carvedilol, chlorothiazide, chlorthalidone, cilnidipine, clevidipine, diltiazem, doxazosin, enalapril, epitizide, eplerenone, eprosartan, ethacrynic acid, felodipine, Fimasartan, fosinopril, furosemide, hydrochlorothiazide, indapamide, indoramin, irbesartan, isradipine, labetalol, lercanidipine, levamlodipine, lisinopril, losartan, methyclothiazide, metolazone, metoprolol, moexipril, nadolol, nebivolol, nicardipine, nifedipine, nimodipine, nisoldipine, nitrendipine, olmesartan, oxprenolol, penbutolol, perindopril, pindolol, phenoxybenzamine, phentolamine, polythiazide, prazosin, propranolol, quinapril, ramipril, spironolactone, telmisartan, terazosin, timolol, tolazoline, torsemide, trandolapril, triamterene, valsartan, and verapamil.

In certain embodiments, the polymers described herein, or a pharmaceutical composition thereof, are administered in combination with one or more additional pharmaceutical agents described herein. In certain embodiments, the additional pharmaceutical agent is an anti-cancer agent. In certain embodiments, the additional pharmaceutical agent is an anti-hypertension agent.

In certain embodiments, the methods described herein include contacting a cell with an effective amount of the polymers described herein, or a pharmaceutical composition thereof. In certain embodiments, the cell is in vitro. In certain embodiments, the cell is in vivo.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Figure 1B:
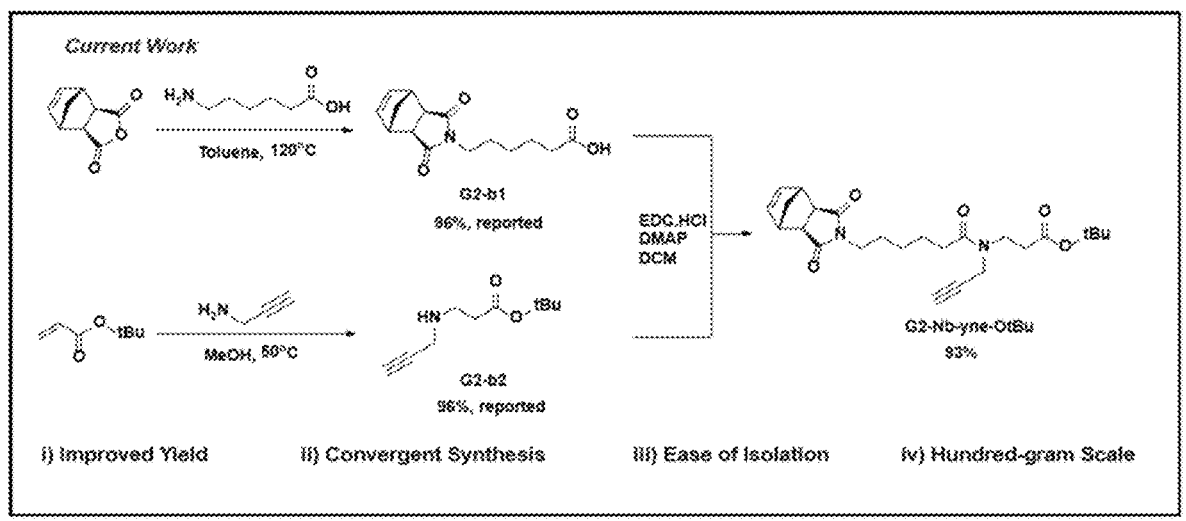
Figure 1C:
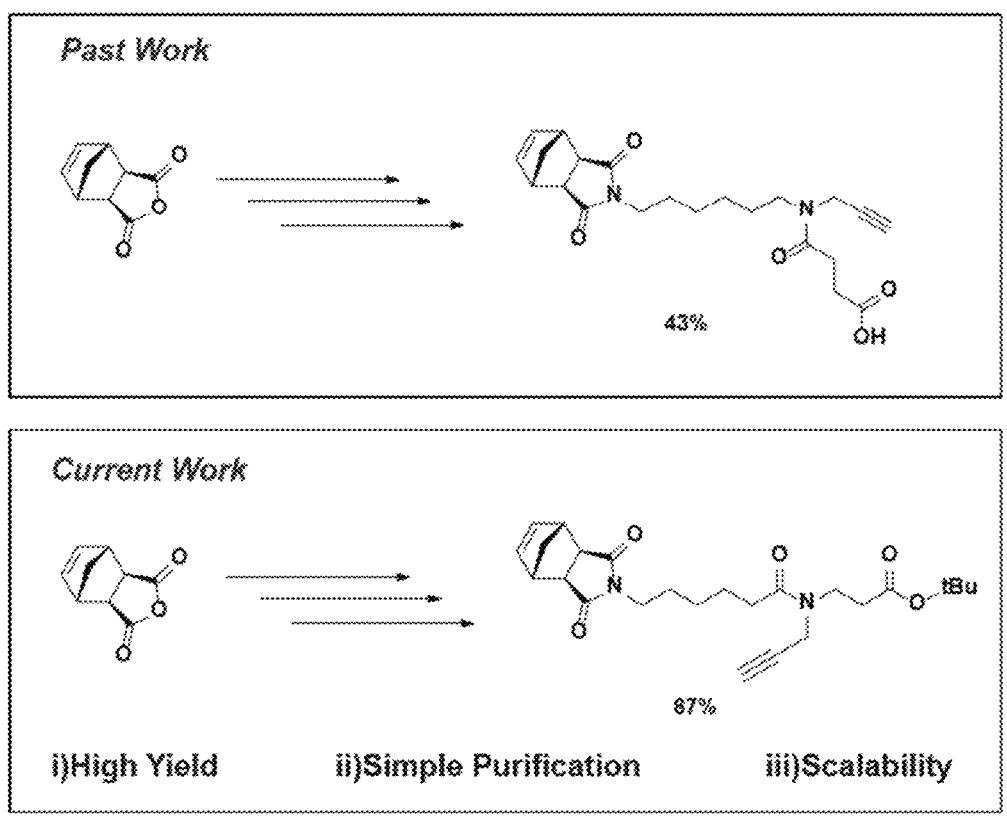
Figure 2:
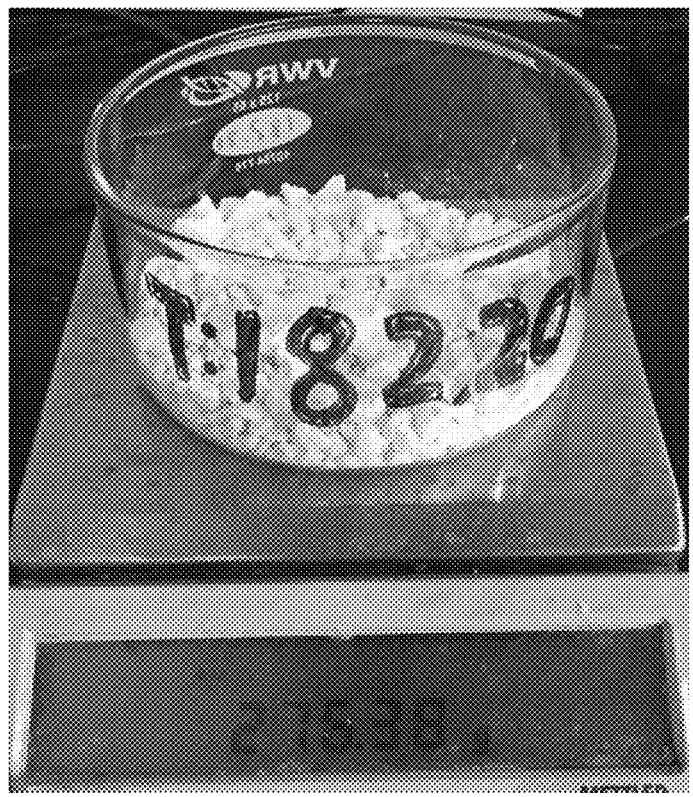
FIG. 2 shows an exemplary large-scale synthesis of G2-M resulting in hundreds of grams of product.

In some examples, the polymerizable norbornene-containing fragment was prepared according to reported procedures[30] with modifications from commercially available cis-5-norbornene-exo-2,3-dicarboxylic anhydride and 6-aminohexanoic acid under reflux conditions in toluene (FIG. 1B). Pure product G2-b2 was easily purified via liquid-liquid extraction. The alkyne and acid-containing fragment was also prepared following literature procedures[31] from commercially available propargyl amine and tert-butyl acrylate (FIG. 1B); conjugated addition readily proceeded at 50° C. in methanol. Rotary evaporation was sufficient to remove the solvent, affording the clean product G2-b1, with no significant amounts of by-product observed. The acid functional group was protected using common tert-butyl protection chemistry, avoiding undesired interference with the remaining steps or any subsequent incompatibilities that may arise during functionalization of the alkyne site.[32] The two fragments, G2-b1 and G2-b2, were then coupled using carbodiimide chemistry with N-(3-dimethylaminopropyl)-N'-ethylcarbodiimide hydrochloride (EDC.HCl) and 4-dimethylaminopyridine (DMAP), yielding the tert-butyl protected G2-M, or G2-Nb-yne-OtBu (FIG. 1B). The product was purified using column chromatography on small scale, yet required an extra liquid-liquid extraction beforehand on large scale, as insoluble by-product was present in sufficient quantities to prevent direct efficient column chromatography. Exemplary full synthetic procedures are described herein. G2-M was designated as an end-product where the protected acid served to avoid any potential subsequence chemical incompatibility while affording a solid, easily handled material (FIG. 2) compared to the previous viscous gel-like G1-M counterpart; the protecting group can be easily removed without any extensive isolation effort and moved forward to the next step (vide infra).[29] This 3-step convergent synthesis afforded G2-M in 87% overall yield, a significant improvement from 43% yield in the previous design.[29] Furthermore, product purification efforts were heavily reduced while giving much better scalability up to hundred-gram scale (FIGS. 1A-B, 2). This synthesis would allow easy-access, both in academic and industrial settings, to ROMP-compatible monomers which also contain two orthogonal functionalities for further incorporation of agents (e.g., small molecules, therapeutic agents, diagnostic agents, prophylactic agents) and polymers of interest onto this backbone.

Figure 3:
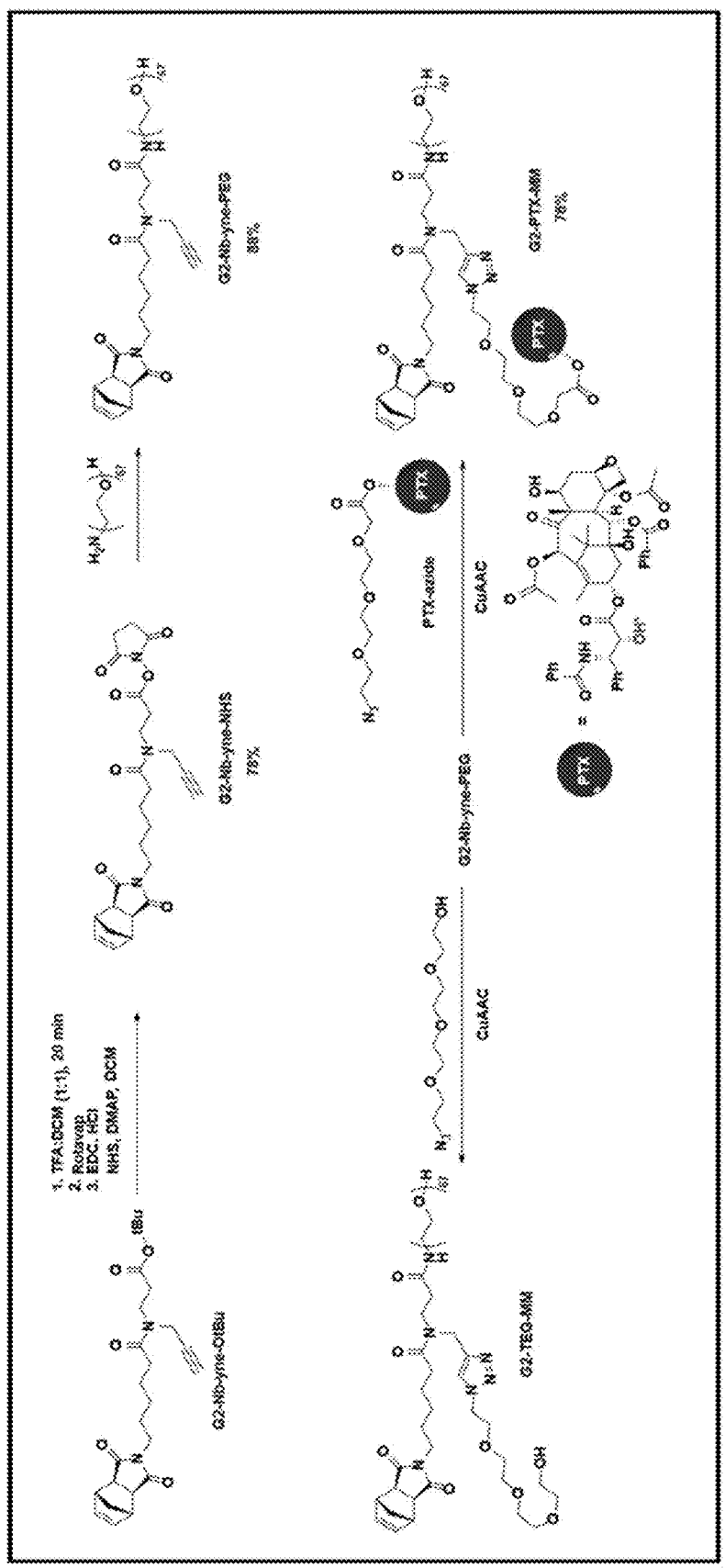
FIG. 3 shows the synthesis of G2-PTX-MM and G2-TEG-MM for BASP formation via brush-first ring opening metathesis polymerization (BF-ROMP).

It was next sought to determine if G2-M can be conveniently functionalized and subsequently converted into useful multifunctional brush star-armed polymer (BASP) NPs and/or well-ordered BBCPs in an analogous manner to the previous systems.[9,27,33] For BASP NPs, generation 2 macromonomers (G2-MMs) where the acid group is conjugated onto a polyethylene glycol (PEG) chain, and the alkyne is "clicked" (e.g., reacted through click chemistry) onto an agent, optionally through a cleavable linker, may be needed (FIG. 3).[8,11,16,29] To achieve this, de-protection of G2-M was performed, e.g., in trifluoroacetic acid/dichloromethane solution (TFA:DCM, 1:1 ratio), affording the acid intermediate G2-Nb-yne-COOH, which was isolated by rotary evaporation. EDC.HCl, DMAP, and N-hydroxysuccinimide (NHS) in DCM was then used to acquire the activated ester G2-Nb-yne-NHS. Amine-terminated PEG was next conjugated onto the activated ester, and the alkyne-containing MM G2-yne-PEG was obtained by precipitation. Using CuAAC chemistry with copper(I) acetate in DCM, paclitaxel-conjugated tetraethylene glycol azide PTX-$N_3$ was readily "clicked" onto the MM, yielding G2-PTX-MM after preparative GPC. Similarly, onto G2-yne-PEG, tetraethylene glycol azide TEG-$N_3$ without PTX can be "clicked" as the blank MM G2-TEG-MM. Exemplary synthetic details are described herein.

Figure 4A:
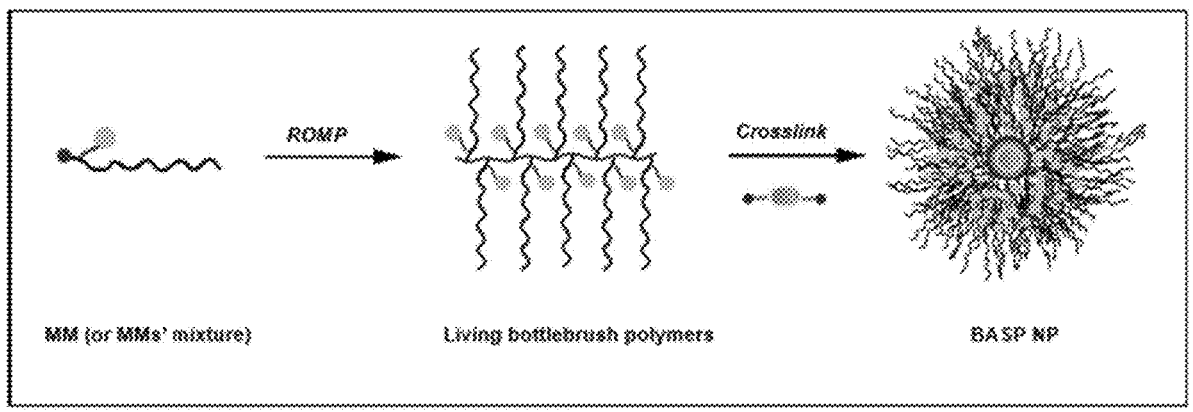
FIGS. 4A to 4C show.
Figure 4B:
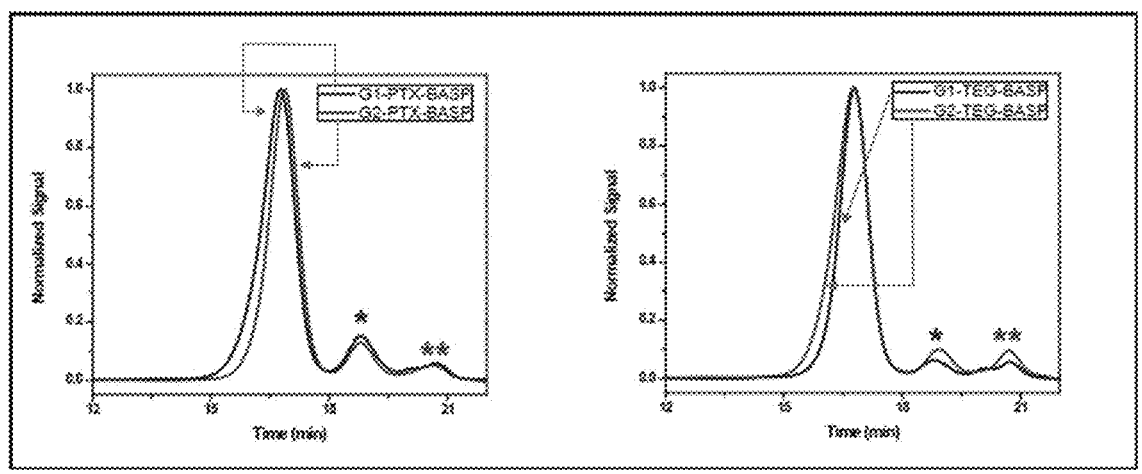
Figure 4C:
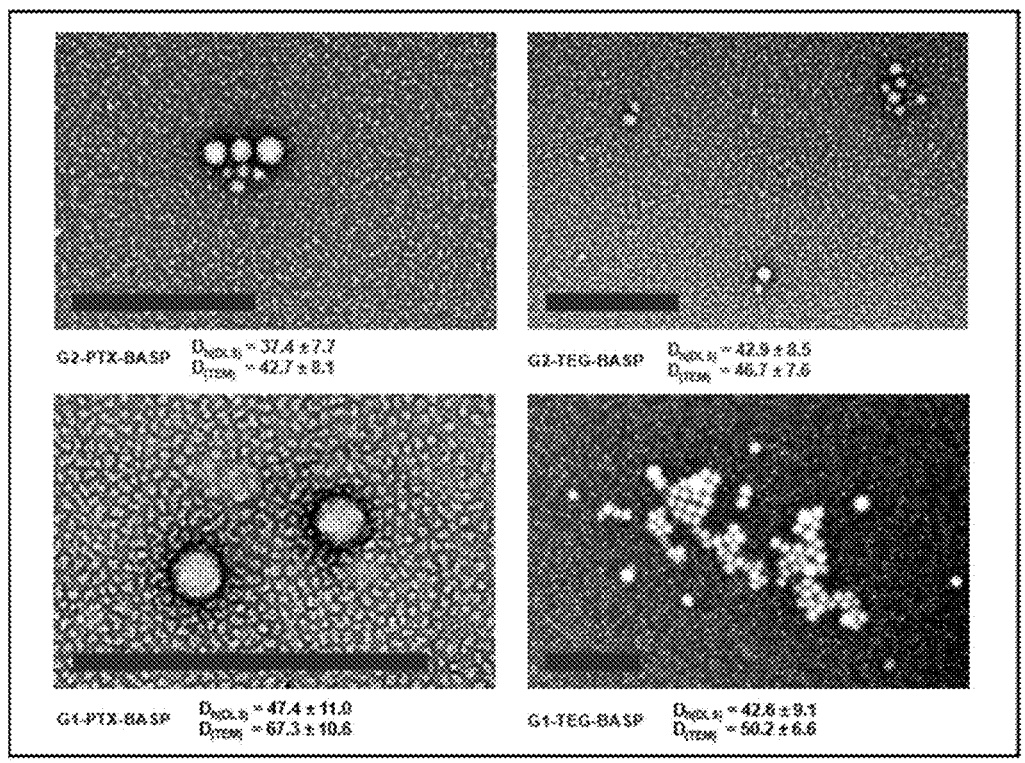
Figure 6:
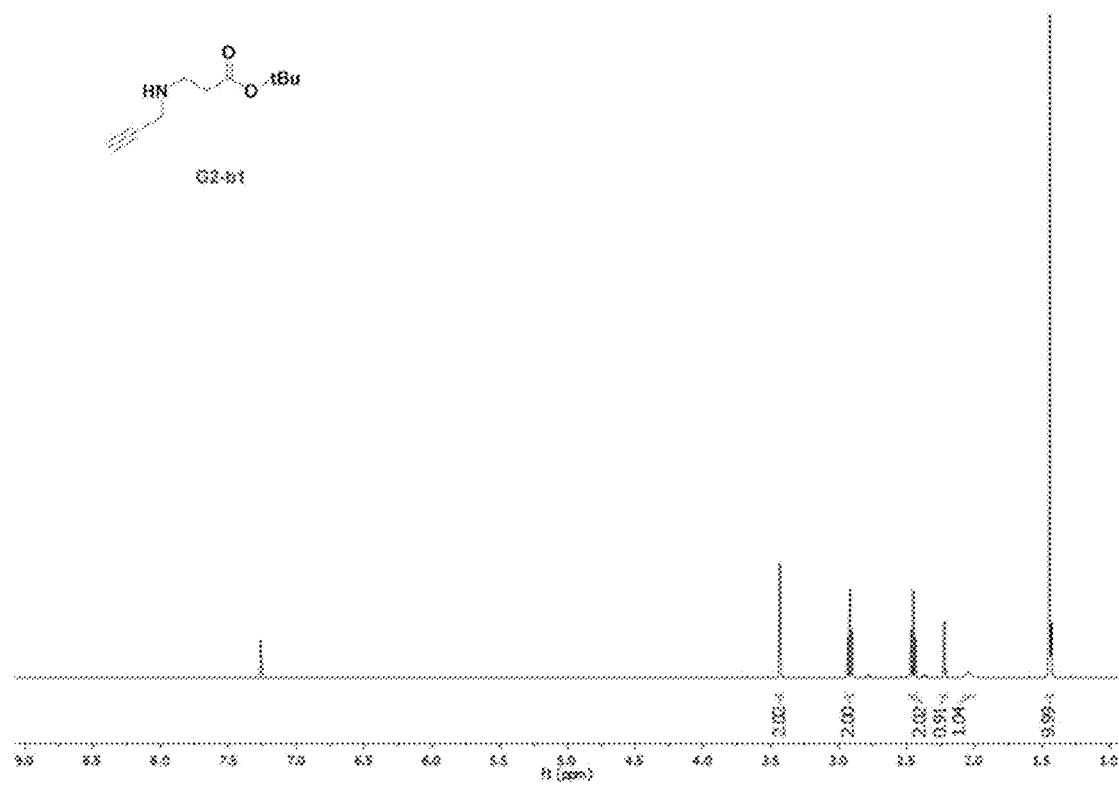
FIG. 6 shows the $^1$H NMR spectrum of G2-b1 in $CDCl_3$.

BF-ROMP was utilized for BASP formation (FIG. 4A). In some examples, MMs in THF were reacted with G3-Cat in a 7:1 ratio to form short living bottlebrush polymers with degree of polymerization (DP) of 7. After 30 minutes, the living polymers were added onto 20 equivalences (eq) of cross-linker (XL), forming the desired BASP. BF-ROMP was also done using the previous design of generation 1 MMs (G1-MMs) for comparison purposes. Reaction mixtures as analyzed by gel permeation chromatography (GPC) indicated similar and efficient formation of BASPs from both G2-MMs and G1-MMs (FIG. 4B). Furthermore, co-polymerization of the branched MMs with unbranched PEG-MM[11,27] at the brush forming stage, followed by cross-linking to afford BASPs also yielded GPC traces that were similar between BASPs starting with G2-MMs or G1-MMs (FIG. 6). This would potentially allow for formation of bottlebrushes containing multiple MMs for multi-component BASP or NP loading adjustments, as previously reported for G1 systems.[8,26,29] Furthermore, the generated BASP NPs were characterized by dynamic light scattering (DLS) and transmission electron microscope (TEM) (FIG. 4C). Hydrodynamic diameter ($D_h$) as determined by DLS suggested NPs in the 30-50 nm range, a highly desirable particle size for in vivo therapeutics/imaging applications (FIG. 4C).[34-37] TEM revealed an agreeable albeit slightly larger NP size in the 40-70 nm range, which, as previously reported, arose from potential PEG-aggregation during TEM sample preparation (FIG. 4C).[8,11,27] Altogether, these results strongly suggest compatible performance between MMs generated from G2-M to the previous design while gaining the advantage of extremely simple, rapid, and scalable synthesis.

Next the G2-M was functionalized with two polymers conjugated onto the orthogonal functional groups. This would subsequently afford A-branch-B BBCPs post-ROMP, which have previously been shown to self-assemble in an interesting manner for three different combinations of polymers.[9] Here, a PS-branch-PLA macromonomer (BMM) was synthesized based on literature procedures.[38] Starting from G2-M-NHS, the activated ester was displaced with 3-amino-propan-1-ol, and an azide-terminated PS was then reacted with the alkyne via CuAAC. The azide-terminated PS was synthesized according to previous procedures.[9] Polylactide was subsequently grown from the primary alcohol using tin (II) ethyl-2-hexanoate catalyzed polymerization of DL-lactide to furnish the branched PS-branch-PLA macromonomer (G2-Nb-PS-branch-PLA).

Figure 5A:
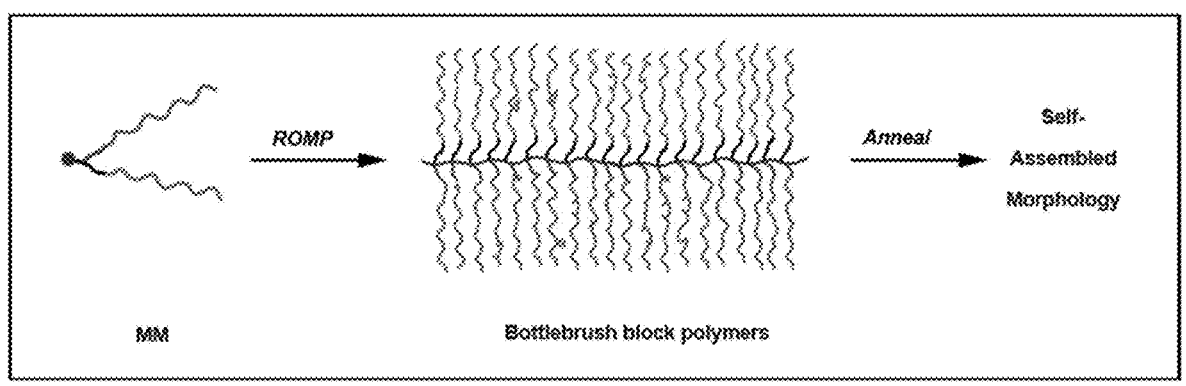
FIGS. 5A to 5C show (FIG. 5A) Schematic of the synthesis and self-assembly of BBCP.
Figure 5C:
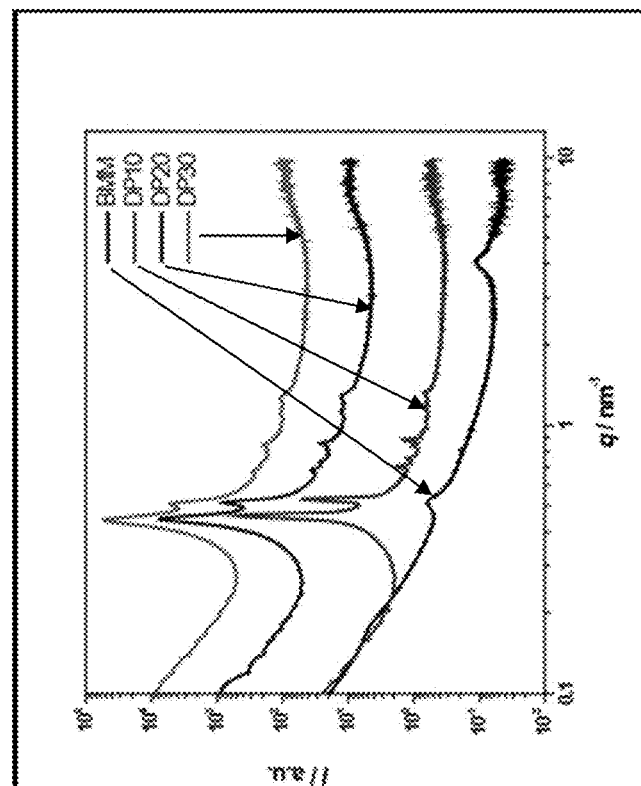
Figure 5B:
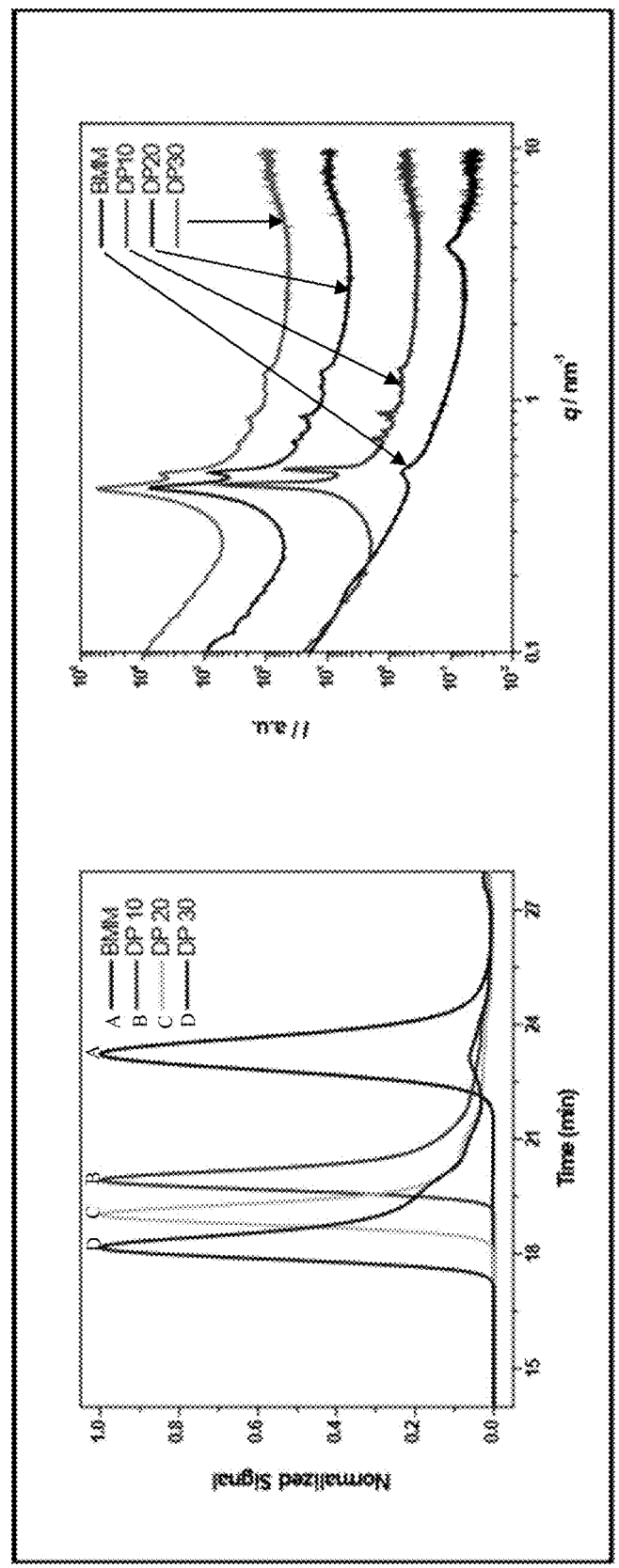

Graft-through ROMP was then employed to prepare BBCP from the G2-Nb-PS-branch-PLA BMM in an analogous manner to the aforementioned polymerization, with the absence of the cross-linking step (FIG. 5A). GPC of reaction mixtures revealed highly efficient conversion from BMM to BBCP across all DPs under examination (10, 20, and 30) (FIG. 5B). Small-angle X-ray scattering (SAXS) was performed at the Advanced Photon Source to study the self-assemble behavior of thermally annealed (145° C. in a vacuum oven for 6 h) G2-Nb-PS-branch-PLA BMM and its corresponding BBCPs. While for the SAXS profile for BMM showed a disordered morphology, as BBCPs became longer, the gyroid morphology were clearly observed for DP=10, 20, and 30 (FIG. 5C). This is consistent with the previous observations of the norbornene polymer backbone providing a pre-organized interface between the two immiscible polymer chains. Furthermore, this demonstrates the compatibility between the 2 generations of monomers.

In summary, a synthesis of a norbornene-based ROMP-compatible monomer system containing 2 or more (e.g., 3, 4, or 5) orthogonal functional groups for convenient conjugation of polymers and/or small molecules is reported herein. The synthesis may be rapid, simple, and/or hundred-gram scale. The resulting MMs can undergo graft-through ROMP and successfully formed BASP NPs and self-assembled BBCPs, both of which are exciting platforms for a diverse array of applications ranging from biomedical and drug delivery to polymer morphology. This synthetically straightforward tri-functional system can now readily be accessed from both an academic and industrial standpoint, allowing for further exploration of its immense potentials. Simple, Rapid and Scalable Synthesis of Branched Norbornene for ROMP Materials, General Methods, and Instrumentation All reagents were purchased from commercial suppliers and used without further purification unless stated otherwise. Grubbs 3$^{rd}$ generation bispyridyl catalyst G3-Cat,[39] 1$^{st}$ generation macromonomer (G1-MM) precursors G1-Nb-yne-PEG,[40] PEG-MM,[41] crosslinker XL,[41] TEG-azide,[42] acid-TEG-azide[42], and chex-azide[28] were prepared according to literature procedures. Liquid chromatography mass spectrometry (LC/MS) and preparative HPLC were performed on an Agilent 1260 LC system equipped with a Zorbax SB-C18 rapid resolution HT column (LC/MS) and a Zorbax SB-C18 semi-preparative column (prep-HPLC) using a binary solvent system (MeCN and $H_2O$ with 0.1% $CH_3COOH$). Recycling preparative HPLC was performed on a LaboACE system (Japan Analytical Industry) using a JAIGEL-2.5HR column. Size exclusion chromatography (SEC) analyses were performed on an Agilent 1260 Infinity setup with two Shodex KD-806M columns in tandem and a 0.025M LiBr DMF mobile phase run at 60° C. The differential refractive index (dRI) of each compound was monitored using a Wyatt Optilab T-rEX detector. For polystyrene-containing samples, Gel Permeation Chromatography (GPC) was performed with a concentration of 0.1-1.0 mg/mL on an Agilent 1260 Infinity system in THF, calibrated with monodisperse linear polystyrene standards and equipped with a UV diode array detector and a differential refractive index (dRI) detector. The GPC was run at a flow rate of 1 mL/minute at 35° C. and three columns were assembled in series: Agilent Technologies PLgel 5 μm 10E5A, 10E4A, and 10E3A, all of which are 300×7.5 mm in dimension. Column chromatography was carried out on silica gel 60F (EMD Millipore, 0.040-0.063 mm). Nuclear magnetic resonance (NMR) spectra were recorded on Bruker AVANCE III-400 spectrometer, with working frequencies of 400 ($^1$H), and 100 ($^{13}$C) MHz, AVANCE-600 spectrometer with working frequencies of 600 ($^1$H), and 151 ($^{13}$C) MHz, or Varian Inova 500 spectrometer with 500 ($^1$H), and 125 ($^{13}$C) MHz. Chemical shifts are reported in ppm relative to the signals corresponding to the residual non-deuterated solvents: $CDCl_3$: $\delta_H$=7.26 ppm and $\delta_C$=77.16 ppm. High-resolution mass spectra (HRMS) were measured on a Bruker Daltonics APEXIV 4.7 Tesla Fourier Transform Ion Cyclotron Resonance Mass Spectrometer (FT-ICR-MS) using an electrospray ionization (ESI) source. Matrix-assisted laser desorption/ionization time-of-flight (MALDI-TOF) analyses were collected on a Bruker OmniFlex instrument using sinapinic acid as the matrix. Dynamic light scattering (DLS) measurements were performed using a Wyatt Technology Mobius DLS instrument. Samples were prepared at 1.0 mg/mL in either nanopure water (MilliQ), PBS buffer, or 5% glucose solution (also in nanopure water); disposable polystyrene cuvettes pre-cleaned with compressed air were used; the resulting solutions were passed through a 0.4 μm Nalgene filter (PES membrane) into disposable polystyrene cuvettes, which were pre-cleaned with compressed air. Measurements were made in sets of 10 acquisitions, and the average hydrodynamic diameters were calculated using the DLS correlation function via a regularization fitting method (Dynamics 7.4.0.72 software package from Wyatt Technology). TEM images were acquired using a FEI Tecnai Multipurpose TEM (G2 Spirit TWIN, 12 kV)

at the MIT Center for Materials Science and Engineering. Sample preparation consisted of the following: 5 μL of a 1.0 mg/mL aqueous solution of BASP nanoparticles was pipetted onto a carbon film-coated 200-mesh copper grid (Electron Microscopy Sciences) placed on a piece of parafilm. Next, the solution was carefully absorbed at the base of the droplet using the edge of a Kimwipe, leaving behind the nanoparticles on the TEM grid. The samples were then stained negatively by adding a drop of 2 wt % uranyl acetate (Electronic Microscopy Sciences). After 3 min, the residual uranyl acetate solution was carefully absorbed onto a Kimwipe, and the samples were allowed to dry completely before analysis. For SAXS measurements, dried samples from ROMP reactions were wet with 15-50 μL of THF to form thick, barely dissolved solutions. A small amount of the material was removed with a spatula or pipet tip and used to fill the hole of a circular washer that acted as a sample holder (outer diameter: 24 mm, inner diameter: 2 mm, thickness: 1 mm). Samples were then placed in a vacuum oven, evacuated, and heated to 145° C. for 6 h. The vacuum oven was allowed to cool overnight and then vented to the atmosphere. Transmission SAXS was conducted at the Advanced Photon Source at Argonne National Lab. The sample to detector distance used was 1.9081 m and the wavelength of the beam was 0.886 Å. Electron Paramagnetic Resonance (EPR) spectra were acquired at the University of Nebraska using a Bruker CW X-band spectrometer equipped with a frequency counter. The spectra were obtained using a dual mode cavity; all spectra were recorded using an oscillating magnetic field perpendicular ($TE_{102}$) to the swept magnetic field. DPPH powder (g=2.0037) was used as a g-value reference. Spectra computations were obtained with the main computation parameters (program by Budil et al.[47]) listed in the following table, that is, the correlation time for the rotational motion of the nitroxide, τ, in ns, which measures the microviscosity around the nitroxide, and the Heisenberg exchange frequency, Wex, in $10^7$ $s^{-1}$, which increases with the increase of the local concentration of colliding nitroxide labels. The other parameters could be assumed constant since the fitting did not improve by changing them. In detail, the gii values for the coupling between the electron spin and the magnetic field were 2.009, 2.006 and 2.0037; the Aii values for the coupling between the electron spin and the nitrogen nuclear spin were 6 G, 6 G and 32 G; and the intrinsic line width, W1, was 3 G.

Synthetic Protocols

1) Generation 2 Branched Norbornene Precursors

Example 1: Synthesis of G2-b1

Scheme 1: Synthesis of G2-b1.

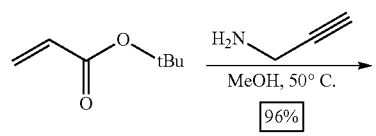

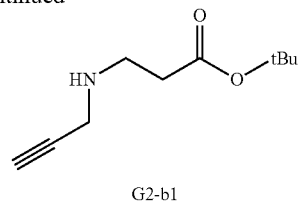

G2-b1

G2-b1 was prepared following a literature procedure with slight modifications.[43] To a round-bottom flask (RBF), propargylamine (7.2 mL, 6.2 g, 0.11 mol, 2.2 eq) and tert-butyl acrylate (7.6 mL, 6.7 g, 0.052 mol, 1.0 eq) were added. Methanol (120 mL) was added, and the reaction mixture was stirred under nitrogen for 24 hours at 50° C. The solution was then concentrated under vacuum, affording G2-b1 as an orange liquid (9.1 g, 96% yield).

Large Scale Synthesis of G2-b1.

Figure 7:
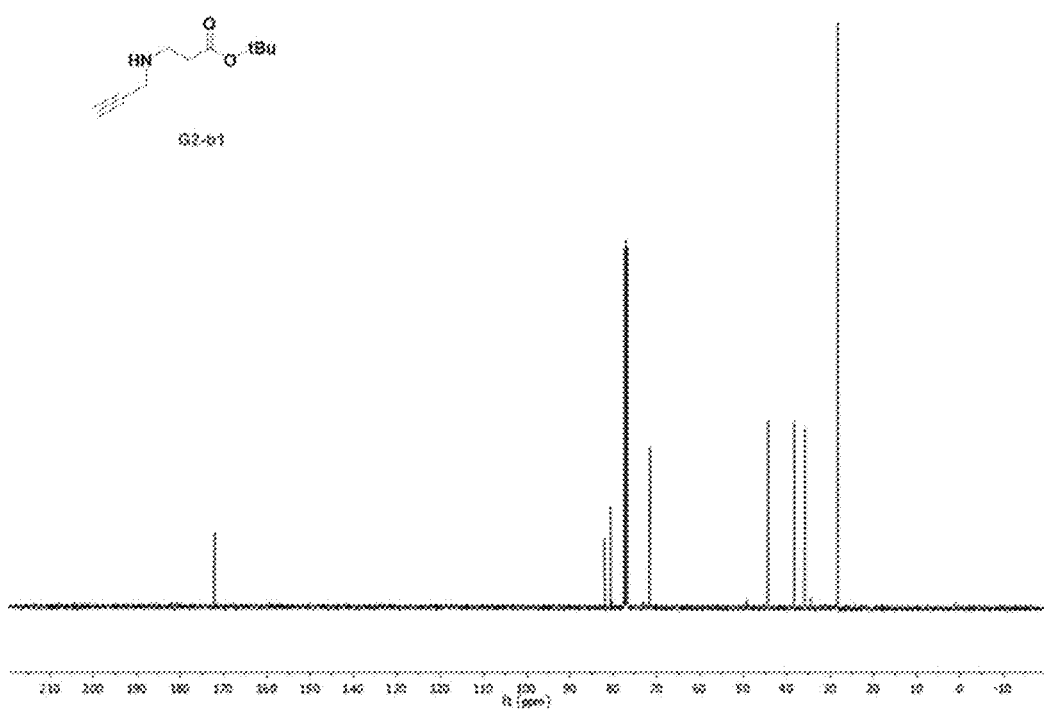
FIG. 7 shows the $^{13}$C NMR spectrum of G2-b1 in $CDCl_3$.

To a RBF, propargylamine (43.2 mL, 37.1 g, 0.674 mol, 2.16 eq) and tert-butyl acrylate (45.7 mL, 40.0 g, 0.312 mol, 1.00 eq) were added. Methanol (720 mL) was added, and the reaction mixture was stirred under nitrogen for 24 hours at 50° C. The solution was then concentrated under vacuum, affording G2-b1 as an orange liquid (56.1 g, 98% yield). HRMS-ESI: Calculated for $C_{10}H_{17}NO_2$: m/z=184.1338 $[M+H]^+$; Found: 184.1346 $[M+H]^+$. $^1$H NMR (400 MHz, CDCl$_3$, ppm) $\delta_H$ 3.43 (d, J=2.4 Hz, 2H), 2.92 (t, J=6.4 Hz, 2H), 2.45 (t, J=6.4 Hz, 2H), 2.22 (t, J=2.4 Hz, 1H), 2.04 (b, 1H), 1.44 (s, 9H).$^{13}$C NMR (100 MHz, CDCl$_3$, ppm): $\delta_C$ 172.1, 82.1, 80.8, 71.5, 44.3, 38.3, 35.8, 28.3. The $^1$H and $^{13}$C NMR spectra data for G2-b1 are shown in FIGS. 6 and 7, respectively.

Example 2: Synthesis of G2-b2

Scheme 2: Synthesis of G2-b2.

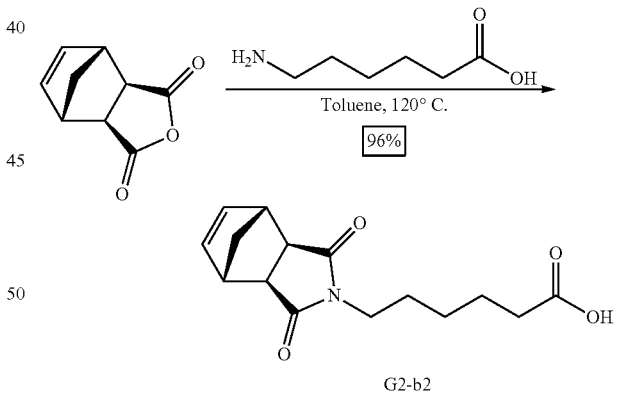

G2-b2

G2-b2 was prepared following a literature procedure with slight modifications.[44] cis-5-norbornene-exo-2,3-dicarboxylic anhydride (0.50 g, 3.0 mmol, 1.0 eq) and 6-aminohexanoic acid (0.48 g, 3.7 mmol, 1.2 eq) were added to a RBF fitted with a condenser. Toluene (15 mL) was then added, and the solution was stirred overnight at 120° C. The mixture was then allowed to cool to room temperature, and concentrated under vacuum. DCM was then added, and the solution was washed with 1M HCl, water, and brine. The organic layer was collected, dried over Na$_2$SO$_4$, and concentrated under vacuum, affording the product as a white solid (0.83 g, 96% yield).

Large Scale Synthesis of G2-b2.

Figure 8:
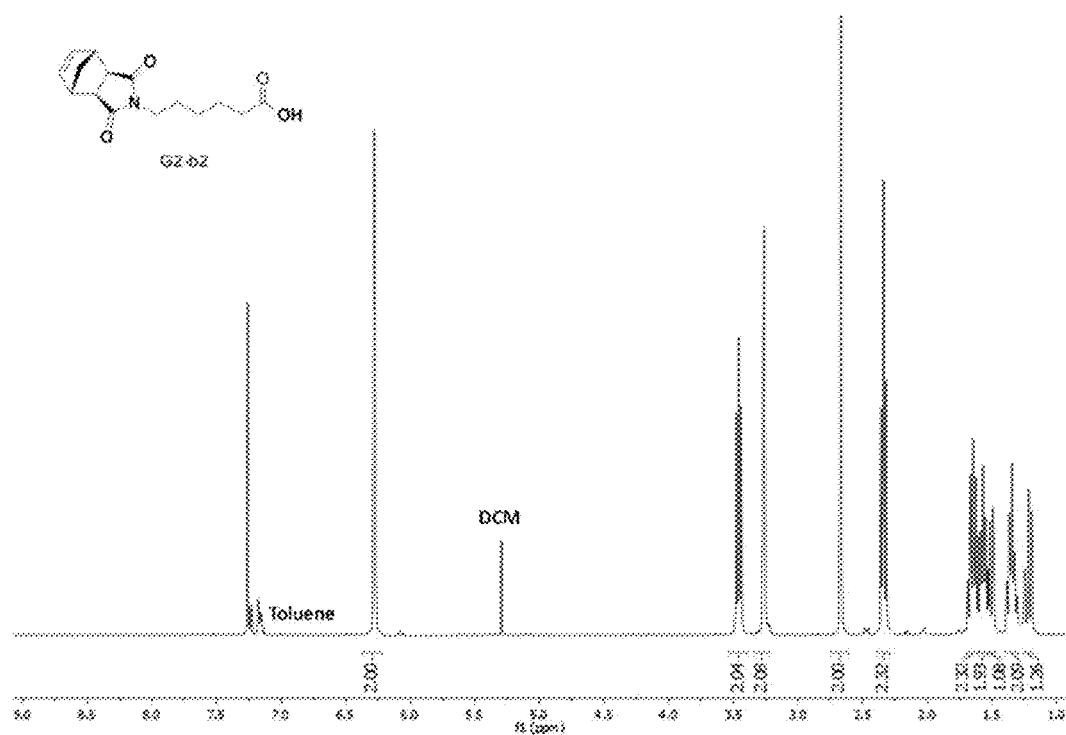
FIG. 8 shows the $^1$H NMR spectrum of G2-b2 in $CDCl_3$.
Figure 9:
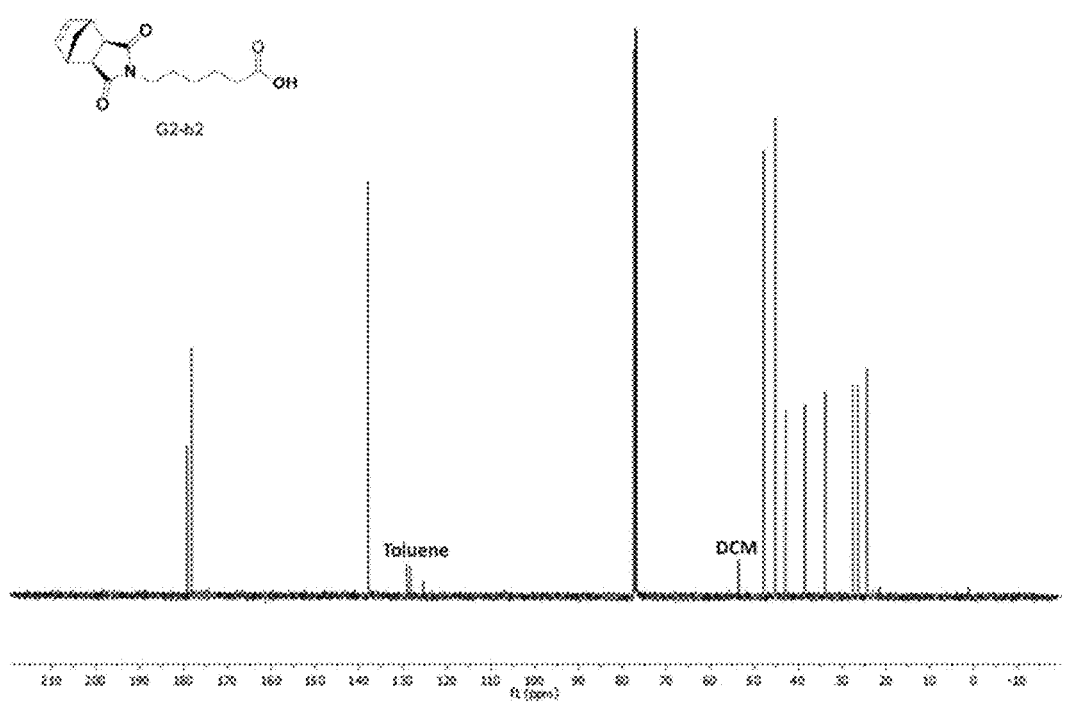
FIG. 9 shows the $^{13}$C NMR spectrum of G2-b2 in $CDCl_3$.

Cis-5-norbornene-exo-2,3-dicarboxylic anhydride (75.0 g, 0.456 mol, 1.00 eq) and 6-aminohexanoic acid (71.9 g, 0.548 mol, 1.20 eq) were added to a RBF fitted with a condenser. Toluene (2.25 L) was then added, and the solution was stirred overnight at 120° C. The mixture was then allowed to cool to room temperature, and concentrated under vacuum. DCM was then added, and the solution was washed with 1M HCl, water, and brine. The organic layer was collected, dried over $Na_2SO_4$, and concentrated under vacuum, affording the product as a white solid (121.5 g, 96% yield). HRMS-ESI: Calculated for $C_{15}H_{19}NO^-_4$: m/z=276.1241 [M−H]⁻; Found: 276.1234 [M−H]⁻. ¹H NMR (400 MHz, $CDCl_3$, ppm) $\delta_H$ 6.28 (t, J=1.8 Hz, 2H), 3.46 (t, J=7.4 Hz, 2H), 3.27 (t, J=1.6 Hz, 2H), 2.67 (d, J=1.2 Hz, 2H), 2.34 (t, J=7.6 Hz, 2H), 1.69-1.61 (m, 2H), 1.59-1.53 (m, 2H), 1.52-1.49 (dt, J=9.6, 1.6, 1H), 1.38-1.31 (m, 2H), 1.25-1.19 (m, 1H). ¹³C NMR (100 MHz, $CDCl_3$, ppm): $\delta_C$ 179.2, 178.2, 137.9, 47.9, 45.3, 42.8, 38.5, 33.8, 27.5, 26.5, 24.3. The ¹H and ¹³C NMR spectra data for G2-b2 are shown in FIGS. 8 and 9, respectively.

Example 3: Synthesis of G2-Nb-Yne-OtBu

Scheme 3: Synthesis of G2-Nb-yne-OtBu.

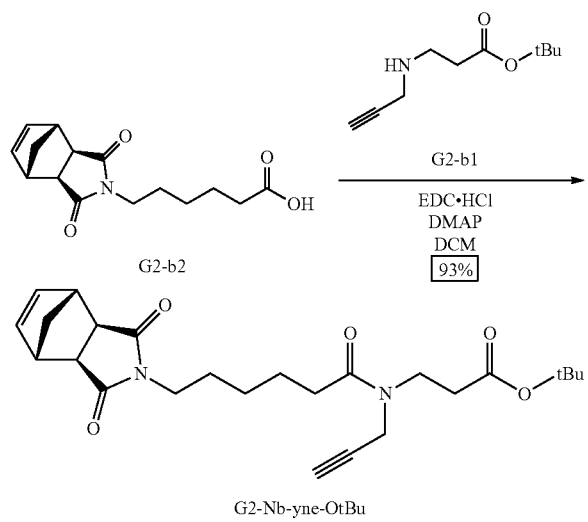

Into a RBF, G2-b1 (400 mg, 2.18 mmol, 1.0 eq), G2-b2 (908 mg, 3.27 mmol, 1.5 eq), N-(3-dimethylaminopropyl)-N'-ethylcarbodiimide hydrochloride (EDC.HCl) (628 mg, 3.27 mmol, 1.5 eq), 4-dimethylaminopyridine (DMAP) (133 mg, 1.09 mmol, 0.5 eq), and DCM (90 mL) were added. The reaction mixture were stirred overnight and then concentrated under vacuum. Column chromatography (MeOH/DCM) of the crude mixture yielded product as a white solid (899 mg, 93% yield).

Large Scale Synthesis of G2-b2.

Figure 10:
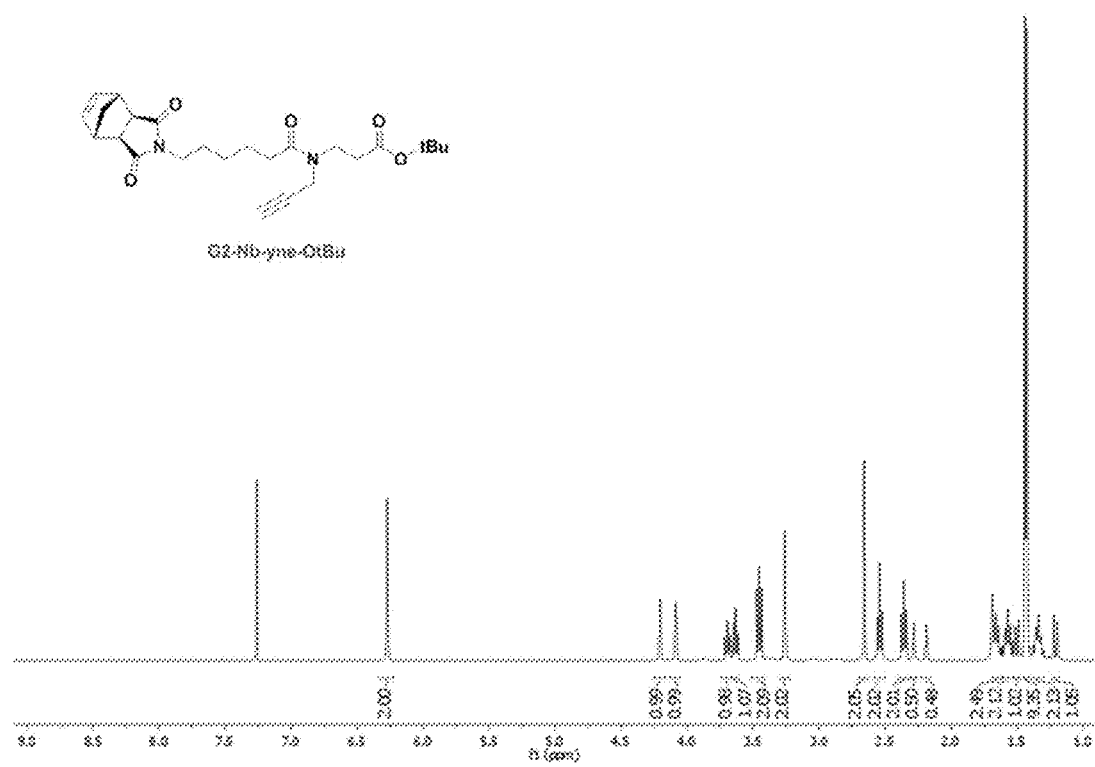
FIG. 10 shows the $^1$H NMR spectrum of G2-Nb-yne-OtBu in $CDCl_3$.
Figure 11:
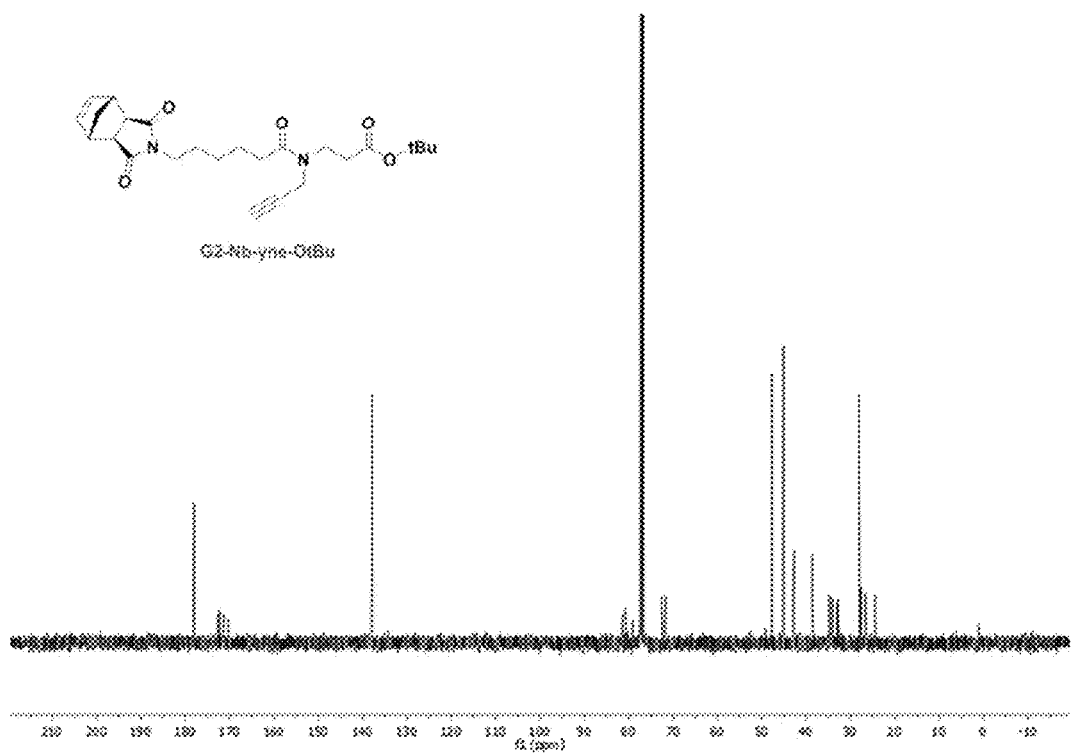
FIG. 11 shows the $^{13}$C NMR spectrum of G2-Nb-yne-OtBu in $CDCl_3$.

Into a RBF, G2-b1 (45.0 g, 0.246 mol, 1.0 eq), G2-b2 (102 g, 0.368 mol, 1.5 eq), EDC.HCl (70.6 g, 0.368 mol, 1.5 eq), DMAP (15.0 mg, 0.123 mol, 0.5 eq), and DCM (4.50 L) were added. The reaction mixture were stirred overnight and then concentrated under vacuum. DCM was then added, and the crude mixture was washed with water and brine. The organic layer was collected, dried over $Na_2SO_4$, and concentrated under vacuum. Column chromatography (EtOAc/hexane) of the crude mixture yielded product as an off-white solid (94.2 g, 87% yield). HRMS-ESI: Calculated for $C_{25}H_{34}N_2O_5$: m/z=443.2540 [M+H]⁺; Found: 443.2556 [M+H]⁺. ¹H NMR (400 MHz, $CDCl_3$, ppm) $\delta_H$ 6.27 (t, J=2.0 Hz, 2H), 4.21 (d, J=2.8 Hz, 1H), 4.09 (d, J=2.4 Hz, 1H), 3.69 (t, J=7.2 Hz, 1H), 3.63 (t, J=6.8 Hz, 1H), 3.45 (t, J=7.6 Hz, 2H), 3.26 (t, J=1.8 Hz, 2H), 2.66 (d, J=1.2 Hz, 2H), 2.54 (td, J=7.1, 1.3 Hz, 2H), 2.36 (t, J=7.4 Hz, 2H), 2.28 (t, J=2.4 Hz, 0.5H), 2.19 (t, J=2.6 Hz, 0.5H), 1.69-1.62 (m, 2H), 1.59-1.53 (m, 2H), 1.51-1.49 (dt, J=10.0, 1.6 Hz, 1H), 1.43 (d, J=6.0 Hz, 9H), 1.38-1.30 (m, 2H), 1.22-1.20 (m, 1H). ¹³C NMR (100 MHz, $CDCl_3$, ppm): $\delta_C$ 178.1, 172.6, 172.3, 171.4, 170.3, 137.8, 81.4, 80.7, 79.1, 78.9, 72.6, 71.8, 47.8, 45.2, 43.0, 42.8, 42.7, 38.5, 34.7, 34.1, 34.0, 33.0, 32.8, 28.1, 28.0, 27.6, 26.7, 24.6, 24.4. The ¹H and ¹³C NMR spectra data for G2-Nb-yne-OtBu are shown in FIGS. 10 and 11, respectively.

Example 4: Synthesis of G2-Nb-Yne-NHS

Scheme 4: Synthesis of G2-Nb-yne-NHS.

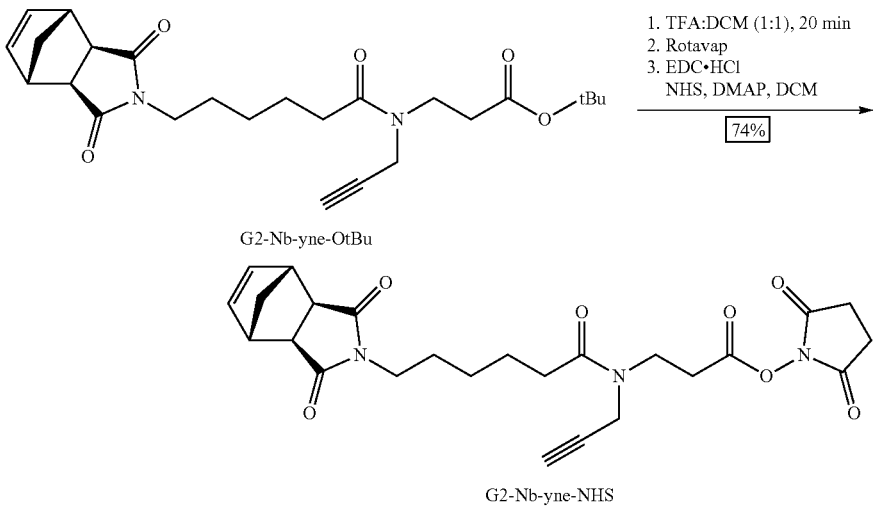

Deprotection of OtBu.

Figure 12:
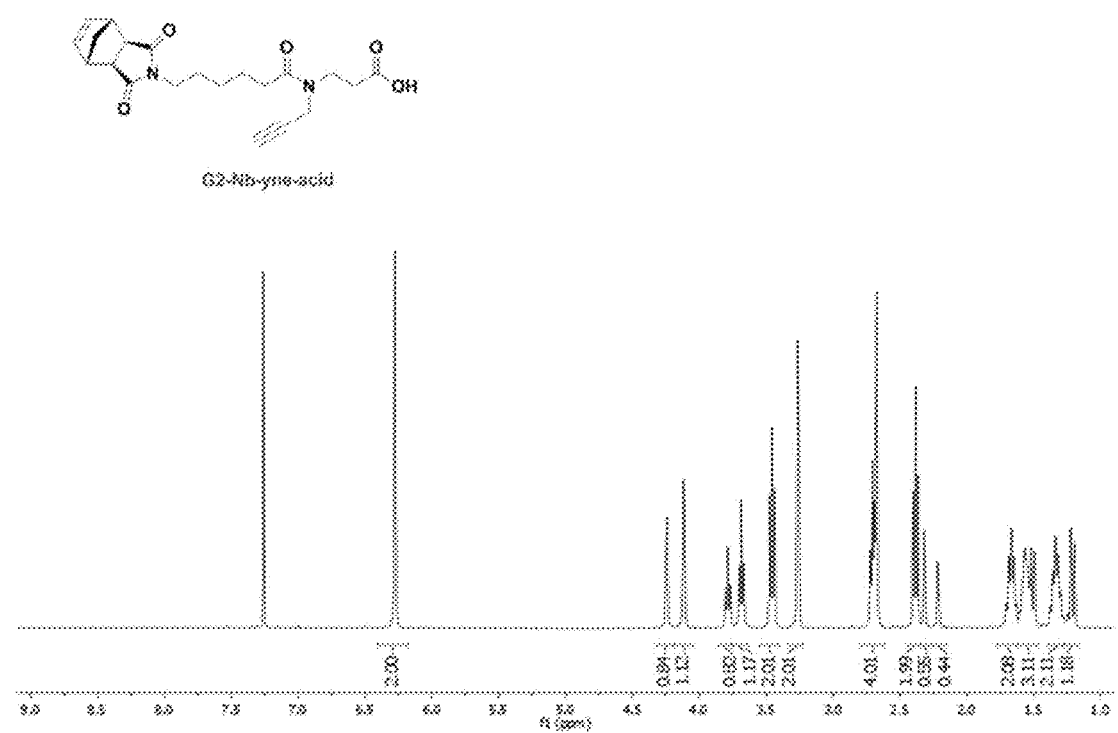
FIG. 12 shows the $^1$H NMR spectrum of G2-Nb-yne-acid in $CDCl_3$.
Figure 13:
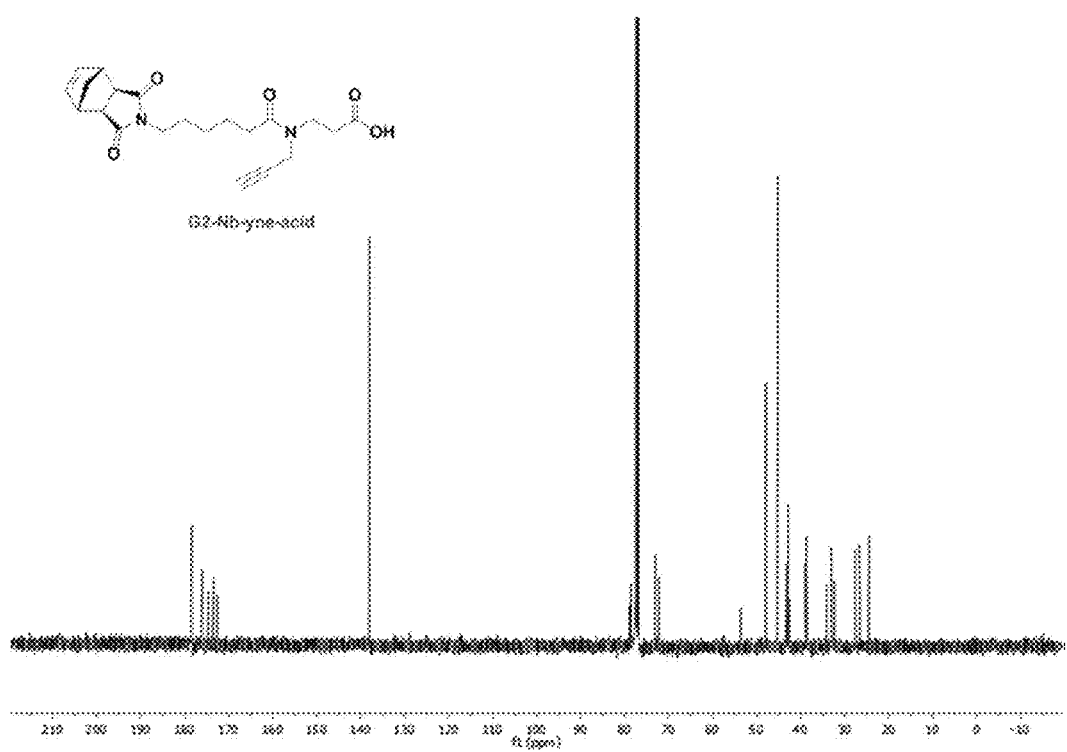
FIG. 13 shows the $^{13}$C NMR spectrum of G2-Nb-yne-acid in $CDCl_3$.

G2-Nb-yne-OtBu (200 mg) was added into a RBF. A solution of TFA and DCM (1:1) was then added (13 mL). The mixture was stirred for 20 minutes, resulting in the complete deprotection of G2-Nb-yne-OtBu. The solution was then concentrated under vacuum, yielding G2-Nb-yne-COOH, which can then be directly used for the synthesis of G2-Nb-yne-NHS. For characterization purposes, the concentrated G2-Nb-yne-COOH was re-dissolved in DCM, washed with 1M HCl, water, and brine. The organic layer was collected, dried over $Na_2SO_4$, and concentrated under vacuum, affording G2-Nb-yne-COOH as a white solid (166 mg, 94% yield). HRMS-ESI: Calcd for $C_{21}H_{26}N_2O_5$: m/z=387.1914 $[M+H]^+$; Found: 387.1926 $[M+H]^+$. $^1$H NMR (400 MHz, $CDCl_3$, ppm) $\delta_H$ 6.28 (t, J=2.0 Hz, 2H), 4.25 (d, J=2.4 Hz, 0.8H), 4.12 (d, J=2.4 Hz, 1.2H), 3.79 (t, J=7.0 Hz, 0.8H), 3.69 (t, J=6.6 Hz, 1.2H), 3.46 (t, J=7.4 Hz, 2H), 3.26 (t, J=1.8 Hz, 2H), 2.72-2.67 (overlap, 4H), 2.38 (t, J=7.4 Hz, 2H), 2.32 (t, J=2.4 Hz, 0.6H), 2.22 (t, J=2.6 Hz, 0.4H), 1.70-1.63 (m, 2H), 1.60-1.54 (m, 2H), 1.52-1.49 (d, J=10.0 Hz, 1H), 1.38-1.28 (m, 2H), 1.22-1.20 (d, J=9.2 Hz, 1H). $^{13}$C NMR (100 MHz, $CDCl_3$, ppm): $\delta_C$ 178.6, 178.3, 176.0, 174.6, 173.5, 172.7, 138.0, 79.0, 78.7, 73.1, 72.3, 48.0, 47.9, 45.3, 43.2, 42.9, 42.7, 38.9, 38.7, 34.1, 33.2, 33.0, 32.9, 32.4, 27.7, 27.5, 26.7, 26.6, 24.5, 24.4. The $^1$H and $^{13}$C NMR spectra data for G2-Nb-yne-COOH are shown in FIGS. 12 and 13, respectively.

Synthesis of G2-Nb-yne-NHS.

Figure 14:
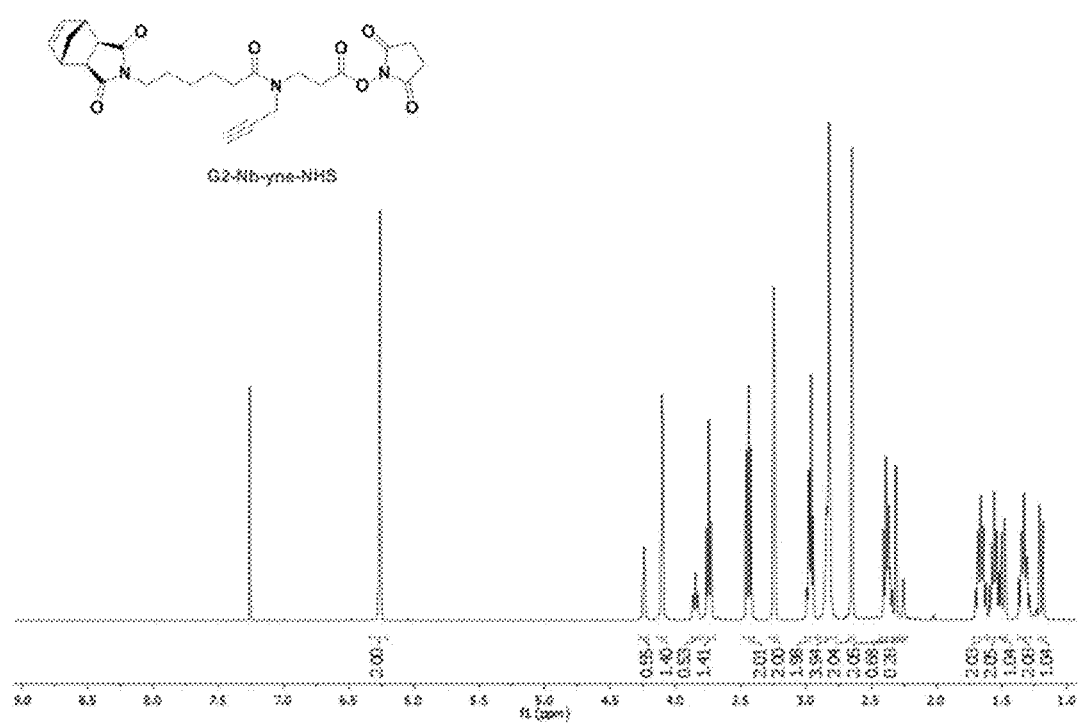
FIG. 14 shows the $^1$H NMR spectrum of G2-Nb-yne-NHS in $CDCl_3$.
Figure 15:
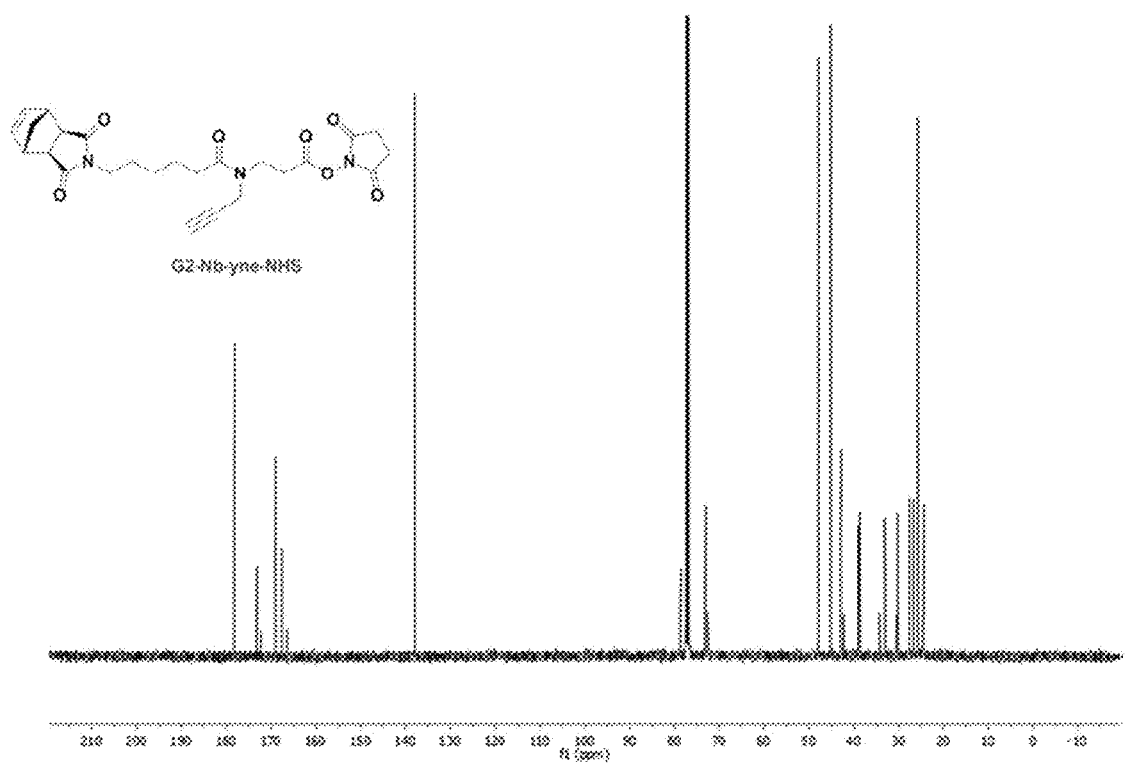
FIG. 15 shows the $^{13}$C NMR spectrum of G2-Nb-yne-NHS in $CDCl_3$.

Into a RBF, G2-Nb-yne-COOH (175 mg, 0.452 mmol, 1.0 eq), N-hydroxysuccinimide (NHS) (78.0 mg, 0.678 mmol, 1.5 eq), EDC.HCl (130 mg, 0.678 mmol, 1.5 eq), DMAP (27.6 mg, 0.226 mmol, 0.5 eq), and DCM (5 mL) were added. The reaction mixture were stirred overnight and then concentrated under vacuum. Column chromatography (EtOAc/hexane) of the crude mixture yielded product as a white solid (171 mg, 78% yield). HRMS-ESI: Calcd for $C_{25}H_{29}N_3O_7$: m/z=483.2078 $[M+H]^+$; Found: 484.2056 $[M+H]^+$. $^1$H NMR (400 MHz, $CDCl_3$, ppm) $\delta_H$ 6.26 (t, J=2.0 Hz, 2H), 4.24 (d, J=2.8 Hz, 0.6H), 4.10 (d, J=2.4 Hz, 1.4H), 3.85 (t, J=7.2 Hz, 0.6H), 3.74 (t, J=6.4 Hz, 1.4H), 3.44 (t, J=7.4 Hz, 2H), 3.25 (t, J=1.8 Hz, 2H), 2.99-2.95 (m, 2H), 2.82 (s, 4H), 2.65 (s, 2H), 2.40-2.34 (m, 2H), 2.31 (t, J=2.4 Hz, 0.7H), 2.25 (t, J=2.4 Hz, 0.3H), 1.70-1.62 (q, J=7.5 Hz, 2H), 1.60-1.52 (m, 2H), 1.50-1.48 (dt, J=10.0, 1.6 Hz, 1H), 1.38-1.28 (m, 2H), 1.21-1.18 (d, J=10.0, 1.6 Hz, 1H). $^{13}$C NMR (100 MHz, $CDCl_3$, ppm): $\delta_C$ 178.2, 173.2, 172.3, 169.1, 168.9, 167.6, 166.4, 137.9, 78.8, 78.6, 73.1, 72.7, 47.9, 45.3, 43.0, 42.9, 42.4, 39.1, 38.7, 38.6, 34.3, 33.1, 32.9, 30.6, 30.2, 27.7, 26.7, 25.7, 24.5, 24.4. The $^1$H and $^{13}$C NMR spectra data for G2-Nb-yne-NHS are shown in FIGS. 14 and 15, respectively.

Example 5: Synthesis of G2-Nb-Yne-NHS

Scheme 5: Synthesis of G2-Nb-yne-propanol.

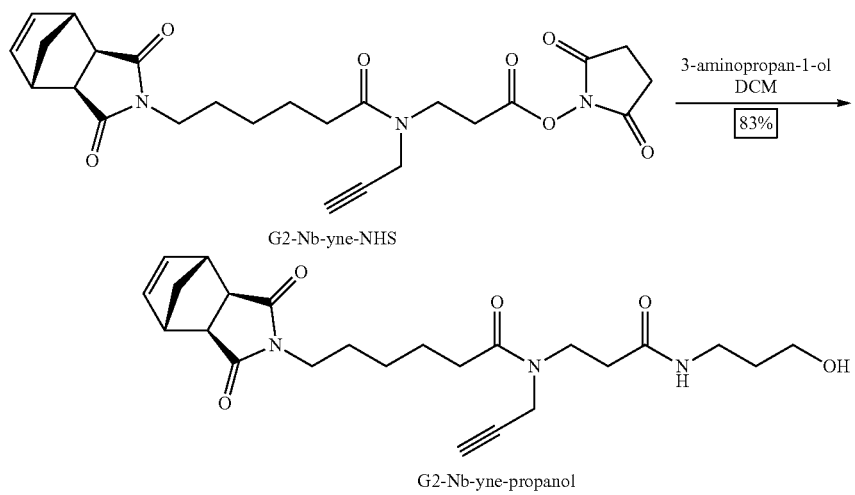

Figure 16:
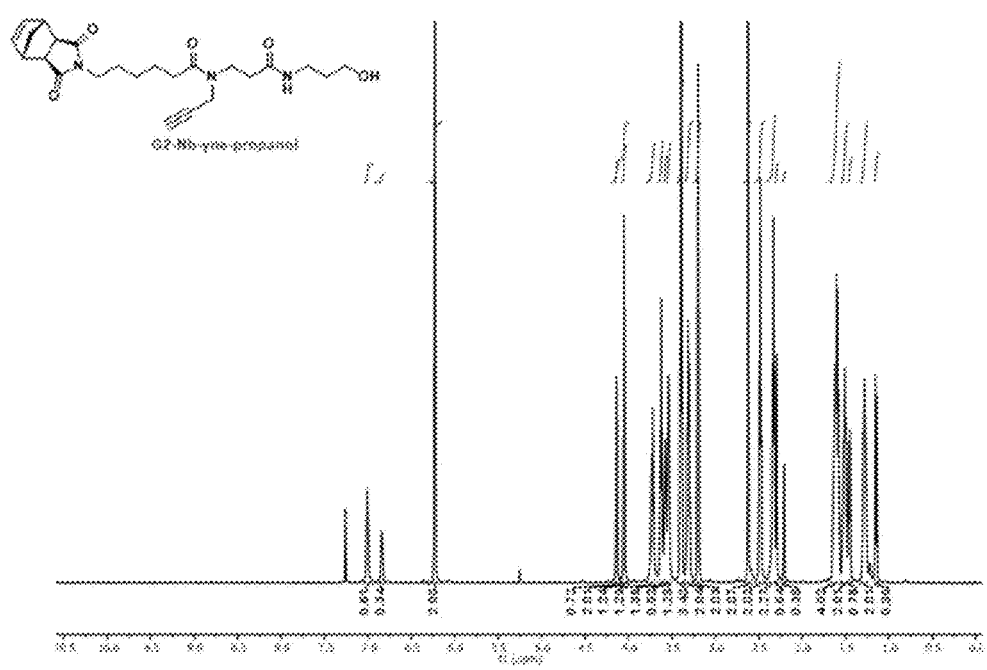
FIG. 16 shows the $^1$H NMR spectrum of G2-Nb-yne-propanol in $CDCl_3$.
Figure 17:
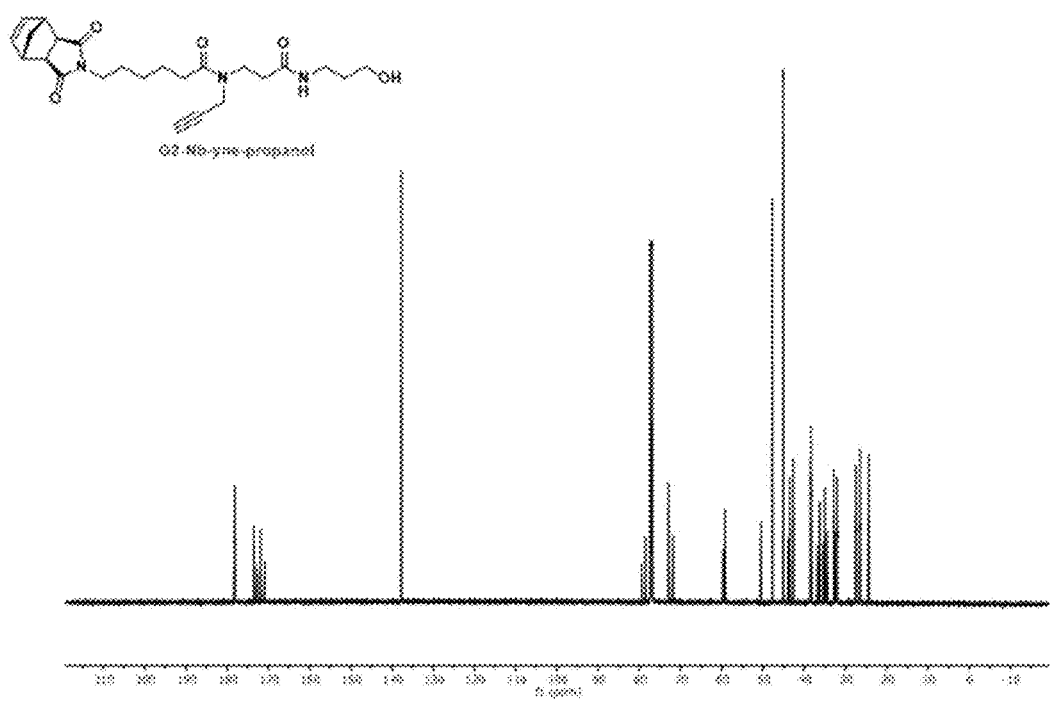
FIG. 17 shows the $^{13}$C NMR spectrum of G2-Nb-yne-propanol in $CDCl_3$.

G2-Nb-yne-NHS (640 mg, 1.32 mmol, 1.0 eq) was dried in a 20 mL glass vial and the vial was evacuated and backfilled with $N_2$ three times. The starting material was dissolved in 13 mL of anhydrous DCM. Neat 3-aminopropan-1-ol (150 mg, 2.0 mmol, 1.5 eq) was added via syringe, upon which a white precipitate formed. After 20 minutes, the reaction was determined to be complete by LCMS and the reaction mixture was loaded directly onto a silica column. The material was chromatographed using a 0→8% MeOH/DCM gradient and the product eluted at approximately 6% MeOH. The product was isolated as a colorless, viscous oil (483 mg, 83% yield). HRMS-ESI: $^1$H NMR (600 MHz, $CDCl_3$) $\delta$ 7.01 (m, 0.61H), 6.84 (t, J=6.0 Hz, 0.34H), 6.23 (t, J=1.8 Hz, 2H), 4.14 (d, J=2.5 Hz, 0.72H), 4.05 (d, J=2.5 Hz, 1.24H), 3.72 (t, J=7.0 Hz, 1.29H), 3.62 (t, J=6.6 Hz, 1.35H), 3.57 (t, J=5.8 Hz, 0.92H), 3.54 (t, J=5.7 Hz, 1.29H), 3.40 (t, J=6.9 Hz, H), 3.32 (m, 2H), 3.20 (s, 1H), 2.62 (s, 2H), 2.48 (t, J=6.5 Hz, 2H), 2.33 (t, J=7.5 Hz, 2H), 2.30 (d, J=2.4 Hz, 0.64H), 2.21 (d, J=2.5 Hz, 0.36H), 1.56-1.66 (m, 4H), 1.51 (p, J=7.4, 6.8 Hz, 2H), 1.46 (d, J=9.8 Hz, 1H), 1.32-1.23 (m, 2H), 1.15 (d, J=9.8 Hz, 1H). $^{13}$C NMR (151 MHz, $CDCl_3$) $\delta$ 178.20, 178.13, 173.47, 172.72, 171.86, 170.85, 137.77, 79.47, 78.53, 77.34, 77.12, 76.91, 72.90, 71.88, 59.72, 59.26, 50.48, 47.78, 45.11, 43.91, 43.50, 42.73, 42.70, 38.51, 38.42, 38.41, 36.83, 36.30, 35.53, 35.02, 34.55, 32.90, 32.41, 32.08, 31.89, 27.48, 27.39, 26.51, 26.45, 24.44, 24.33. The $^1$H and $^{13}$C NMR spectra data for G2-Nb-yne-propanol are shown in FIGS. 16 and 17, respectively.

2) Generation 2 Multi-Click Norbornene Precursors

Example 6: Synthesis of G2-Nb-Yne₂-OtBu

Scheme 6: Synthesis of G2-Nb-yne₂-OtBu.

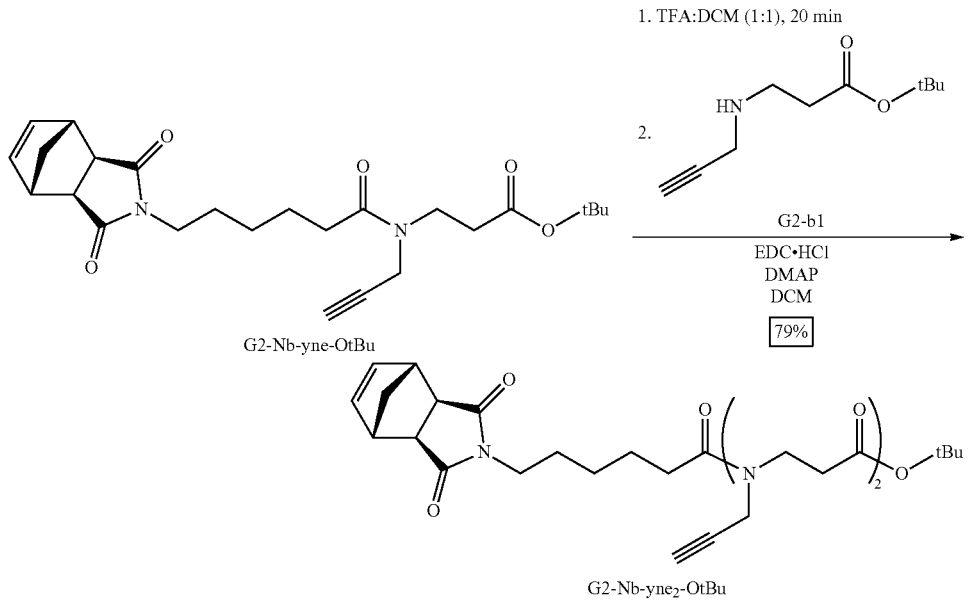

G2-Nb-yne-OtBu was deprotected following the same procedure reported above using a solution of TFA and DCM (1:1). The mixture was stirred for 20 minutes, resulting in the complete deprotection of G2-Nb-yne-OtBu. The solution was then washed with 1M HCl, water, and brine. The organic layer was collected, dried over Na₂SO₄, and concentrated under vacuum, affording G2-Nb-yne-COOH as a white solid.

Figure 64:
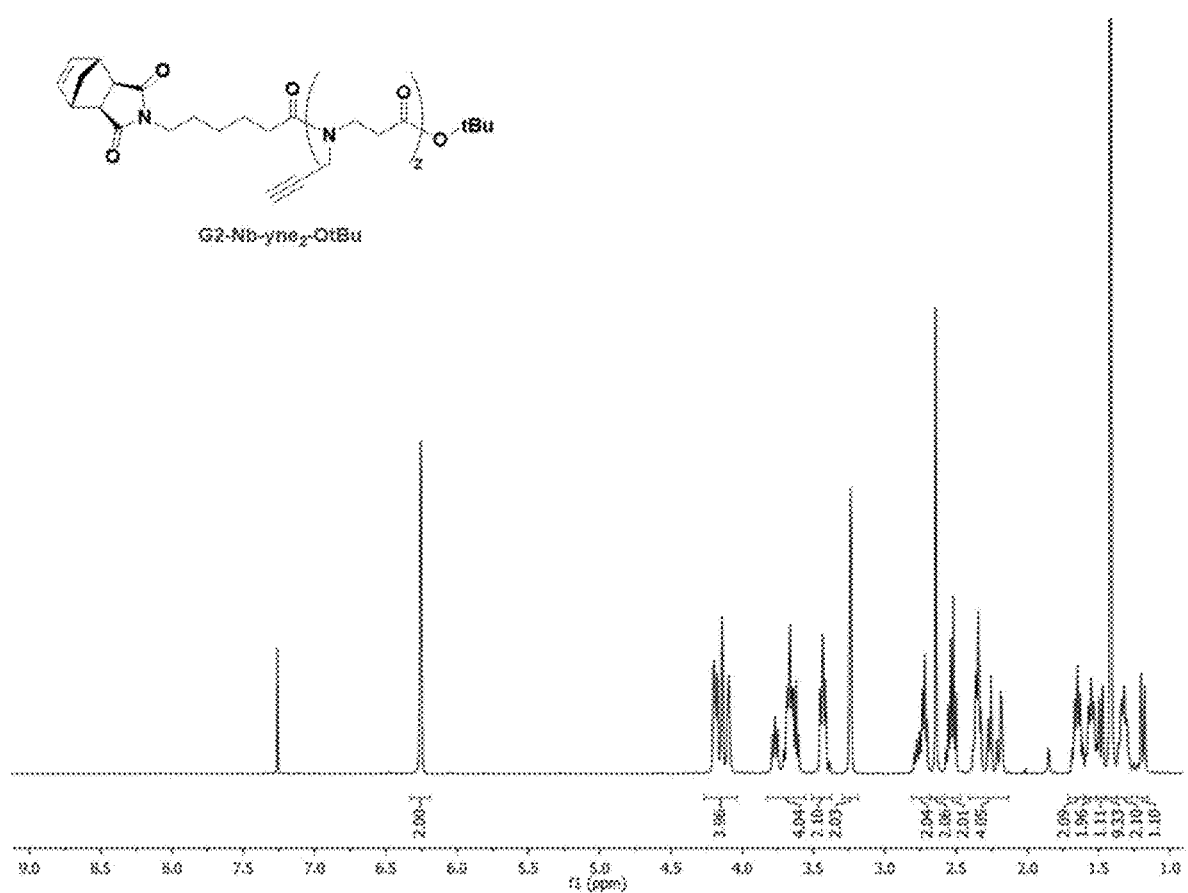
FIG. 64 shows the $^1$H NMR spectrum of G2-Nb-yne$_2$-OtBu in CDCl$_3$.
Figure 65:
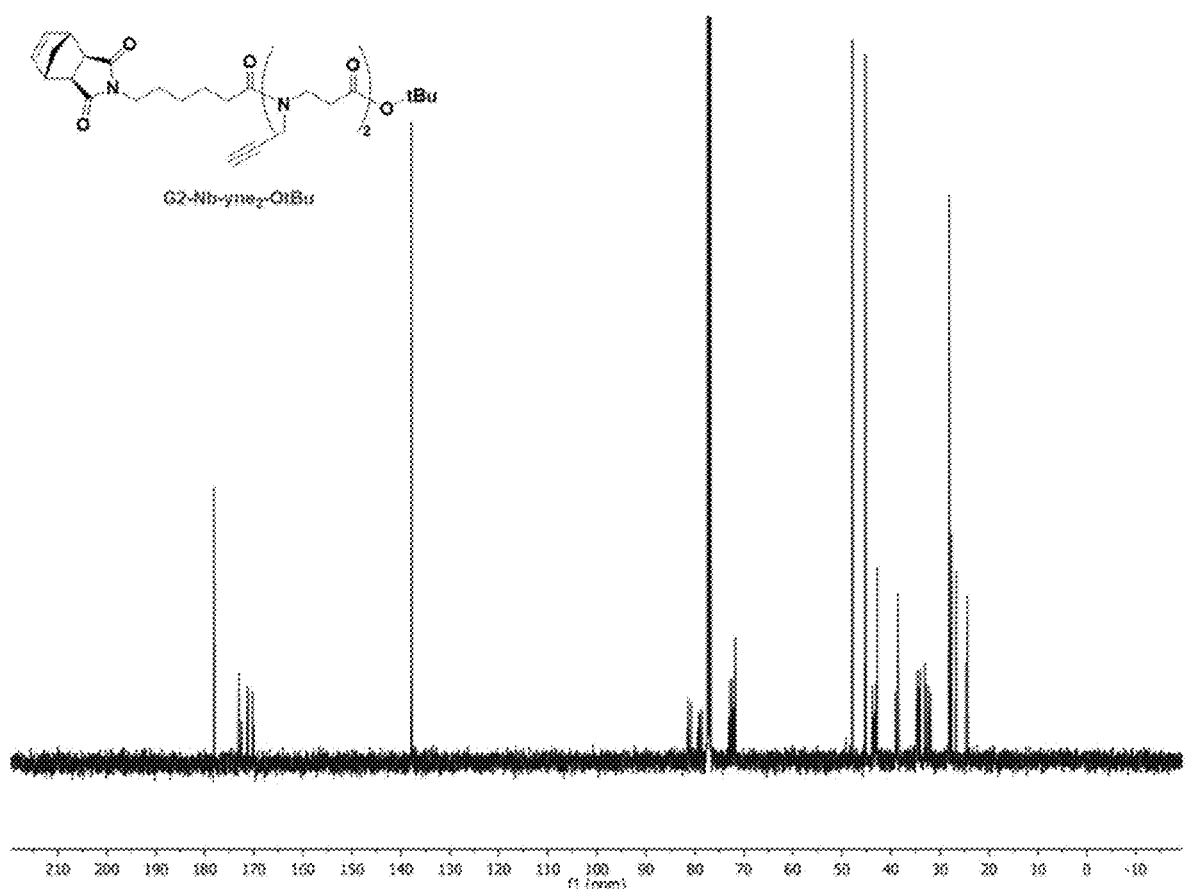
FIG. 65 shows the $^{13}$C NMR spectrum of G2-Nb-yne$_2$-OtBu in CDCl$_3$.

Into a RBF, G2-Nb-yne-COOH (1.49 g, 3.86 mmol, 1.0 eq), EDC.HCl (0.740 g, 3.86 mmol, 1.0 eq), DMAP (0.267 g, 2.19 mmol, 0.6 eq), G2-b1 (0.530 g, 2.89 mmol, 0.75 eq) and DCM (100 mL) were added. The reaction mixture was stirred overnight and then concentrated under vacuum. Column chromatography (EtOAc/hexane) of the crude mixture yielded product as a light yellow viscous oil (1.34 g, 84% yield, 79% yield from G2-Nb-yne-OtBu). HRMS-DART: Calcd for $C_{31}H_{42}N_3O_6$: m/z=552.3068 [M+H]⁺; Found: 552.3044 [M+H]⁺. ¹H NMR (400 MHz, CDCl₃, ppm): $\delta_H$ 6.26 (t, J=1.8 Hz, 2H), 4.21-4.09 (m, 4H), 3.79-3.60 (m, 4H), 3.46-3.41 (m, 2H), 3.24 (t, J=1.8 Hz, 2H), 2.79-2.70 (m, 2H), 2.64 (s, 2H), 2.57-2.50 (m, 2H), 2.38-2.32 (m, 2H), 2.28-2.25 (m, 1H), 2.21-2.17 (m, 1H), 1.68-1.61 (m, 2H), 1.59-1.52 (m, 2H), 1.50-1.47 (dt, J=10.0, 1.6 Hz, 1H), 1.42 (s, 9H), 1.36-1.28 (m, 2H), 1.19 (1H, d, J=9.6 Hz). ¹³C NMR (100 MHz, CDCl₃, ppm): $\delta_C$ 178.1, 173.0, 172.5, 172.4, 171.4, 171.2, 171.1, 170.3, 170.2, 170.1, 137.9, 81.6, 81.4, 81.0, 80.9, 79.5, 79.2, 79.1, 78.7, 77.4, 73.1, 72.8, 72.5, 72.2, 71.9, 71.8, 47.9, 45.2, 43.8, 43.7, 43.6, 43.5, 43.3, 43.30, 42.9, 42.8, 39.1, 38.6, 38.5, 34.7, 34.6, 34.4, 34.2, 34.1, 33.1, 32.9, 32.3, 32.0, 31.9, 28.2, 28.1, 27.7, 26.8, 24.7, 24.5. The ¹H and ¹³C NMR spectra data for G2-Nb-yne₂-OtBu are shown in FIGS. 64 and 65, respectively.

Example 7: Synthesis of G2-Nb-Yne₂-NHS

Scheme 7: Synthesis of G2-Nb-yne₂-NHS.

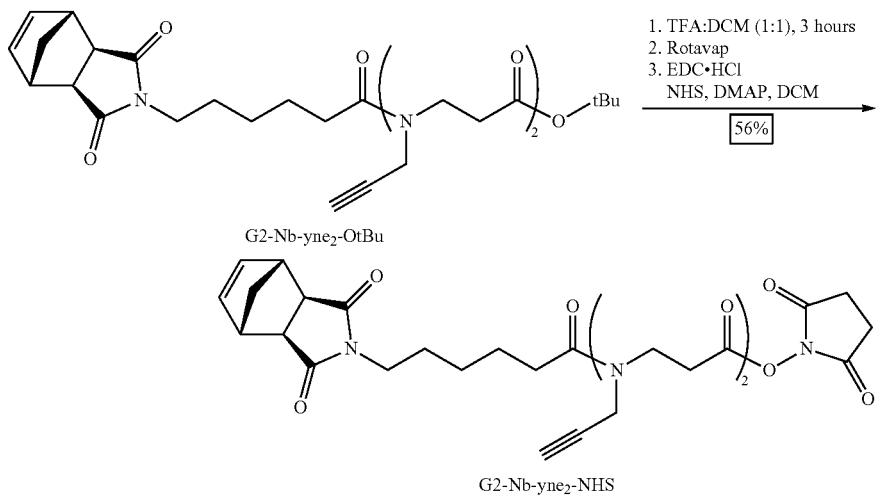

G2-Nb-yne$_2$-OtBu (7.02 g, 12.7 mmol) was deprotected following similar procedure as reported above using a solution of TFA and DCM (1:1, 30 mL TFA in 30 mL DCM). The mixture was stirred for 3 hours, resulting in the complete deprotection of G2-Nb-yne$_2$-OtBu. DCM (70 mL) was then added to the reaction mixture, and the solution was washed with 1M HCl, water, and brine. The organic layer was collected, dried over Na$_2$SO$_4$, and concentrated under vacuum, affording G2-Nb-yne$_2$-COOH as an off-white solid (6.24 g, 99% yield).

Figure 66:
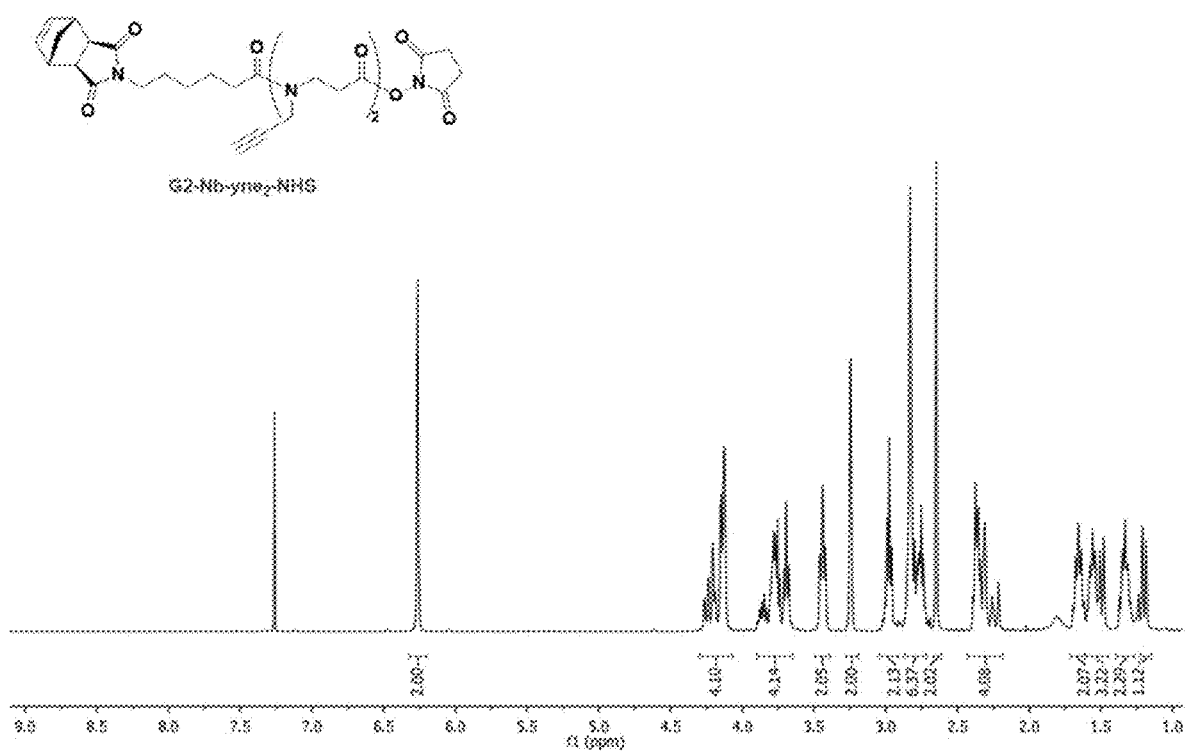
FIG. 66 shows the $^1$H NMR spectrum of G2-Nb-yne$_2$-NHS in CDCl$_3$.
Figure 67:
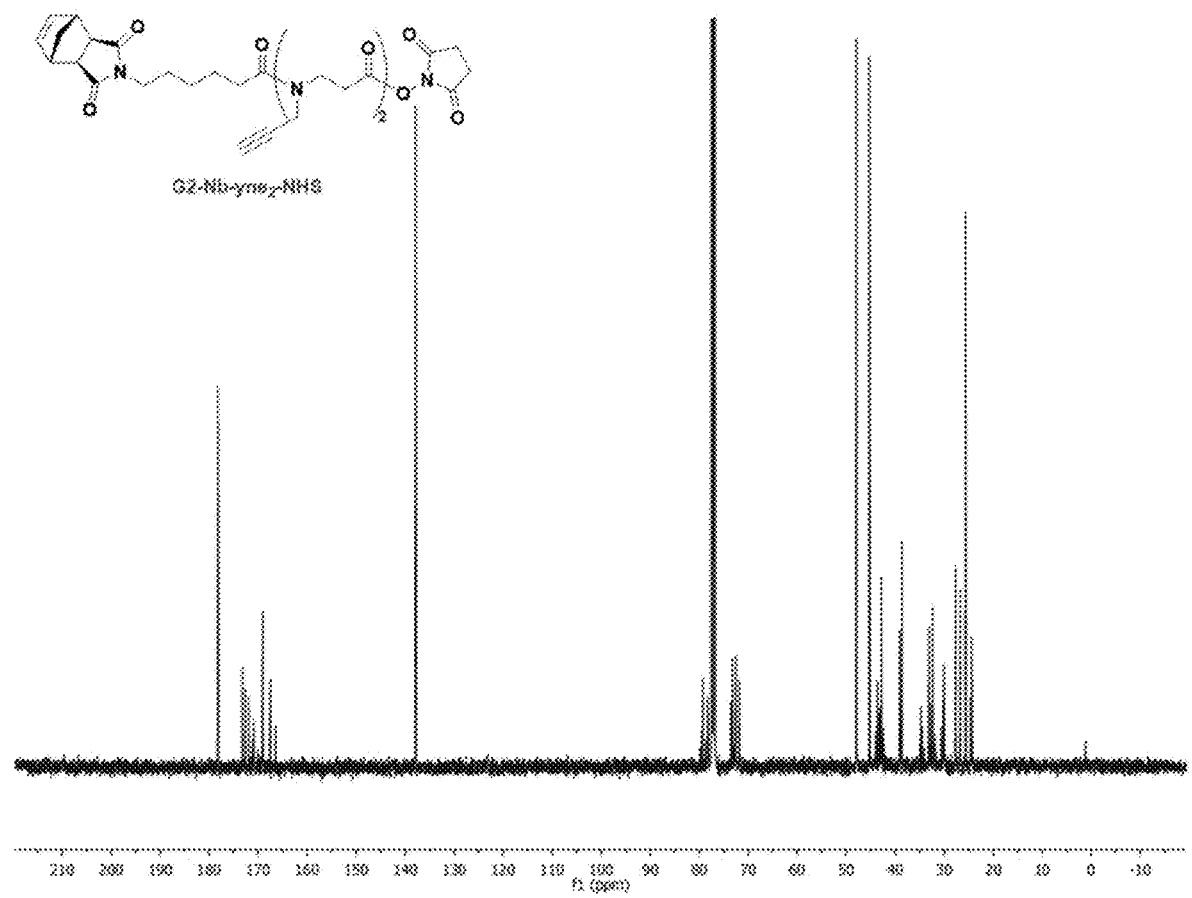
FIG. 67 shows the $^{13}$C NMR spectrum of G2-Nb-yne$_2$-NHS in CDCl$_3$.

Into a RBF, G2-Nb-yne$_2$-COOH (1.87 g, 3.77 mmol, 1.0 eq), EDC.HCl (1.09 g, 5.67 mmol, 1.5 eq), DMAP (0.114 g, 0.94 mmol, 0.25 eq), NHS (0.653 g, 5.68 mmol, 1.5 eq) and DCM (100 mL) were added. The reaction mixture was stirred overnight and then concentrated under vacuum. Column chromatography (EtOAc/hexane) of the crude mixture yielded product as a white solid (1.27 g, 57% yield, 56% yield from G2-Nb-yne$_2$-OtBu). HRMS-DART: Calcd for C$_{31}$H$_{37}$N$_4$O$_8$: m/z=593.2606 [M+H]$^+$; Found: 593.2617 [M+H]$^+$. $^1$H NMR (400 MHz, CDCl$_3$, ppm): δ$_H$ 6.26 (t, J=1.6 Hz, 2H), 4.27-4.12 (m, 4H), 3.90-3.68 (m, 4H), 3.44 (td, J=7.4, 2.4 Hz, 2H), 3.24 (s, 2H), 3.02-2.96 (m, 2H), 2.85-2.73 (m, 6H), 2.65 (s, 2H), 2.39-2.21 (m, 4H), 1.69-1.62 (m, 2H), 1.59-1.52 (m, 2H), 1.51-1.48 (dt, J=9.6, 1.7 Hz, 1H), 1.37-1.29 (m, 2H), 1.20 (1H, d, J=9.6 Hz). $^{13}$C NMR (100 MHz, CDCl$_3$, ppm): δ$_C$ 178.2, 173.1, 172.6, 171.9, 171.1, 170.9, 169.1, 168.9, 167.5, 166.4, 137.9, 79.8, 79.6, 79.3, 78.7, 78.3, 78.2, 77.4, 73.6, 73.3, 73.1, 72.7, 72.6, 71.9, 47.9, 45.3, 44.0, 43.8, 43.6, 43.4, 43.1, 42.9, 42.8, 42.4, 42.3, 39.2, 39.1, 39.0 38.6, 35.0, 34.8, 34.5, 34.1, 33.1, 32.9, 32.8, 32.4, 32.3, 31.9, 30.6, 30.4, 30.2, 30.1, 27.7, 26.9, 26.8, 25.7, 24.7, 24.5. The $^1$H and $^{13}$C NMR spectra data for G2-Nb-yne$_2$-NHS are shown in FIGS. 66 and 67, respectively.

Example 8: Synthesis of G2-Nb-yne$_3$-OtBu

G2-Nb-yne$_2$-OtBu was deprotected following the same procedure reported above using a solution of TFA and DCM. The mixture was stirred for 3 hours, resulting in the complete deprotection of G2-Nb-yne$_2$-OtBu. The solution was then washed with 1M HCl, water, and brine. The organic layer was collected, dried over Na$_2$SO$_4$, and concentrated under vacuum, affording G2-Nb-yne$_2$-COOH as a an off-white solid.

Figure 68:
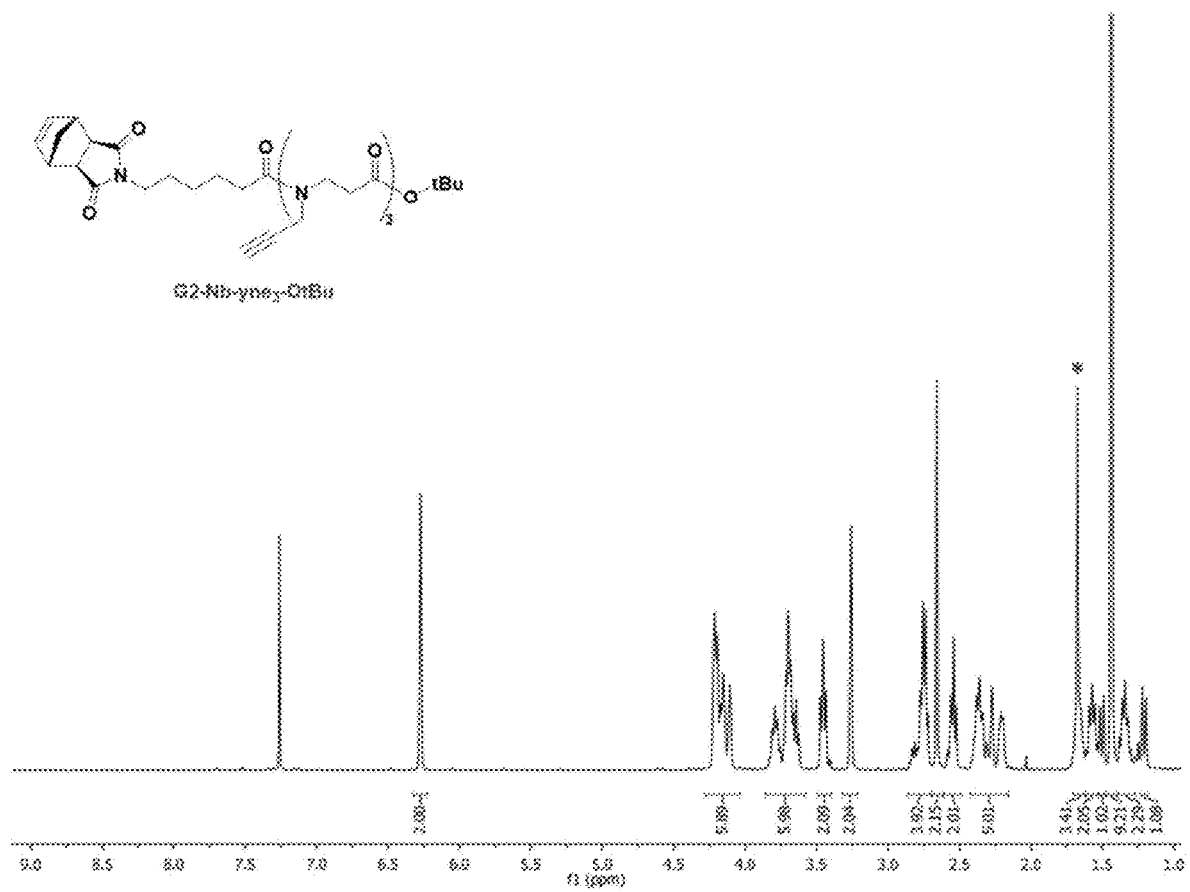
FIG. 68 shows the $^1$H NMR spectrum of G2-Nb-yne$_3$-OtBu in CDCl$_3$, * denotes minor solvent impurity.
Figure 69:
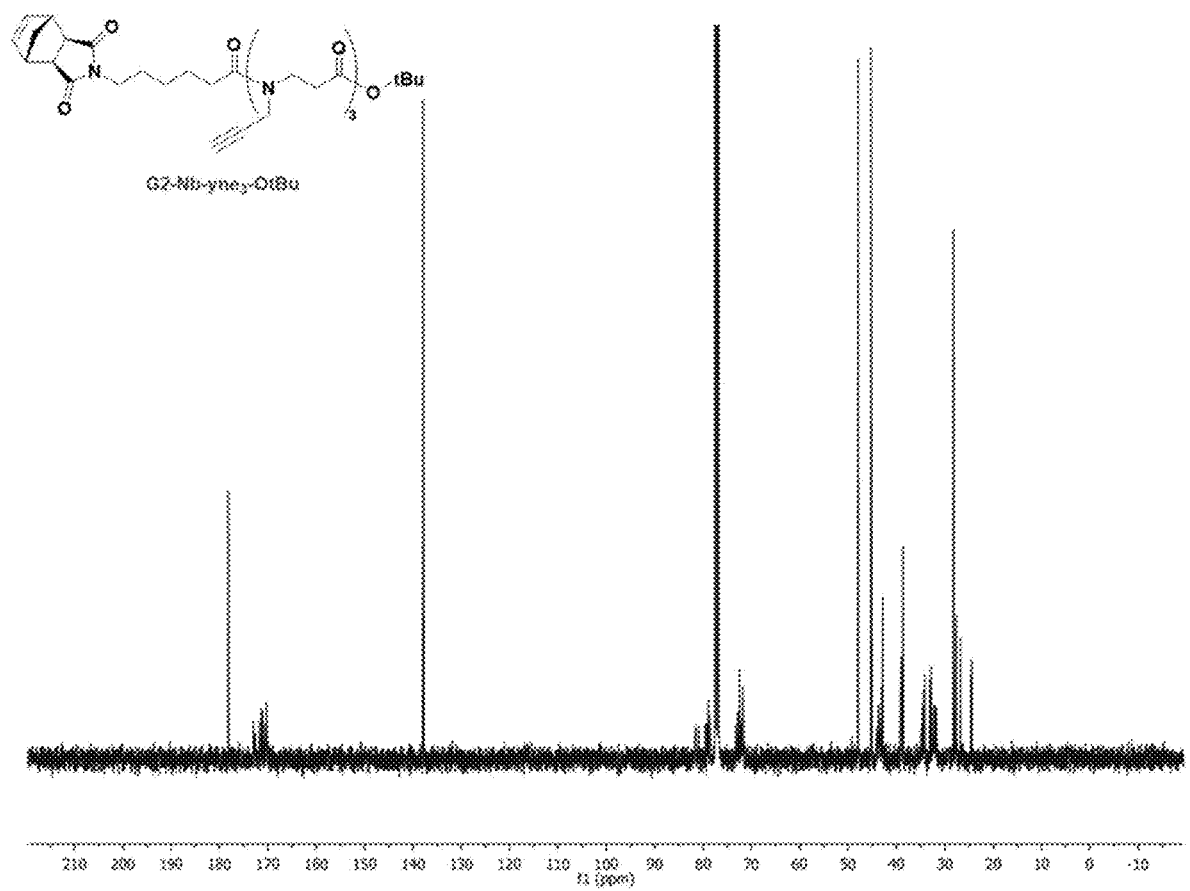
FIG. 69 shows the $^{13}$C NMR spectrum of G2-Nb-yne$_3$-OtBu in CDCl$_3$.

Into a RBF, G2-Nb-yne$_2$-COOH (0.458 g, 0.92 mmol, 1.0 eq), EDC.HCl (0.196 g, 1.02 mmol, 1.1 eq), DMAP (0.070 g, 0.57 mmol, 0.6 eq), G2-b1 (0.130 g, 0.71 mmol, 0.75 eq) and DCM (20 mL) were added. The reaction mixture was stirred overnight and then concentrated under vacuum. Column chromatography (EtOAc/hexane) of the crude mixture yielded product as a yellow viscous oil (0.340 g, 55% yield, 54% yield from G2-Nb-yne$_2$-OtBu). HRMS-DART: Calcd for C$_{37}$H$_{49}$N$_4$O$_7$: m/z=661.3596 [M+H]$^+$; Found: 661.3589 [M+H]$^+$. $^1$H NMR (400 MHz, CDCl$_3$, ppm): δ$_H$ 6.27 (t, J=1.8 Hz, 2H), 4.22-4.10 (m, 6H), 3.82-3.63 (m, 6H), 3.47-3.41 (m, 2H), 3.26 (s, 2H), 2.85-2.72 (m, 4H), 2.66 (s, 2H), 2.59-2.53 (m, 2H), 2.42-2.18 (m, 5H), 1.71-1.63 (m, 2H), 1.61-1.54 (m, 2H), 1.52-1.49 (d, J=10.0, 1H), 1.43 (s, 9H), 1.39-1.27 (m, 2H), 1.21 (d, J=9.6 Hz, 1H). $^{13}$C NMR (100 MHz, CDCl$_3$, ppm): δ$_C$ 178.2, 173.0, 172.6, 172.5, 171.8, 171.7, 171.3, 171.2, 171.0, 170.7, 170.3, 170.2, 137.9, 81.6, 81.4, 81.0, 80.9, 79.6, 79.3, 79.1, 78.9, 78.7, 77.3, 73.2, 72.9, 72.7, 72.6, 72.2, 71.9, 71.8, 49.3, 47.9, 45.3, 43.8, 43.6, 43.4, 43.1, 42.9, 39.2, 39.0, 38.7, 38.6, 34.6, 34.4, 34.2, 34.1, 33.1, 32.9, 32.4, 32.2, 32.0, 31.8, 28.2, 28.1, 27.7, 26.8, 24.7, 24.5. The $^1$H and $^{13}$C NMR spectra data for G2-Nb-yne$_3$-OtBu are shown in FIGS. 68 and 69, respectively.

Scheme 8: Synthesis of G2-Nb-yne$_3$-OtBu.

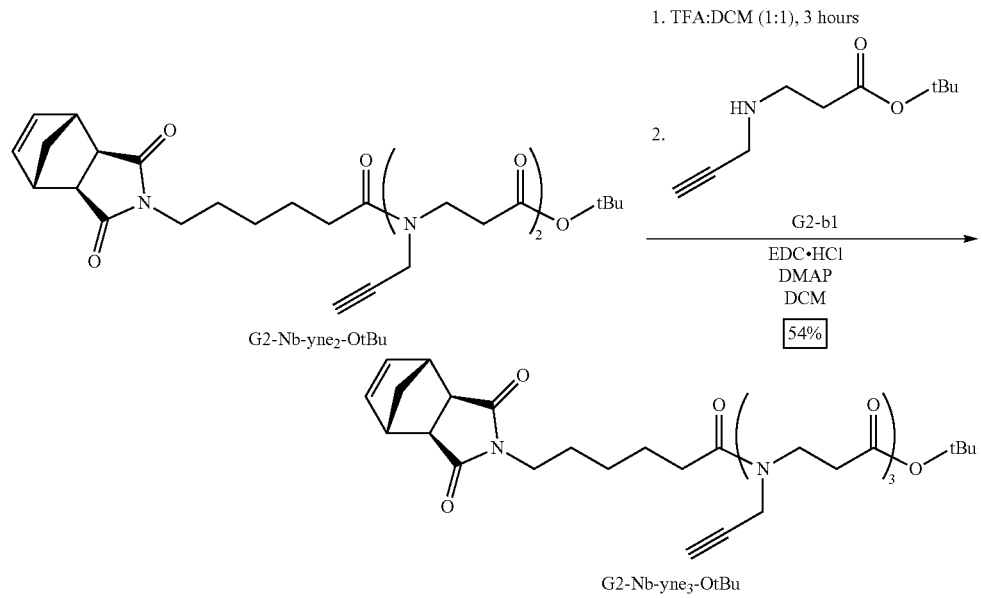

Example 9: Synthesis of G2-Nb-Yne₃-NHS

Scheme 9: Synthesis of G2-Nb-yne₃-NHS.

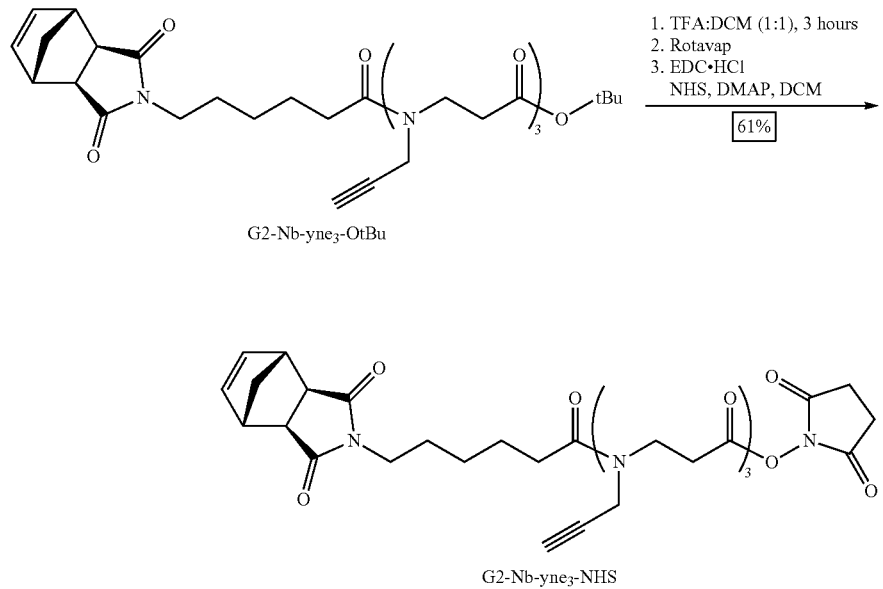

G2-Nb-yne₃-OtBu (1.68 g, 2.54 mmol) was deprotected following similar procedure as reported above using a solution of TFA and DCM (1:1, 20 mL TFA in 20 mL DCM). The mixture was stirred for 3 hours, resulting in the complete deprotection of G2-Nb-yne₃-OtBu. DCM (40 mL) was then added to the reaction mixture, and the solution was washed with 1M HCl, water, and brine. The organic layer was collected, dried over Na₂SO₄, and concentrated under vacuum, affording G2-Nb-yne₃-COOH as an off-white solid (1.50 g, 97% yield).

Figure 70:
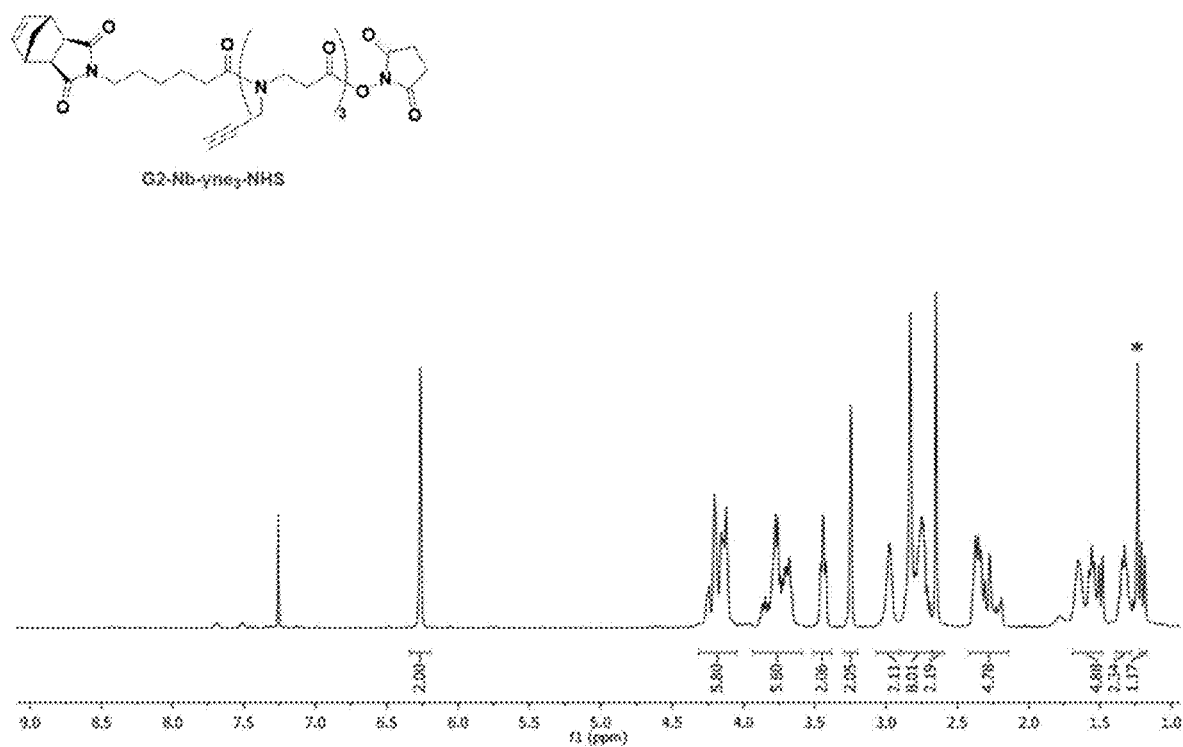
FIG. 70 shows the $^1$H NMR spectrum of G2-Nb-yne$_3$-NHS in CDCl$_3$, * denotes minor solvent impurity.
Figure 71:
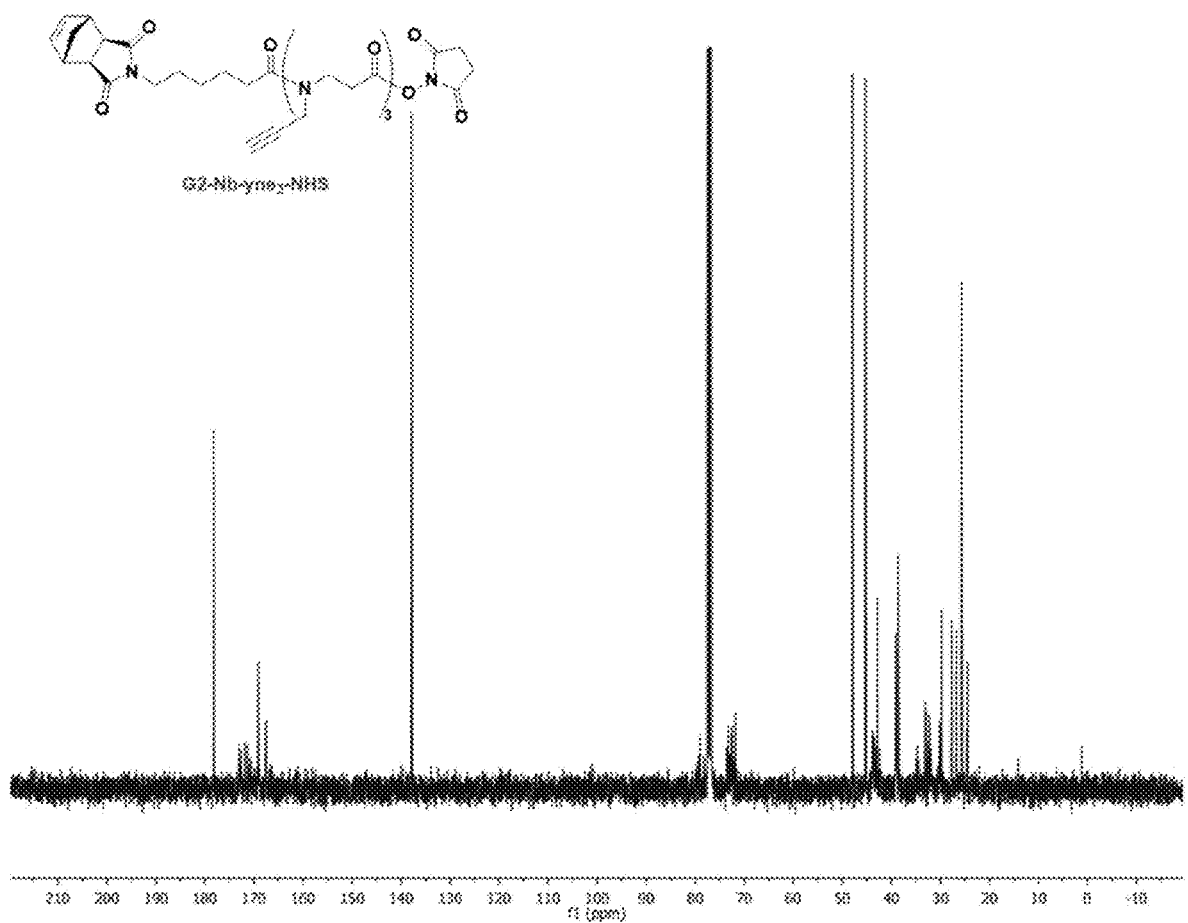
FIG. 71 shows the $^{13}$C NMR spectrum of G2-Nb-yne$_3$-NHS in CDCl$_3$.

Into a RBF, G2-Nb-yne₃-COOH (1.50 g, 2.48 mmol, 1.0 eq), EDC.HCl (0.713 g, 3.72 mmol, 1.5 eq), DMAP (0.151 g, 1.24 mmol, 0.5 eq), NHS (0.428 g, 3.72 mmol, 1.5 eq) and DCM (100 mL) were added. The reaction mixture was stirred overnight and then concentrated under vacuum. Column chromatography (EtOAc/hexane) of the crude mixture yielded product as a white solid (1.10 g, 63% yield, 61% yield from G2-Nb-yne₃-OtBu). HRMS-DART: Calcd for $C_{37}H_{44}N_5O_9$: m/z=702.3134 [M+H]⁺; Found: 702.3132 [M+H]⁺. ¹H NMR (400 MHz, CDCl₃, ppm): $\delta_H$ 6.27 (s, 2H), 4.26-4.12 (m, 6H), 3.88-3.66 (m, 6H), 3.44 (td, J=7.6, 2.4 Hz, 2H), 3.25 (s, 2H), 3.03-2.95 (m, 2H), 2.86-2.69 (m, 8H), 2.65 (s, 2H), 2.39-2.18 (m, 5H), 1.69-1.48 (m, 5H), 1.37-1.27 (m, 2H), 1.20 (d, J=11.6 Hz, 1H). ¹³C NMR (100 MHz, CDCl₃, ppm): $\delta_C$ 178.2, 173.0, 172.9, 172.6, 171.8, 171.7, 171.3, 169.1, 168.9, 167.6, 137.9, 79.8, 79.6, 79.3, 79.0, 78.3, 78.2, 77.4, 73.6, 73.3, 73.1, 72.8, 72.7, 72.6, 72.5, 71.9, 47.9, 45.3, 43.9, 43.8, 43.5, 43.4, 43.1, 42.9, 42.8, 42.4, 39.2, 39.1, 38.6, 35.0, 34.9, 34.4, 34.1, 33.1, 32.9, 32.4, 32.3, 32.2, 30.2, 30.1, 29.8, 27.7, 26.8, 25.7, 24.7, 24.5. The ¹H and ¹³C NMR spectra data for G2-Nb-yne-propanol are shown in FIGS. 70 and 71, respectively.

3) Azide Precursors

Example 10: Synthesis of PTX-Azide

Scheme 10: Synthesis of PTX-azide.

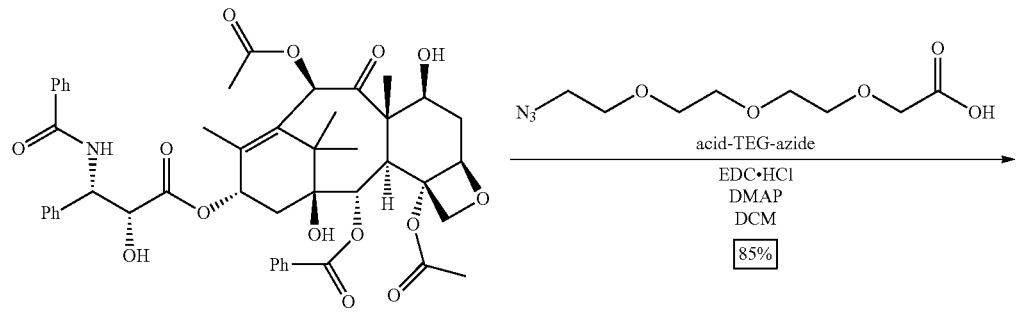

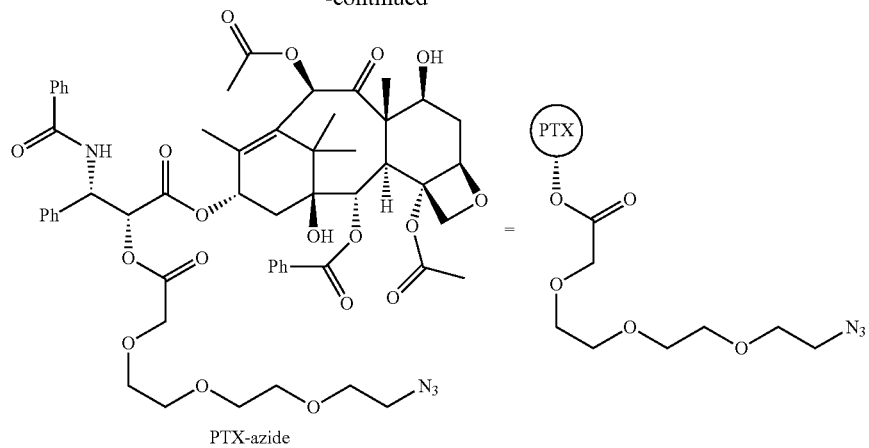

PTX-azide

Figure 20:
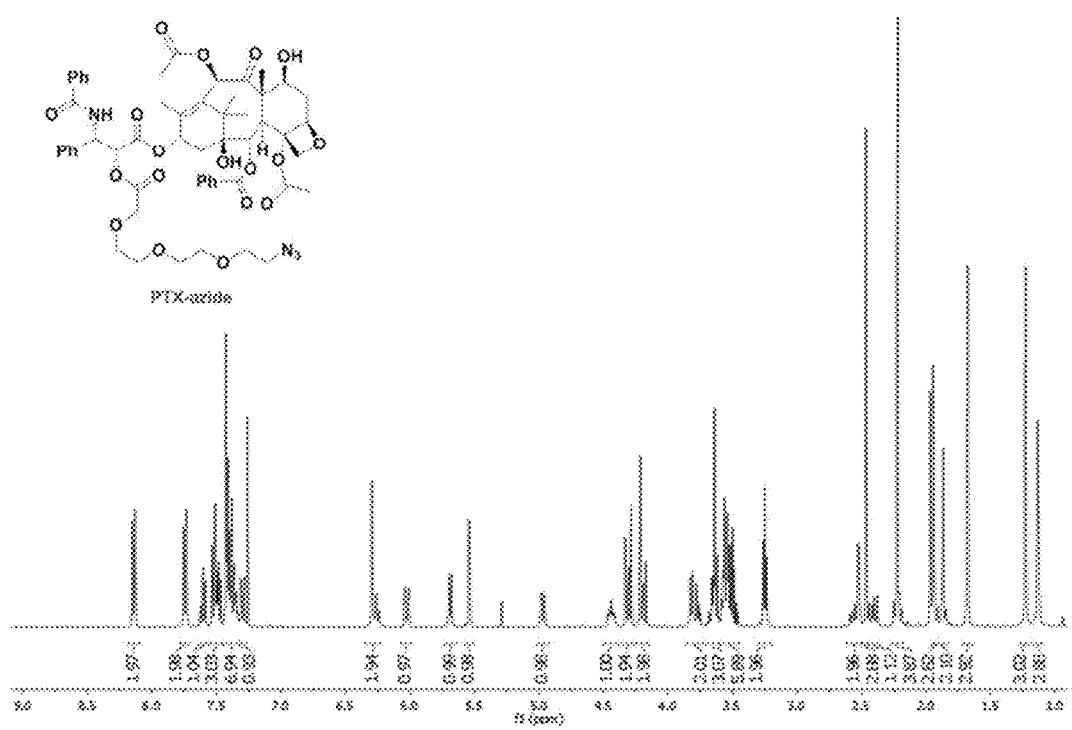
FIG. 20 shows the $^1$H NMR spectrum of PTX-azide in $CDCl_3$.
Figure 21:
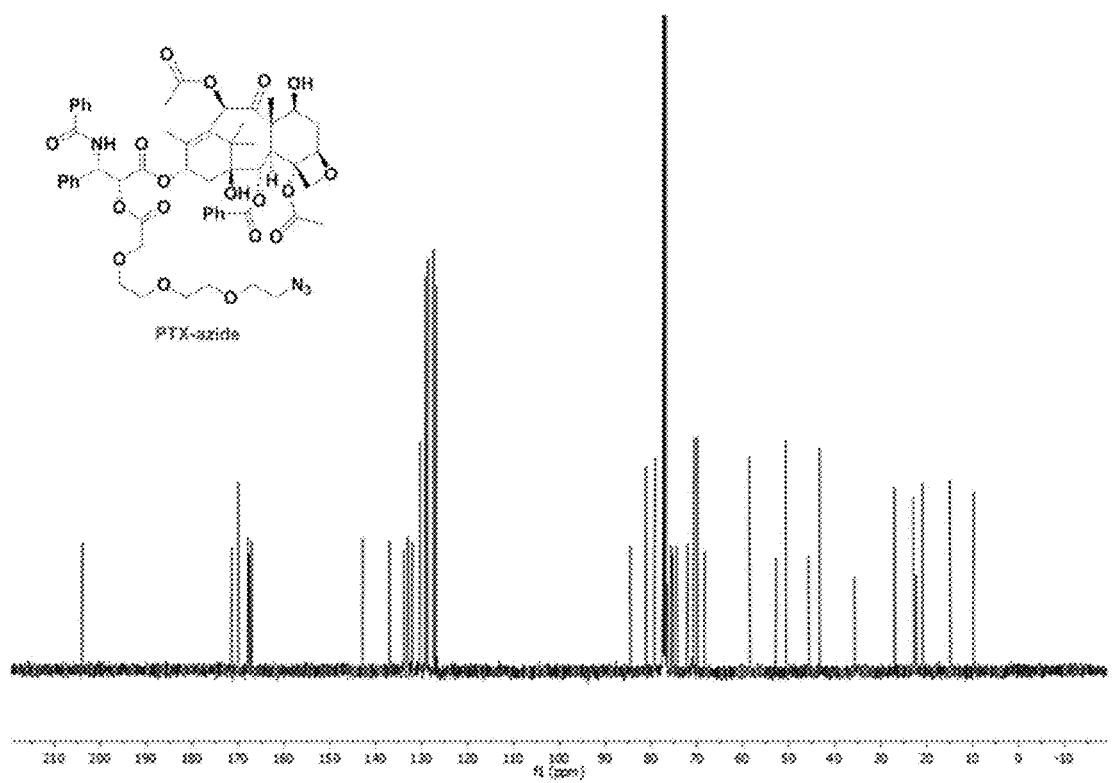
FIG. 21 shows the $^{13}$C NMR spectrum of PTX-azide in $CDCl_3$.

Into a RBF, Paclitaxel (260 mg, 0.304 mmol, 1.0 eq), acid-TEG-azide (107 mg, 0.457 mmol, 1.5 eq), EDC.HCl (87.6 mg, 0.457 mmol, 1.5 eq), DMAP (18.6 mg, 0.152 mmol, 0.5 eq), and DCM (40 mL) were added. The reaction mixture were stirred overnight and then concentrated under vacuum. Column chromatography (EtOAc/hexane) of the crude mixture yielded product as a white solid (275 mg, 85% yield). HRMS-ESI: Calcd for $C_{55}H_{64}N_4O_{18}$: m/z= 1091.4108 [M+Na]$^+$; Found: 1091.4129 [M+Na]$^+$. $^1$H NMR (400 MHz, CDCl$_3$, ppm) $\delta_H$ 8.14 (d, J=7.2 Hz, 2H), 7.74 (d, J=7.2 Hz, 2H), 7.60 (tt, J=7.4, 1.7 Hz, 1H), 7.53-7.47 (overlap, 3H), 7.43-7.33 (overlap, 7H), 7.30 (d, J=4.8 Hz, 1H), 6.29 (s, 1H), 6.26 (t, J=9.2 Hz, 1H), 6.03 (dd, J=9.2, 2.8 Hz, 1H), 5.69 (d, J=7.2 Hz, 1H), 5.54 (d, J=2.8 Hz, 1H), 4.97 (dd, J=7.6, 2.2 Hz, 1H), 4.44 (m, 1H), 4.30 (t, 2H), 4.19 (t, 2H), 3.83-3.75 (overlap, 2H), 3.68-3.62 (overlap, 3H), 3.59-46 (overlap, 6H), 3.25 (t, J=5.0 Hz, 2H), 2.59-2.52 (overlap, 2H), 2.46 (s, 3H), 2.41 (dd, J=15.6, 9.2 Hz, 1H), 2.25-2.19 (t, J=6.0 Hz, 1H), 2.20 (s, 3H), 1.94 (s, 3H), 1.91-1.84 (m, 2H), 1.68 (s, 3H), 1.23 (s, 3H), 1.13 (s, 3H). $^{13}$C NMR (100 MHz, CDCl$_3$, ppm): $\delta_C$, 203.9, 171.4, 169.9, 167.9, 167.5, 167.1, 142.8, 137.0, 133.9, 133.8, 132.9, 132.0, 130.4, 129.3, 129.2, 128.9, 128.7, 128.6, 127.4, 126.9, 84.6, 81.2, 79.2, 77.4, 76.6, 75.7, 75.2, 74.5, 72.2, 72.1, 71.0, 70.8, 70.7, 70.6, 69.9, 68.4, 58.6, 52.9, 50.6, 45.7, 43.3, 35.7, 35.6, 26.9, 22.8, 22.3, 20.9, 14.9, 9.7. The $^1$H and $^{13}$C NMR spectra data for PTX-azide are shown in FIGS. 20 and 21, respectively.

Example 11: Synthesis of ChexW-N$_3$

Scheme 11: Synthesis of ChexW-N$_3$.

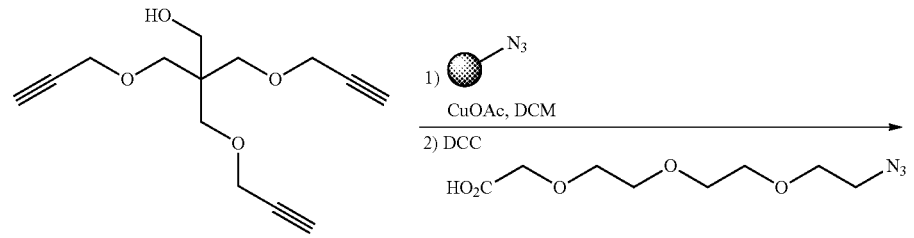

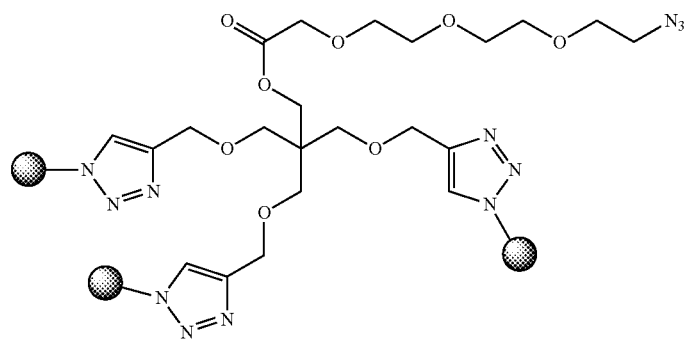

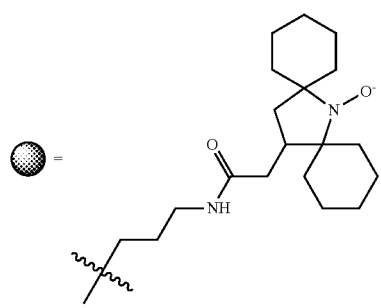

Chex-N₃ (0.267 g, 0.77 mmol, 3.2 mmol) was loaded to a small vial with yne₃-OH (0.060 g, 0.241 mmol, 1.0 equiv). The vial was transported to a glove box where CuOAc (0.005 g, 0.041 mmol, 0.17 mmol) and anhydrous DCM (3 mL) was added. The reaction was stirred at room temperature for 1 hour, after which time LC-MS indicated the reaction was complete. The reaction was filtered over a silica plug (10:1 DCM:MeOH). This material was used directly in the next step without purification. To a small vial containing DCC (0.096 g, 0.465 mmol), 14-azido-3,6,9,12-tetraoxatetradecanoic acid (0.092 g, 0.332 mmol). The reaction was stirred overnight, after which time LC-MS indicated a considerable amount of starting material still present. DMAP (0.022 g) was then added to the reaction, and the reaction was complete within three hours. Filtration and purification by preparative gel permeation chromatography afforded the ChexW-N₃ as an orange oil (0.165 g, 0.11 mmol, 46% yield over two steps).

Example 12: Synthesis of PTXW-N₃

Scheme 12: Synthesis of yne₃-NHS.

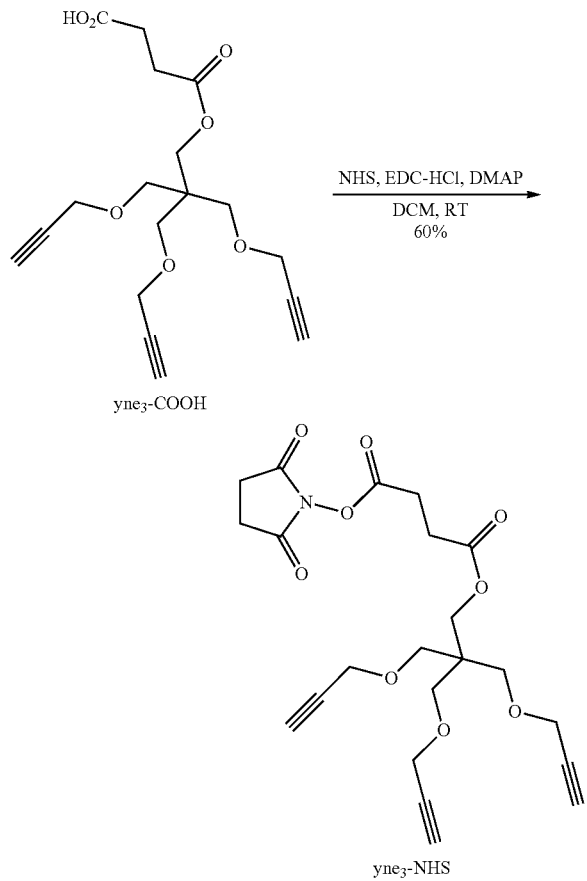

Procedure for yne₃-NHS:

yne₃-COOH (0.400 g, 1.14 mmol, 1 equiv), EDC-HCl (0.332 g, 1.74 mmol, 1.5 equiv), DMAP (0.0741 g, 0.61 mmol, 0.54 equiv) and N-hydroxysuccinimide (0.370 g, 3.22 mmol, 2.9 equiv) were mixed for 12 hours in DCM at room temperature. After evaporation of the volatiles, the residue was purified on silica using a 20:1 DCM:MeOH eluent. Subsequent purification using preparative gel permeation chromatography (CHCl₃) afforded yne₃-NHS as a white powder (0.306 g, 0.68 mmol, 60%). ¹H NMR (CDCl₃, 400 MHz): 4.19 (s, 2H), 4.10 (t, 6H, J=2.6 Hz), 3.51 (s, 6H), 2.98 (t, 2H, J=7.2 Hz), 2.83 (s, 4H), 2.76 (t, 2H, 7.2 Hz), 2.43 (t, 3H, J=2.4 Hz)¹³C NMR (CDCl₃, 100 MHz): 170.6, 168.9, 167.7, 79.8, 74.4, 68.7, 64.1, 58.7, 44.0, 28.8, 26.3, 25.6 HRMS-ESI: Calcd for C₂₂H₂₅NO₉: m/z=470.1422 [M+Na]⁺; Found: 470.1426 [M+Na]⁺.

Figure 46:
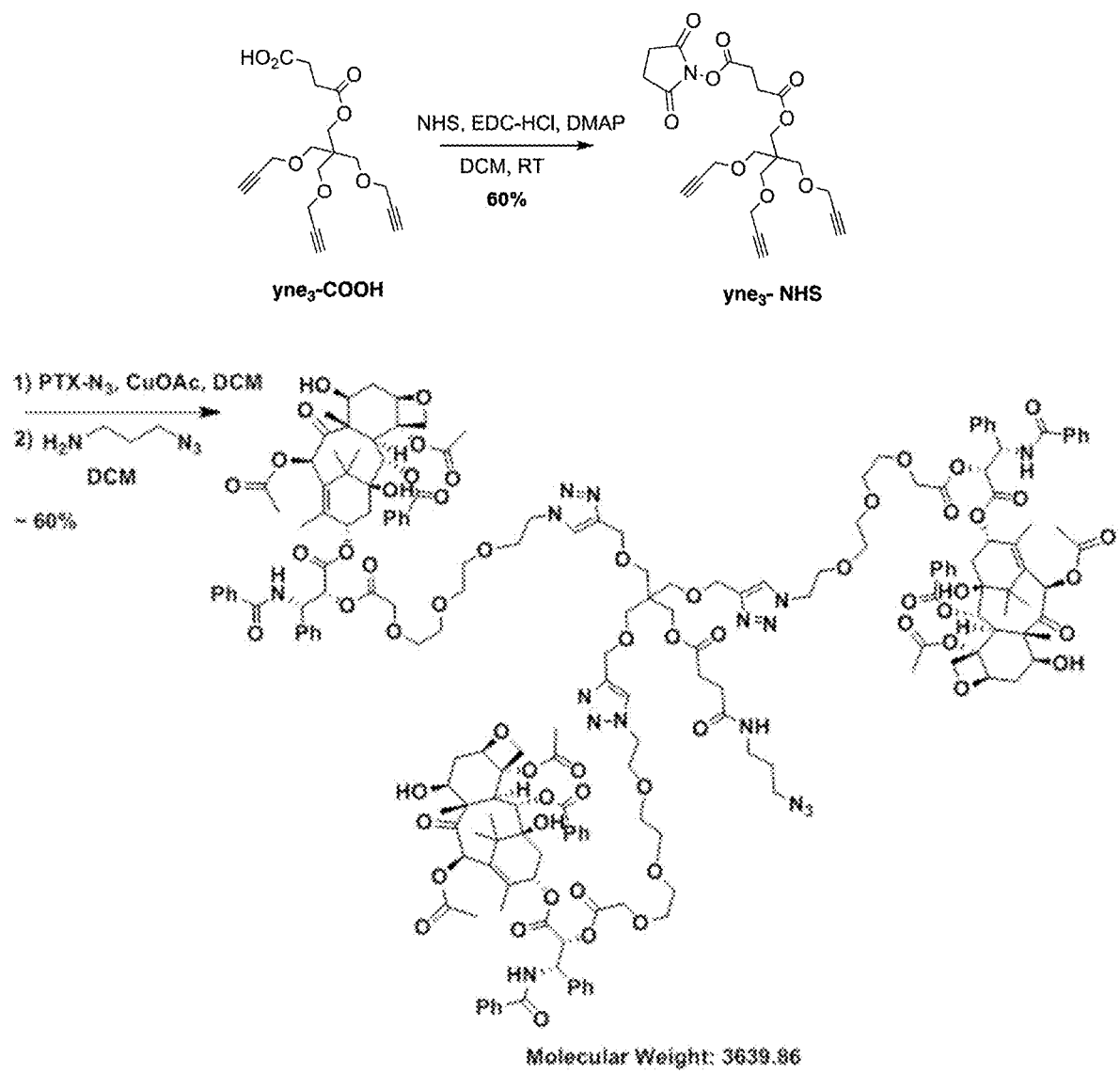
FIG. 46 shows the synthesis of an azide containing three Paclitaxel moieties (PTX-amide-N3).
Figure 46:
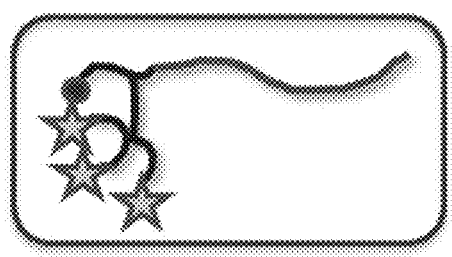

Procedure for PTXW-N₃:

yne₃-NHS (0.048 g, 0.107 mmol, 1 equiv), PTX-N₃, (0.375 g, 0.350 mmol, 3.3 equiv), tris(benzyltriazolylmethyl)amine (TBTA, 0.027 g, 0.040 mmol, 0.4 equiv), and tetrakis(acetonitrile)copper(i) hexafluorophosphate (0.0265 g, 0.050 mmol, 0.5 equiv) were added to a small vial and dissolved in CHCl₃ (1.5 mL). Two additions of tetrakis(acetonitrile)copper(i) hexafluorophosphate (0.0202 g+0.0200 g) were added over the next 24 hours, and after 2 hours the reaction was complete by LC-MS. The solution was filtered over alumina and purified by preparative gel permeation chromatography (CHCl₃) to afford the PTX₃-NHS intermediate as a white powder (0.232 g, 0.063 mmol, 59% yield). A portion of this intermediate (0.223 g, 0.061 mmol, 1 equiv) was dissolved in CHCl₃ and 11-azido-3-6-9-trioxaundecaneamine (0.033 g, 0.151 mmol, 2.5 equiv) was added in 0.2 mL of CHCl₃. The reaction was stirred for 12 house at room temperature and purified by preparative gel permeation chromatography (CHCl₃) to yield PTXW-N₃ as a colorless powder (0.154 g, 0.041 mmol, 67% yield). The MALDI spectrum for PTXW-N₃ is shown in FIG. 46.

Example 13: Synthesis of TelW-N₃

Scheme 13: Synthesis of TelW-N₃.

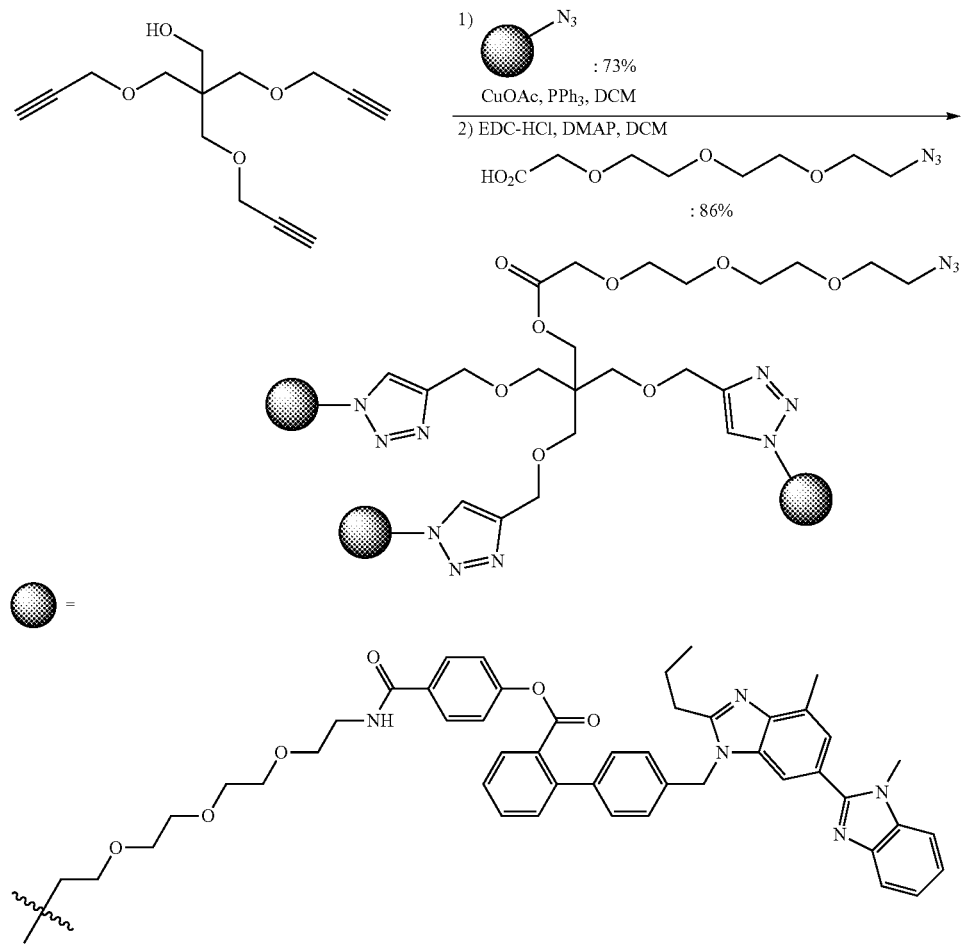

Tel-N₃ (0.802 g, 0.959 mmol, 3.2 equiv) and yne₃-OH (0.075 g, 0.300 mmol, 1 equiv) were loaded to a vial and transported to a glovebox where 10 mL of a freshly prepared solution of CuOAc/PPh₃ (3 mM and 6 mM, respectively) in DCM was added. The reaction was stirred at room temperature for 12 hours at which time LC-MS indicated the reaction was complete. The reaction was then filtered over silica (10:1 DCM:MeOH) to afford the Tel₃OH intermediate which was used in the next step without purification (0.560 g). A portion of this material (0.501 g, ~0.181 mmol) was added to a vial with EDC-HCl (0.120 g, 1.00 mmol), azido-3,6,9,12-tetraoxatetradecanoic acid (0.132 g, 0.477 mmol) and DMAP (. DCM (10 mL) was added and the reaction was stirred at room temperature for 3 hours after which time LC-MS indicated the reaction to be complete. The volatiles were evaporated and the residue was purified by preparative gel permeation chromatography (CHCl₃) to afford Tel as a white powder (0.512 g, 0.178 mmol, 59% over two steps).

4) Generation 2 Branched Norbornene Macromonomers

Example 14: Synthesis of G2-Nb-Yne-PEG

Scheme 14: Synthesis of G2-Nb-yne-PEG.

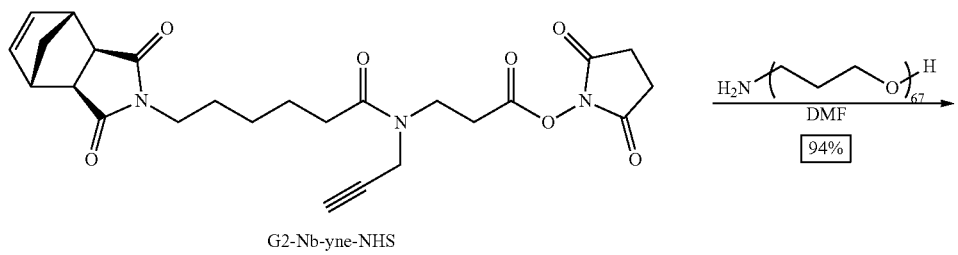

G2-Nb-yne-NHS

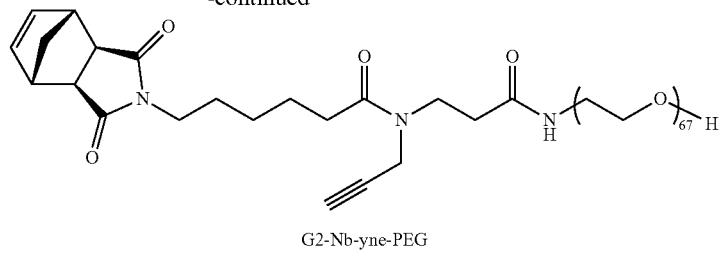

G2-Nb-yne-PEG

Figure 18:
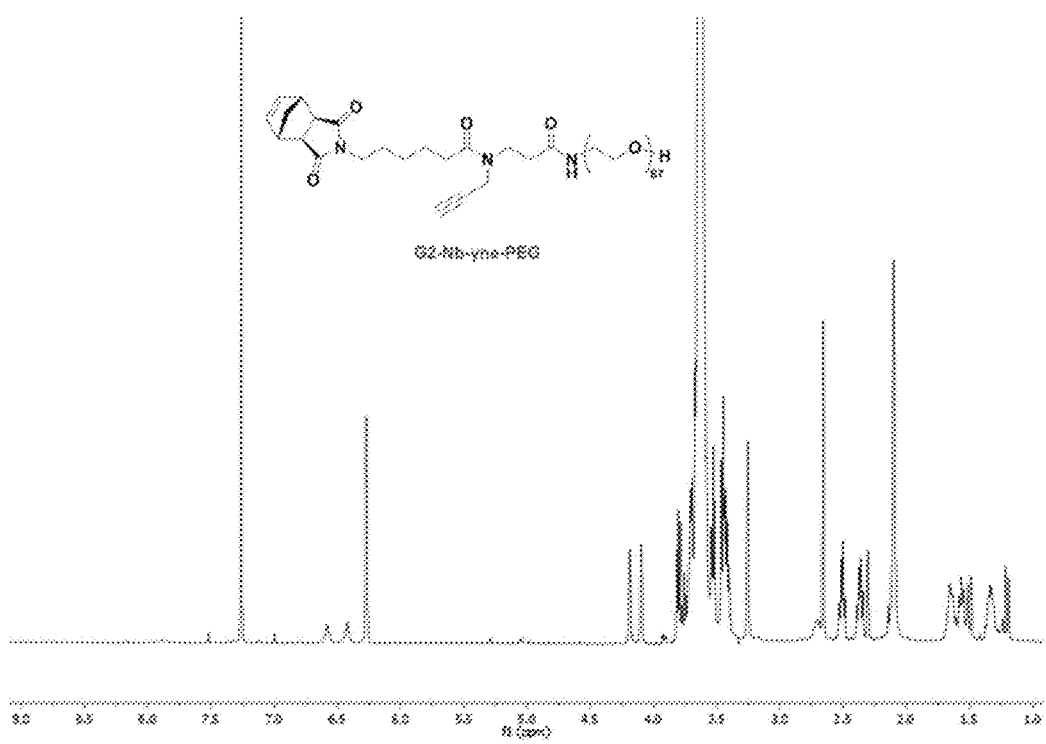
FIG. 18 shows the $^1$H NMR spectrum of G2-Nb-yne-PEG in $CDCl_3$.
Figure 19:
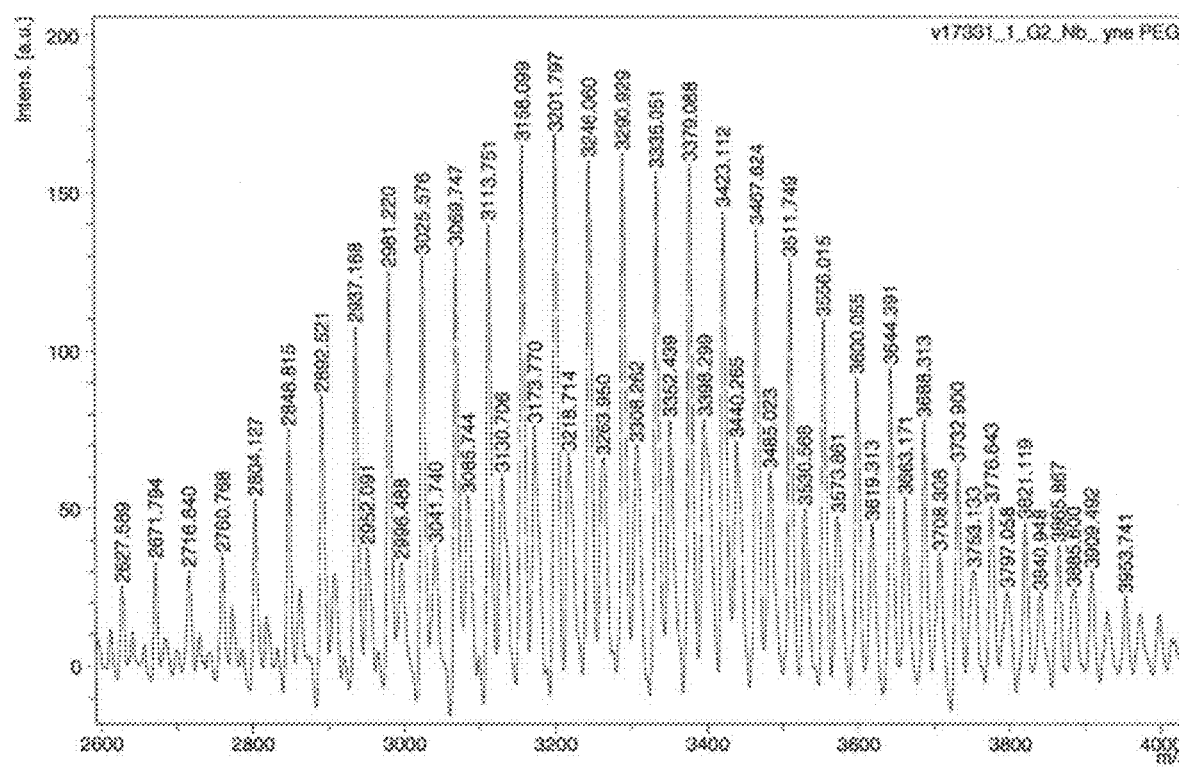
FIG. 19 shows the MALDI spectrum of G2-Nb-yne-PEG. $C_{157}H_{300}N_3O_{72}$: Calculated m/z=3380.24; Found: 3379.088 $[M+H]^+$. $C_{157}H_{302}N_3O_{73}$: Calculated m/z=3398.25; Found: 3398.299 $[M+H_3O]^+$.

G2-Nb-yne-PEG was prepared following a literature procedure with slight modifications.[40] Into a round-bottom flask (RBF), G2-Nb-yne-NHS (0.260 g, 0.538 mmol, 1.24 eq) and O-(2-aminoethyl)poly(ethylene glycol) (1.30 g, 0.434 mmol, 1.0 eq) were added. DMF (26.0 mL) was then added, and the resulting solution was stirred overnight. The solution was then added dropwise into stirring diethyl ether (300 mL), affording G2-Nb-yne-PEG as a white precipitate. The mixture was then subjected to centrifugation (4000 rpm, 15 min), and the ether can then be decanted. The white solid was washed with ether followed by centrifugation and decantation another 2 times, affording pure G2-Nb-yne-PEG as a white solid (1.37 g, 94% yield). $^1$H NMR and MALDI spectra are shown in FIGS. 18 and 19, respectively.

Example 15: Synthesis of G2-Nb-TEG-MM

Scheme 15: Synthesis of G2-Nb-TEG-MM.

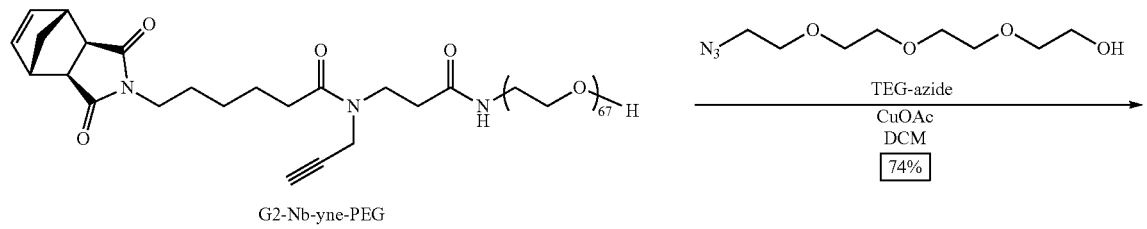

G2-Nb-yne-PEG

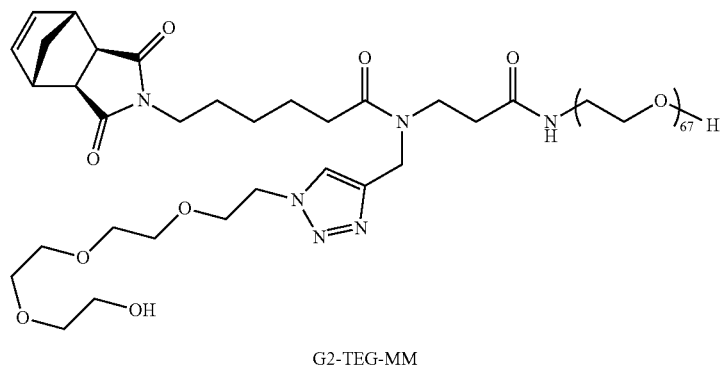

G2-TEG-MM

Figure 22:
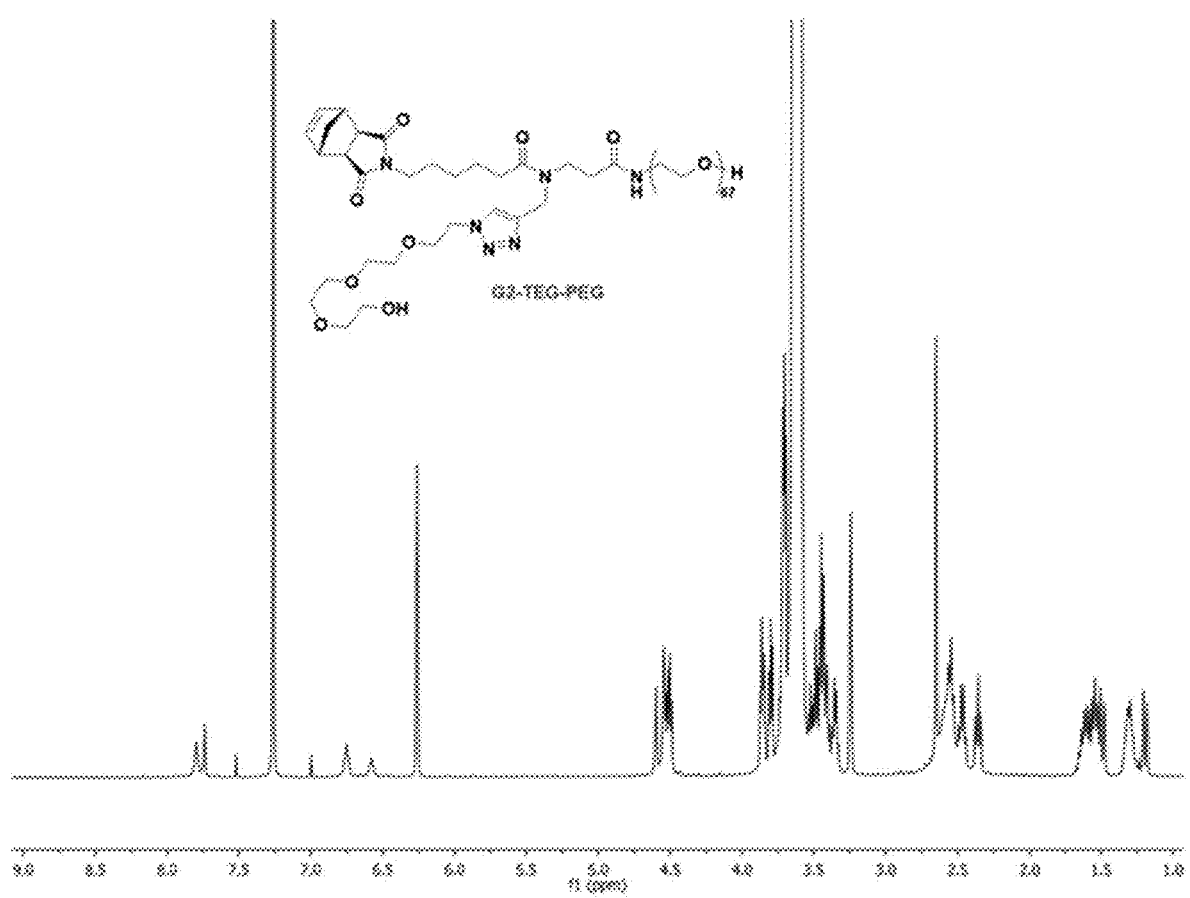
FIG. 22 shows the $^1$H NMR spectrum of G2-TEG-PEG in $CDCl_3$.
Figure 23:
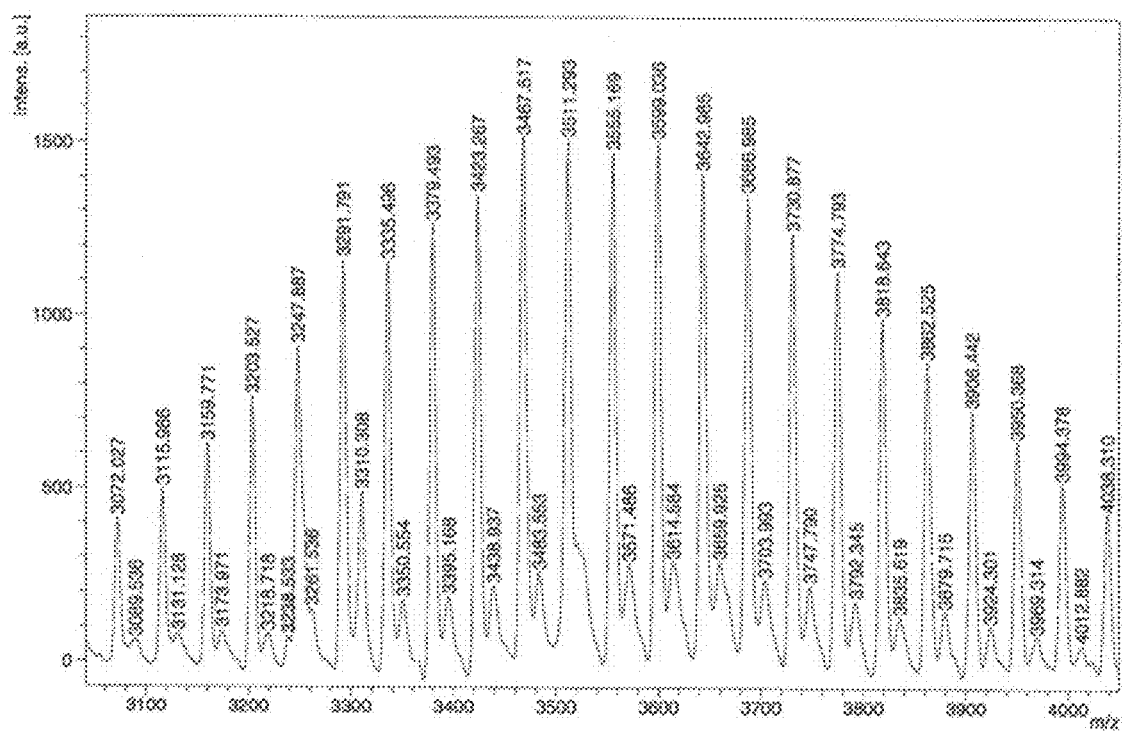
FIG. 23 shows the MALDI spectrum of G2-TEG-PEG. $C_{165}H_{317}N_6O_{76}$. Calculated m/z=3599.36; Found: 3599.036 $[M+H]^+$. $C_{165}H_{319}N_6O_{77}$. Calculated m/z=3616.35; Found: 3614.584 $[M+H_3O]^+$.

To a vial, G2-Nb-yne-PEG (150.0 mg, 0.044 mmol, 1.0 eq), TEG-azide (14.5 mg, 0.066 mmol, 1.5 eq) and DCM (2.0 mL) were added. Copper(I) acetate (CuOAc) (a pinch) was then added, and the reaction mixture was stirred under nitrogen. Completion of the click reaction was followed by LC-MS, and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (119 mg, 74% yield). $^1$H NMR and MALDI spectra are shown in FIGS. 22 and 23, respectively.

Example 16: Synthesis of G2-PTX-MM

Scheme 16: Synthesis of G2-PTX-MM.

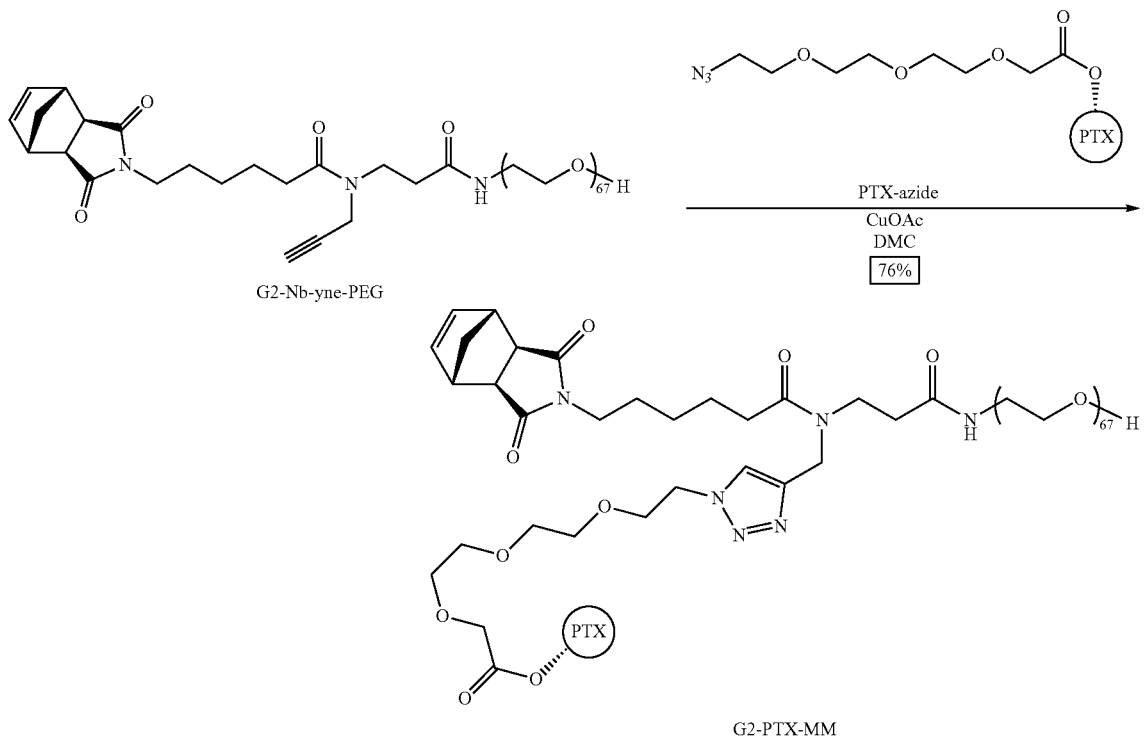

Figure 24:
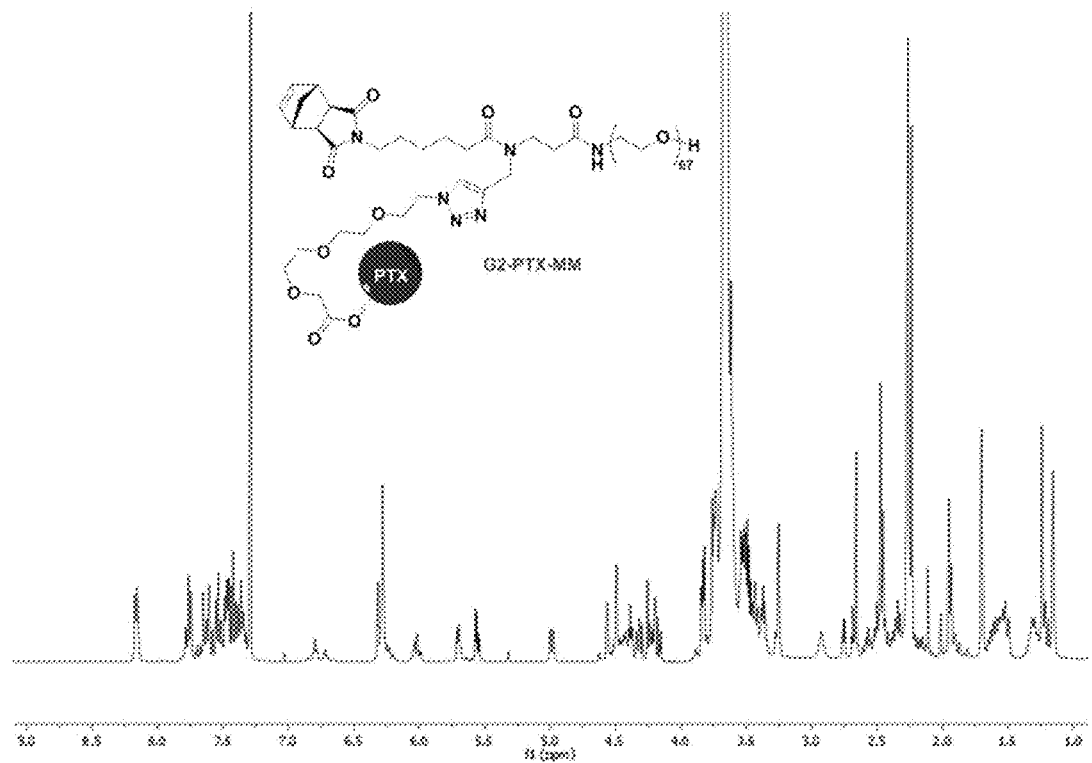
FIG. 24 shows the $^1$H NMR spectrum of G2-PTX-MM in $CDCl_3$.
Figure 25:
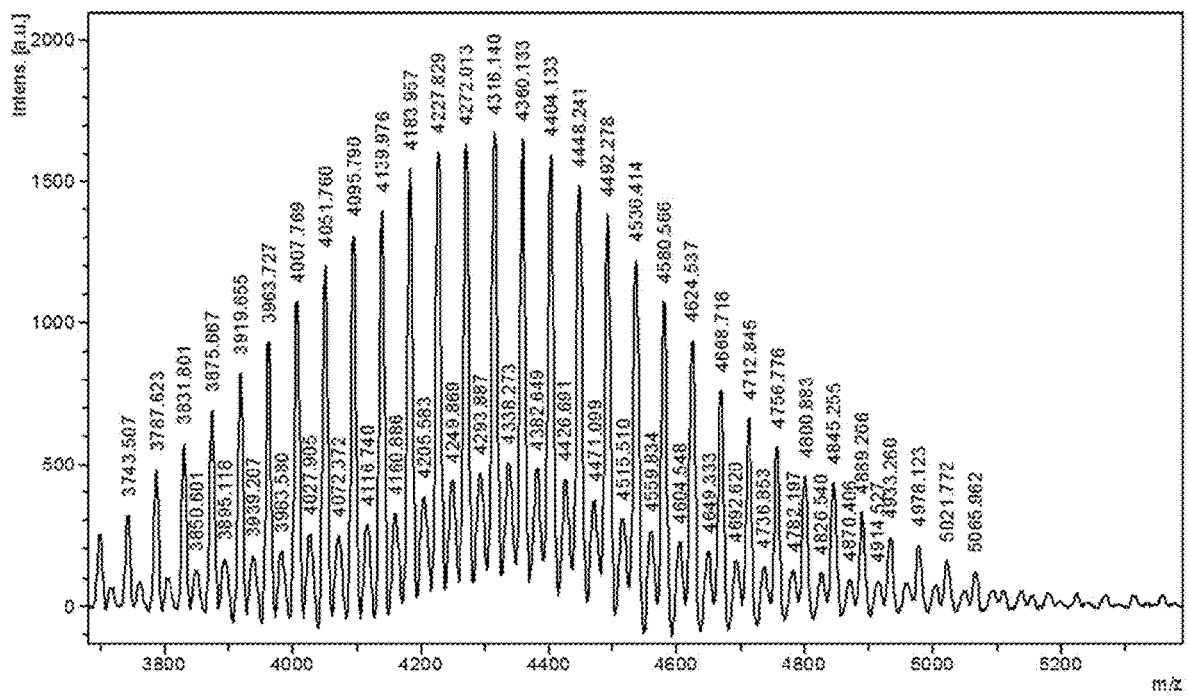
FIG. 25 shows the MALDI spectrum of G2-PTX-MM. $C_{210}H_{359}N_7O_{89}$: Calculated m/z=4404.385 $[M+H]^+$; Found: 4404.133 $[M+H]^+$. Calculated m/z=4426.367 $[M+Na]^+$; Found: 446.691 $[M+Na]^+$.

To a vial, G2-Nb-yne-PEG (113.6 mg, 0.033 mmol, 1.0 eq), PTX-azide (50.0 mg, 0.047 mmol, 1.4 eq) and DCM (2 mL) were added. A pinch of CuOAc was then added, and the reaction mixture was stirred under nitrogen. Completion of the click reaction was followed by LC-MS, and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (114 mg, 76% yield). $^1$H NMR and MALDI spectra are shown in FIGS. 24 and 25, respectively.

Example 17: Synthesis of G2-Nb-Yne$_2$-PEG

Scheme 17: Synthesis of G2-Nb-yne$_2$-PEG.

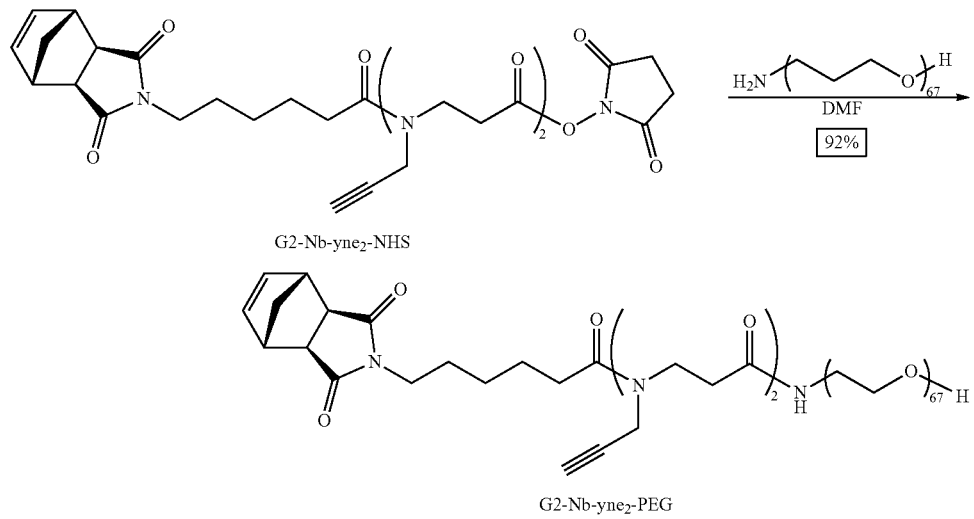

Figure 72:
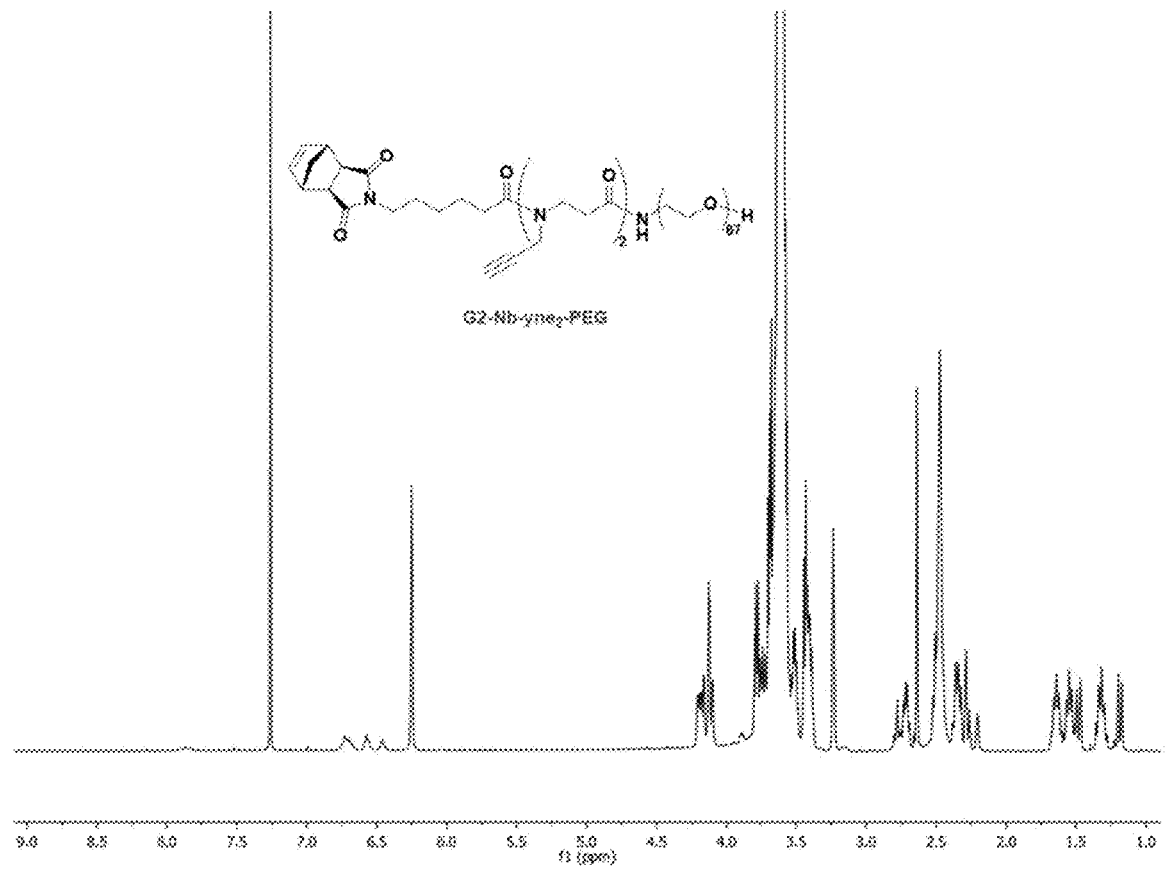
FIG. 72 shows the $^1$H NMR spectrum of G2-Nb-yne$_2$-PEG in CDCl$_3$.
Figure 73:
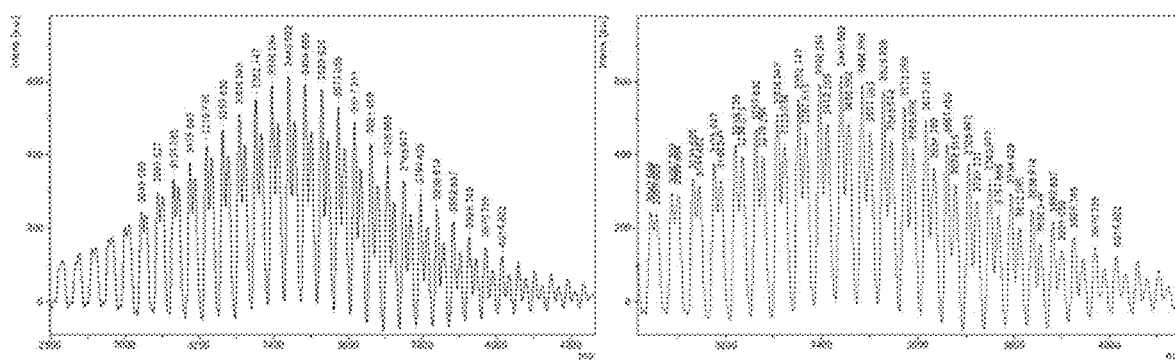
FIG. 73 shows the MALDI spectrum of G2-Nb-yne$_2$-PEG. $C_{163}H_{306}N_4O_{73}K$ calcd m/z=3527.24; Found: 3528.928 [M+K]$^+$. $C_{163}H_{306}N_4O_{73}$: calcd m/z=3545.25; Found: 3545.544 [M+H$_2$O+K]$^+$.

G2-Nb-yne$_2$-PEG was prepared following a literature procedure with slight modifications.[40] Into a round-bottom flask (RBF), G2-Nb-yne$_2$-NHS (70 mg, 0.118 mmol, 1.2 eq) and O-(2-aminoethyl)poly(ethylene glycol) (295.3 mg, 0.098 mmol, 1.0 eq) were added. DMF (4.0 mL) was then added, and the resulting solution was stirred overnight. The solution was then added dropwise into stirring diethyl ether (150 mL), affording G2-Nb-yne$_2$-PEG as a white precipitate. The mixture was then subjected to centrifugation (4000 rpm, 15 min), and the ether can then be decanted. The white solid was washed with ether followed by centrifugation and decantation another 2 times, affording pure G2-Nb-yne$_2$-PEG as a white solid (313.3 mg, 94% yield). $^1$H NMR and MALDI spectra are shown in FIGS. 72 and 73, respectively.

Example 18: Synthesis of G2-Nb-yne$_3$-PEG

Scheme 18: Synthesis of G2-Nb-yne$_3$-PEG.

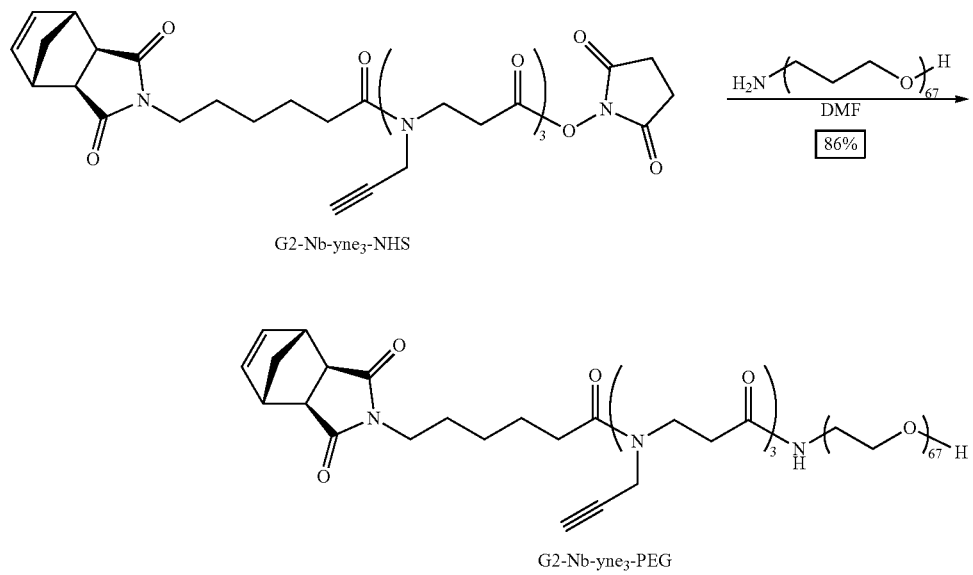

Figure 74:
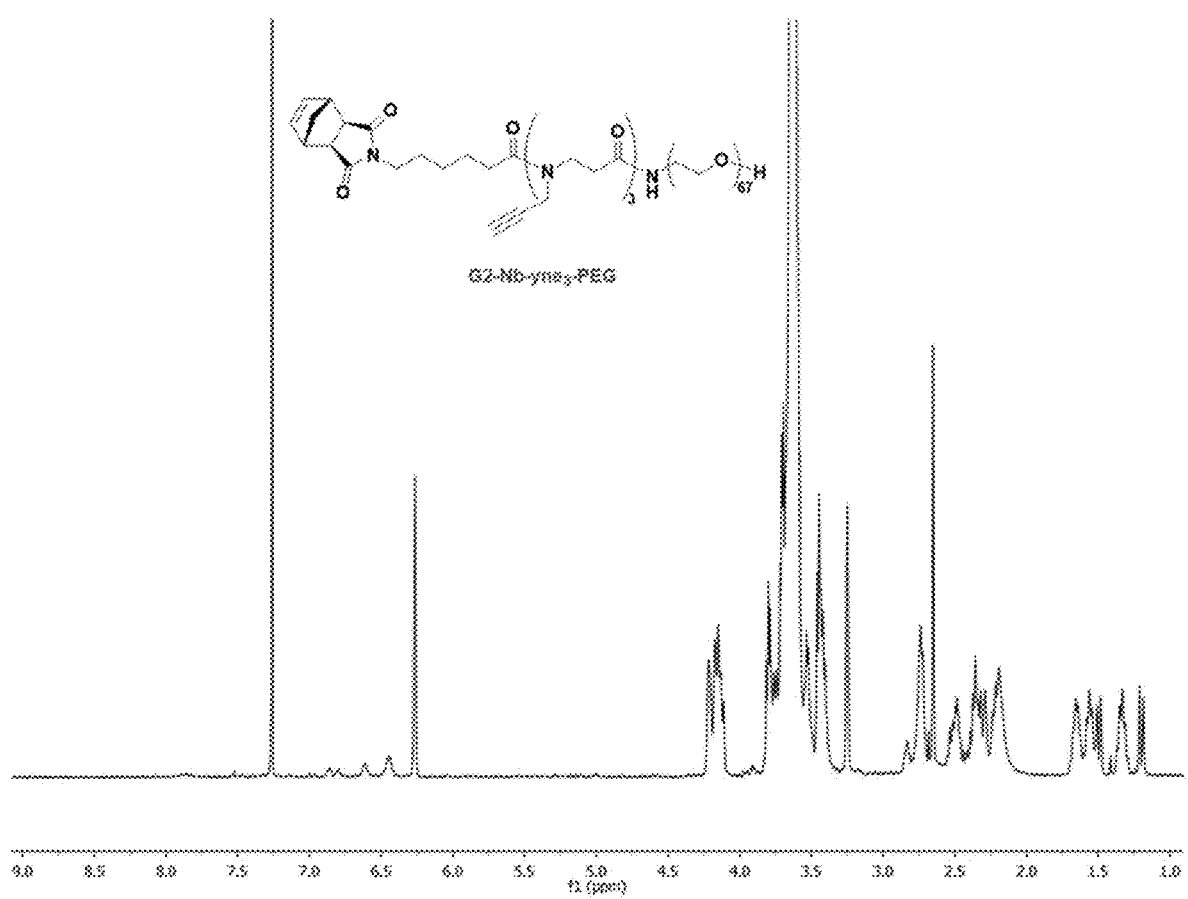
FIG. 74 shows the $^1$H NMR spectrum of G2-Nb-yne$_3$-PEG in CDCl$_3$.
Figure 75:
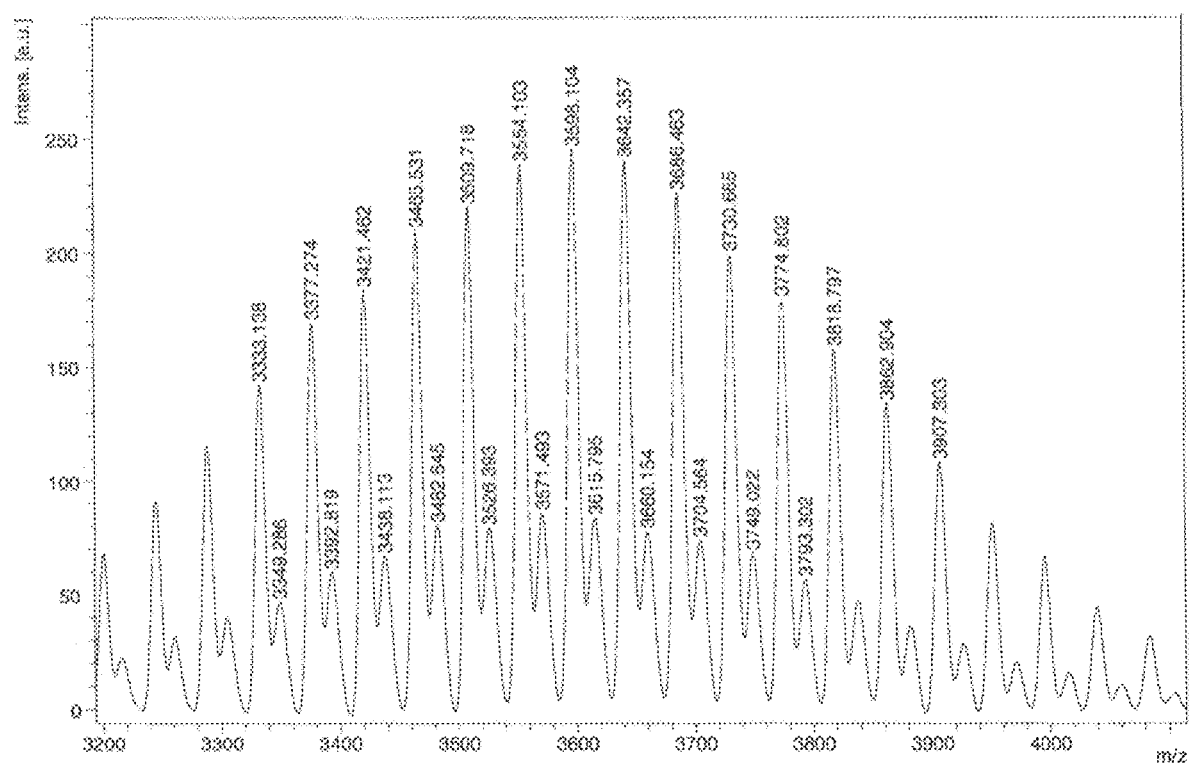
FIG. 75 shows the MALDI spectrum of G2-Nb-yne$_3$-PEG. $C_{169}H_{314}N_5O_{74}$: calcd m/z=3598.34; Found: 3598.104 [M+H]$^+$. $C_{169}H_{316}N_5O_{75}$: calcd m/z=3616.35; Found: 3615.795 [M+H$_3$O]$^+$.
Figure 76:
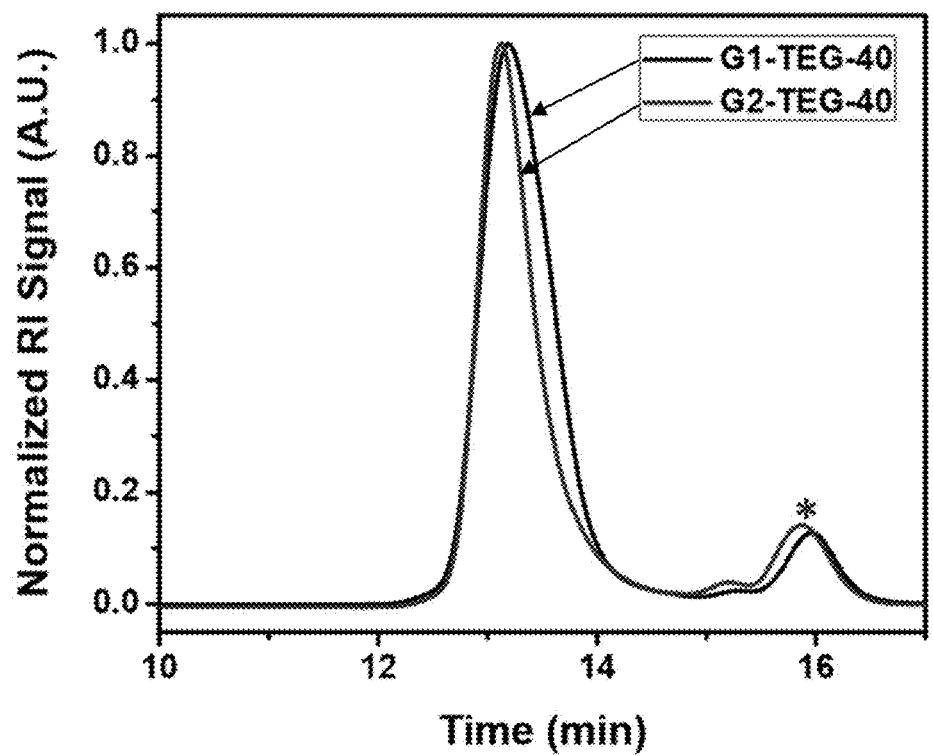
FIG. 76 shows the GPC traces of G1-TEG-40 and G2-TEG-40. * indicates residual MM. The MM-to-BP conversions were determined be >90% for all polymerizations.

G2-Nb-yne$_3$-PEG was prepared following a literature procedure with slight modifications.[40] Into a round-bottom flask (RBF), G2-Nb-yne$_3$-NHS (0.767 g, 1.09 mmol, 1.2 eq) and O-(2-aminoethyl)poly(ethylene glycol) (2.74 g, 0.913 mmol, 1.0 eq) were added. DMF (44.0 mL) was then added, and the resulting solution was stirred overnight. The solution was then added dropwise into stirring diethyl ether (150 mL), affording G2-Nb-yne$_3$-PEG as a white precipitate. The mixture was then subjected to centrifugation (4000 rpm, 15 min), and the ether can then be decanted. The white solid was washed with ether followed by centrifugation and decantation another 2 times, affording pure G2-Nb-yne$_2$-PEG as a white solid (2.81 g, 86% yield). $^1$H NMR and MALDI spectra are shown in FIGS. 74 and 75, respectively.

Example 19: Synthesis of G2-Nb-TEG-PEG

Scheme 19: Synthesis of G2-Nb-TEG-PEG.

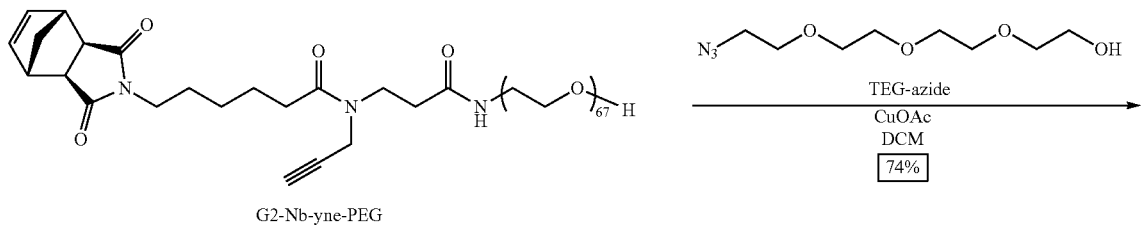

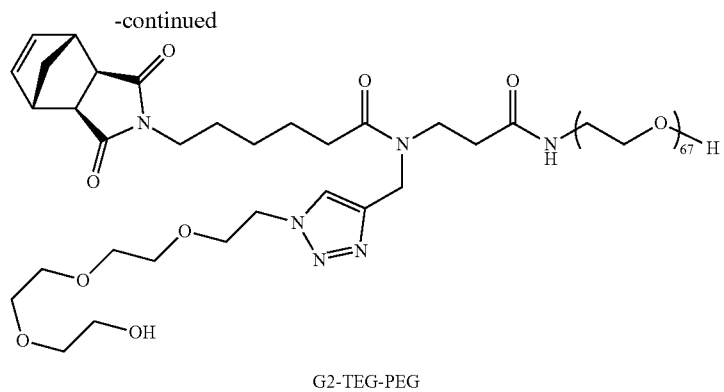

G2-TEG-PEG

To a vial, G2-Nb-yne-PEG (150.0 mg, 0.044 mmol, 1.0 eq), TEG-azide (14.5 mg, 0.066 mmol, 1.5 eq) and DCM (2.0 mL) were added. Copper(I) acetate (CuOAc) (a pinch) was then added, and the reaction mixture was stirred under nitrogen. Completion of the click reaction was followed by LC-MS (~1 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (119 mg, 74% yield).

Example 20: Synthesis of G2-Nb-TEG$_2$-PEG

Scheme 20: Synthesis of G2-Nb-TEG$_2$-PEG.

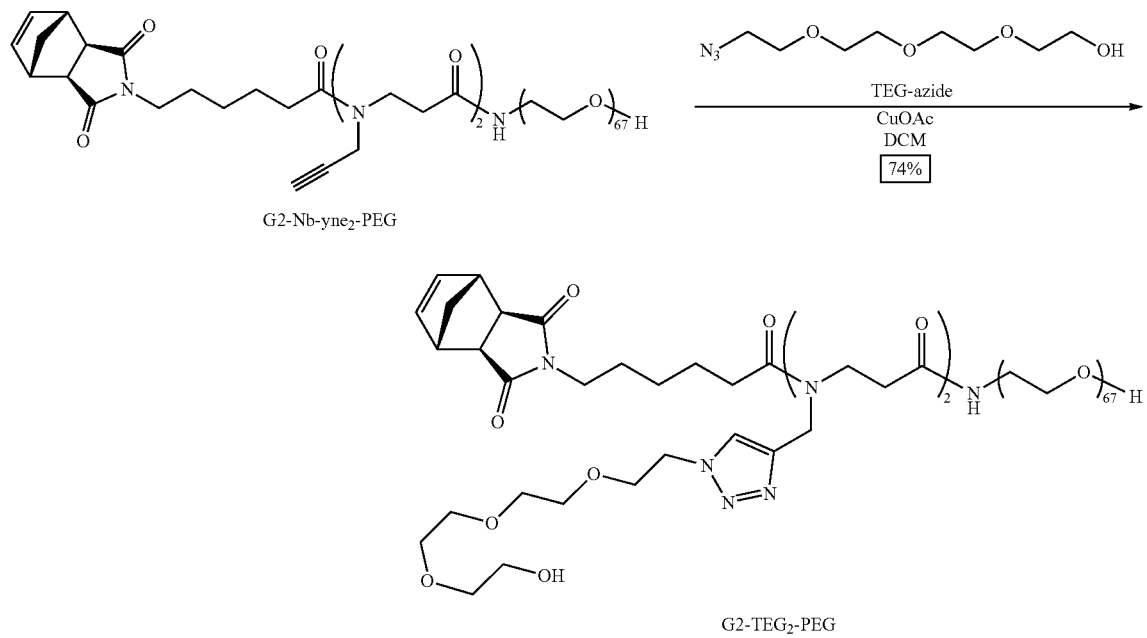

Figure 77:
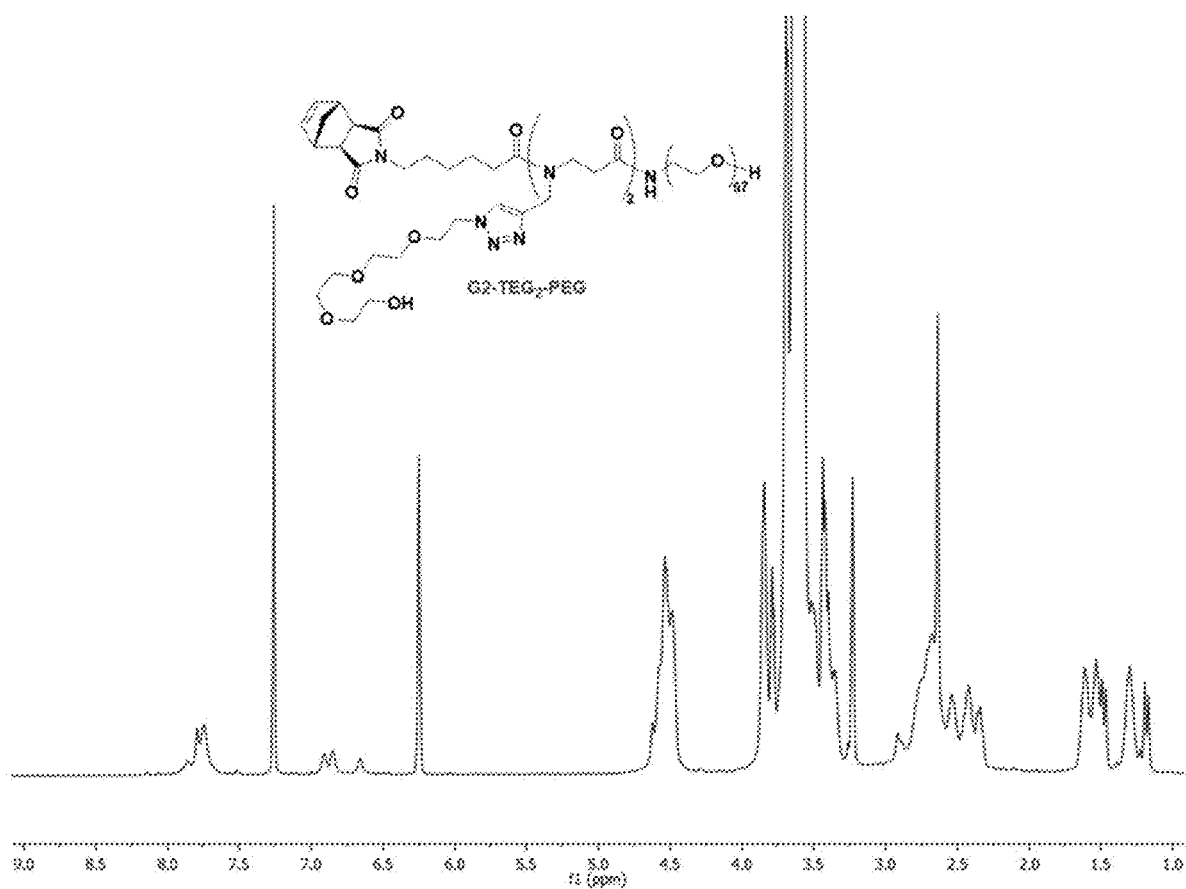
FIG. 77 shows the $^1$H NMR spectrum of G2-TEG$_2$-PEG in CDCl$_3$.
Figure 78:
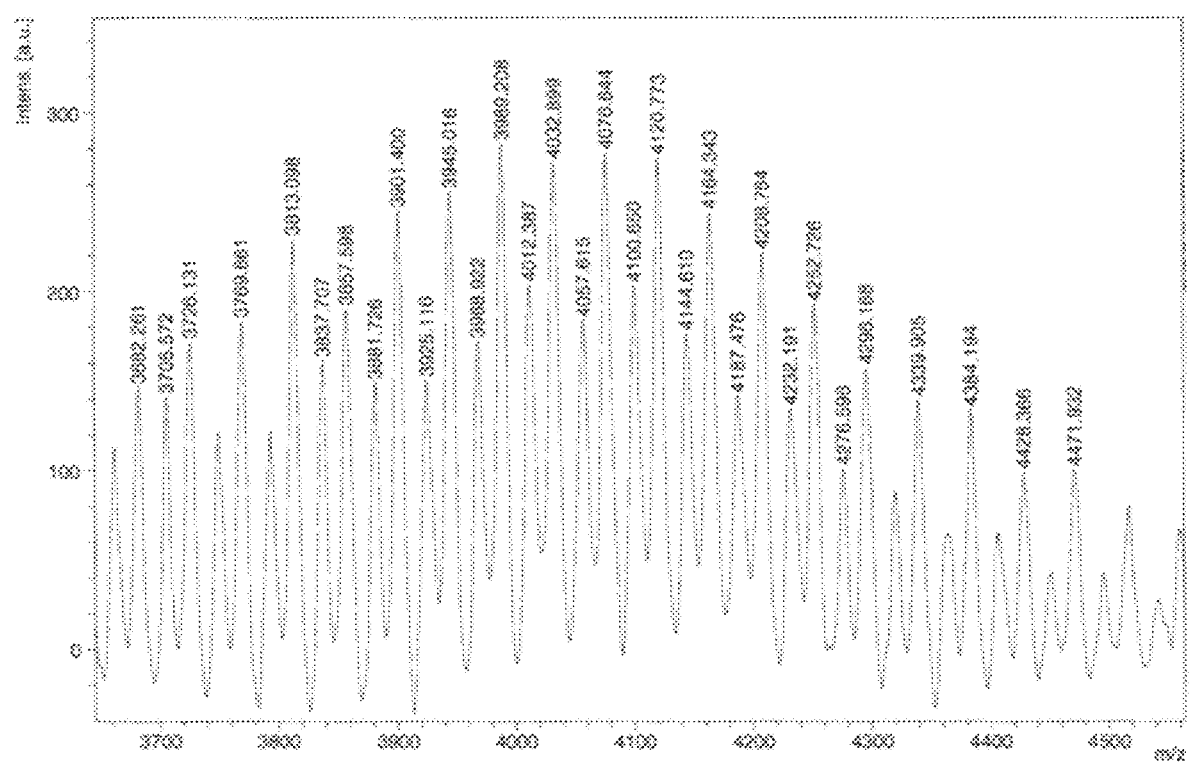
FIG. 78 shows the MALDI spectrum of G2-TEG$_2$-PEG. $C_{179}H_{341}N_{10}O_{81}$: calcd m/z=3927.53; Found: 3925.116 [M+H]$^+$. $C_{179}H_{343}N_{10}O_{82}$: calcd m/z=3945.54; Found: 3945.016 [M+H$_3$O]$^+$.

To a vial, G2-Nb-yne$_2$-PEG (130.0 mg, 0.037 mmol, 1.0 eq), TEG-azide (19.7 mg, 0.090 mmol, 2.4 eq) and DCM (3.0 mL) were added. Copper(I) acetate (CuOAc) (a pinch) was then added, and the reaction mixture was stirred under nitrogen. Completion of the click reaction was followed by LC-MS (~2.5 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (110 mg, 75% yield). $^1$H NMR and MALDI spectra are shown in FIGS. 77 and 78, respectively.

Example 21: Synthesis of G2-Nb-TEG₃-PEG

Scheme 21: Synthesis of G2-Nb-TEG₃-PEG.

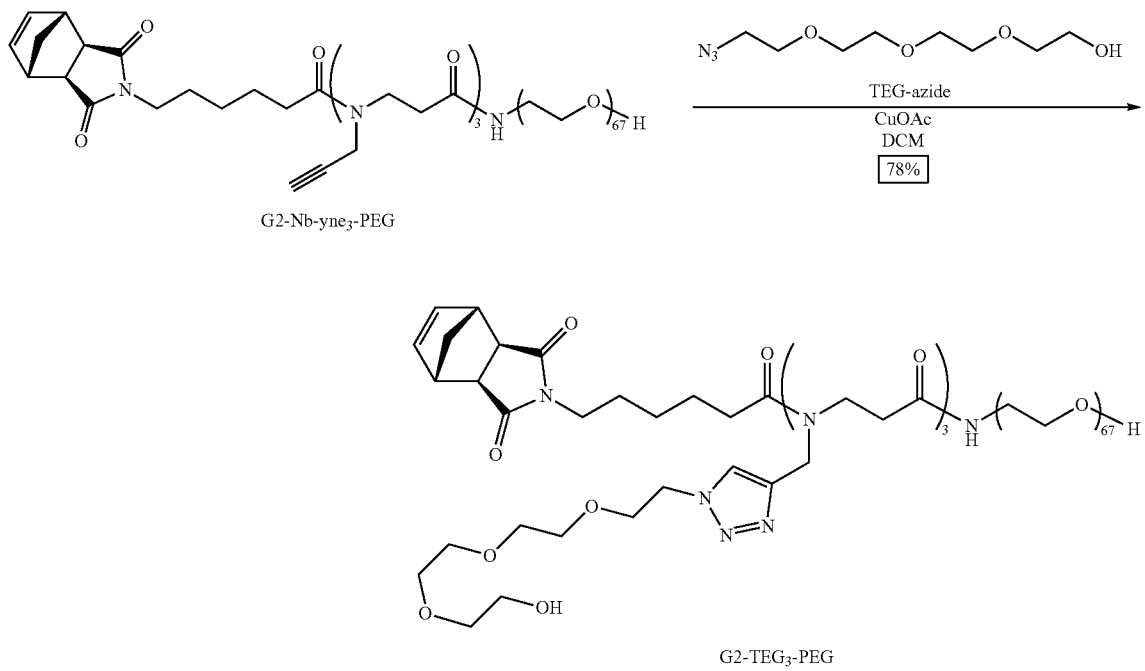

Figure 79:
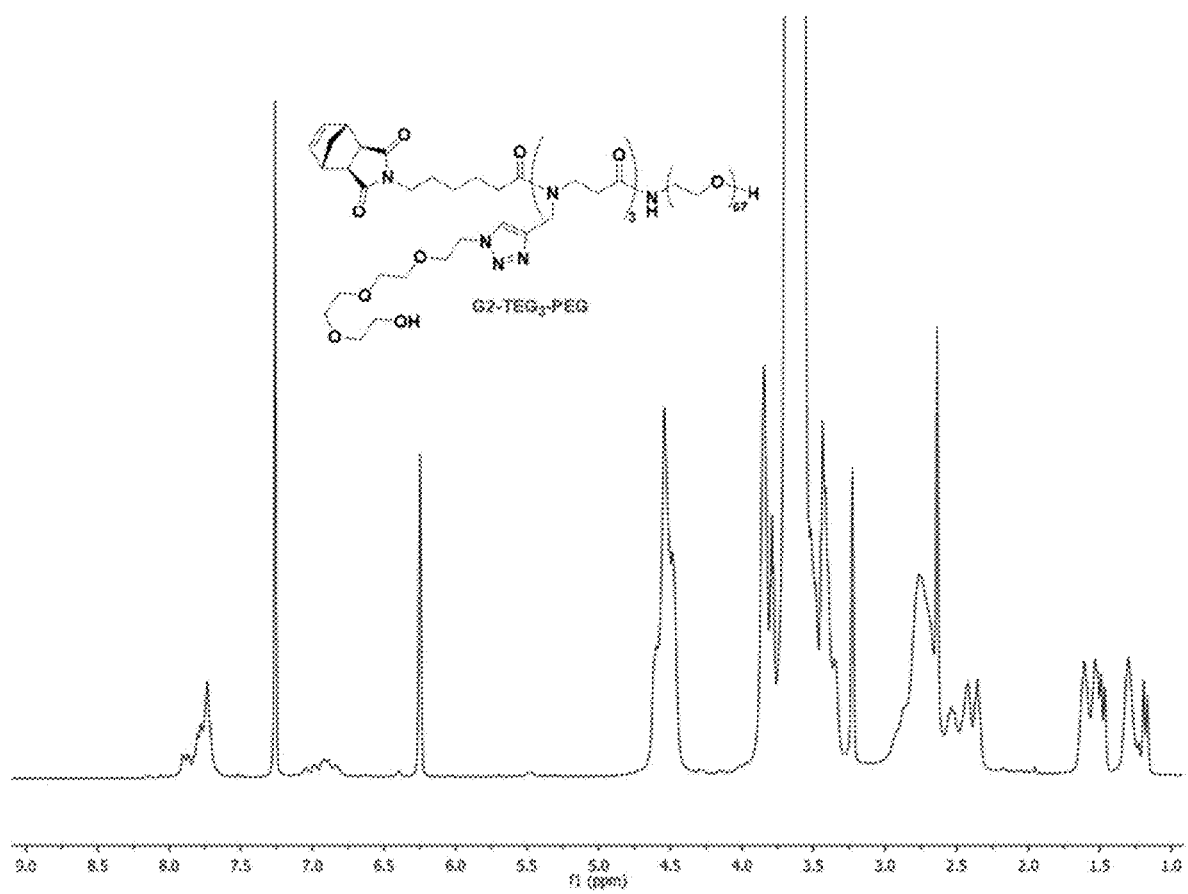
FIG. 79 shows the $^1$H NMR spectrum of G2-TEG$_3$-PEG in CDCl$_3$.
Figure 80:
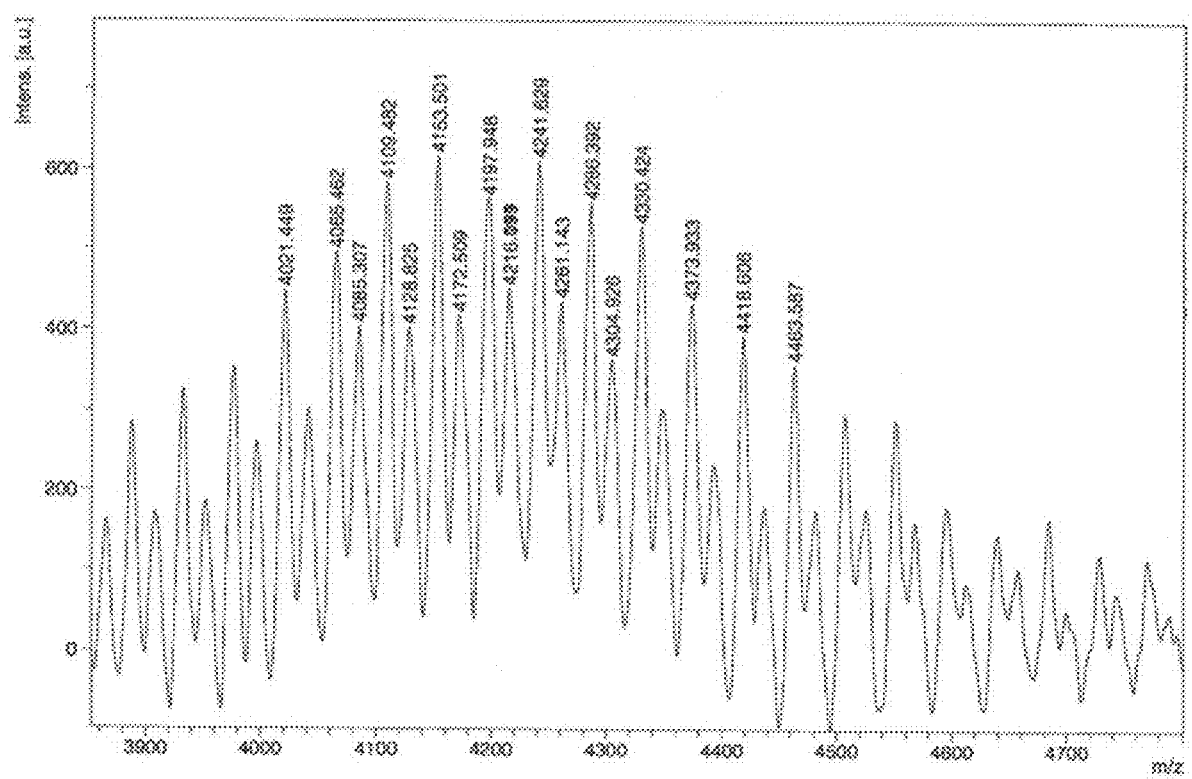
FIG. 80 shows the MALDI spectrum of G2-TEG$_3$-PEG. $C_{193}H_{364}N_{14}O_{86}Li$ calcd m/z=4261.71; Found: 4261.143 [M+Li]$^+$. $C_{194}H_{369}N_{14}O_{87}$: calcd m/z=4287.73; Found: 4286.392 [M+MeOH+H]$^+$.

To a vial, G2-Nb-yne$_2$-PEG (130.0 mg, 0.036 mmol, 1.0 eq), TEG-azide (28.6 mg, 0.130 mmol, 3.6 eq) and DCM (3.0 mL) were added. Copper(I) acetate (CuOAc) (a pinch) was then added, and the reaction mixture was stirred under nitrogen. Completion of the click reaction was followed by LC-MS (~3 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (120.4 mg, 78% yield). $^1$H NMR and MALDI spectra are shown in FIGS. 79 and 80, respectively.

Example 22: Synthesis of G2-Nb-chex-PEG

Scheme 22: Synthesis of G2-Nb-chex-PEG.

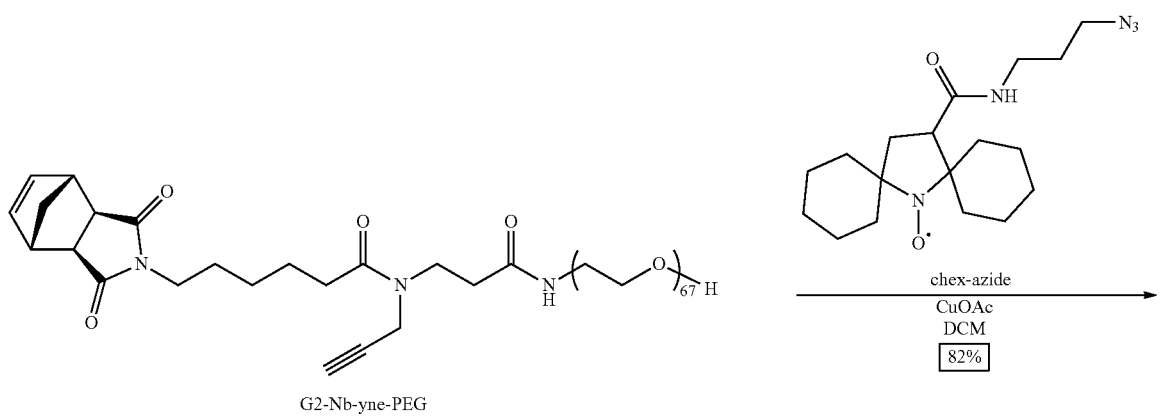

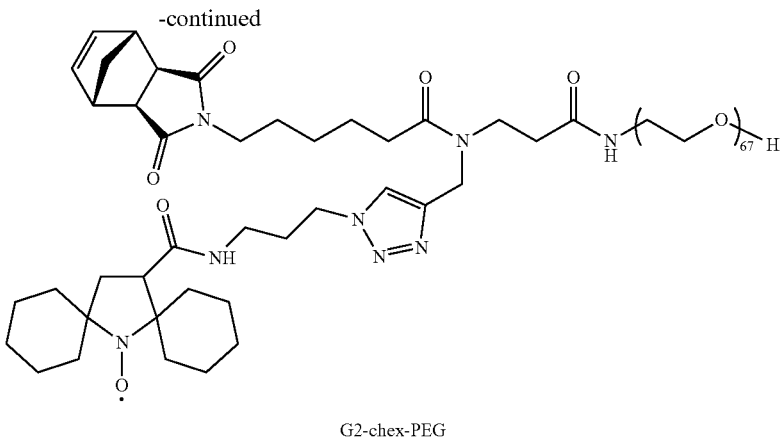

G2-chex-PEG

Figure 81:
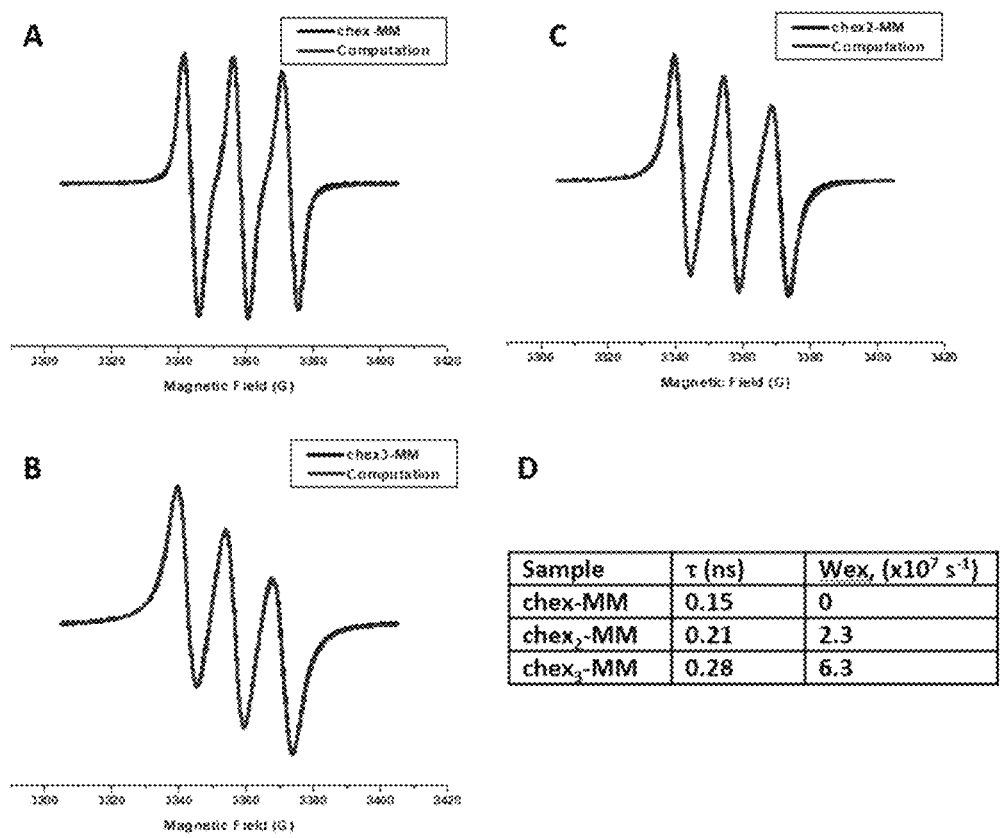
FIGS. 81A to 81D show the computational analysis of EPR spectra of G2-chex-MM, G2-chex$_2$-MM, and G2-chex$_3$-MM.
Figure 82:
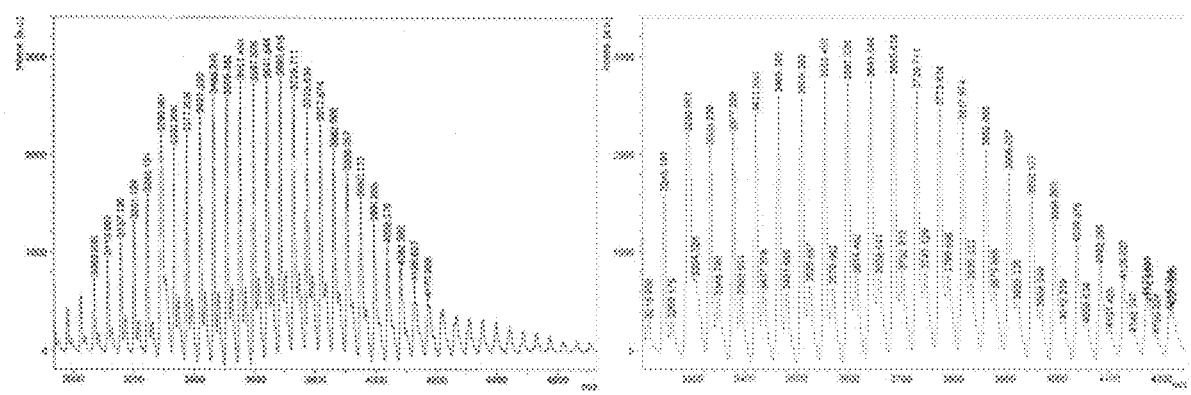
FIG. 82 shows the MALDI spectrum of G2-chex-MM. $C_{175}H_{330}N_8O_{74}$: calcd m/z=3728.48; Found: 3729.711 [M+H]$^+$. $C_{175}H_{332}N_8O_{75}$: calcd m/z=3746.49; Found: 3747.129 [M+H$_3$O]$^+$.

To a vial, G2-Nb-yne-PEG (99.0 mg, 0.029 mmol, 1.0 eq), chex-azide (12.3 mg, 0.035 mmol, 1.2 eq) and DCM (2.0 mL) were added. Copper(I) acetate (CuOAc) (a pinch) was then added, and the reaction mixture was stirred under nitrogen. Completion of the click reaction was followed by LC-MS (~1 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (90.0 mg, 82% yield). EPR and MALDI spectra are shown in FIGS. 81A and 82, respectively.

Example 23: Synthesis of G2-Nb-chex$_2$-PEG

Scheme 23: Synthesis of G2-Nb-chex$_2$-PEG.

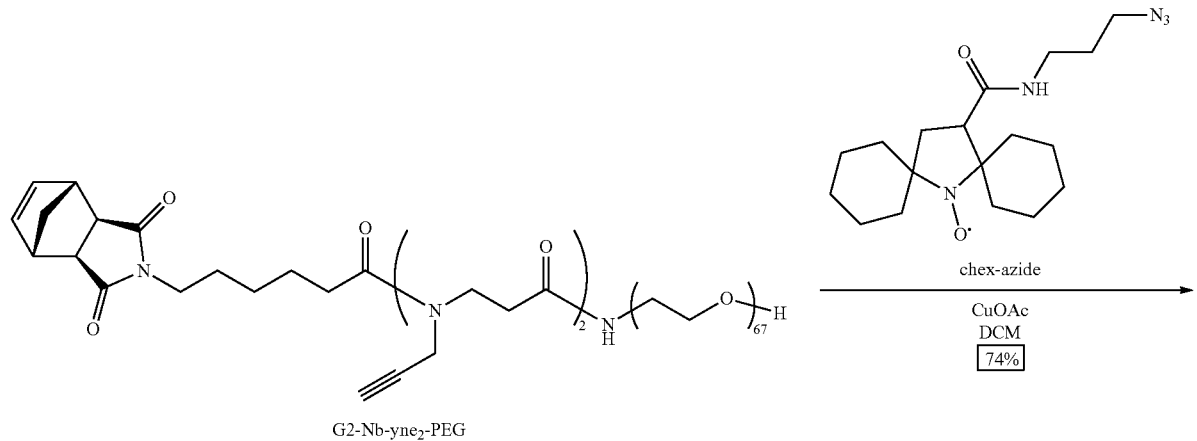

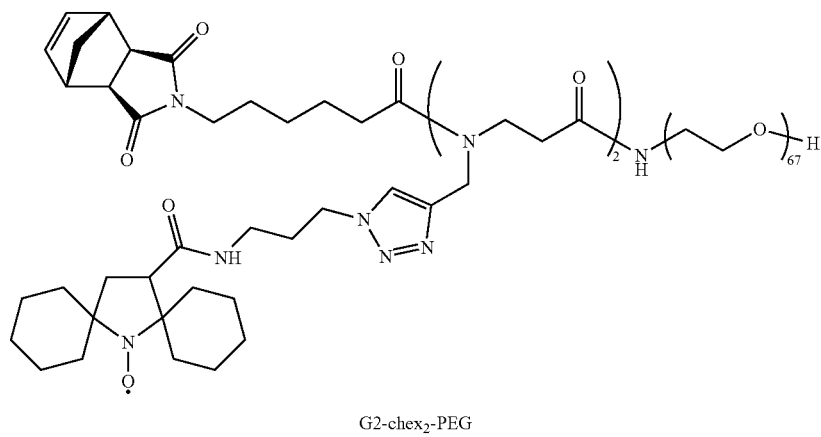

G2-chex$_2$-PEG

Figure 83:
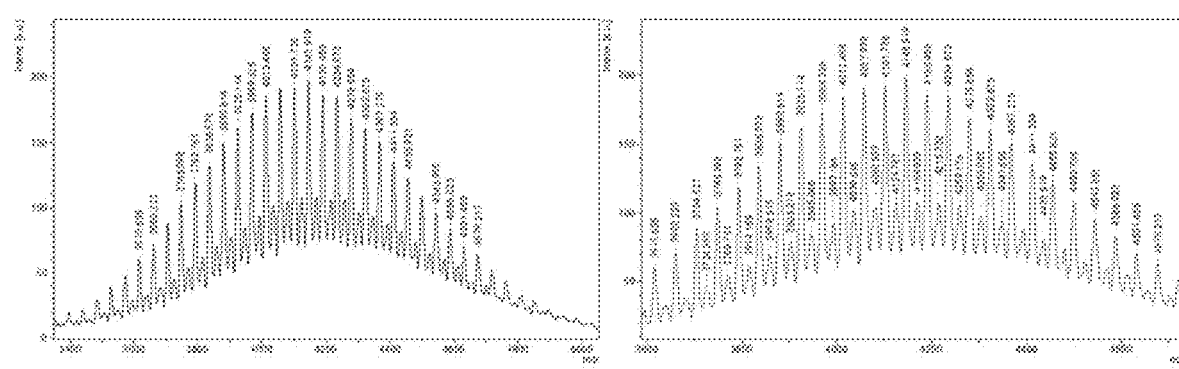
FIG. 83 shows the MALDI spectrum of G2-chex$_2$-MM. $C_{199}H_{366}N_{14}O_{77}$: calcd m/z=4191.78; Found: 4190.456 [M+Li]$^+$. $C_{199}H_{366}N_{14}O_{77}$: calcd m/z=4217.8; Found: 4215.330 [M+MeOH+H]$^+$.

To a vial, G2-Nb-yne$_2$-PEG (150.0 mg, 0.043 mmol, 1.0 eq), chex-azide (46.0 mg, 0.132 mmol, 3.0 eq) and DCM (5.0 mL) were added. Copper(I) acetate (CuOAc) (a pinch) was then added, and the reaction mixture was stirred under nitrogen. Completion of the click reaction was followed by LC-MS (~3 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (150 mg, 83% yield). EPR and MALDI spectra are shown in FIGS. 81B and 83, respectively.

Example 24: Synthesis of G2-Nb-chex$_3$-PEG

Scheme 24: Synthesis of G2-Nb-chex$_3$-PEG.

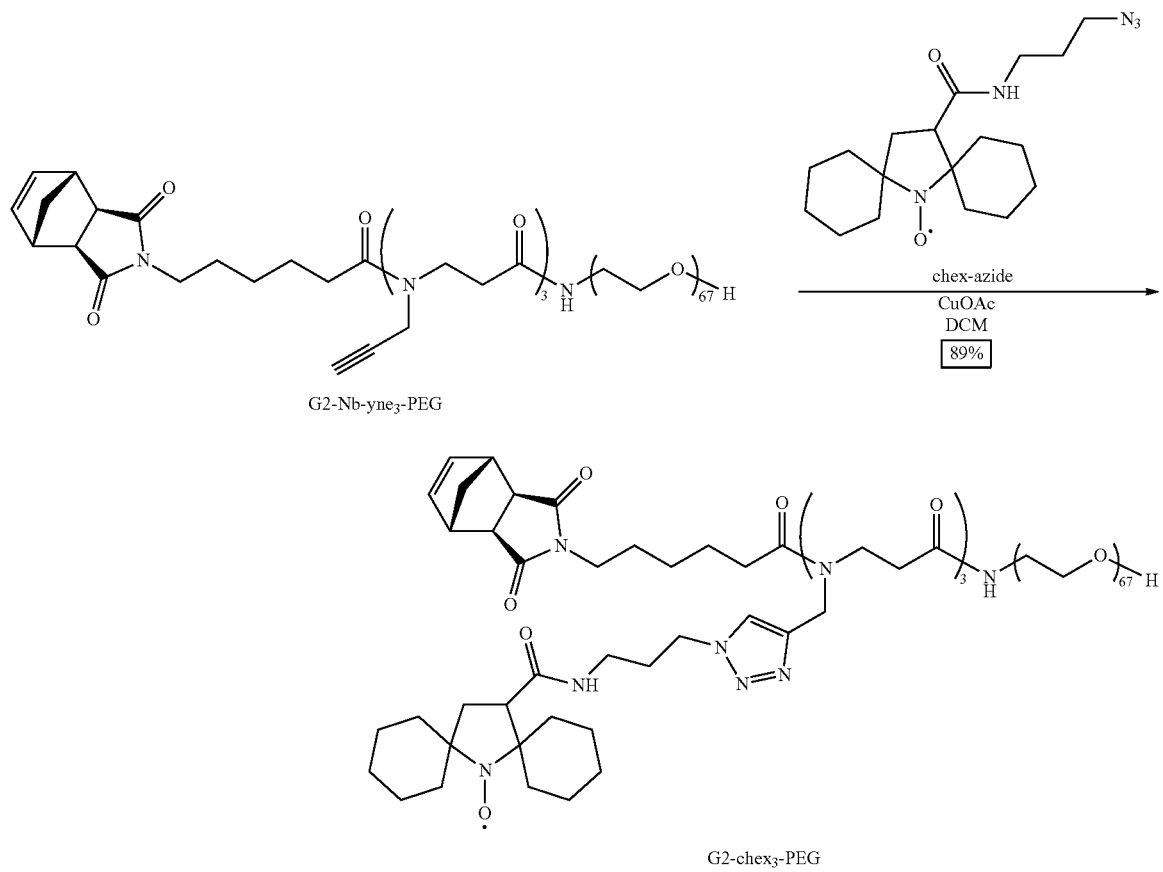

G2-Nb-yne$_3$-PEG

G2-chex$_3$-PEG

Figure 84:
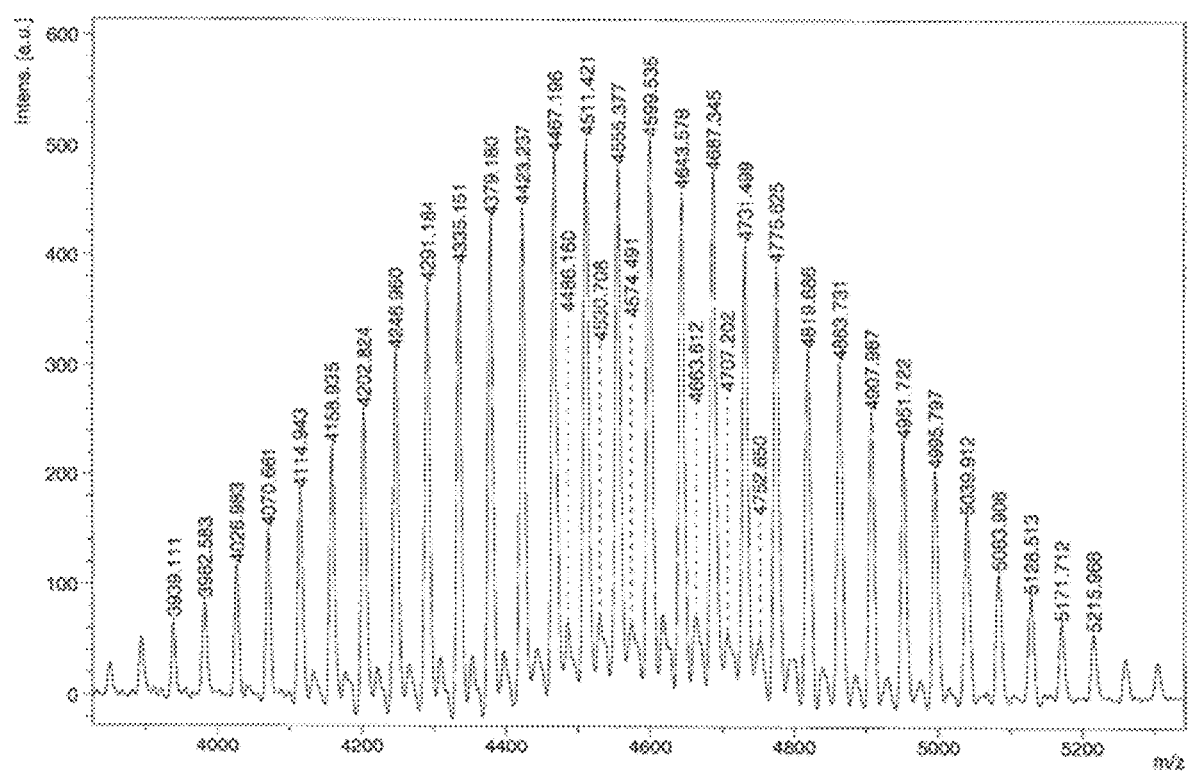
FIG. 84 shows the MALDI spectrum of G2-chex$_3$-MM. $C_{223}H_{404}N_{20}O_{80}$: calcd m/z=4643.06; Found: 4643.578 [M+H]$^+$. $C_{223}H_{403}N_{20}O_{80}Na$: calcd m/z=4665.0; Found: 4663.612 [M+Na]$^+$.
Figure 85:
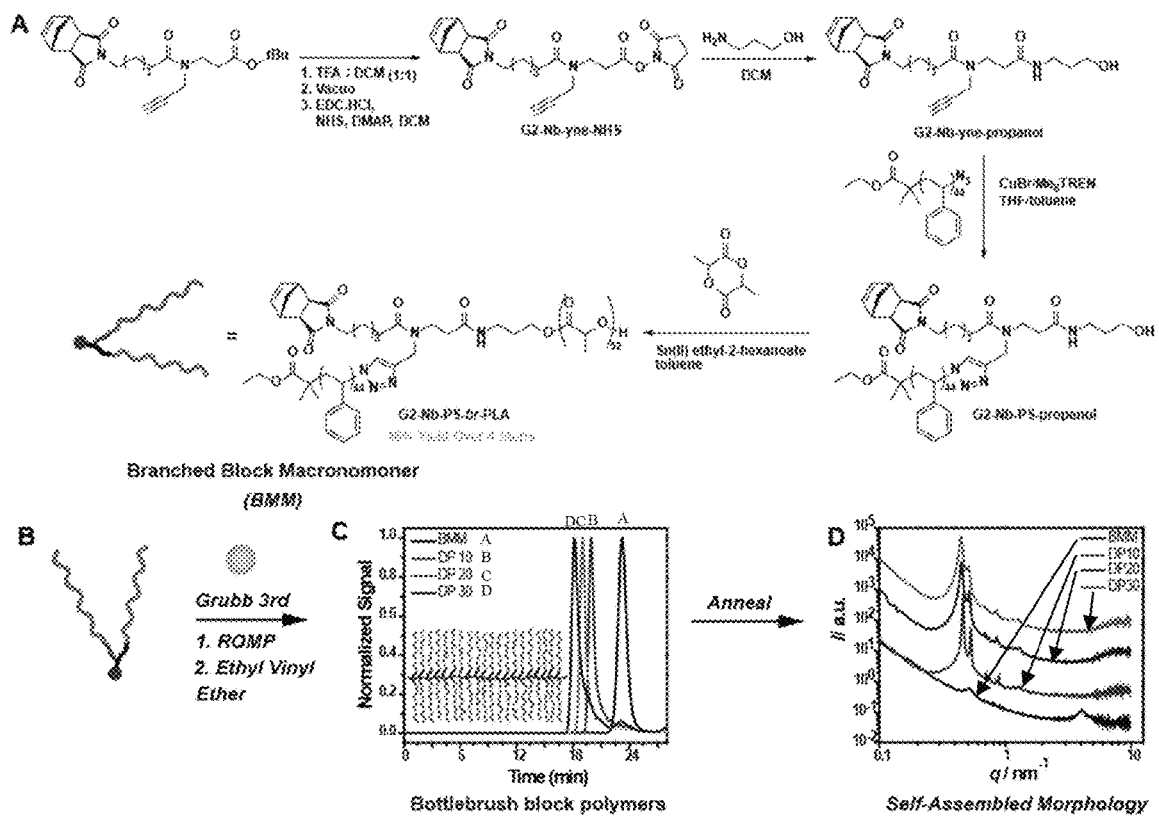
FIGS. 85A to 85D show.
Figure 86:
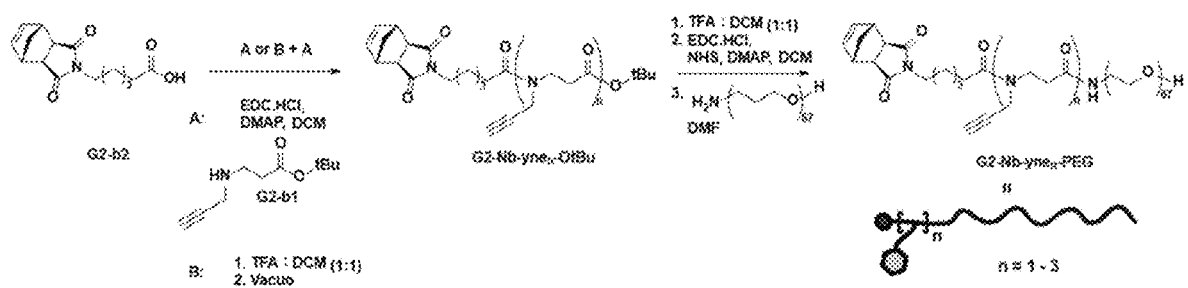
FIG. 86 shows the synthesis of MMM (multi-click macromonomer) precursors.
Figure 87:
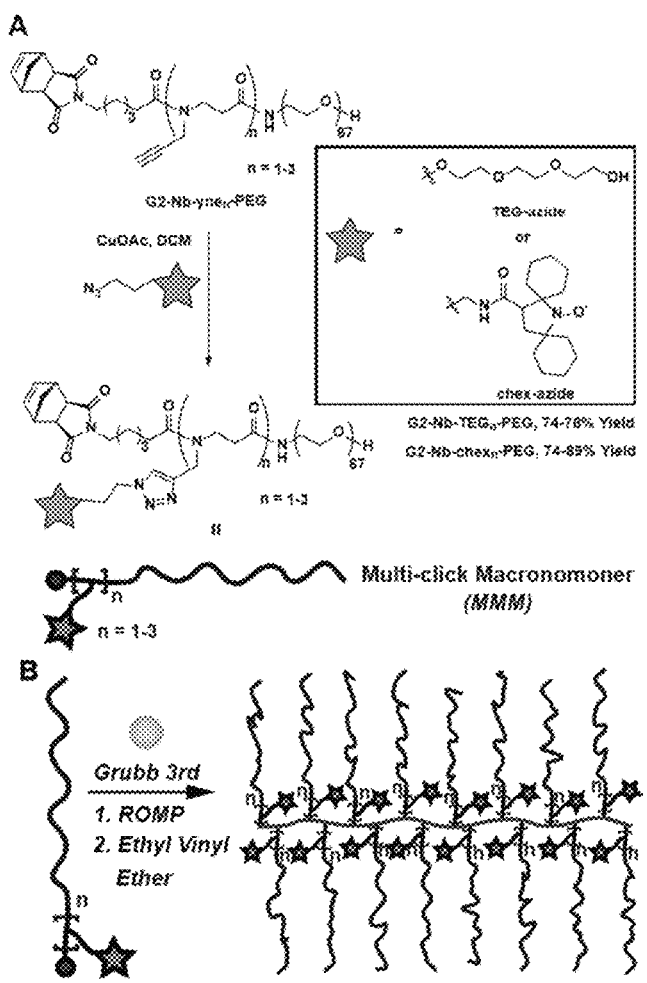
FIGS. 87A to 87B show.
Figure 88:
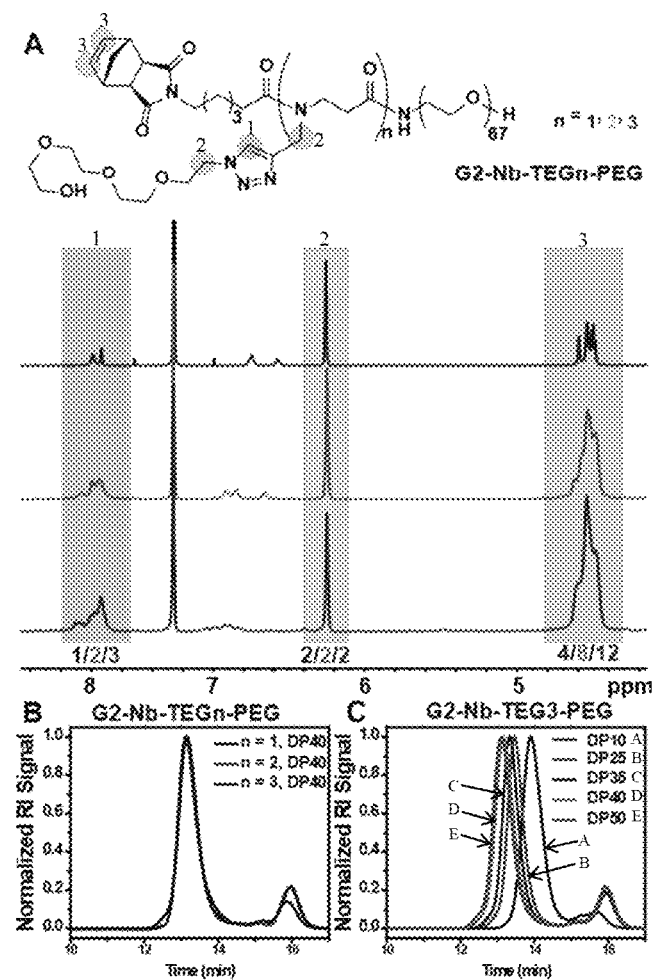
FIGS. 88A to 88C show.

To a vial, G2-Nb-yne$_3$-PEG (591.1 mg, 0.166 mmol, 1.0 eq), chex-azide (207.8 mg, 0.596 mmol, 3.6 eq) and DCM (9.0 mL) were added. Copper(I) acetate (CuOAc) (a pinch) was then added, and the reaction mixture was stirred under nitrogen. Completion of the click reaction was followed by LC-MS (~6 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (682 mg, 89% yield). EPR and MALDI spectra are shown in FIGS. 81C and 84, respectively.

Example 25: Synthesis of ChexWI-MM

To a vial, G2-Nb-yne-PEG (10.0 mg, 3.0 μmol, 1.0 eq), ChexW-N$_3$ (6.0 mg, 4.0 μmol, 1.3 eq) and DCM (0.1 mL) were added. Copper(I) acetate (CuOAc) (a pinch) was then added, and the reaction mixture was stirred under nitrogen. Completion of the click reaction was followed by LC-MS (~2 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a light yellow solid.

Example 26: Synthesis of PTXWI-MM

Figure 47:
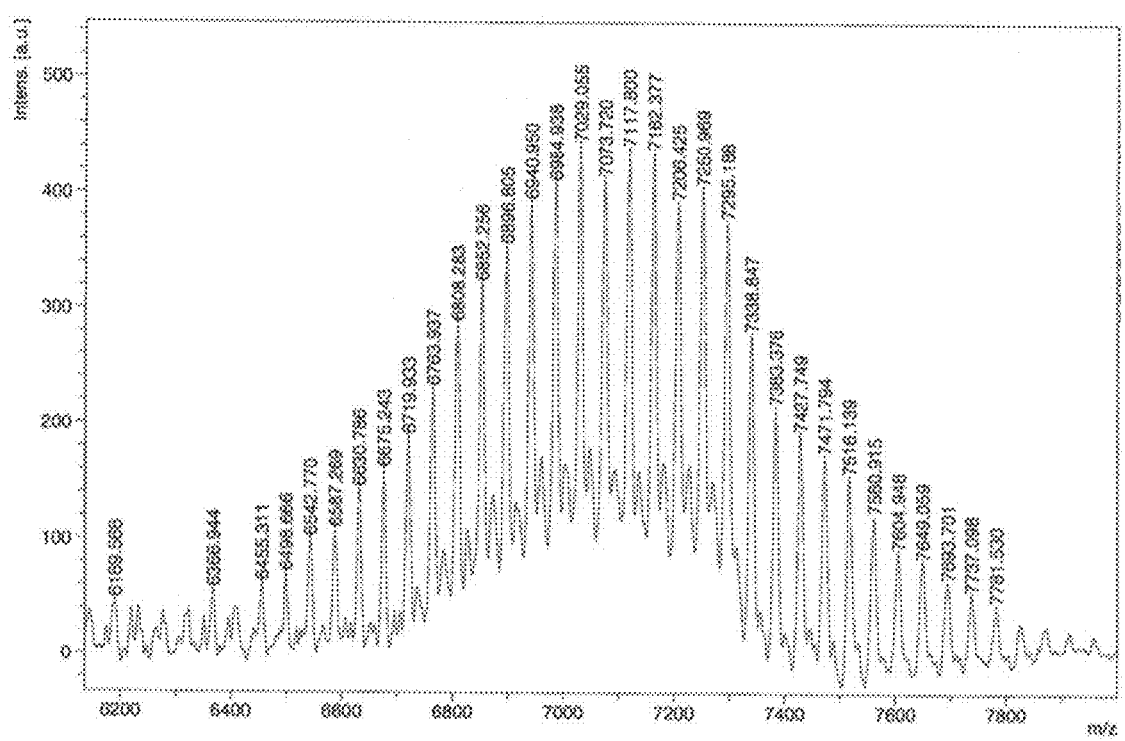
FIG. 47 shows the MALDI spectrum of PTXIII-amide-MM.
Figure 48:
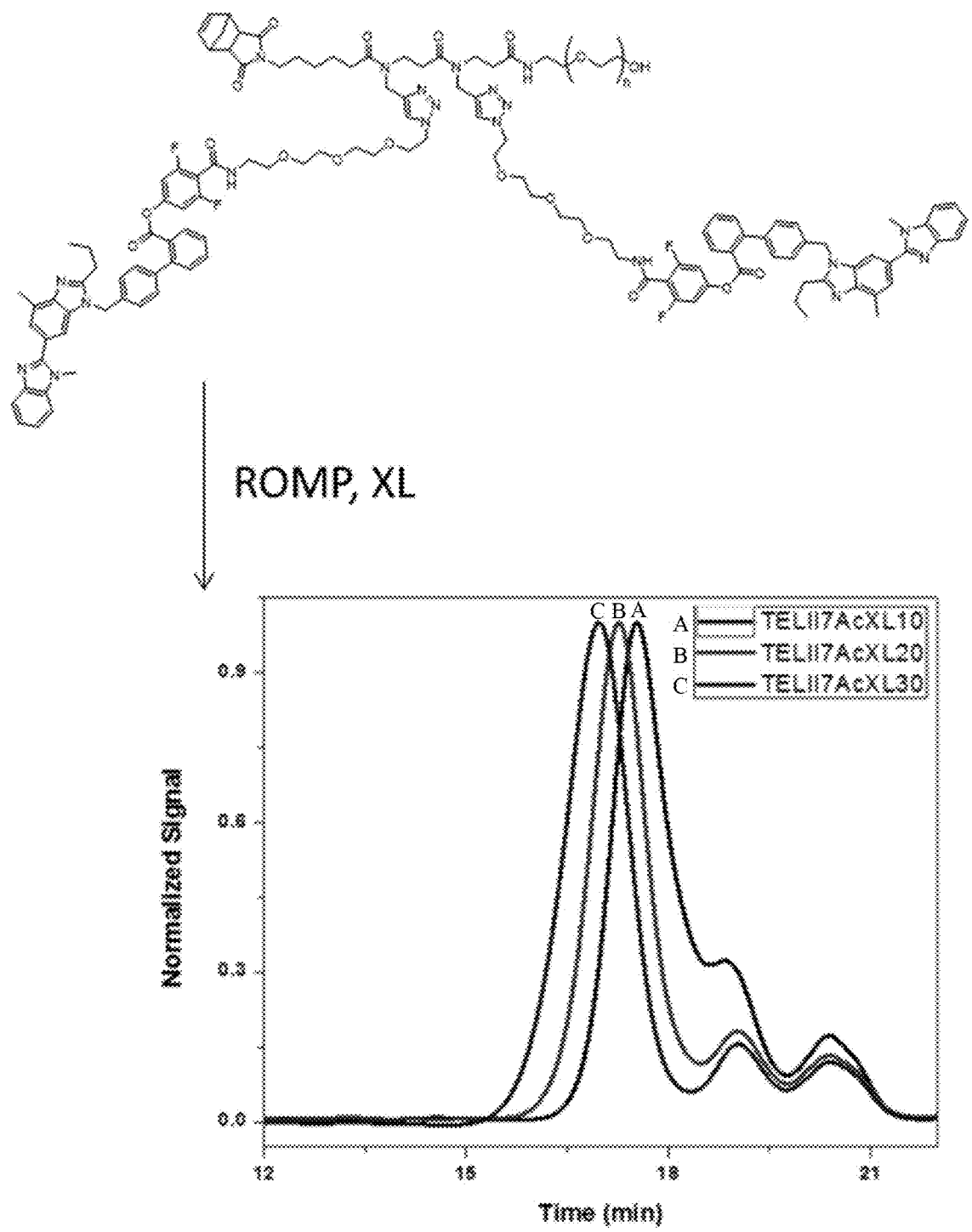
FIG. 48 shows the structure of F-TELII MM, which is used to synthesize the following BASPs: TELII7AcXL10, TELIIAcXL20, and TELII7AcXL30. The GPC traces for TELII7AcXL10, TELIIAcXL20, and TELII7AcXL30 are provided.

To a vial, G2-Nb-yne-PEG (60.0 mg, 0.018 mmol, 1.0 eq), PTXW-N$_3$ (100.0 mg, 0.027 mmol, 1.5 eq) and DCM (3.0 mL) were added. Copper(I) acetate (CuOAc) (12.1 mg) was then added, and the reaction mixture was stirred under nitrogen. Completion of the click reaction was followed by LC-MS (19 hour), and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (88.7 mg, 70% yield). MALDI spectrum of PTXWI-MM is shown in FIG. 47.

Example 27: Synthesis of TelII-MM

Figure 49:
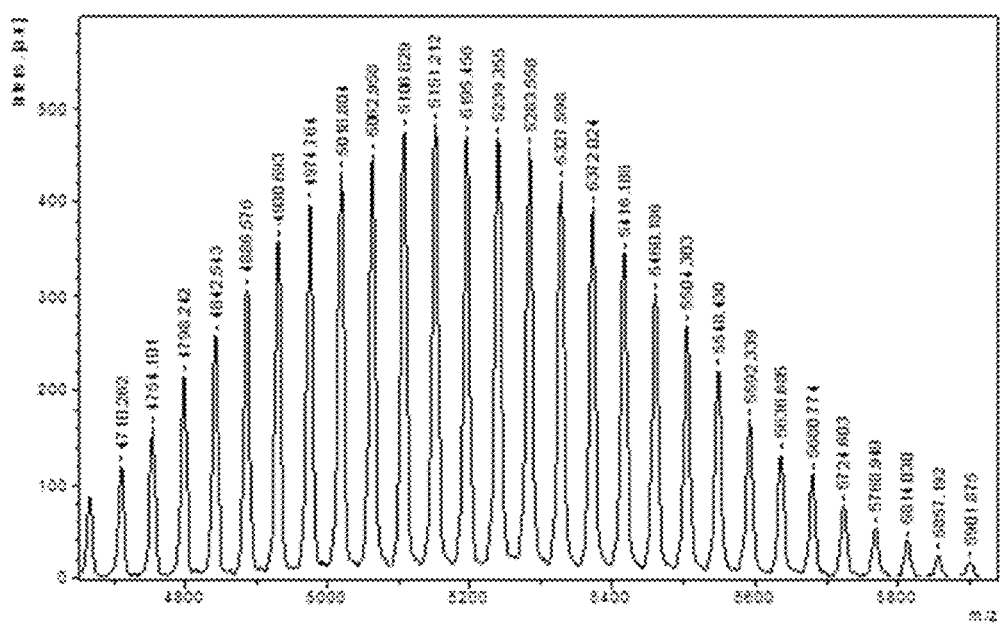
FIG. 49 shows the MALDI spectrum of F-TELII MM.
Figure 50:
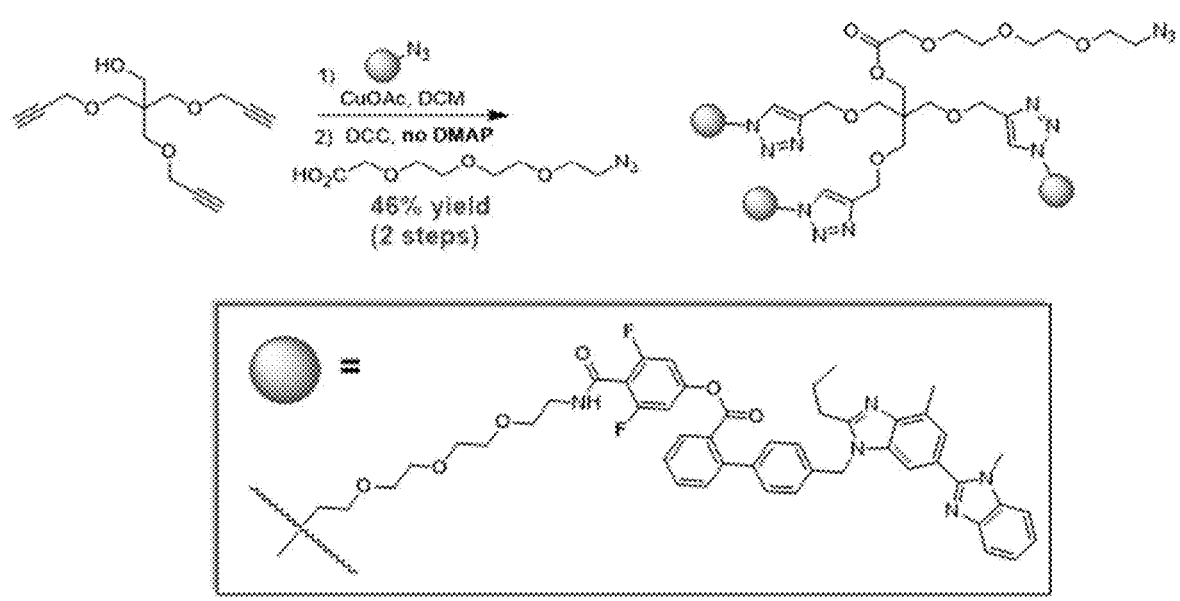
FIG. 50 shows the synthesis of F-TELIII-N3.
Figure 51:
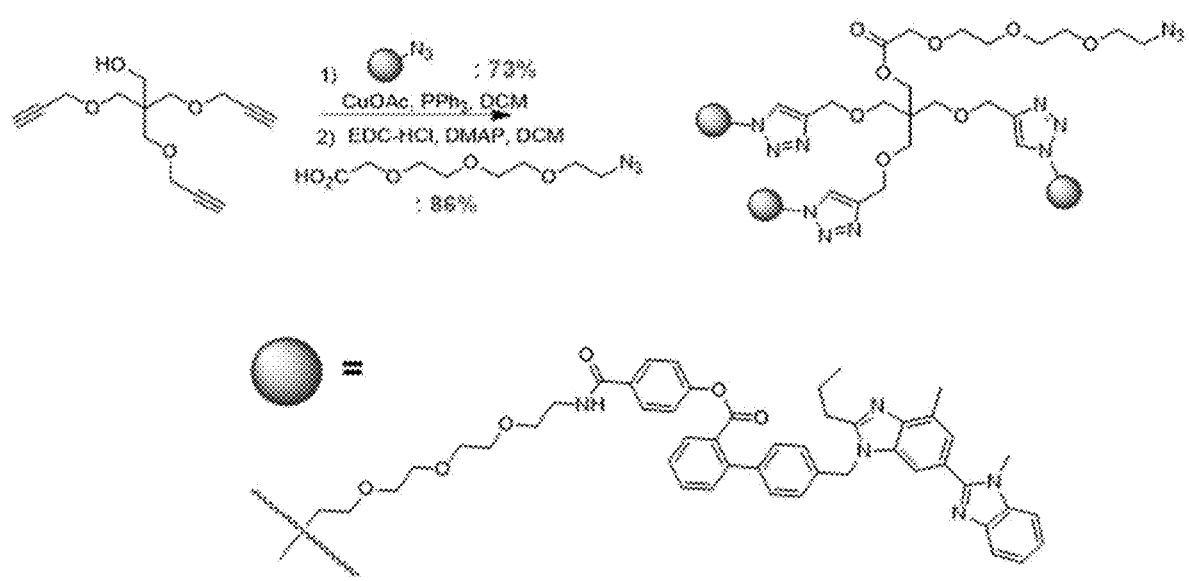
FIG. 51 shows the synthesis of $Tel_3$-$N_3$.
Figure 52:
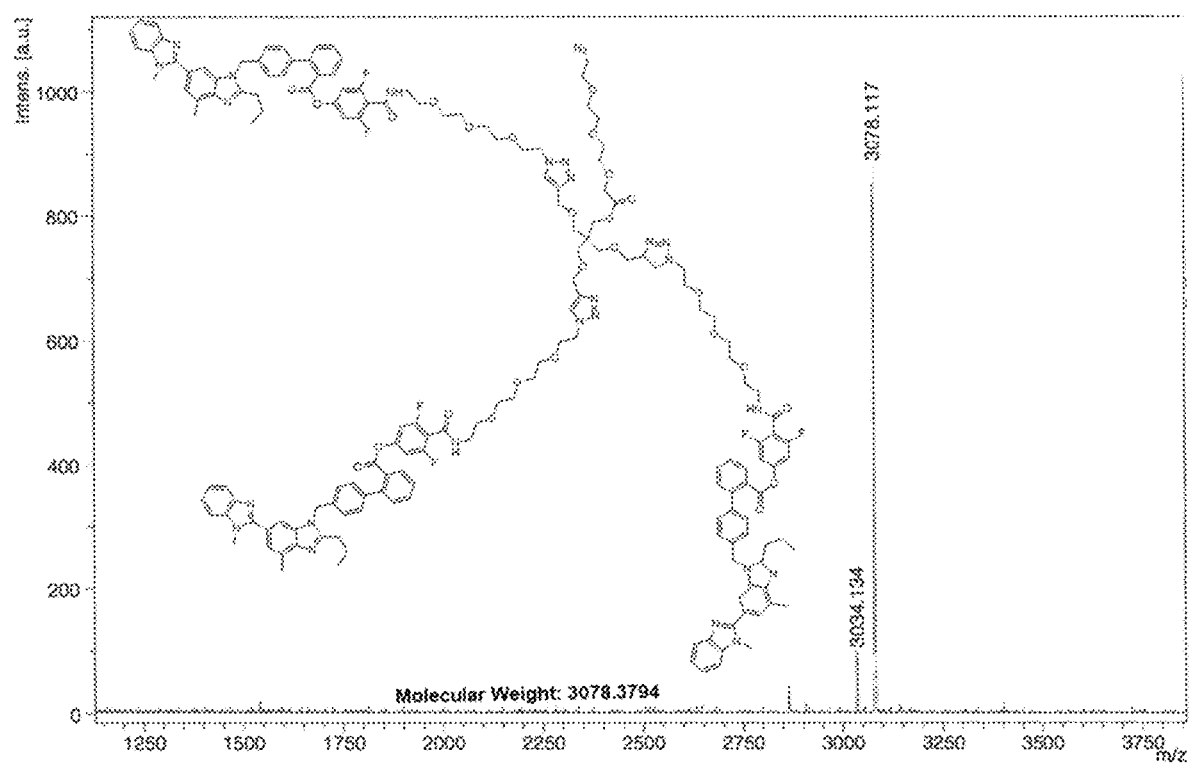
FIG. 52 shows the MALDI spectrum of F-TELIII-N3.
Figure 53:
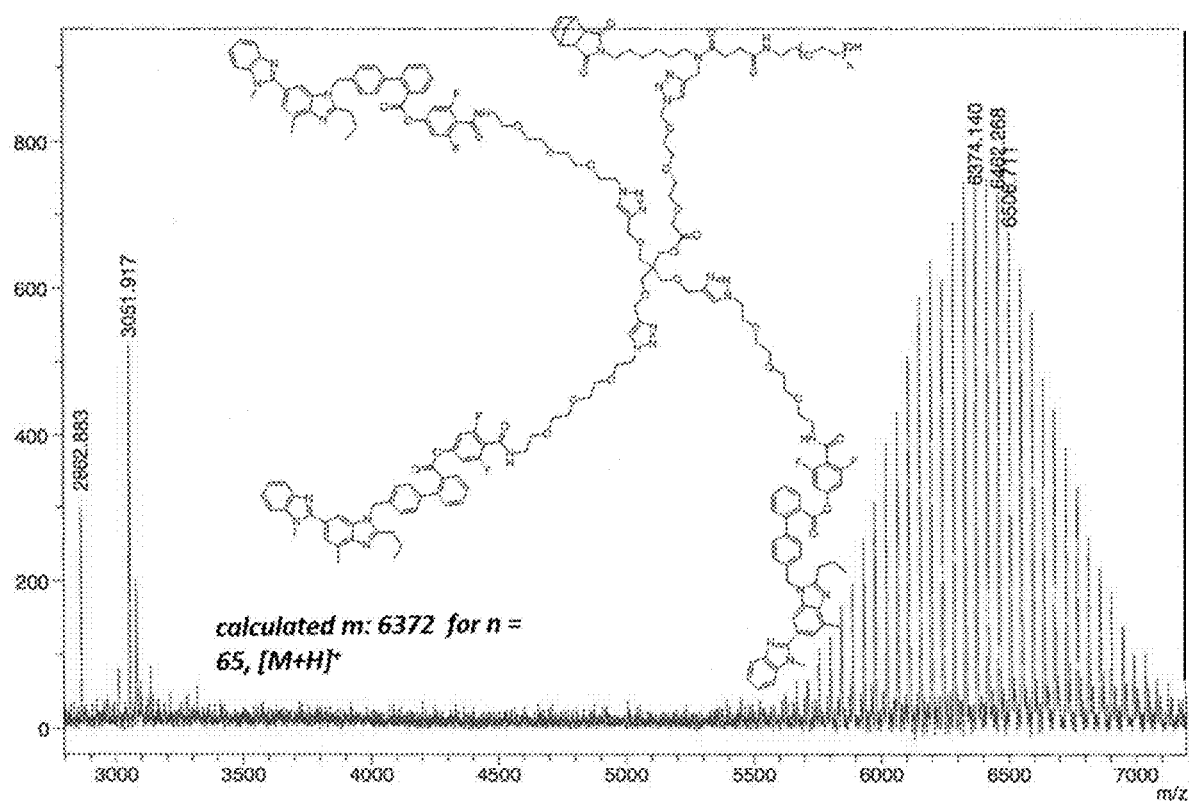
FIG. 53 shows the structure and MALDI spectrum of TELWI-MM (n=65), which is synthesized using F-TELIII-N3.

To a vial, G2-Nb-yne$_2$-PEG (400.0 mg, 0.115 mmol, 1.0 eq), Tel-N$_3$ (250.0 mg, 0.287 mmol, 2.5 eq) and DCM (20 mL) were added. Copper(I) acetate (CuOAc) (28.2 mg, 0.230 mmol, 2.0 eq) was then added, and the reaction mixture was stirred under nitrogen. Completion of the click reaction was followed by LC-MS (~4 hour), and the reaction mixture was filtered through a 0.45 µm filter (Nalgene) upon complete conversion. The crude mixture was concentrated under vacuum, redissolved in chloroform, and subjected to recycling preparative HPLC, affording the pure product as a light yellow solid. MALDI spectrum of TelII-MM is shown in FIG. 49.

Example 28: Synthesis of TelW-MM

Figure 54:
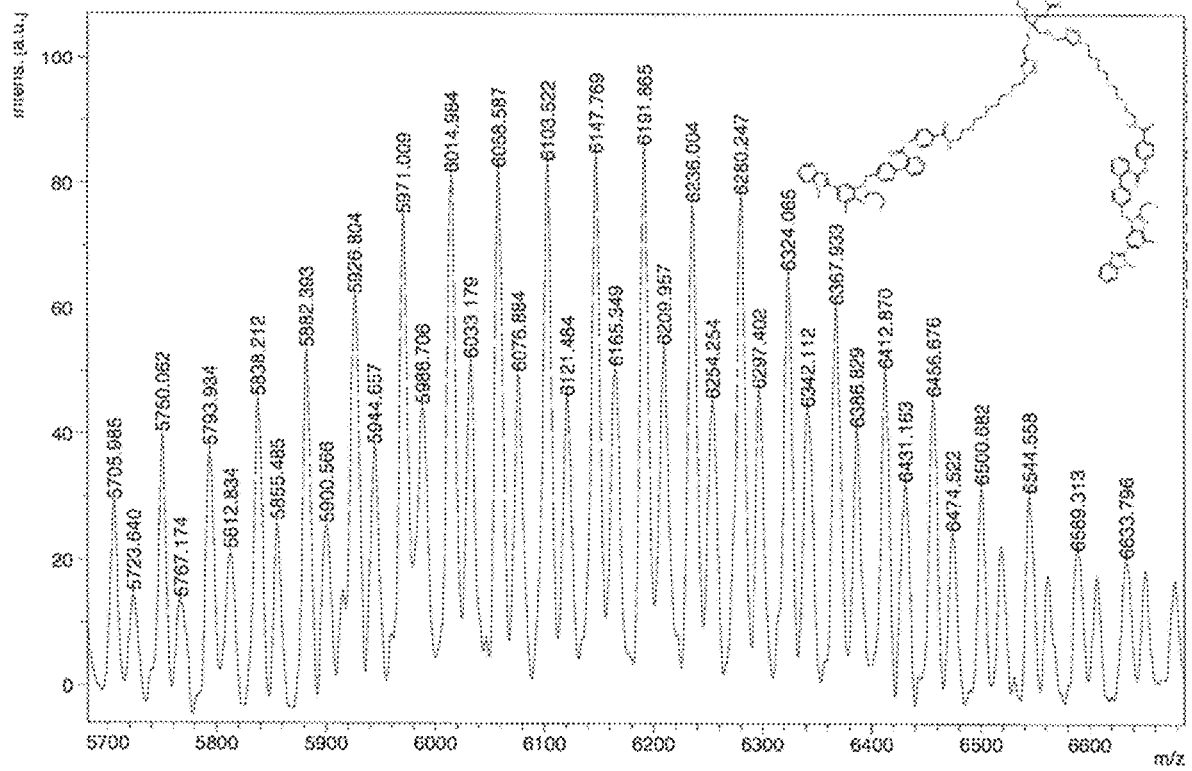
FIG. 54 shows the structure and MALDI spectrum of $Tel_3MM$ (n=62), which is synthesized from $Tel_3$-$N_3$.
Figure 55:
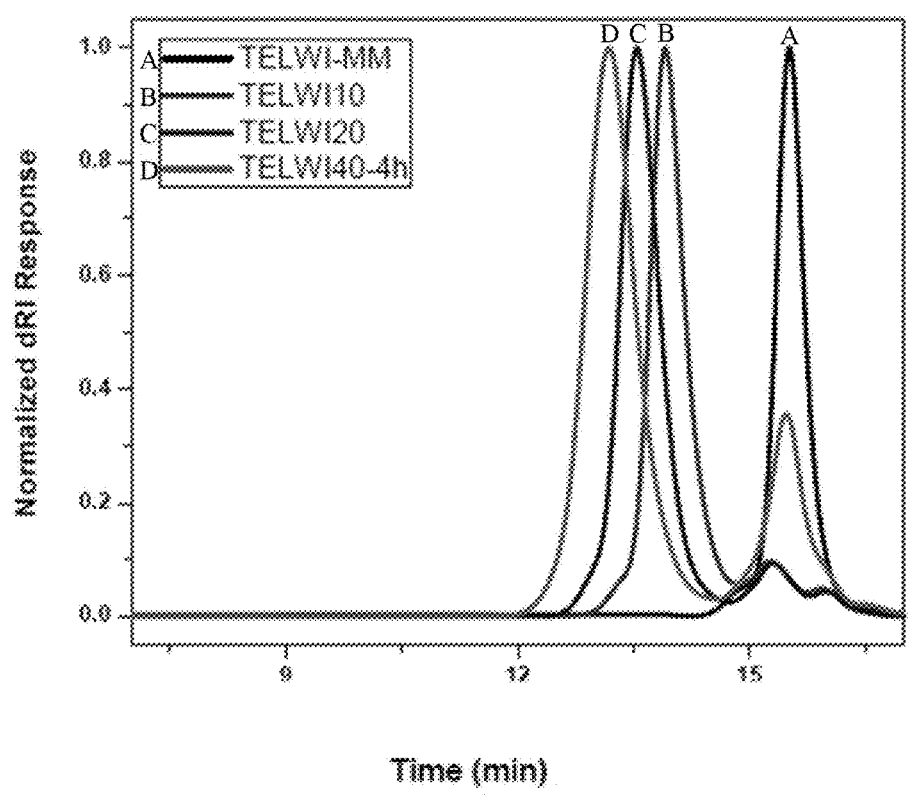
FIG. 55 shows GPC traces of TELWI-MM, TEL TELWI20, and TEL $D_H$=15.8 nm for TEL and $D_H$=16.4 nm for TELWI20.
Figure 56:
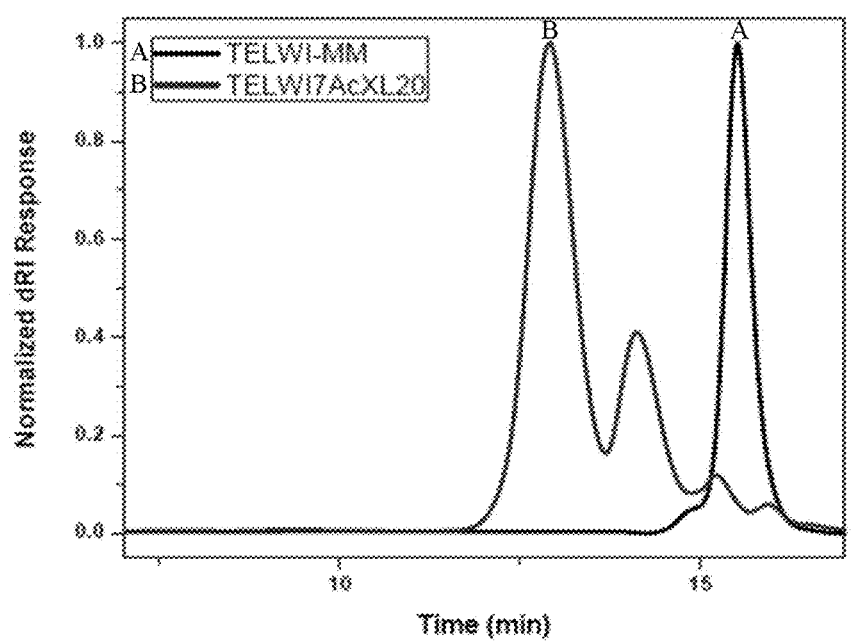
FIG. 56 shows GPC traces of TELWI-MM and TELWI7AcXL20.
Figure 57:
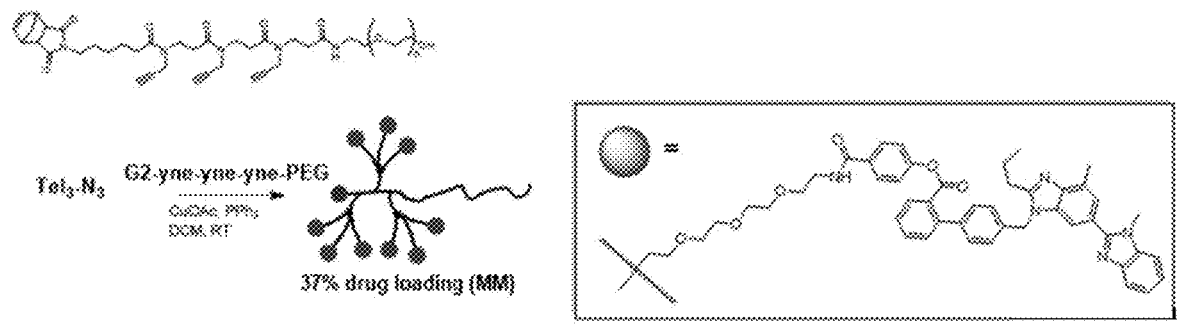
FIG. 57 shows the synthesis of G2-yne3-Tel3-MM with 37% drug loading from $Tel_3$-$N_3$ and G2-yne-yne-yne-PEG.
Figure 58:
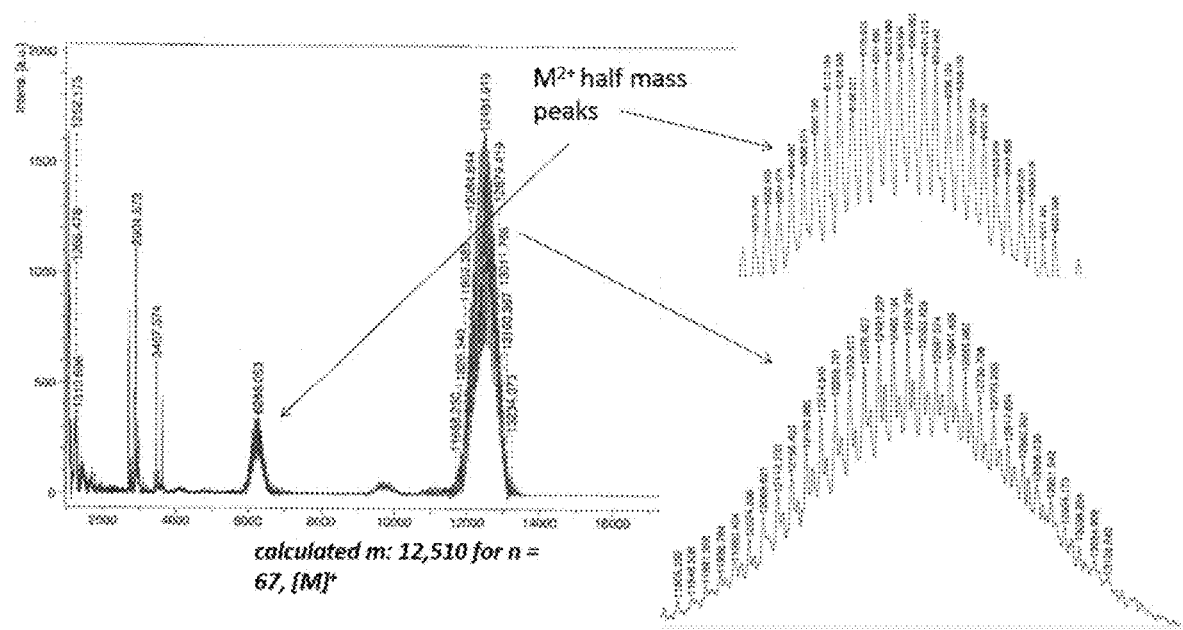
FIG. 58 shows the MALDI spectrum of G2-yne3-Tel3-MM.
Figure 59:
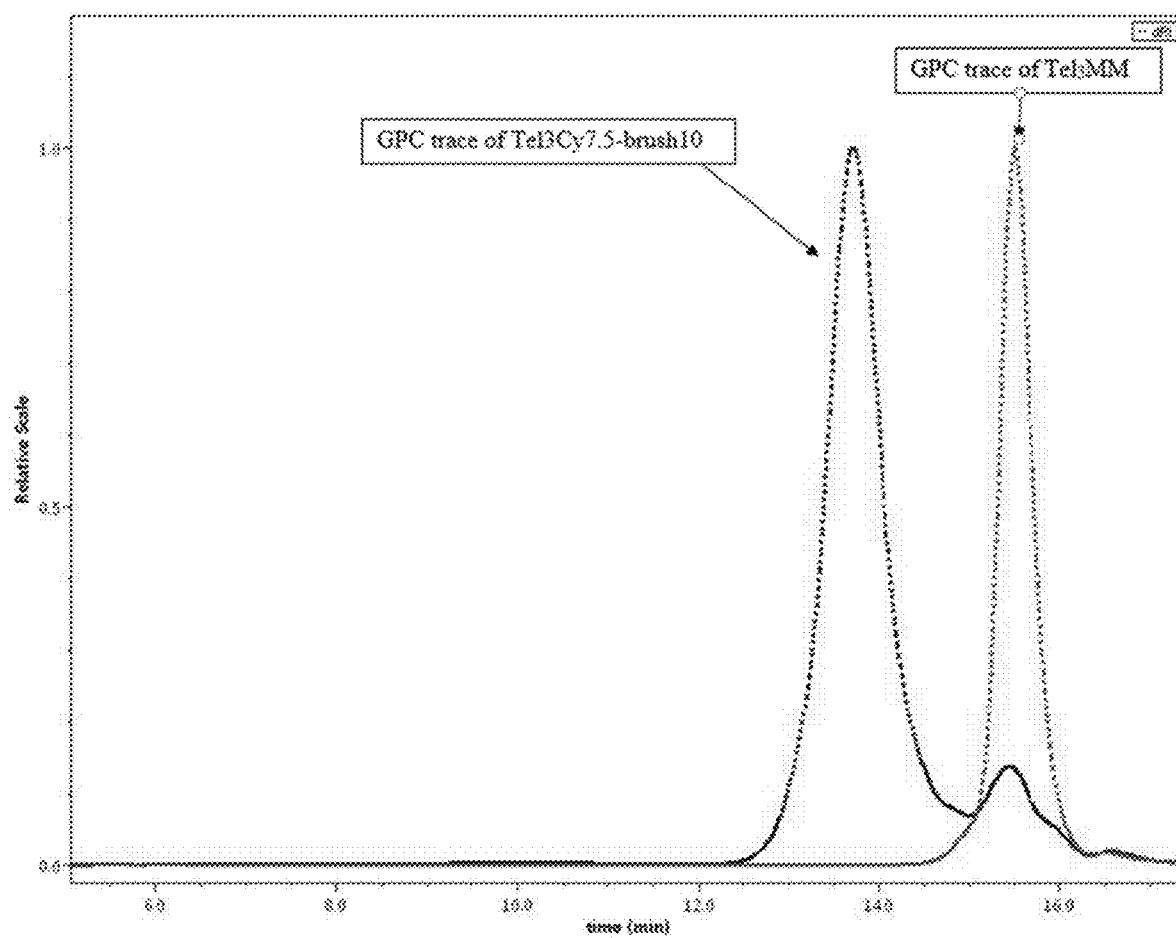
FIG. 59 shows GPC traces of $Tel_3MM$ and $Tel_3Cy7.5$-brush10.
Figure 60:
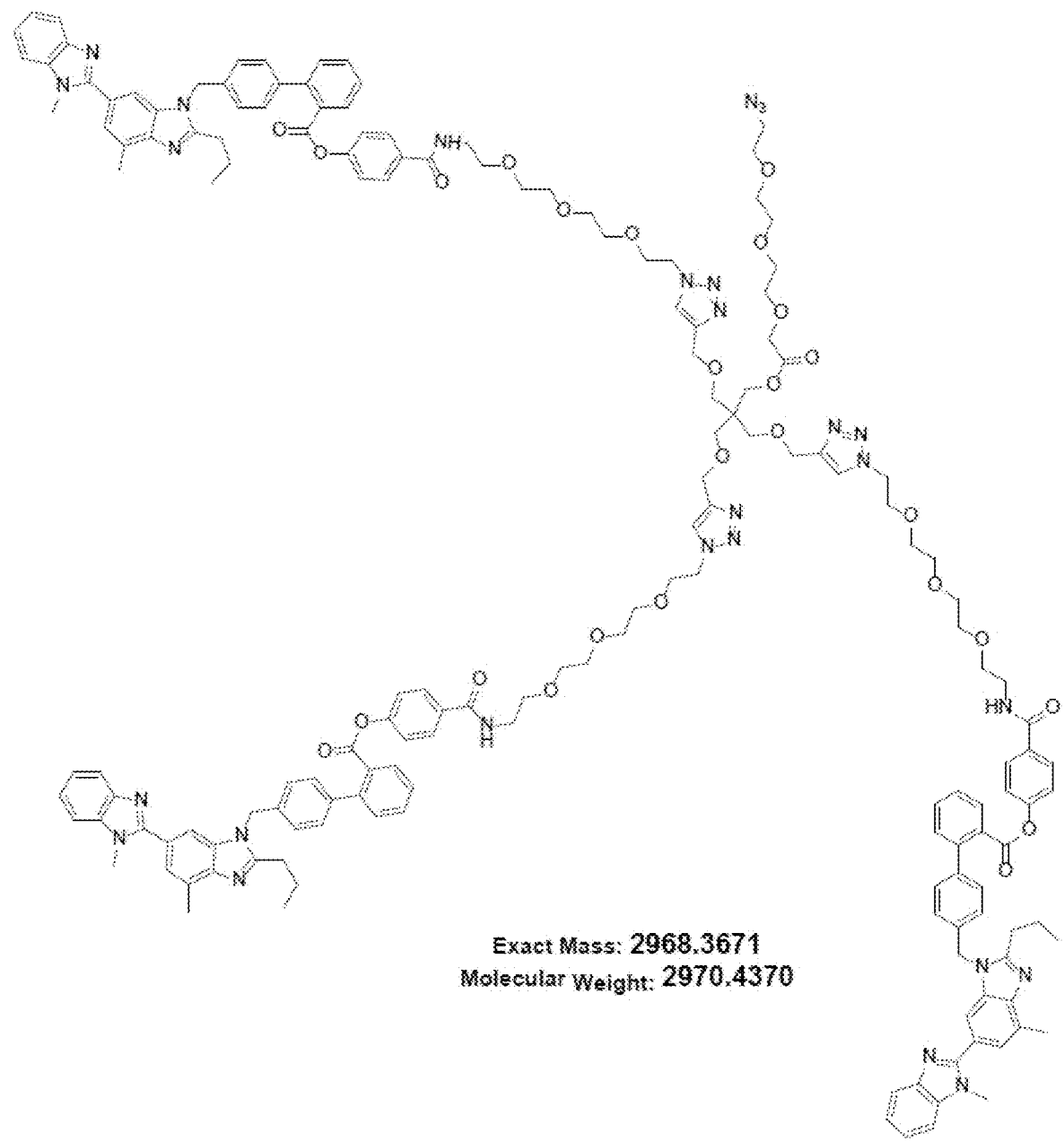
FIG. 60 shows the structure, exact mass, and molecular weight of $Tel_3$-$N_3$.
Figure 61:
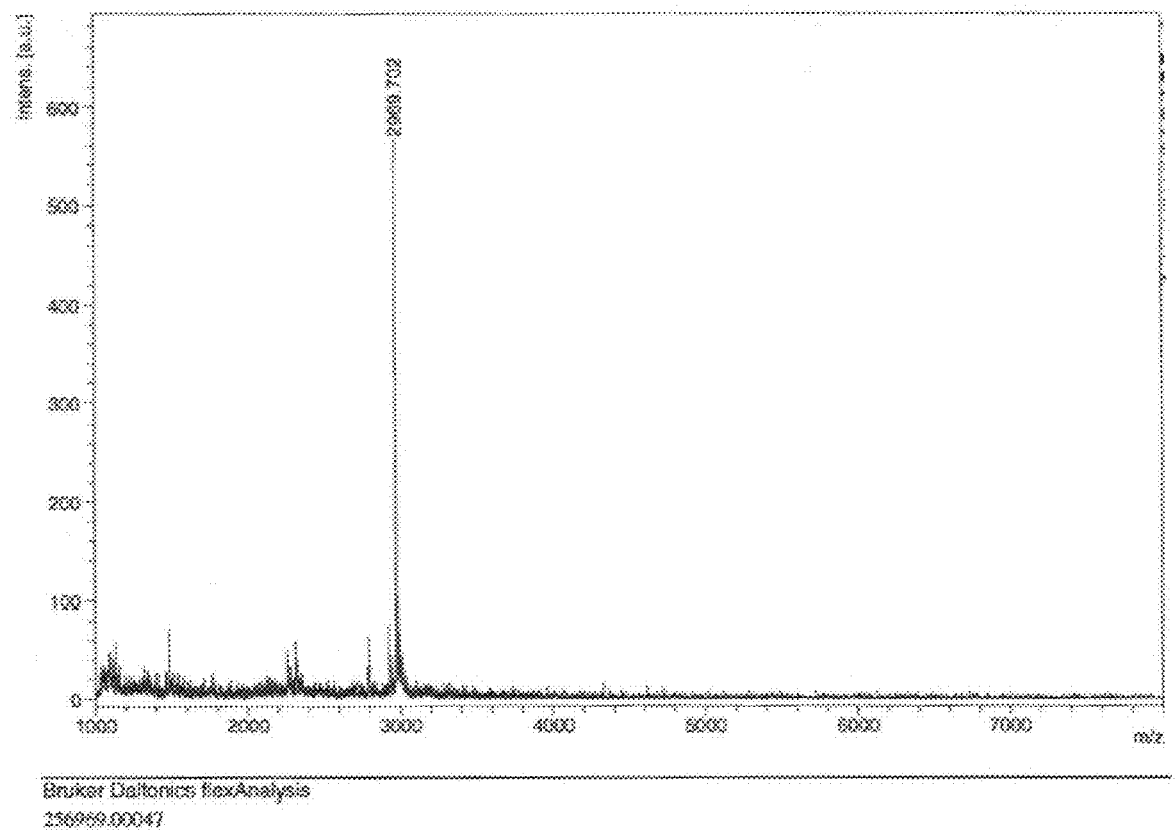
FIG. 61 shows the MALDI spectrum of $Tel_3$-$N_3$.
Figure 62:
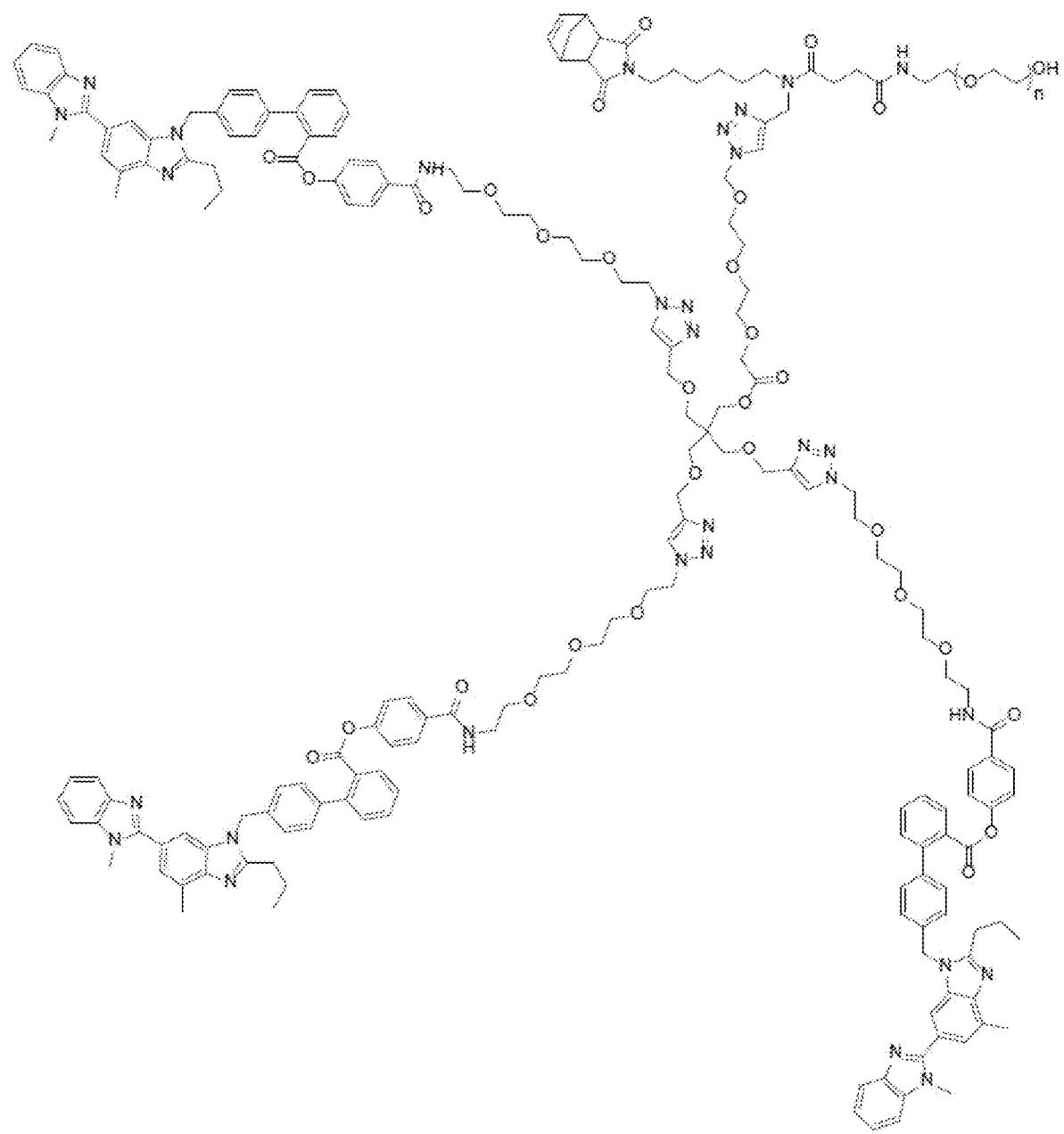
FIG. 62 shows the structure of $Tel_3MM$.
Figure 63:
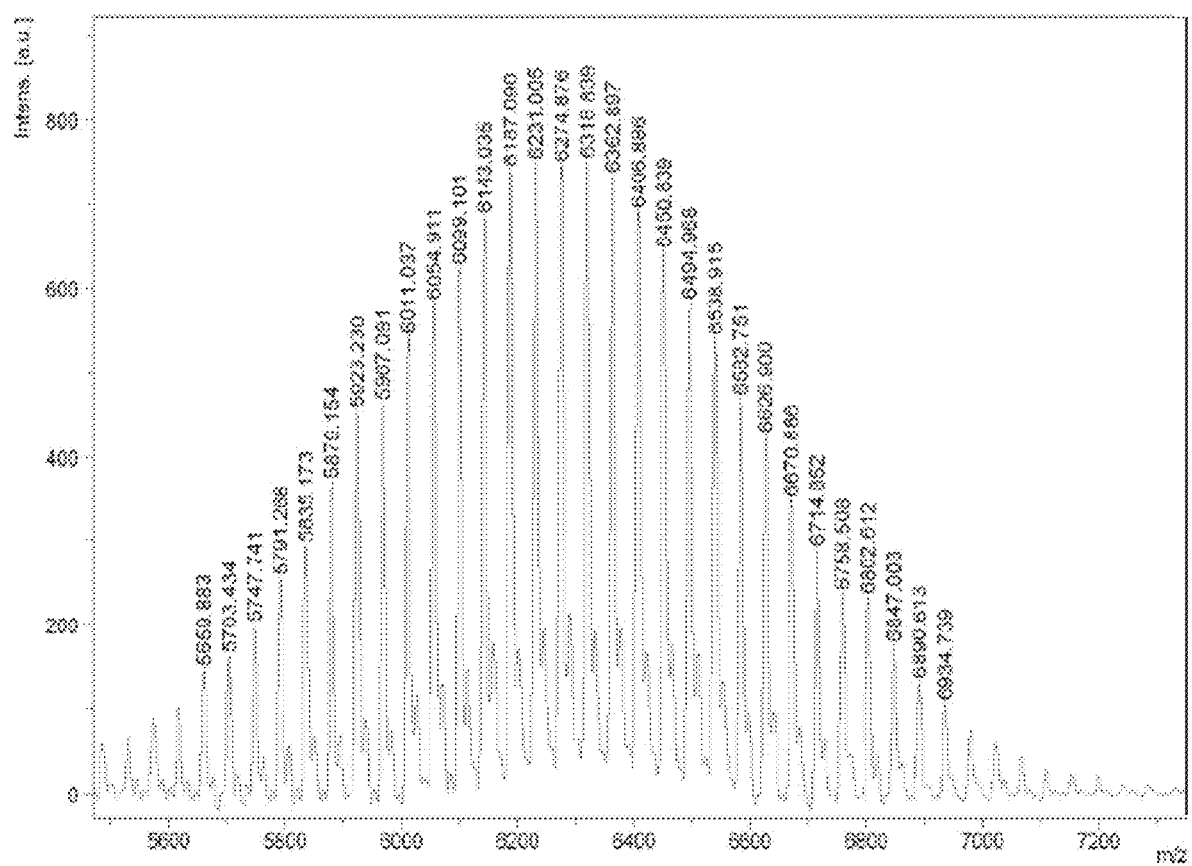
FIG. 63 shows the MALDI spectrum of Tel$_3$MM.

To a vial, G1-Nb-yne-PEG (100.0 mg, 0.03 mmol, 1.0 eq), TelPhW-N$_3$ (135.0 mg, 0.045 mmol, 1.5 eq) and DCM (3.0 mL) were added. Copper(I) acetate (CuOAc) (5.5 mg, 0.045 mmol, 1.5 eq) and triphenylphosphine (PPh$_3$) (24.0 mg, 0.092 mmol, 3.0 eq) were then added, and the reaction mixture was stirred under nitrogen. Completion of the click reaction was followed by LC-MS (overnight), and the reaction mixture was filtered through a 0.45 µm filter (Nalgene) upon complete conversion. The crude mixture was concentrated under vacuum, redissolved in chloroform, and subjected to recycling preparative HPLC, affording the pure product as a light yellow solid. MALDI spectrum of TelW-MM is shown in FIG. 54.

Example 29: Synthesis of Tel

To a vial, G2-Nb-yne$_3$-PEG (10.0 mg, 2.79 mol, 1.0 eq), TelPhW-N$_3$ (42.0 mg, 14.0 mol, 5.0 eq) and DCM (0.9 mL) were added. Copper(I) acetate (CuOAc) (1.7 mg, 14.0 mol, 5.0 eq) and triphenylphosphine (PPh$_3$) (7.3 mg, 28.0 mol, 10.0 eq) were then added, and the reaction mixture was stirred under nitrogen. Completion of the click reaction was followed by LC-MS (overnight), and the reaction mixture was filtered through a 0.45 µm filter (Nalgene) upon complete conversion. The crude mixture was concentrated under vacuum, redissolved in chloroform, and subjected to recycling preparative HPLC, affording the pure product as a light yellow solid.

5) Generation 1 Branched Norbornene Macromonomers

Example 30: Synthesis of G1-TEG-MM

Scheme 25: Synthesis of G1-TEG-MM.

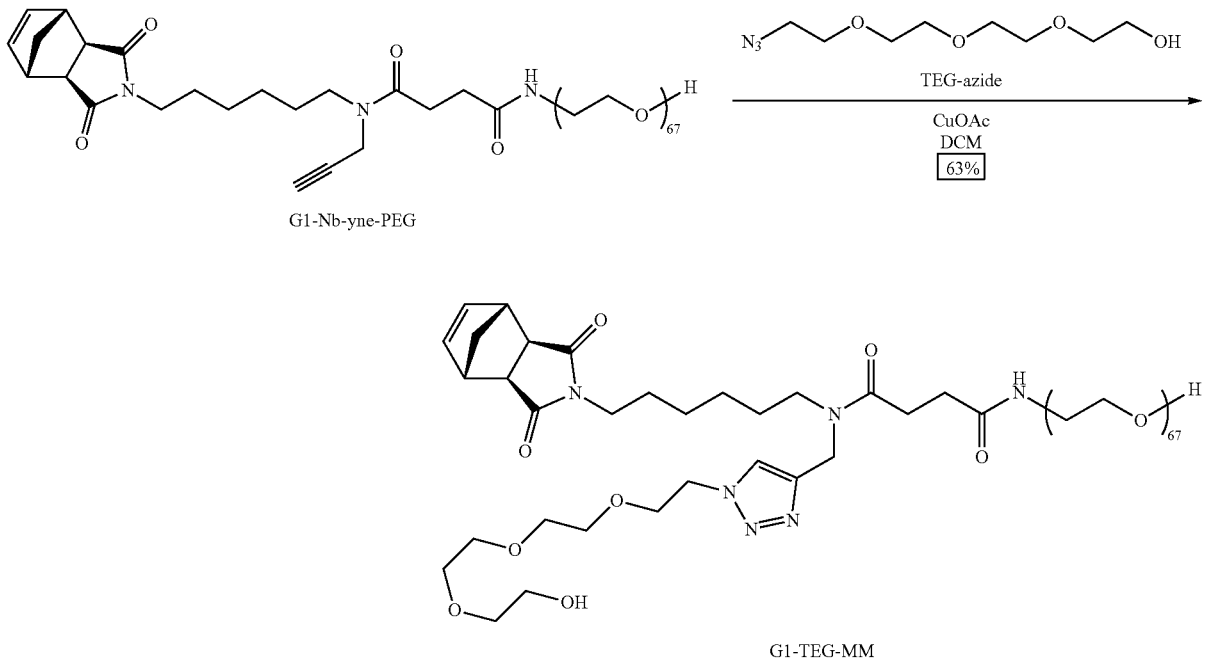

G1-TEG-MM

Figure 26:
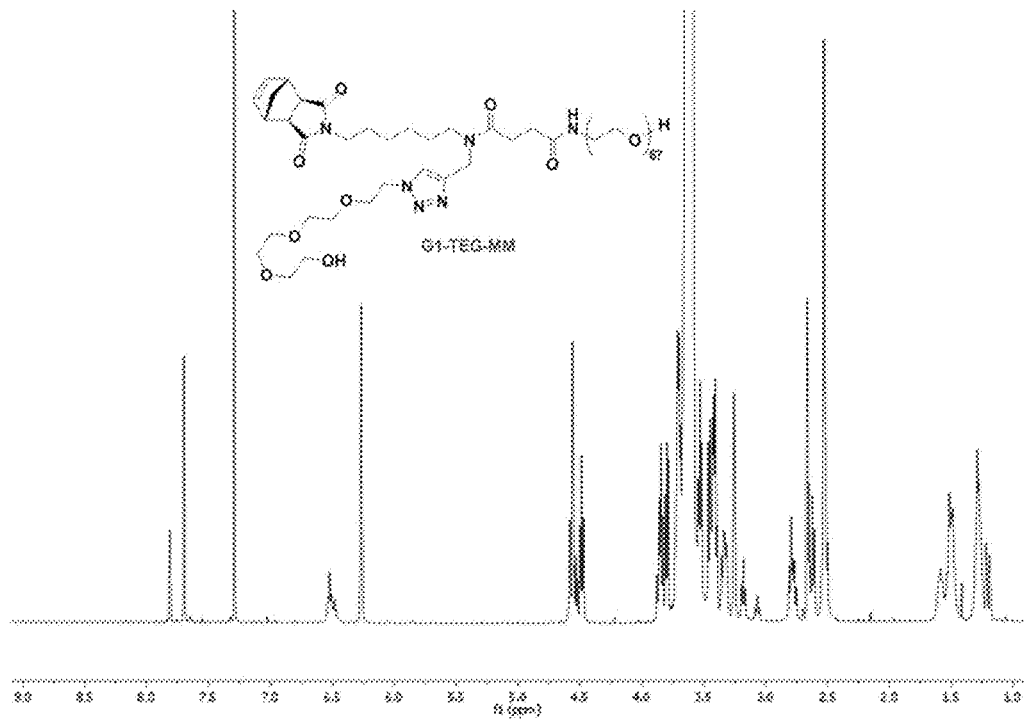
FIG. 26 shows the $^1$H NMR spectrum of G1-TEG-MM in $CDCl_3$.
Figure 27:
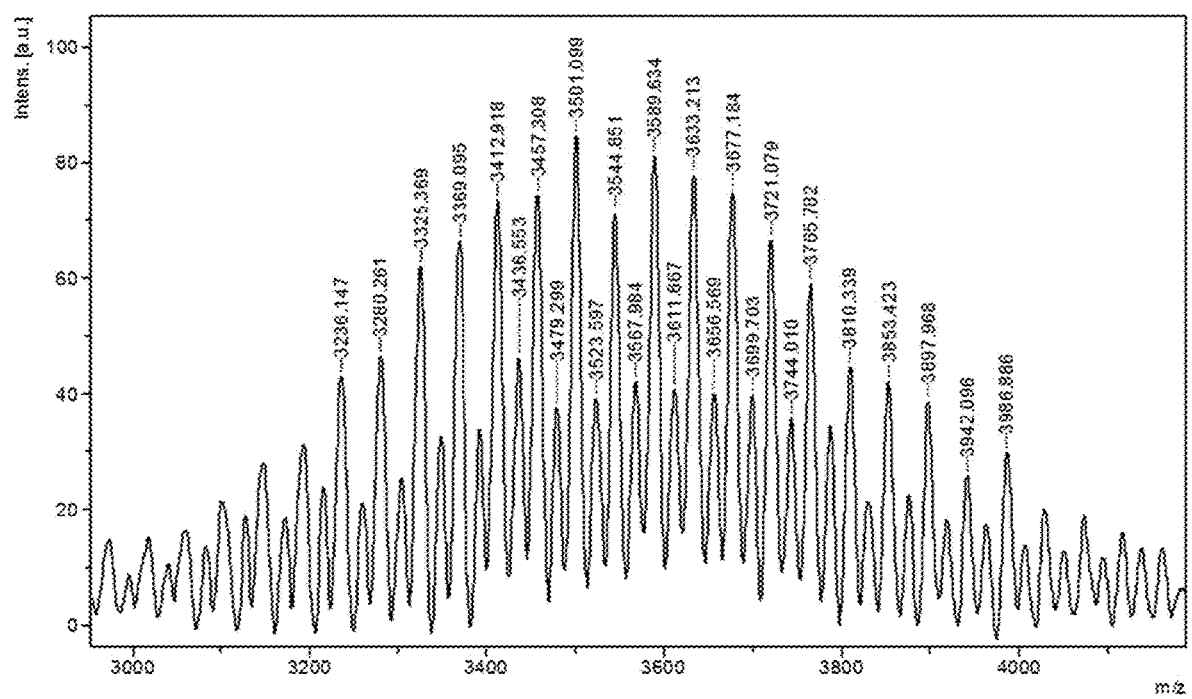
FIG. 27 shows the MALDI spectrum of G1-TEG-MM. $C_{164}H_{314}N_6O_{75}$: Calculated m/z=3591.082 [M+Na]+; Found: 3589.634 [M+Na]+. Calculated m/z=3569.100 [M+H]+; Found: 3567.984 [M+H]+.

To a vial, G1-Nb-yne-PEG (340.0 mg, 0.1 mmol, 1.0 eq), TEG-azide (33.0 mg, 0.15 mmol, 1.5 eq) and DCM (2 mL) were added. A pinch of CuOAc was then added, and the reaction mixture was stirred under nitrogen. Completion of the click reaction was followed by LC-MS, and the reaction mixture was filtered through a 0.45 µm filter (Nalgene) upon complete conversion. The crude mixture was concentrated under vacuum, redissolved in chloroform, and subjected to recycling preparative GPC, affording the pure product as a white solid (227 mg, 63% yield). $^1$H NMR and MALDI spectra of G1-TEG-MM are shown in FIGS. 26 and 27, respectively.

Example 31: Synthesis of G1-PTX-MM

Scheme 26: Synthesis of G1-PTX-MM.

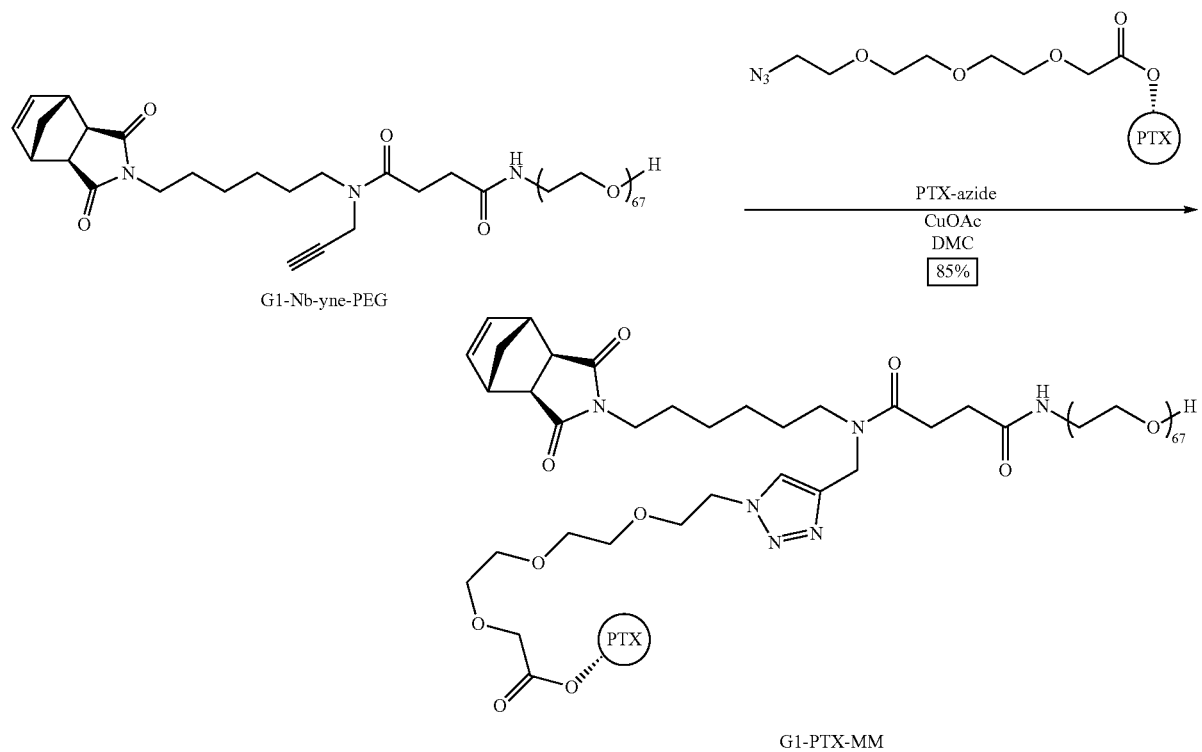

Figure 28:
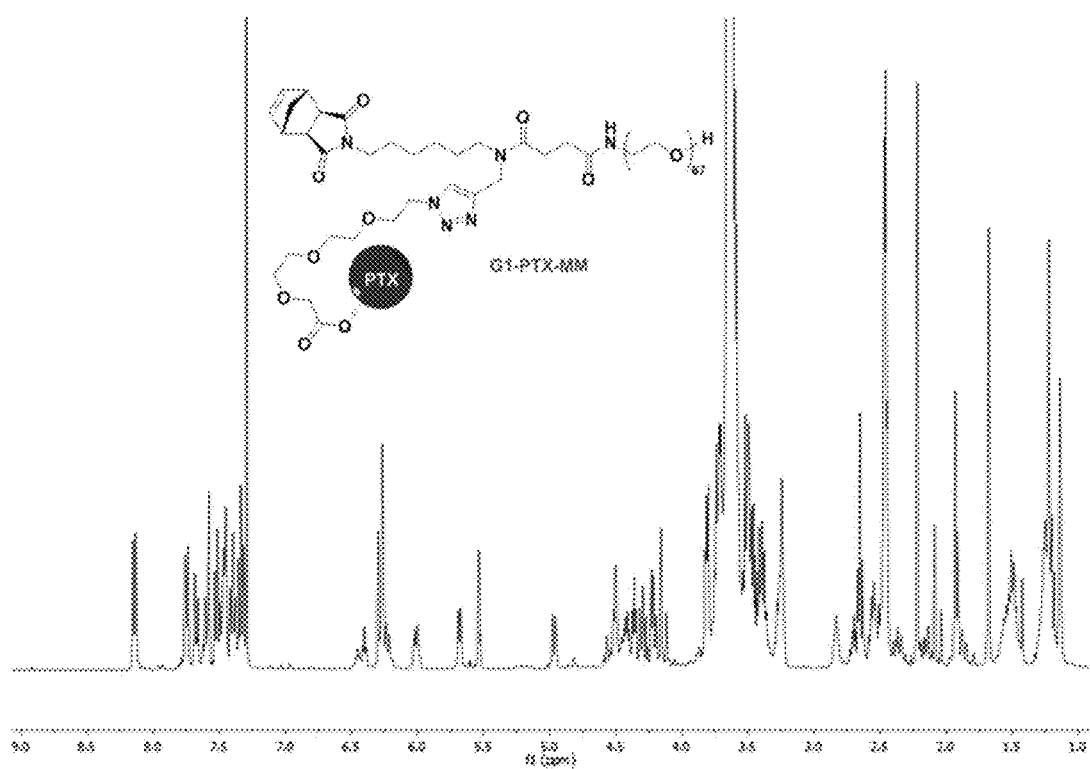
FIG. 28 shows the $^1$H NMR spectrum of G1-PTX-MM in $CDCl_3$.
Figure 29:
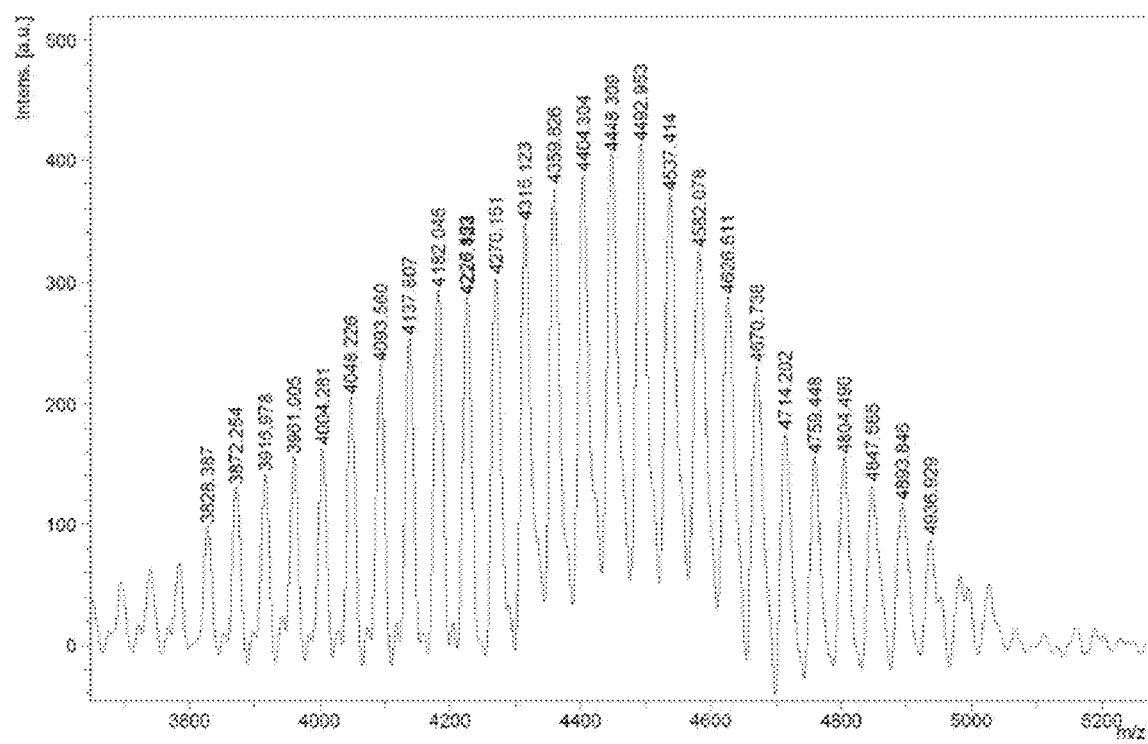
FIG. 29 shows the MALDI spectrum of G1-PTX-MM. $C_{211}H_{361}N_7O_{89}$: Calculated m/z=4448.3926 $[M+H_2O+Na]^+$; Found: 4448.309 $[M+H_2O+Na]^+$.

To a vial, G1-Nb-yne-PEG (113.6 mg, 0.033 mmol, 1.0 eq), PTX-azide (50.0 mg, 0.047 mmol, 1.00 eq) and DCM (2 mL) were added. A pinch of CuOAc was then added, and the reaction mixture was stirred under nitrogen. Completion of the click reaction was followed by LC-MS, and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (127 mg, 85% yield). $^1$H NMR and MALDI spectra of G1-PTX-MM are shown in FIGS. 28 and 29, respectively.

Example 32: Synthesis of G1-TEG-PEG

Scheme 27: Synthesis of G1-TEG-PEG

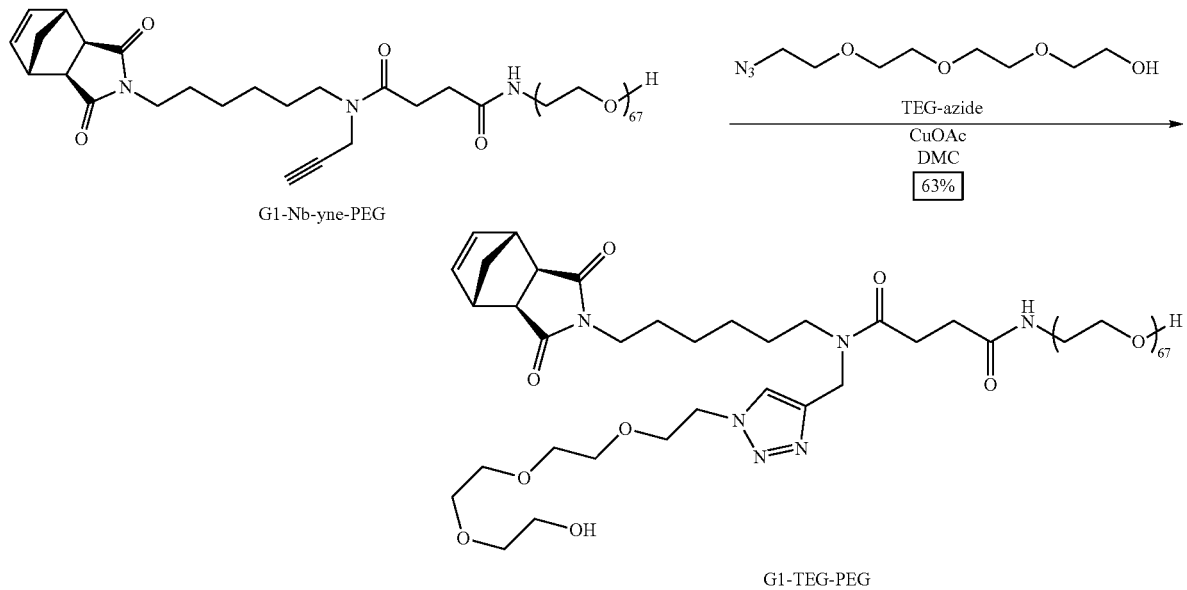

To a vial, G1-Nb-yne-PEG (340.0 mg, 0.1 mmol, 1.0 eq), TEG-azide (33.0 mg, 0.15 mmol, 1.5 eq) and DCM (2 mL) were added. A pinch of CuOAc was then added, and the reaction mixture was stirred under nitrogen. Completion of the click reaction was followed by LC-MS, and the reaction mixture was filtered through a 0.45 μm filter (Nalgene) upon complete conversion. The crude mixture was concentrated under vacuum, redissolved in chloroform, and subjected to recycling preparative HPLC, affording the pure product as a white solid (227 mg, 63% yield). $^1$H NMR and MALDI spectra of G1-TEG-MM are shown in FIGS. 26 and 27, respectively.

6) Generation 2 Branched Norbornene Block Macromonomers

Example 33: Synthesis of G2-Nb-PS-propanol

Scheme 28: Synthesis of G2-Nb-PS-propanol.

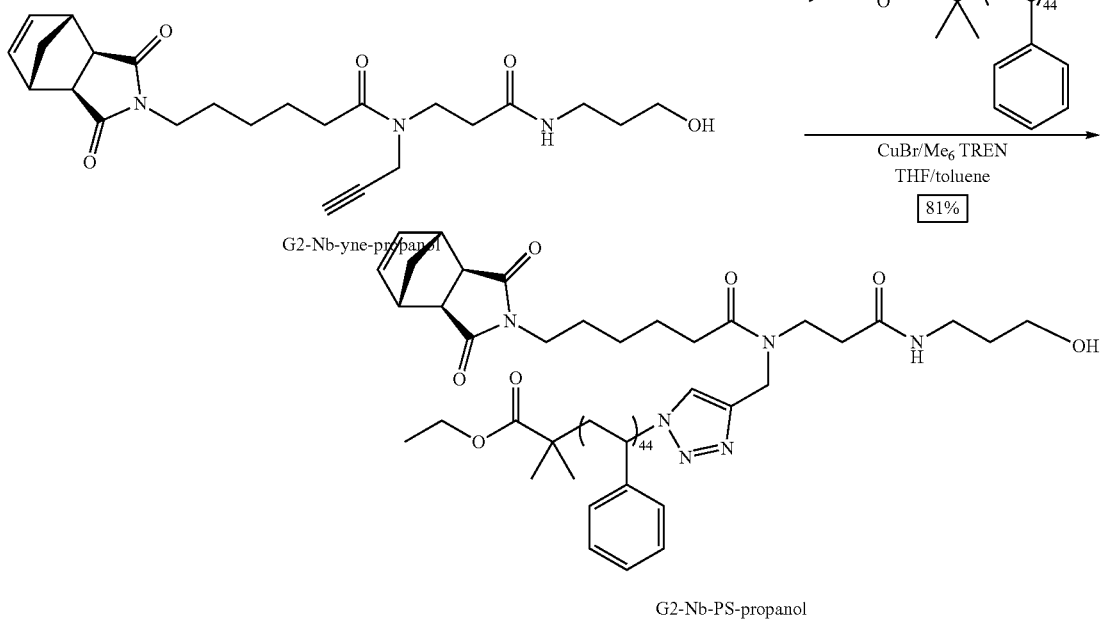

G2-Nb-PS-propanol

Figure 30:
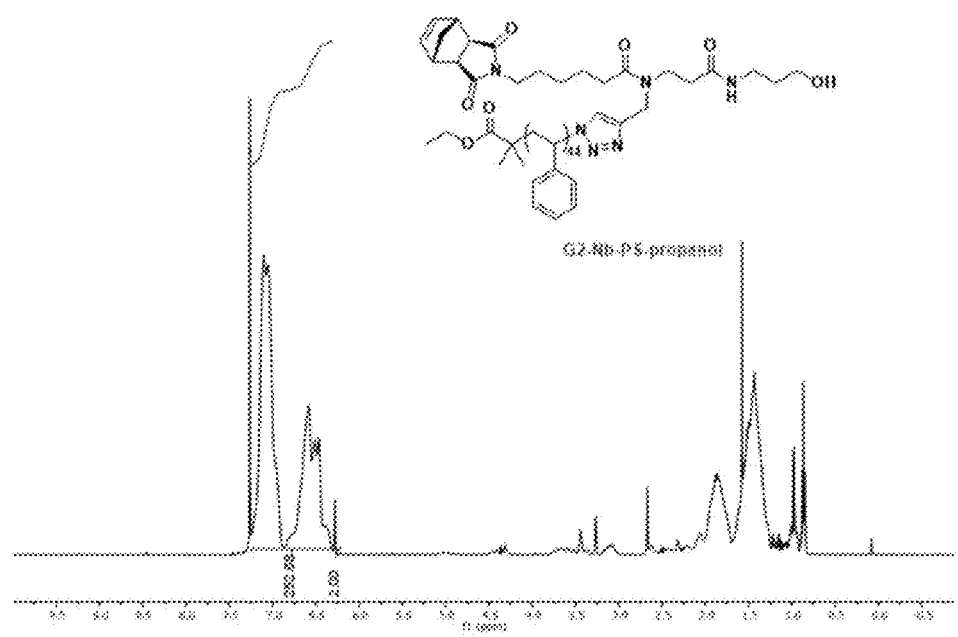
FIG. 30 shows the $^1$H NMR spectrum of G2-Nb-PS-propanol in $CDCl_3$.
Figure 32:
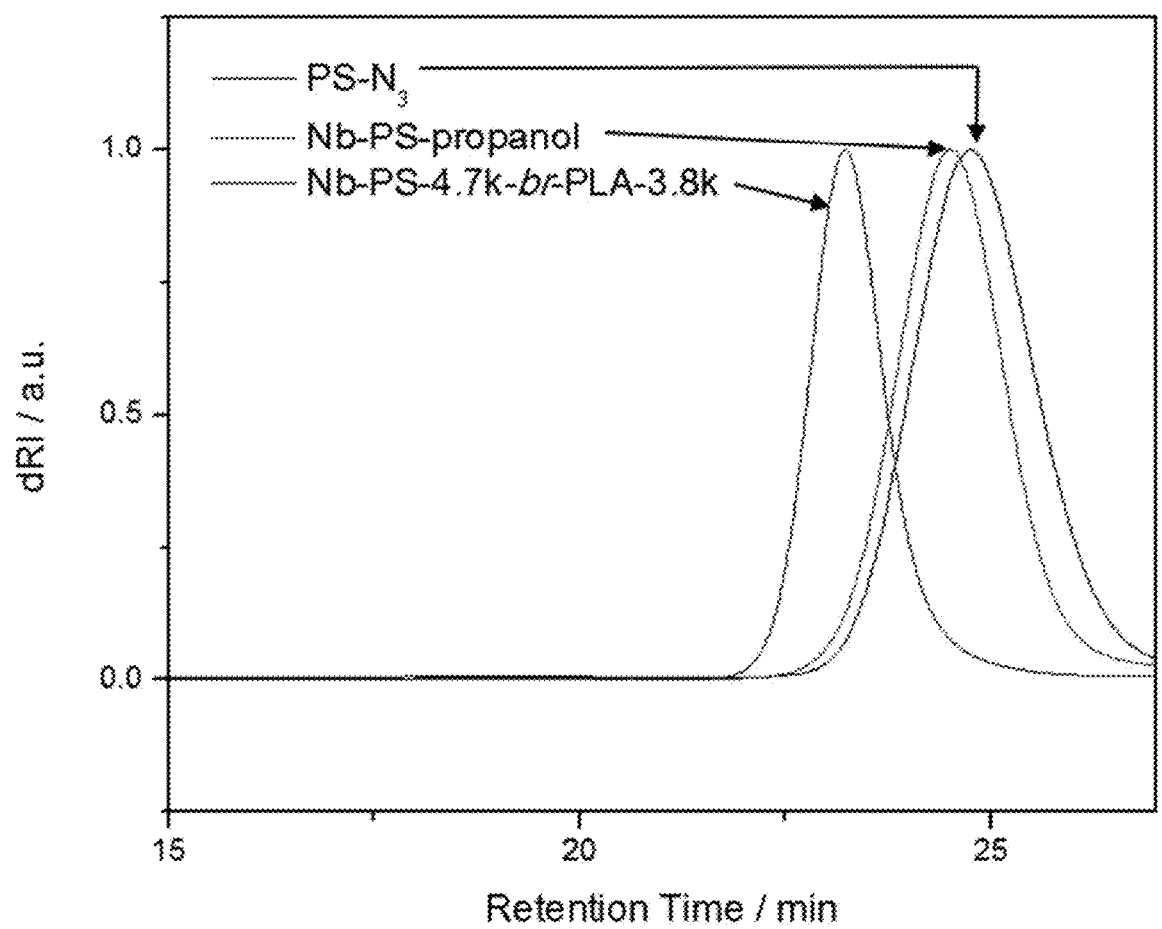
FIG. 32 shows GPC traces of G2-Nb-PS-branch-PLA.
Figure 33:
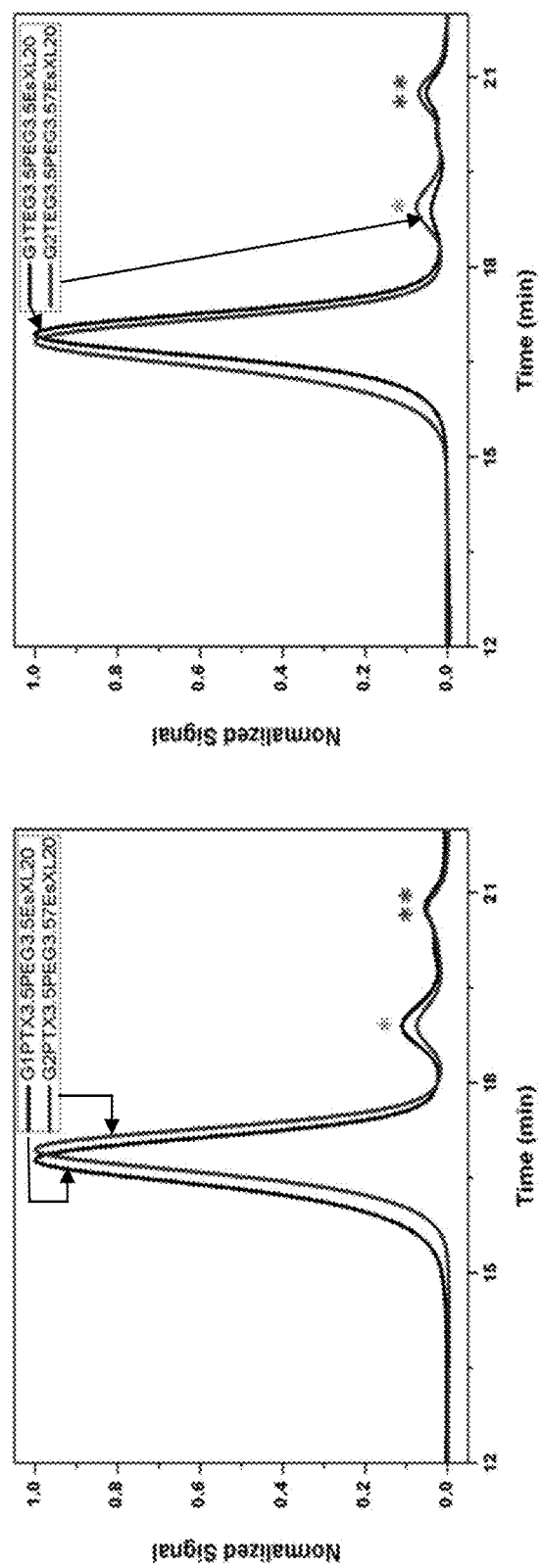
FIG. 33 shows GPC traces of BASP-forming reaction mixture of G2-MMs in comparison with their G1-MMs counterparts, with living bottlebrushes prepared from a mixture of MMs of the same generation. * denotes residual unconverted brushes, and ** denotes residual MMs.
Figure 34:
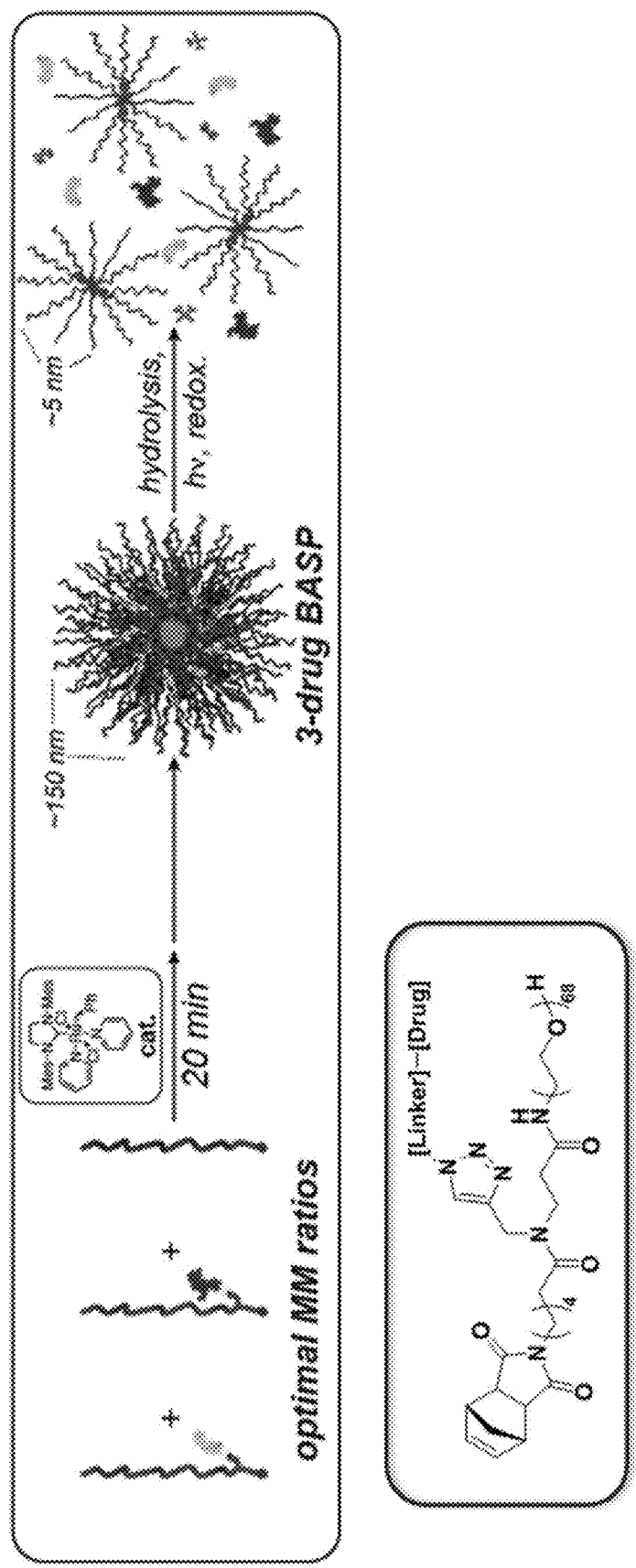
FIG. 34 shows a schematic of optimal MM ratios such as one click site per macromonomer and one drug per azide to optimize the BASP platform (Liao, L.; Liu, J.; Dreaden, E. C.; Morton, S. W.; Shopsowitz, K. E.; Hammond, P. T; Johnson, J. A. JACS 2014, 136, 5896 and Barnes, J. C.; Bruno, P. M.; Nguyen, H. V.-T.; Liao, L.; Liu, J.; Hemann, M. T.; Johnson, J. A. JACS, 2016, 138, 12494).
Figure 35:
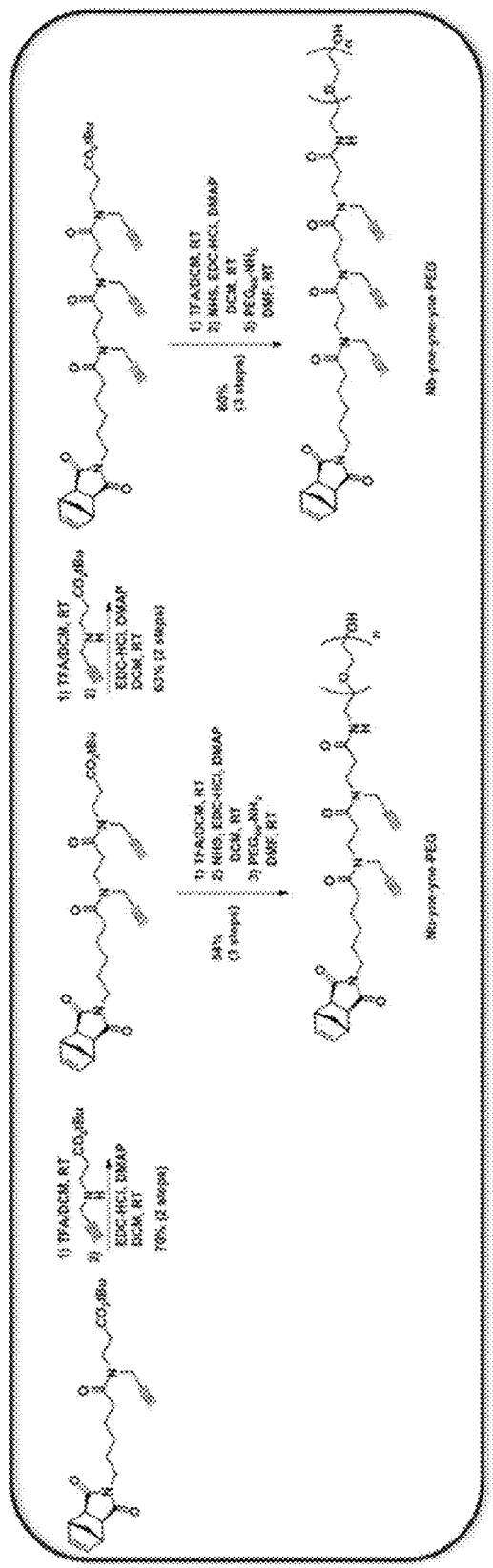
FIG. 35 shows the synthesis of multi-alkyne MMs made possible by the synthetic strategy outlined in FIG. 1B.
Figure 36:
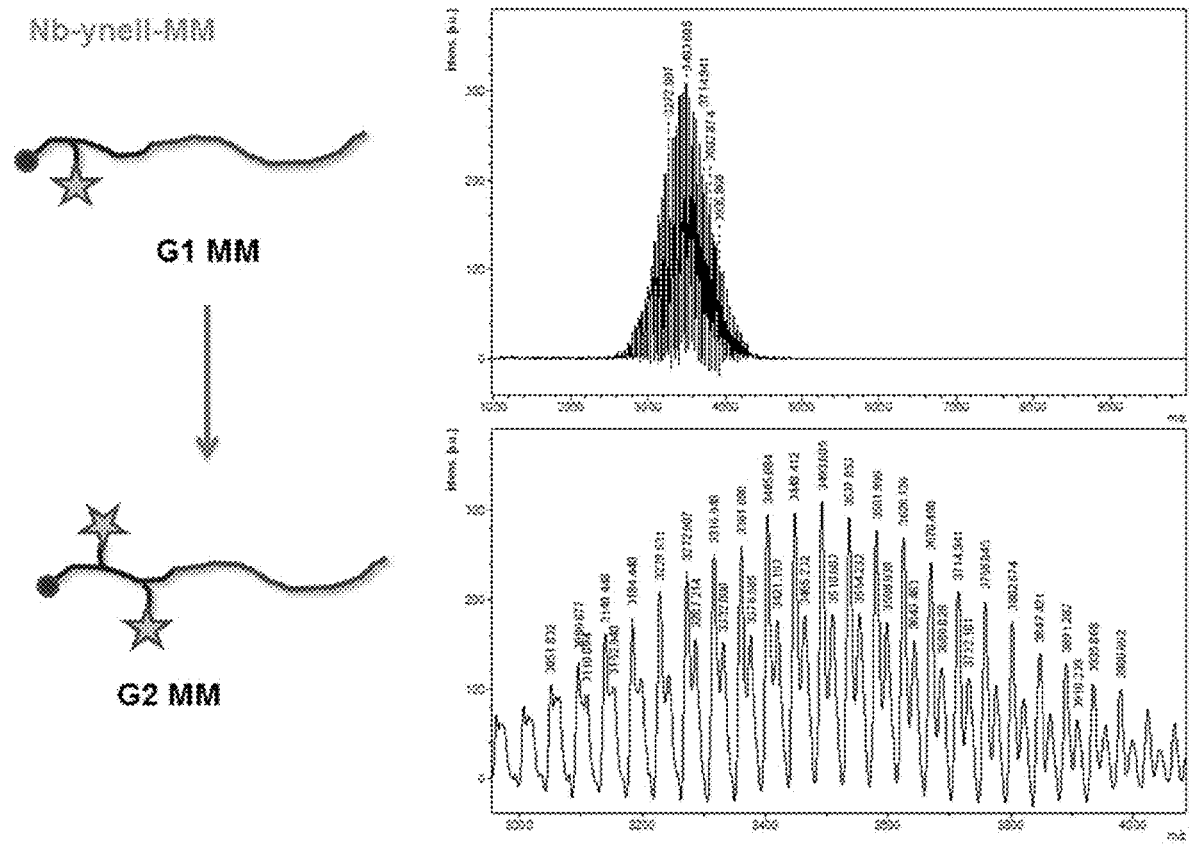
FIG. 36 shows the MALDI spectrum for Nb-yneII-MM.
Figure 37A:
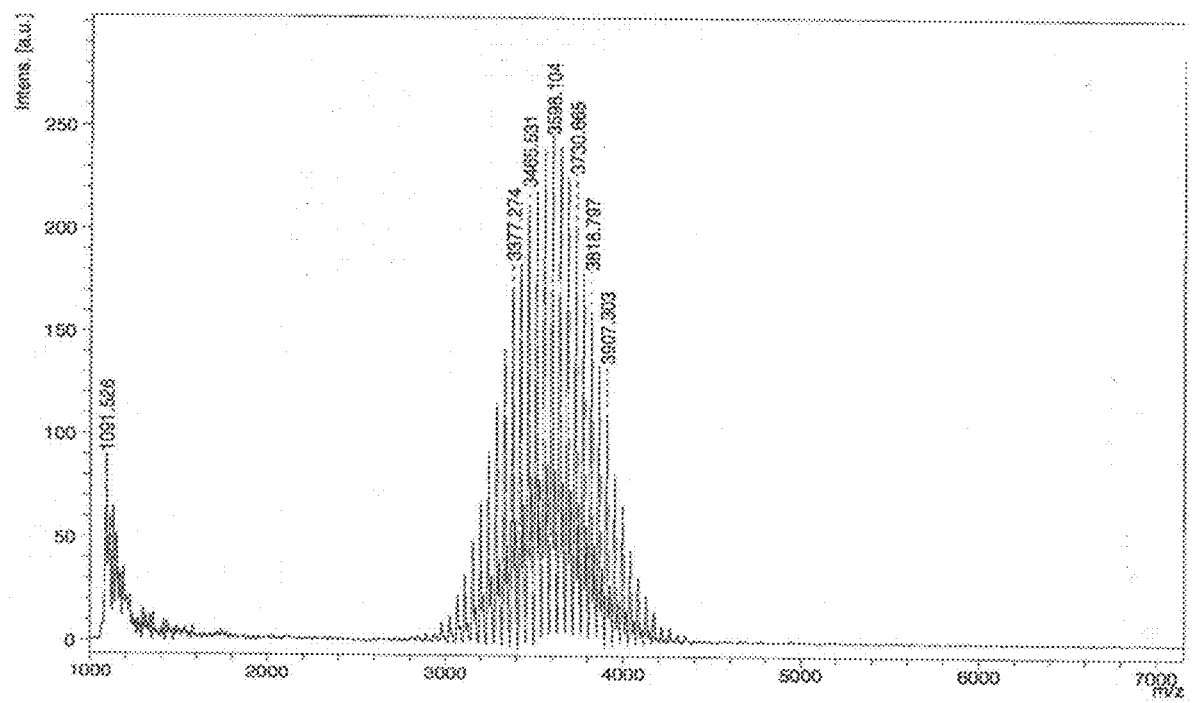
FIGS. 37A to 37B show the MALDI spectrum for Nb-yneIII-MM.
Figure 37B:
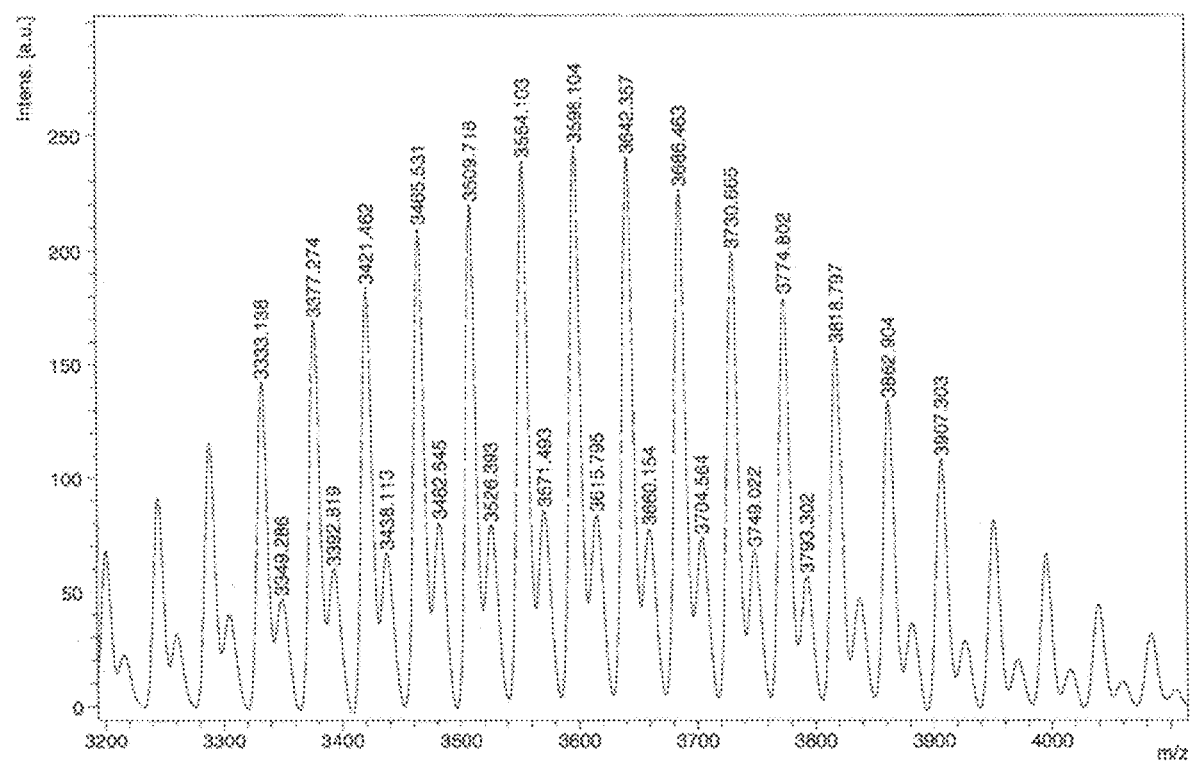
Figure 38:
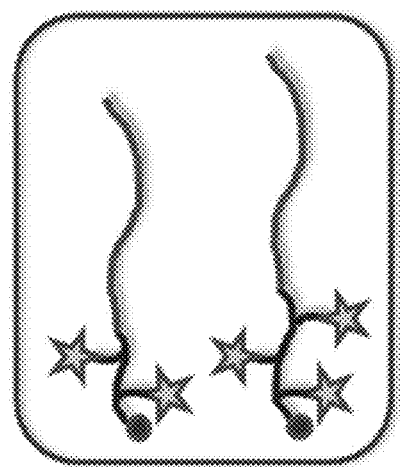
FIG. 38 shows the synthesis of ChexII-BASP from chexII-MM and the synthesis of ChexIII-BASP from chexIII-MM.
Figure 38:
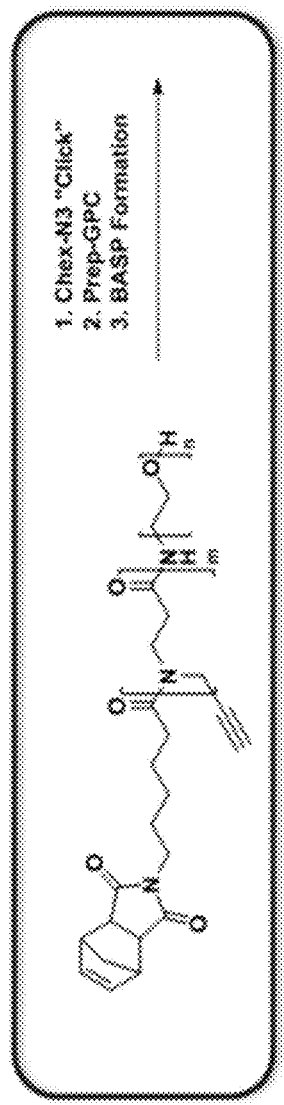
Figure 39:
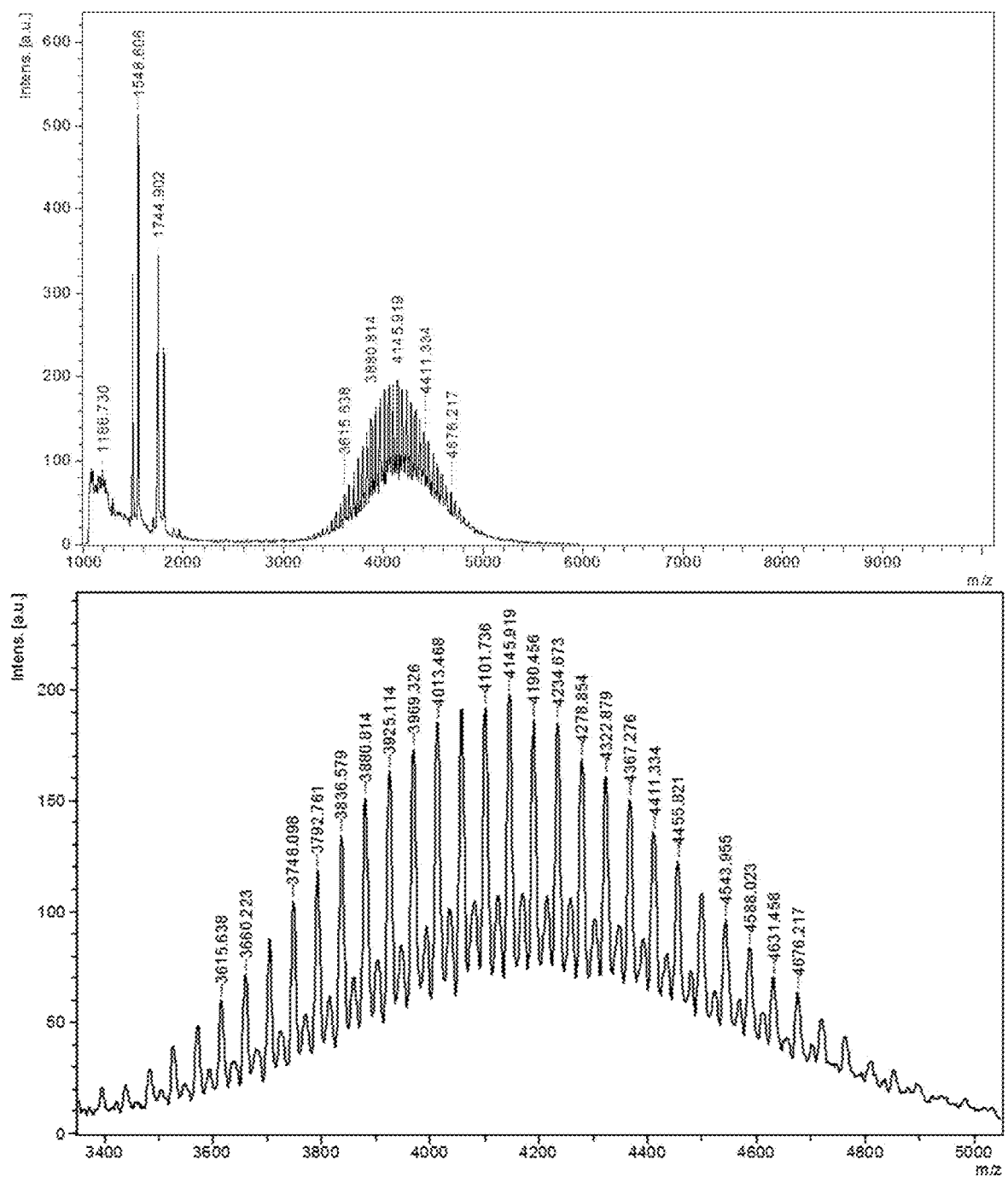
FIG. 39 shows the MALDI spectrum for chexII-MM.
Figure 40:
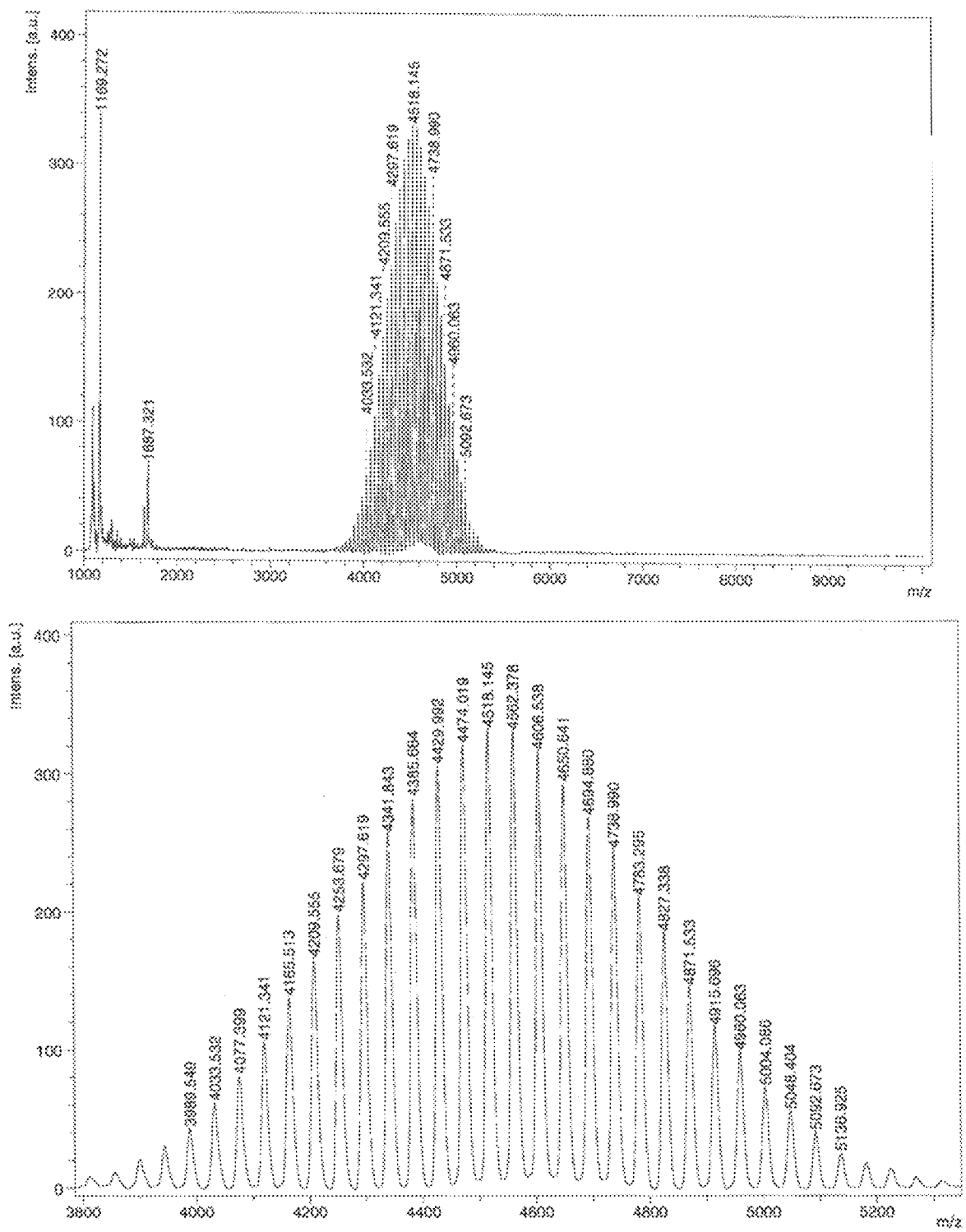
FIG. 40 shows the MALDI spectrum for chexIII-MM.
Figure 41:
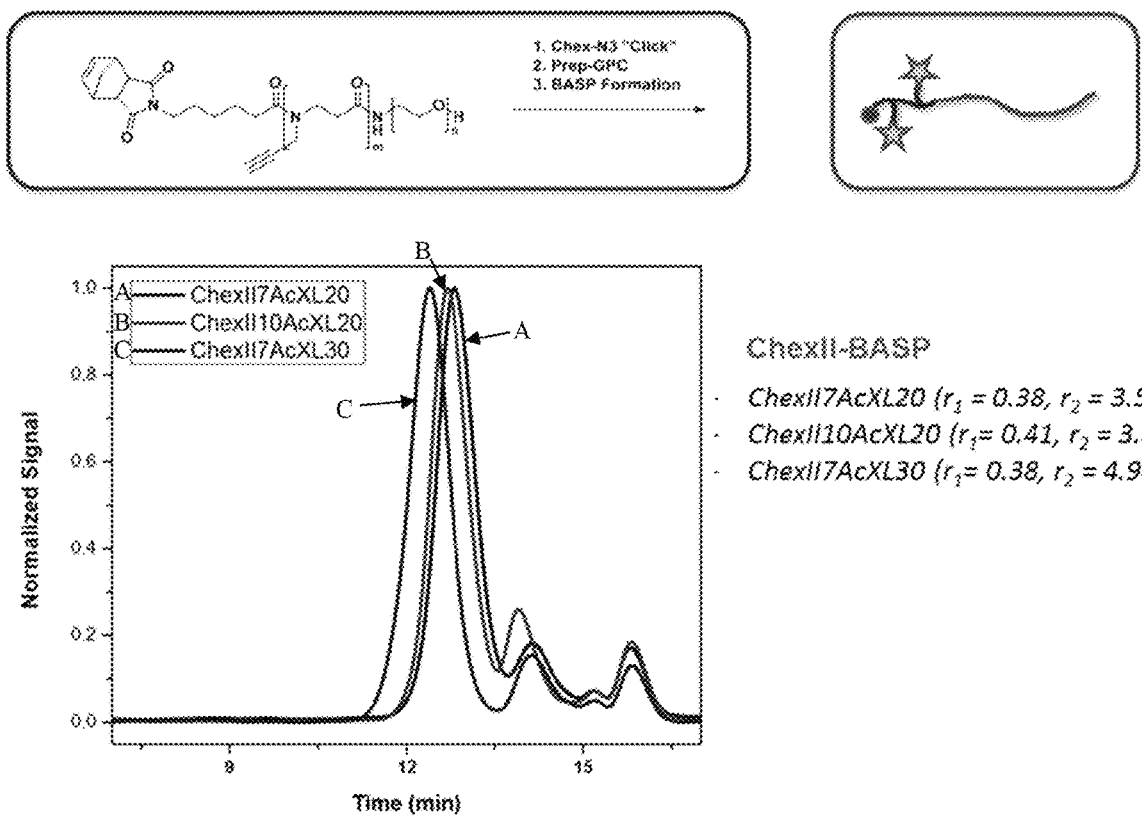
FIG. 41 shows the GPC trace of ChexII-BASP.
Figure 42:
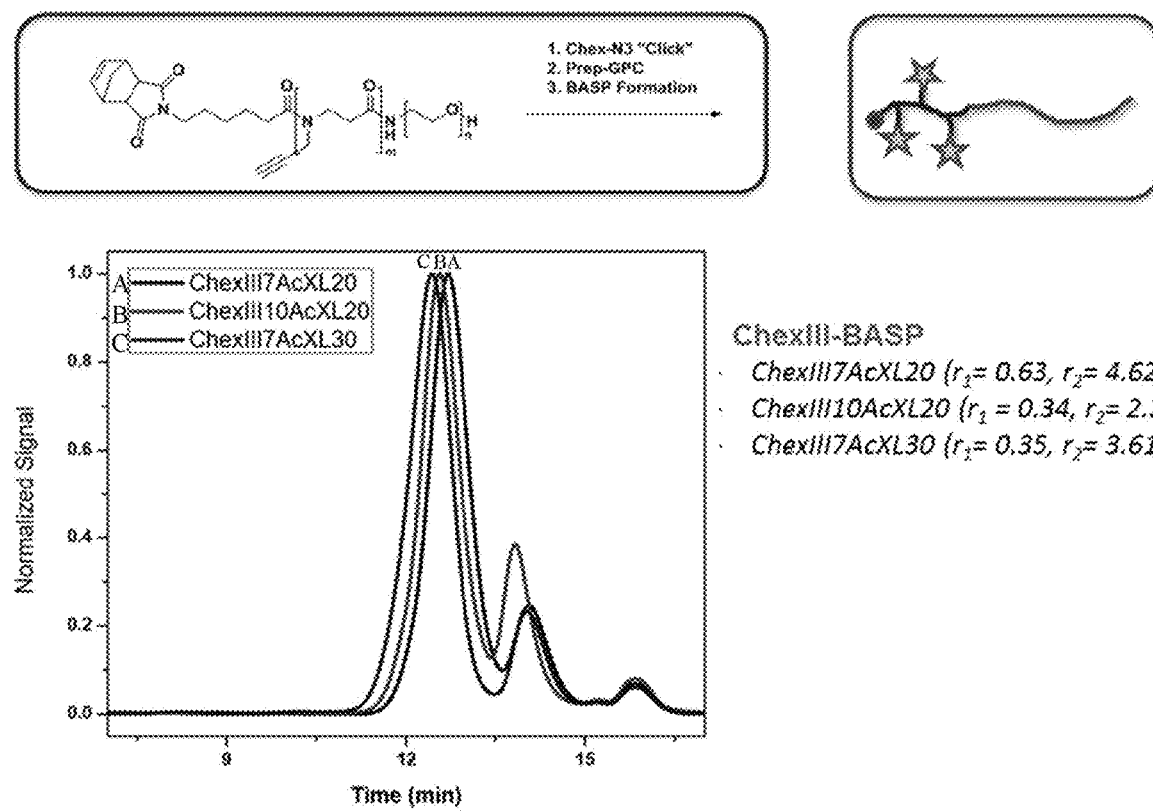
FIG. 42 shows the GPC trace of ChexIII-BASP.
Figure 43:
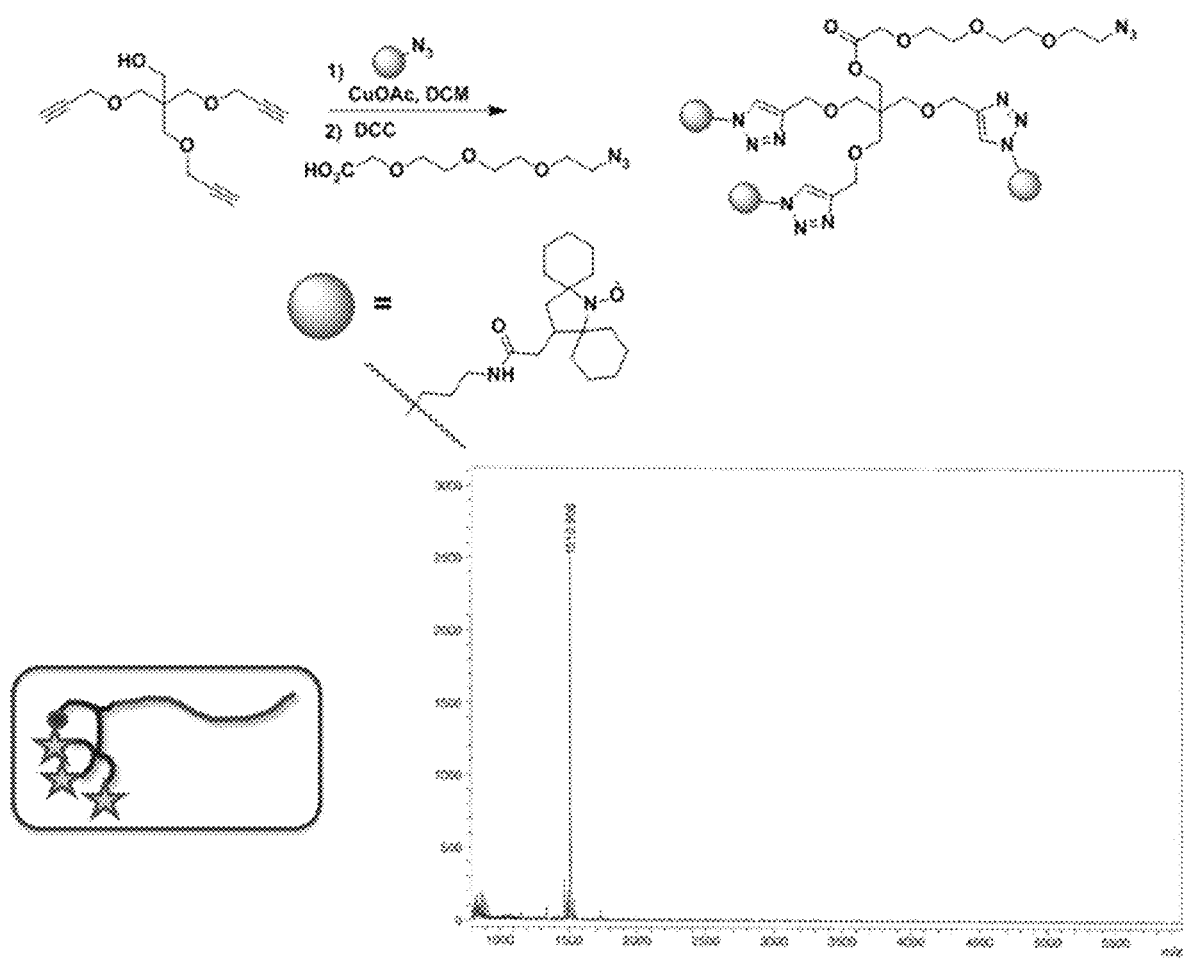
FIG. 43 shows the synthesis of an azide (ChexW-N3) capable of achieving 3-fold loading of a spirocyclohexyl nitroxide agent per alkyne. A MALDI spectrum for the azide is also provided.
Figure 44:
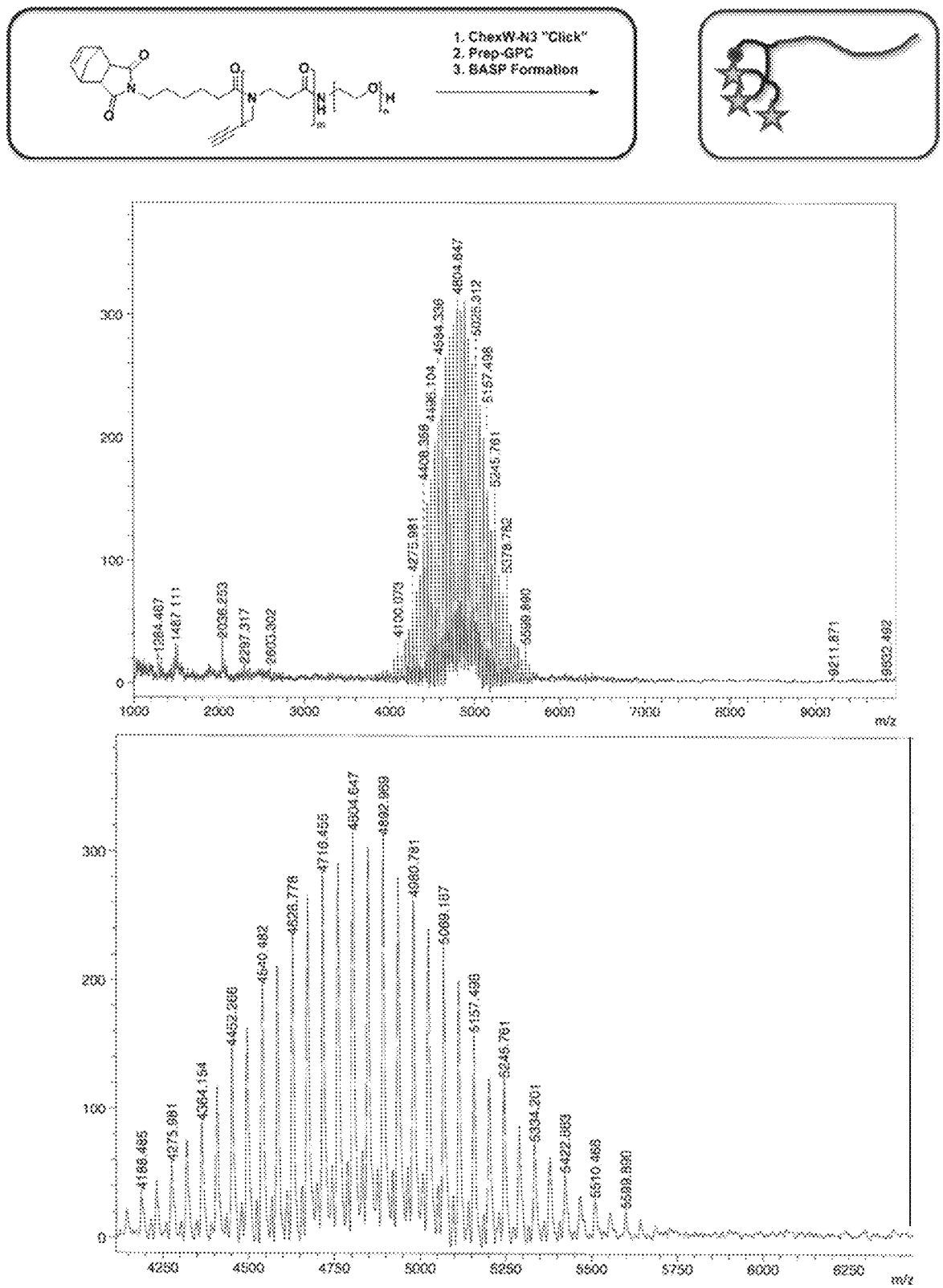
FIG. 44 shows the synthesis of BASP ChexWI and a MALDI spectrum of chexW-MM (product formed from the first step of the synthesis of ChexWI).
Figure 45:
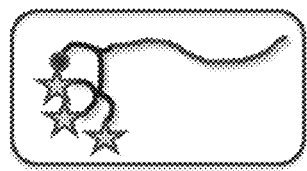
FIG. 45 shows the GPC trace of ChexWI.
Figure 45:
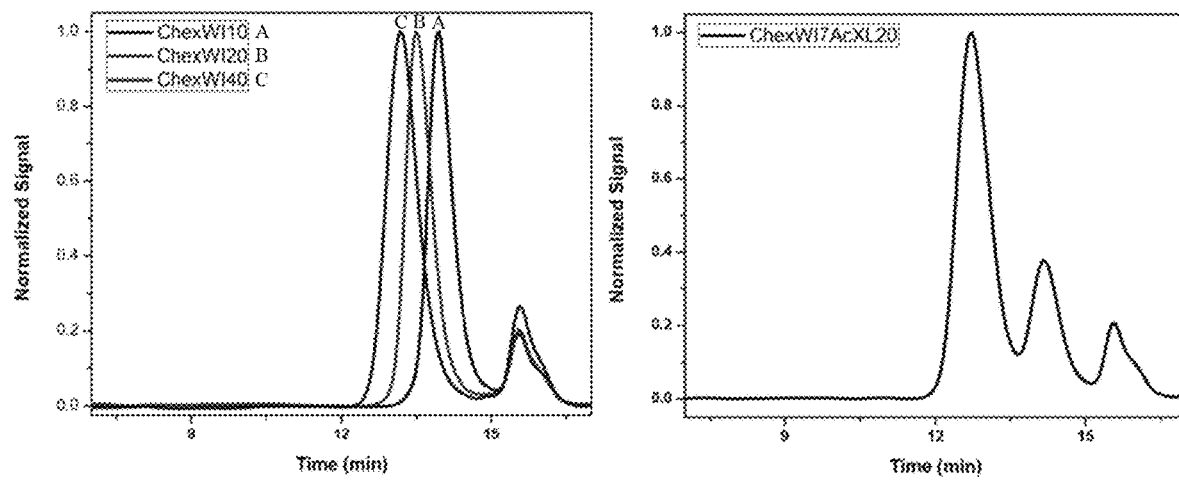

G2-Nb-yne-propanol (287 mg, 0.71 mmol, 1.0 eq) was reacted with PS—N$_3$ (M$_n$=4700 Da, Đ=1.19, synthesized according to previously published procedures)[45] (3.99 g, 0.848 mmol, 1.2 eq) according to a previously published procedure.[45] The product was isolated as a white solid (2.92 g, 81% yield). $^1$H NMR spectrum and GPC trace are shown in FIGS. 30 and 32, respectively Example 34: Synthesis of G2-Nb-PS-branch-PLA Scheme 29: Synthesis of G2-Nb-PS-branch-PLA.

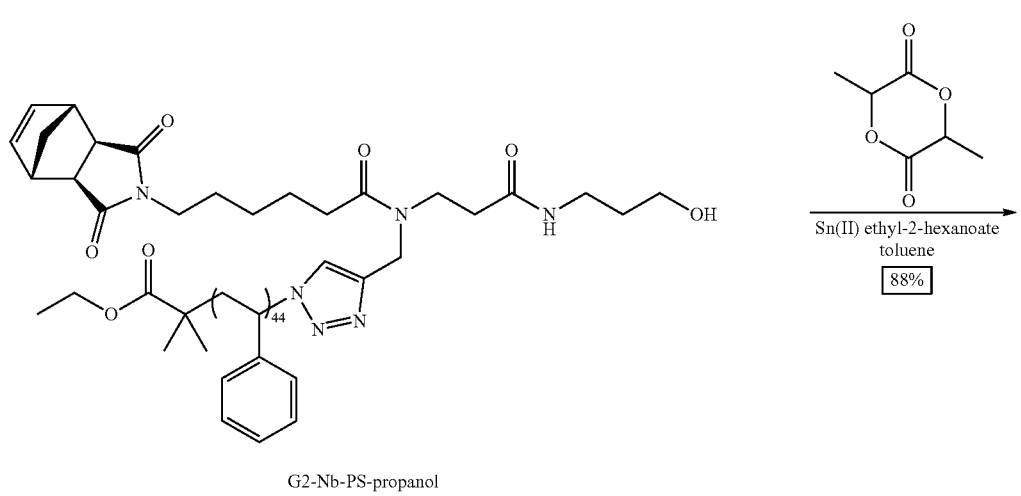

G2-Nb-PS-propanol

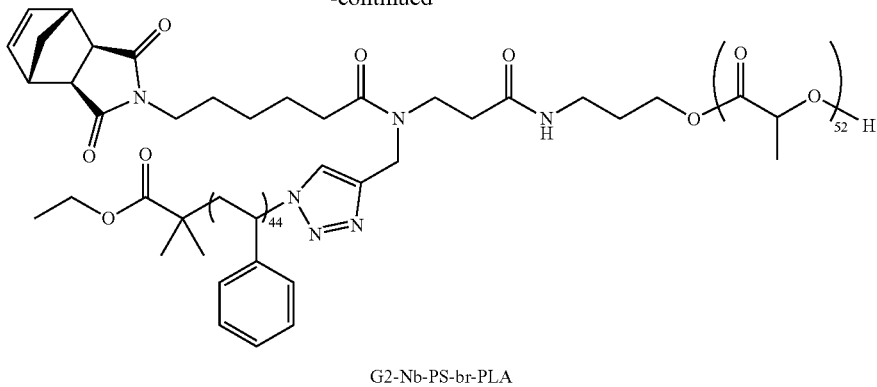

G2-Nb-PS-br-PLA

Figure 31:
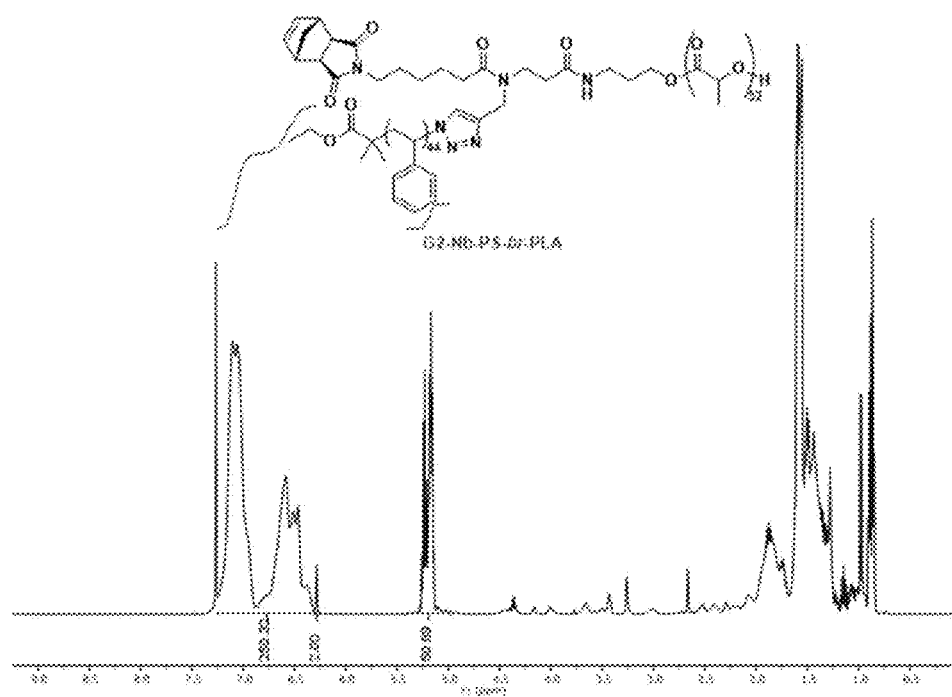
FIG. 31 shows the $^1$H NMR Spectrum of G2-Nb-PS-br-PLA in $CDCl_3$.

G2-Nb-PS-propanol (1.36 g, 0.267 mmol, 1.0 eq) was used as a macroinitiator for the tin(II) ethyl-2-hexaonate catalyzed ring opening polymerization of DL-lactide (1.54 g, 10.6 mmol, 39.7 eq). The polymerization was carried out according to previously published procedures.[46] The $M_n$ of PLA was determined to be 3.8 kDa by $^1$H NMR. $^1$H NMR spectrum and GPC trace are shown in FIGS. 31 and 32, respectively.

7) General Procedure for Brush-Arm Star Polymer (BASP) and Bottlebrush Block Copolymer (BBCP) Syntheses All BASP syntheses were performed in a glovebox under $N_2$ atmosphere; however, similar results are expected under ambient conditions. All ROMP reactions followed the same general procedure, which was modified from previously published literature.[28,40-45]

Example 35: Synthesis of G2-TEG-BASP

To the XL vial containing a stir bar, XL (4.7 mg, 7.96 mol, 20.0 eq) was added. To the MM vial containing a stir bar, G2-TEG-MM (10.0 mg, 2.79 mol, 7.0 eq) was added. To a third vial, a solution of Grubbs $3^{rd}$ generation bispyridyl catalyst G3-Cat (0.02M in THF) was freshly prepared. THF (35.8 µL) was then added to the MM vial, followed by the addition of G3-Cat solution (19.9 µL, 0.40 mol, 1.0 eq) to give the desired MM:G3-Cat ratio of 7:1, while achieving a total MM concentration of 0.05M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 36: Synthesis of G2-TEG-PEG-BASP

To the XL vial containing a stir bar, XL (6.6 mg, 11.15 mol, 20.0 eq) was added. To the MM vial containing a stir bar, G2-TEG-MM (7.0 mg, 1.95 mol, 3.5 eq) and PEG-MM (6.3 mg, 1.95 mol, 3.5 eq) were added. To a third vial, a solution of Grubbs $3^{rd}$ generation bispyridyl catalyst G3-Cat (0.02M in THF) was freshly prepared. THF (50.2 µL) was then added to the MM vial, followed by the addition of G3-Cat solution (27.9 µL, 0.56 mol, 1.0 eq) to give the desired MM:G3-Cat ratio of 7:1, while achieving a total MM concentration of 0.05M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 37: Synthesis of G2-PTX-BASP

To the XL vial containing a stir bar, XL (3.8 mg, 6.44 mol, 20.0 eq) was added. To the MM vial containing a stir bar, G2-PTX-MM (10.0 mg, 2.25 mol, 7.0 eq) was added. To a third vial, a solution of Grubbs $3^{rd}$ generation bispyridyl catalyst G3-Cat (0.02M in THF) was freshly prepared. THF (29.0 µL) was then added to the MM vial, followed by the addition of G3-Cat solution (16.1 µL, 0.32 mol, 1.0 eq) to give the desired MM:G3-Cat ratio of 7:1, while achieving a total MM concentration of 0.05M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 38: Synthesis of G2-PTX-PEG-BASP

To the XL vial containing a stir bar, XL (5.3 mg, 9.01 mol, 20.0 eq) was added. To the MM vial containing a stir bar, G2-PTX-MM (7.0 mg, 1.58 mol, 3.5 eq) and PEG-MM (5.1 mg, 1.58 mol, 3.5 eq) were added. To a third vial, a solution of Grubbs $3^{rd}$ generation bispyridyl catalyst G3-Cat (0.02 M in THF) was freshly prepared. THF (40.6 µL) was then added to the MM vial, followed by the addition of G3-Cat solution (22.5 µL, 0.45 mol, 1.0 eq) to give the desired MM:G3-Cat ratio of 7:1, while achieving a total MM concentration of 0.05 M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 39: Synthesis of G1-TEG-BASP

To the XL vial containing a stir bar, XL (4.7 mg, 7.93 mol, 20.0 eq) was added. To the MM vial containing a stir bar, G1-TEG-MM (10.0 mg, 2.78 mol, 7.0 eq) was added. To a third vial, a solution of Grubbs $3^{rd}$ generation bispyridyl catalyst G3-Cat (0.02 M in THF) was freshly prepared. THF (35.7 µL) was then added to the MM vial, followed by the addition of G3-Cat solution (19.8 µL, 0.40 mol, 1.0 eq) to give the desired MM:G3-Cat ratio of 7:1, while achieving a total MM concentration of 0.05 M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 40: Synthesis of G1-TEG-PEG-BASP

To the XL vial containing a stir bar, XL (6.5 mg, 11.11 mol, 20.0 eq) was added. To the MM vial containing a stir bar, G1-TEG-MM (7.0 mg, 1.94 mol, 3.5 eq) and PEG-MM (6.3 mg, 1.94 mol, 3.5 eq) were added. To a third vial, a solution of Grubbs $3^{rd}$ generation bispyridyl catalyst G3-Cat (0.02 M in THF) was freshly prepared. THF (50.0 µL) was then added to the MM vial, followed by the addition of G3-Cat solution (27.8 µL, 0.55 mol, 1.0 eq) to give the desired MM:G3-Cat ratio of 7:1, while achieving a total MM concentration of 0.05 M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 41: Synthesis of G1-PTX-BASP

To the XL vial containing a stir bar, XL (3.8 mg, 6.42 mol, 20.0 eq) was added. To the MM vial containing a stir bar, G1-PTX-MM (10.0 mg, 2.25 mol, 7.0 eq) was added. To a third vial, a solution of Grubbs $3^{rd}$ generation bispyridyl catalyst G3-Cat (0.02 M in THF) was freshly prepared. THF (29.0 µL) was then added to the MM vial, followed by the addition of G3-Cat solution (16.0 µL, 0.32 mol, 1.0 eq) to give the desired MM:G3-Cat ratio of 7:1, while achieving a total MM concentration of 0.05 M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 42: Synthesis of G1-PTX-PEG-BASP

To the XL vial containing a stir bar, XL (5.3 mg, 8.99 mol, 20.0 eq) was added. To the MM vial containing a stir bar, G1-PTX-MM (7.0 mg, 1.57 mol, 3.5 eq) and PEG-MM (5.1 mg, 1.57 mol, 3.5 eq) were added. To a third vial, a solution of Grubbs $3^{rd}$ generation bispyridyl catalyst G3-Cat (0.02 M in THF) was freshly prepared. THF (40.4 µL) was then added to the MM vial, followed by the addition of G3-Cat solution (22.5 µL, 0.45 mol, 1.0 eq) to give the desired MM:G3-Cat ratio of 7:1, while achieving a total MM concentration of 0.05 M, affording a yellow solution. The reaction mixture was allowed to stir for 30 min at room temperature; the living brush solution was then added to the XL vial to start the cross-linking process, and the polymerizing mixture was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 2 mL nanopure water, and the solution was dialyzed against water (100 mL×3, solvent exchange every 6 h). The nanoparticles were then lyophilized to afford a white solid.

Example 43: Synthesis of PS-branch-PLA BBCP

To the BMM vial containing a stir bar, G2-Nb-PS-br-PLA (50.0 mg) was dissolved in 50 µL of THF. To another vial, a solution of Grubbs $3^{rd}$ generation bispyridyl catalyst G3-Cat (5 mg/mL in THF) was freshly prepared. Appropriate volumes of the G3-Cat solution to achieve the desired degrees of polymerization (DP) were then added to the MM vial. The reaction mixture was allowed to stir for 2.5 h at room temperature. To quench the polymerization, a few drop of ethyl vinyl ether was then added.

Example 44: Synthesis of G2-TEG40
(Representative Bottlebrush Synthesis)

To the MM vial containing a stir bar, G2-TEG-MM (15.9 mg, 4.43 mol, 40.0 eq) was added. To another vial, a solution of G3-Cat (0.005 M in THF) was freshly prepared. THF (66.5 µL) was then added to the MM vial, followed by the addition of G3-Cat solution (22.2 µL, 0.11 mol, 1.0 eq) to give the desired DP of 40, while achieving a total MM concentration of 0.05 M, affording a yellow solution. The reaction mixture was allowed to stir for 3 hours at room temperature. To quench the polymerization, a drop of ethyl vinyl ether was then added.

Example 45: Synthesis of G1-TEG40, G2-TEG$_2$40, G2-chex40, G2-chex$_2$40

Polymers were prepared in the same manner as reported for G2-TEG40. Bottlebrushes of DP 40 were prepared using 0.005 M G3-Cat solution and the appropriate MM solution to ensure final MM concentration of 0.05 M and MM-to-G3-Cat ratio of 40:1 (DP=40).

Example 46: Synthesis of G2-TEG$_3$ and G2-Chex$_3$ with Varying DP

Polymers were prepared in the same manner as reported for G2-TEG40. Bottlebrushes of the appropriate DPs (10, 25, 40, 55, 70) were prepared using 0.005 M G3-Cat solution and the appropriate MM solution to ensure final MM concentration of 0.05 M and desired MM-to-G3-Cat ratio (DP). Bottlebrushes of DP 10 was prepared using 0.02 M G3-Cat and allowed to stir for 60 minutes. Bottlebrushes of DP 55 and 70 were allowed to stir for 6 hours.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the terth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Rzayev, J.: Molecular Bottlebrushes: New Opportunities in Nanomaterials Fabrication. *ACS Macro Letters* 2012, 1, 1146-1149.
2. Sheiko, S. S.; Sumerlin, B. S.; Matyjaszewski, K.: Cylindrical molecular brushes: Synthesis, characterization, and properties. *Progress in Polymer Science* 2008, 33, 759-785.
3. Lee, H.-i.; Pietrasik, J.; Sheiko, S. S.; Matyjaszewski, K.: Stimuli-responsive molecular brushes. *Progress in Polymer Science* 2010, 35, 24-44.
4. Xia, Y.; Olsen, B. D.; Kornfield, J. A.; Grubbs, R. H.: Efficient Synthesis of Narrowly Dispersed Brush Copolymers and Study of Their Assemblies: The Importance of Side Chain Arrangement. *Journal of the American Chemical Society* 2009, 131, 18525-18532.
5. Xia, Y.; Kornfield, J. A.; Grubbs, R. H.: Efficient Synthesis of Narrowly Dispersed Brush Polymers via Living Ring-Opening Metathesis Polymerization of Macromonomers. *Macromolecules* 2009, 42, 3761-3766.
6. Verduzco, R.; Li, X.; Pesek, S. L.; Stein, G. E.: Structure, function, self-assembly, and applications of bottlebrush copolymers. *Chemical Society Reviews* 2015, 44, 2405-2420.
7. Miyake, G. M.; Piunova, V. A.; Weitekamp, R. A.; Grubbs, R. H.: Precisely Tunable Photonic Crystals From Rapidly Self-Assembling Brush Block Copolymer Blends. *Angewandte Chemie International Edition* 2012, 51, 11246-11248.
8. Barnes, J. C.; Bruno, P. M.; Nguyen, H. V. T.; Liao, L.; Liu, J.; Hemann, M. T.; Johnson, J. A.: Using an RNAi Signature Assay To Guide the Design of Three-Drug-Conjugated Nanoparticles with Validated Mechanisms, In Vivo Efficacy, and Low Toxicity. *Journal of the American Chemical Society* 2016, 138, 12494-12501.
9. Kawamoto, K.; Zhong, M.; Gadelrab, K. R.; Cheng, L.-C.; Ross, C. A.; Alexander-Katz, A.; Johnson, J. A.: Graft-through Synthesis and Assembly of Janus Bottlebrush Polymers from A-Branch-B Diblock Macromonomers. *Journal of the American Chemical Society* 2016, 138, 11501-11504.
10. Ren, J. M.; McKenzie, T. G.; Fu, Q.; Wong, E. H. H.; Xu, J.; An, Z.; Shanmugam, S.; Davis, T. P.; Boyer, C.; Qiao, G. G.: Star Polymers. *Chemical Reviews* 2016, 116, 6743-6836.

11. Liao, L.; Liu, J.; Dreaden, E. C.; Morton, S. W.; Shopsowitz, K. E.; Hammond, P. T.; Johnson, J. A.: A Convergent Synthetic Platform for Single-Nanoparticle Combination Cancer Therapy: Ratiometric Loading and Controlled Release of Cisplatin, Doxorubicin, and Camptothecin. *Journal of the American Chemical Society* 2014, 136, 5896-5899.

12. Sveinbjörnsson, B. R.; Weitekamp, R. A.; Miyake, G. M.; Xia, Y.; Atwater, H. A.; Grubbs, R. H.: Rapid self-assembly of brush block copolymers to photonic crystals. *Proceedings of the National Academy of Sciences* 2012, 109, 14332-14336.

13. Fox, M. E.; Szoka, F. C.; Fréchet, J. M. J.: Soluble Polymer Carriers for the Treatment of Cancer: The Importance of Molecular Architecture. *Accounts of Chemical Research* 2009, 42, 1141-1151.

14. Peer, D.; Karp, J. M.; Hong, S.; Farokhzad, O. C.; Margalit, R.; Langer, R.: Nanocarriers as an emerging platform for cancer therapy. *Nat Nano* 2007, 2, 751-760.

15. Maeda, H.; Bharate, G. Y.; Daruwalla, J.: Polymeric drugs for efficient tumor-targeted drug delivery based on EPR-effect. *European Journal of Pharmaceutics and Biopharmaceutics* 2009, 71, 409-419.

16. Gao, A. X.; Liao, L.; Johnson, J. A.: Synthesis of Acid-Labile PEG and PEG-Doxorubicin-Conjugate Nanoparticles via Brush-First ROMP. *ACS Macro Letters* 2014, 3, 854-857.

17. Duncan, R.: The dawning era of polymer therapeutics. *Nat Rev Drug Discov* 2003, 2, 347-360.

18. Liang, L.; Astruc, D.: The copper(I)-catalyzed alkyne-azide cycloaddition (CuAAC) "click" reaction and its applications. An overview. *Coordination Chemistry Reviews* 2011, 255, 2933-2945.

19. Hein, J. E.; Fokin, V. V.: Copper-catalyzed azide-alkyne cycloaddition (CuAAC) and beyond: new reactivity of copper(i) acetylides. *Chemical Society Reviews* 2010, 39, 1302-1315.

20. Worrell, B. T.; Malik, J. A.; Fokin, V. V.: Direct Evidence of a Dinuclear Copper Intermediate in Cu(I)-Catalyzed Azide-Alkyne Cycloadditions. *Science* 2013, 340, 457-460.

21. Han, S.-Y.; Kim, Y.-A.: Recent development of peptide coupling reagents in organic synthesis. *Tetrahedron* 2004, 60, 2447-2467.

22. Valeur, E.; Bradley, M.: Amide bond formation: beyond the myth of coupling reagents. *Chemical Society Reviews* 2009, 38, 606-631.

23. Dunetz, J. R.; Magano, J.; Weisenburger, G. A.: Large-Scale Applications of Amide
Coupling Reagents for the Synthesis of Pharmaceuticals. *Organic Process Research & Development* 2016, 20, 140-177.

24. El-Faham, A.; Albericio, F.: Peptide Coupling Reagents, More than a Letter Soup. *Chemical Reviews* 2011,111, 6557-6602.

25. Neises, B.; Steglich, W.: Simple Method for the Esterification of Carboxylic Acids. *Angewandte Chemie International Edition* in English 1978, 17, 522-524.

26. Burts, A. O.; Liao, L.; Lu, Y. Y.; Tirrell, D. A.; Johnson, J. A.: Brush-first and Click: Efficient Synthesis of Nanoparticles that Degrade and Release Doxorubicin in Response to Light. *Photochemistry and Photobiology* 2014, 90, 380-385.

27. Liu, J.; Burts, A. O.; Li, Y.; Zhukhovitskiy, A. V.; Ottaviani, M. F.; Turro, N. J.; Johnson, J. A.: "Brush-First" Method for the Parallel Synthesis of Photocleavable, Nitroxide-Labeled Poly(ethylene glycol) Star Polymers. *Journal of the American Chemical Society* 2012, 134, 16337-16344.

28. Sowers, M. A.; McCombs, J. R.; Wang, Y.; Paletta, J. T.; Morton, S. W.; Dreaden, E. C.; Boska, M. D.; Ottaviani, M. F.; Hammond, P. T.; Rajca, A.; Johnson, J. A.: Redox-responsive branched-bottlebrush polymers for in vivo MRI and fluorescence imaging. *Nature Communications* 2014, 5, 5460.

29. Johnson, J. A.; Lu, Y. Y.; Burts, A. O.; Xia, Y.; Durrell, A. C.; Tirrell, D. A.; Grubbs, R. H.: Drug-Loaded, Bivalent-Bottle-Brush Polymers by Graft-through ROMP. *Macromolecules* 2010, 43, 10326-10335.

30. Patel, P. R.; Kiser, R. C.; Lu, Y. Y.; Fong, E.; Ho, W. C.; Tirrell, D. A.; Grubbs, R. H.: Synthesis and Cell Adhesive Properties of Linear and Cyclic RGD Functionalized Polynorbornene Thin Films. *Biomacromolecules* 2012, 13, 2546-2553.

31. Roy, O.; Faure, S.; Thery, V.; Didierjean, C.; Taillefumier, C.: Cyclic β-Peptoids. *Organic Letters* 2008, 10, 921-924.

32. Wuts, P. G. M.; Greene, T. W.: Protection for the Carboxyl Group. In Greene's *Protective Groups in Organic Synthesis*; John Wiley & Sons, Inc., 2006; pp 533-646.

33. Xia, Y.; Li, Y.; Burts, A. O.; Ottaviani, M. F.; Tirrell, D. A.; Johnson, J. A.; Turro, N. J.; Grubbs, R. H.: EPR Study of Spin Labeled Brush Polymers in Organic Solvents. *Journal of the American Chemical Society* 2011, 133, 19953-19959.

34. Joralemon, M. J.; McRae, S.; Emrick, T.: PEGylated polymers for medicine: from conjugation to self-assembled systems. *Chemical Communications* 2010, 46, 1377-1393.

35. Torchilin, V.: Tumor delivery of macromolecular drugs based on the EPR effect. *Advanced Drug Delivery Reviews* 2011, 63, 131-135.

36. Anraku, Y.; Kishimura, A.; Kobayashi, A.; Oba, M.; Kataoka, K.: Size-controlled long-circulating PICsome as a ruler to measure critical cut-off disposition size into normal and tumor tissues. *Chemical Communications* 2011, 47, 6054-6056.

37. Cabral, H.; Matsumoto, Y.; MizunoK; Chen, Q.; Murakami, M.; Kimura, M.; Terada, Y.; Kano, M. R.; Miyazono, K.; Uesaka, M.; Nishiyama, N.; Kataoka, K.: Accumulation of sub-100 nm polymeric micelles in poorly permeable tumours depends on size. *Nat Nano* 2011, 6, 815-823.

38. Burts, A. O.; Gao, A. X.; Johnson, J. A.: Brush-First Synthesis of Core-Photodegradable Miktoarm Star Polymers via ROMP: Towards Photoresponsive Self-Assemblies. *Macromolecular Rapid Communications* 2014, 35, 168-173.

39. Love, J. A.; Morgan, J. P.; Trnka, T. M.; Grubbs, R. H. A Practical and Highly Active
Ruthenium-based Catalyst that Effects the Cross Metathesis of Acrylonitrile. *Angew. Chem. Int. Ed.* 2002, 41, 4035-4037.

40. Johnson, J. A.; Lu, Y. Y.; Burts, A. O.; Xia, Y.; Durrell, A. C.; Tirrell, D. A.; Grubbs, R. H. Drug-loaded, Bivalent-bottle-brush Polymers by Graft-through ROMP. *Macromolecules*. 2010, 43, 10326-10335.

41. Liu, J.; Burts, A. O.; Li, Y.; Zhukhovitskiy, A. V.; Ottaviani, M. F.; Turro, N. J.; Johnson, J. A. "Brush-first" Method for the Parallel Synthesis of Photocleavable, Nitroxide-labeled poly(ethylene glycol) Star Polymers. *J. Am. Chem. Soc.* 2012, 134, 16337-16344.

42. Liao, L.; Liu, J.; Dreaden, E. C.; Morton, S. W.; Shopsowitz, K. E.; Hammond, P. T.; Johnson, J. A. A Convergent Synthetic Platform for Single-nanoparticle Combination Cancer Therapy: Ratiometric Loading and Controlled Release of Cisplatin, Doxorubicin, and Camptothecin. *J. Am. Chem. Soc.* 2014, 136, 5896-5899.

43. Roy, O.; Faure, S.; Thery, V.; Didierjean, C.; Taillefumier, C. Cyclic β-peptoids. *Org. Lett.* 2008, 10, 921-924.

44. Patel, P. R.; Kiser, R. C.; Lu, Y. Y; Fong, E.; Ho, W. C.; Tirrell, D. A.; Grubbs, R. H. Synthesis and cell adhesive properties of linear and cyclic RGD functionalized polynorbornene thin films. *Biomacromolecules.* 2012, 13, 2546-2553.

45. Kawamoto, K.; Zhong, M.; Gadelrab, K. R.; Cheng, L.-C.; Ross, C. A.; Alexander-Katz, A.; Johnson, J. A.: Graft-through Synthesis and Assembly of Janus Bottlebrush Polymers from A-Branch-B Diblock Macromonomers. *J. Am. Chem. Soc.* 2016, 138, 11501-11504.

46. Burts, A. O.; Gao, A. X.; Johnson, J. A. Brush-first Synthesis of Core-photodegradable Miktoarm Star Polymer via ROM: Towards Photoresponsive Self-assemblies. *Macromol. Rap. Commun.* 2014, 35, 168-173.

47. Budil, D. E.; Lee, S.; Saxena, S.; Freed, J. H. Nonlinear-least-square Analysis of Slow-motion EPR Spectra in One and Two Dimensions Using a Modified Levenberg-Marquardt-algorithm. *J. Magn. Reson., Ser. A.* 1996, 120, 155-189.

What is claimed is:

1. A macromonomer of Formula (I):

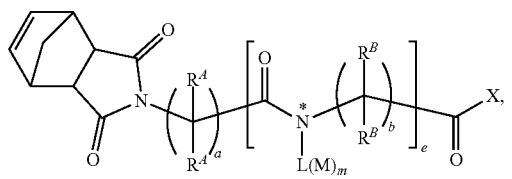

(I)

or a salt thereof, wherein:
each instance of $R^A$ is independently hydrogen, halogen, or substituted or unsubstituted, $C_{1-6}$ alkyl;
a is an integer from 1 to 20, inclusive;
each instance of M is independently hydrogen or an agent, wherein each instance of the agent is independently a therapeutic agent, a diagnostic agent, or a prophylactic agent;
each instance of m is independently an integer from 1 to 10, inclusive;
each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:
  optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
  optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
  provided that when each instance of M is hydrogen, at least one instance of -L(M)$_m$ comprises a click-chemistry handle;
each instance of $R^B$ is independently hydrogen, halogen, or substituted or unsubstituted, $C_{1-6}$ alkyl;
each instance of b is independently an integer from 1 to 20, inclusive;
e is an integer from 1 to 10, inclusive; and
X is $OR^C$ or $N(R^D)_2$, wherein:
  $R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and
  each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group, or two $R^D$ are taken together to form a substituted or unsubstituted heterocyclyl or substituted or unsubstituted heteroaryl moiety.

2. The macromonomer of claim 1, or a salt thereof, wherein at least one instance of L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with

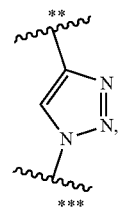

wherein the nitrogen atom labeled with "*" is closer to the attachment point labeled with "" than the attachment point labeled with "*".

3. The macromonomer of claim 1, or a salt thereof, wherein at least two instances of M that are agents are different from each other.

4. The macromonomer of claim 1, or a salt thereof, wherein at least one instance of m is 2, 3, 4, or 5.

5. A method of preparing a macromonomer of claim 1, or a salt thereof, comprising coupling a compound of the formula:

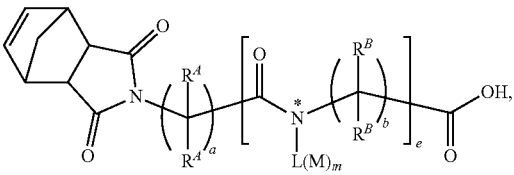
(D)

or a salt thereof, with a compound of the formula: HOR$^C$ or HN(R$^D$)$_2$, or a salt thereof.

6. A polymer prepared by polymerizing a macromonomer of claim 1, or a salt thereof, in the presence of a metathesis catalyst.

7. The polymer of claim 6, wherein the polymer is prepared by polymerizing a first instance of the macromonomer, or a salt thereof, and a second instance of the macromonomer, or a salt thereof, in the presence of a metathesis catalyst, wherein at least one instance of M of the first instance of the macromonomer is different from at least one instance of M of the second instance of the macromonomer.

8. A method of preparing a polymer comprising polymerizing a macromonomer of claim 1, or a salt thereof, in the presence of a metathesis catalyst.

9. The method of claim 8 comprising polymerizing a first instance of the macromonomer, or a salt thereof, and a second instance of the macromonomer, or a salt thereof, in the presence of a metathesis catalyst, wherein at least one instance of M of the first instance of the macromonomer is different from at least one instance of M of the second instance of the macromonomer.

10. A pharmaceutical composition comprising a polymer of claim 6, and optionally a pharmaceutically acceptable excipient, wherein at least one instance of M is a therapeutic agent, a diagnostic agent, or a prophylactic agent.

11. A kit comprising:
a polymer of claim 6; and
instructions for using the polymer.

12. A method of delivering a therapeutic agent, a diagnostic agent, or a prophylactic agent to a subject comprising administering to the subject a polymer of claim 6, wherein at least one instance of M is a therapeutic agent, a diagnostic agent, or a prophylactic agent.

13. A method of delivering a therapeutic agent, a diagnostic agent, or a prophylactic agent to a cell comprising contacting the cell with a polymer of claim 6, wherein at least one instance of M is a therapeutic agent, a diagnostic agent, or a prophylactic agent.

14. A method of treating a disease or condition in a subject in need thereof comprising administering to or implanting in the subject in need thereof a therapeutically effective amount of:
a polymer of claim 6;
wherein at least one instance of M is a therapeutic agent.

15. A method of diagnosing a disease or condition in a subject comprising administering to or implanting in the subject a diagnostically effective amount of:
a polymer of claim 6;
wherein at least one instance of M is a diagnostic agent.

16. The macromonomer of claim 1, or a salt thereof, wherein each instance of R$^A$ is hydrogen.

17. The macromonomer of claim 1, or a salt thereof, wherein a is 4, 5, or 6.

18. The macromonomer of claim 1, or a salt thereof, wherein at least one instance of -L(M)$_m$ is —(CH$_2$)$_p$—C≡CH, wherein each instance of p is independently an integer from 1 to 10, inclusive.

19. The macromonomer of claim 1, or a salt thereof, wherein each instance of M is hydrogen, and each instance of the click-chemistry handle is —C≡CH.

20. The macromonomer of claim 1, or a salt thereof, wherein at least one instance of M is a therapeutic agent, a diagnostic agent, or a prophylactic agent.

21. The macromonomer of claim 1, or a salt thereof, wherein at least one instance of M is an anti-cancer agent.

22. The macromonomer of claim 1, or a salt thereof, wherein each instance of m is 1.

23. The macromonomer of claim 1, or a salt thereof, wherein each instance of R$^B$ is hydrogen.

24. The macromonomer of claim 1, or a salt thereof, wherein each instance of b is independently 2, 3, or 4.

25. The macromonomer of claim 1, or a salt thereof, wherein e is 2, 3, or 4.

26. The macromonomer of claim 1, or a salt thereof, wherein X is N(R$^D$)$_2$.

27. The macromonomer of claim 26, or a salt thereof, wherein at least one instance of R$^D$ is substituted or unsubstituted, C$_{50-1000}$ heteroalkyl.

28. The macromonomer of claim 1, or a salt thereof, wherein the macromonomer is of the formula:

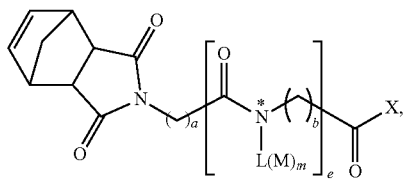

wherein e is an integer from 2 to 10, inclusive.

29. The macromonomer of claim 1, or a salt thereof, wherein the macromonomer is of the formula:

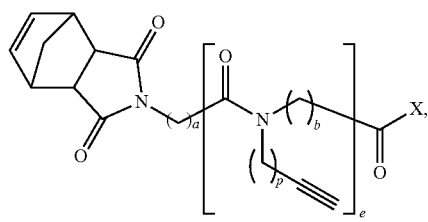

wherein:
each instance of p is independently an integer from 1 to 10, inclusive; and
e is an integer from 2 to 10, inclusive.

30. The macromonomer of claim 1, or a salt thereof, wherein the macromonomer is of the formula:

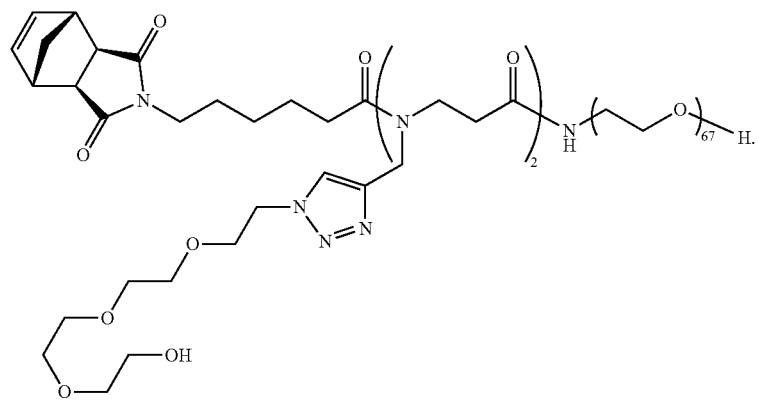
31. The method of claim 14, wherein the disease or condition is cancer, and at least one instance of M is an anti-cancer agent.